US009752142B2

(12) United States Patent
Oestergaard et al.

(10) Patent No.: US 9,752,142 B2
(45) Date of Patent: *Sep. 5, 2017

(54) GAPPED OLIGOMERIC COMPOUNDS COMPRISING 5'-MODIFIED DEOXYRIBONUCLEOSIDES IN THE GAP AND USES THEREOF

(75) Inventors: Michael Oestergaard, Carlsbad, CA (US); Thazha P. Prakash, Carlsbad, CA (US); Punit P. Seth, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 301 days.

This patent is subject to a terminal disclaimer.

(21) Appl. No.: 14/238,094

(22) PCT Filed: Aug. 8, 2012

(86) PCT No.: PCT/US2012/049989
§ 371 (c)(1),
(2), (4) Date: Jul. 1, 2014

(87) PCT Pub. No.: WO2013/022967
PCT Pub. Date: Feb. 14, 2013

(65) Prior Publication Data
US 2014/0309279 A1 Oct. 16, 2014

Related U.S. Application Data

(60) Provisional application No. 61/522,659, filed on Aug. 11, 2011, provisional application No. 61/596,723, filed on Feb. 8, 2012, provisional application No. 61/603,196, filed on Feb. 24, 2012.

(51) Int. Cl.
C12N 15/11 (2006.01)
C07H 21/04 (2006.01)
C12N 15/113 (2010.01)

(52) U.S. Cl.
CPC .......... *C12N 15/113* (2013.01); *C12N 15/111* (2013.01); *C12N 2310/11* (2013.01); *C12N 2310/312* (2013.01); *C12N 2310/315* (2013.01); *C12N 2310/316* (2013.01); *C12N 2310/3125* (2013.01); *C12N 2310/3231* (2013.01); *C12N 2310/3341* (2013.01); *C12N 2310/341* (2013.01); *C12N 2320/34* (2013.01)

(58) Field of Classification Search
CPC . C12N 15/111; C12N 15/113; C12N 2310/11; C12N 2310/341
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,845,205 A | 7/1989 | Huynh Dinh et al. |
| 5,023,243 A | 6/1991 | Tullis |
| 5,130,302 A | 7/1992 | Spielvogel et al. |
| 5,134,066 A | 7/1992 | Rogers et al. |
| 5,175,273 A | 12/1992 | Bischofberger et al. |
| 5,177,198 A | 1/1993 | Spielvogel et al. |
| 5,223,618 A | 6/1993 | Cook et al. |
| 5,256,775 A | 10/1993 | Froehler |
| 5,264,562 A | 11/1993 | Matteucci |
| 5,264,564 A | 11/1993 | Matteucci |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,432,272 A | 7/1995 | Benner |
| 5,434,257 A | 7/1995 | Matteucci |
| 5,457,187 A | 10/1995 | Gmelner et al. |
| 5,459,255 A | 10/1995 | Cook et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,508,270 A | 4/1996 | Baxter et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |

(Continued)

FOREIGN PATENT DOCUMENTS

| | | |
|---|---|---|
| WO | WO 94/02499 | 2/1994 |
| WO | WO 94/17093 | 8/1994 |

(Continued)

OTHER PUBLICATIONS

Abifadel et al., "Mutations and polymorphisms in the proprotein convertase subtilisin kexin 9 (PCSK9) gene in cholesterol metabolism and disease." Hum Mutat. (2009) 30(4): 520-529.

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Alves et al., "Allele-Specific RNA Silencing of Mutant Ataxin-3 Mediates Neuroprotection in a Rat Model of Machado-Joseph Disease" PLoS One (2008) 3(10): e3341.

Beigelman et al., "Synthesis of 5'-C-Methyl-D-allo- & L-Taloribonucleoside 3'-O-Phosphoramidites & Their Incorporation into Hammerhead Ribozymes" Nucleosides Nucleotides Nucleic Acids (1995) 14(3-5): 901-905.

(Continued)

*Primary Examiner* — Dana Shin

(57) ABSTRACT

The present invention provides gapped oligomeric compounds comprising at least one 5'-substituted β-D-2'-deoxyribonucleoside in the gap region. Certain such gapped oligomeric compounds are useful for hybridizing to a complementary nucleic acid, including but not limited to, nucleic acids in a cell. The oligomeric compounds provided herein have improved properties such as selectivity, potency and improved proinflammatory profile. In certain embodiments, hybridization results in modulation of the amount of activity or expression of the target nucleic acid in a cell.

26 Claims, No Drawings

(56) References Cited

U.S. PATENT DOCUMENTS

| | | |
|---|---|---|
| 5,596,091 A | 1/1997 | Switzer |
| 5,602,240 A | 2/1997 | De Mesmaeker et al. |
| 5,610,289 A | 3/1997 | Cook et al. |
| 5,614,617 A | 3/1997 | Cook et al. |
| 5,625,050 A | 4/1997 | Beaton et al. |
| 5,645,985 A | 7/1997 | Froehler et al. |
| 5,646,269 A | 7/1997 | Matteucci |
| 5,681,941 A | 10/1997 | Cook et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,426,220 B1 | 7/2002 | Bennett et al. |
| 6,525,191 B1 | 2/2003 | Ramasamy |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 7,569,686 B1 | 8/2009 | Bhat et al. |
| 2003/0158403 A1 | 8/2003 | Manoharan et al. |
| 2004/0171570 A1 | 9/2004 | Allerson et al. |
| 2005/0130923 A1 | 6/2005 | Bhat et al. |
| 2007/0287831 A1 | 12/2007 | Seth et al. |
| 2008/0039618 A1 | 2/2008 | Allerson et al. |
| 2015/0051389 A1 | 2/2015 | Seth et al. |

FOREIGN PATENT DOCUMENTS

| | | |
|---|---|---|
| WO | WO 94/22890 | 10/1994 |
| WO | WO 99/14226 | 3/1999 |
| WO | WO 02/36743 | 5/2002 |
| WO | WO 2004/106356 | 12/2004 |
| WO | WO 2005/021570 | 3/2005 |
| WO | WO 2007/090071 | 8/2007 |
| WO | WO 2007/134181 | 11/2007 |
| WO | WO 2008/049085 | 4/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2009/135322 | 11/2009 |
| WO | WO 2009/143369 | 11/2009 |
| WO | WO 2010/036698 | 4/2010 |
| WO | WO 2010/048585 | 4/2010 |
| WO | WO 2010/077578 | 7/2010 |
| WO | WO 2011/017521 | 2/2011 |
| WO | WO 2011/115818 | 9/2011 |

OTHER PUBLICATIONS

Braasch et al., "Locked nucleic acid (LNA): fine-tuning the recognition of DNA and RNA" Chem. Biol. (2001) 8:1-7.
Bruijn et al., "Aggregation and Motor Neuron Toxicity of an ALS-Linked SOD1 Mutant Independent from Wild-Type SOD1" Science (1998) 281(5384): 1851-1854.
Chen et al., "Allelic origin of the abnormal prion protein isoform in familial prion diseases." Nat. Med. (1997) 3: 1009-1015.
Chiang et al., "Antisense Oligonucleotides Inhibit Intercellular Adhesion Molecule 1 Expression by Two Distinct Mechanisms" J. Biol. Chem. (1991) 266:18162-18171.
Crooke et al., "Pharmacokinetic Properties of Several Novel Oligonucleotide Analogs in mice" J. Pharmacol. Exp. Ther. (1996) 277(2):923-937.
Daiger et al., "Mutations in known genes account for 58% of autosomal dominant retinitis pigmentosa (adRP)." Adv Exp Med Biol. (2008) 613: 203-209.
Dawson et al., "Rare genetic mutations shed light on the pathogenesis of Parkinson disease" J. Clin. Invest. (2003) 111(2): 145-151.
De Gobbi et al., "A regulatory SNP causes a human genetic disease by creating a new transcriptional promoter." Science (2006) 312(5777): 1215-1217.
De Mesmaeker et al., "Amide-Modified Oligonucleotides with Preorganized Backbone and Furanose Rings: Highly Increased Thermodynamic Stability of the Duplexes Formed with their RNA and DNA Complements" Synlett (1997) 11: 1287-1290.
Dupouy et al., "Watson-Crick Base-Pairing Properties of Nucleic Acid Analogues with Stereocontrolled α and β Torsion Angles (α,β-D-CNAs)" Angew. Chem. Int. Ed. (2006) 45(22): 3623-3627.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Agnew Chem. Int. Ed. Engl. (1991) 30:613-629.
Eppacher et al., "Synthesis and Incorporation of C(5')-Ethynylated Uracil-Derived Phosphoramidites into RNA" Helvetica Chimica Acta (2004) 87(12): 3004-3020.
Ewart-Toland et al., "A gain of function TGFB1 polymorphism may be associated with late stage prostate cancer." Cancer Epidemiol. Biomarkers Prev. (2004) 13(5): 759-764.
Feng et al., "Allele-specific silencing of Alzheimer's disease genes: The amyloid precursor protein genes with Swedish or London mutations" Gene (2006) 371(1): 68-74.
Fontana et al., "P2Y12 H2 Haplotype is Associated With Peripheral Arterial Disease: A Case-Control Study" Circulation (2003) 108: 2971-2973.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Hagemann et al., "Alexander disease-associated glial fibrillary acidic protein mutations in mice induce Rosenthal fiber formation and a white matter stress response." J. Neurosci. (2006) 26(43): 111623-111673.
Harlan et al., "Variants in Apaf-1 segregating with major depression promote apoptosome function" Mol. Psychiatry (2006) 11:76-85.
Hizawa et al., "Functional single nucleotide polymorphisms of the CCL5 gene and nonemphysematous phenotype in COPD patients." Eur. Respir. J. (2008) 32(2): 372-378.
Hu et al., "Serotonin Transporter Promoter Gain-of-Function Genotypes Are Linked to Obsessive-Compulsive Disorder" Am. J. Hum. Genet. (2006) 78: 815-826.
Jones et al., "RNA quantitation by fluorescence-based solution assay: RiboGreen reagent characterization." Anal Biochem. (1998) 265(2): 368-374.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Kabashi et al., "Gain and loss of function of ALS-related mutations of TARDBP (TDP-43) cause motor deficits in vivo." Hum. Mol. Genet. (2010) 19(4): 671-683.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Landgraf, "The involvement of the vasopressin system in stress-related disorders." CNS Neurol. Disord. Drug Targets (2006) 5(2): 167-179.
Letsinger et al., "Cholesteryl-conjugated oligonucleotides: Synthesis, properties, and activity as inhibitors of replication of human immunodeficiency virus in cell culture" PNAS (1989) 86:6553-6556.

(56) References Cited

OTHER PUBLICATIONS

Leumann et al., "DNA Analogues: From Supramolecular Principles to Biological Properties" Bioorganic & Medicinal Chemistry (2002) 10:841-854.

Li et al., "Gain-of-function polymorphism in mouse and human Ltk: implications for the pathogenesis of systemic lupus erythematosus" Hum. Mol. Gen. (2004) 13(2): 171-179.

Manoharan et al., "Chemical Modifications to Improve Uptake and Bioavailability of Antisense Oligonucleotides" Ann. N.Y. Acad. Sci. (1992) 660: 306-309.

Manoharan et al., "Cholic Acid-Oligonucleotide Conjugates for Antisense Applications" Bioorg. Med. Chem. Lett. (1994) 4:1053-1060.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Lipidic Nucleic Acids" Tetrahedron Lett. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5):969-973.

Mantaring et al., "Genotypic variation in ATP-binding cassette transporter-1 (ABCA1) as contributors to the high and low high-density lipoprotein-cholesterol (HDL-C) phenotype." Transl. Res. (2007) 149(4): 205-210.

Marzolini et al., "A common polymorphism in the bile acid receptor farnesoid X receptor is associated with decreased hepatic target gene expression." Mol. Endocrinol. (2007) 21(8): 1769-1780.

McWhinney et al., "Intronic single nucleotide polymorphisms in the RET protooncogene are associated with a subset of apparently sporadic pheochromocytoma and may modulate age of onset." J. Clin. Endocrinol. Metab. (2003) 88(10): 4911-4916.

Mikhailov et al., "Substrate Properties of C'-Methylnucleoside and C'-Methyl-2'-deoxynucleoside 5'-Triphosphates in RNA and DNA Synthesis Reactions Catalysed by RNA and DNA Polymerases" Nucleosides & Nucleotides (1991) 10(1-3): 339-343.

Mishra et al., "Improved leishmanicidal effect of phosphorotioate antisense oligonucleotides by LDL-mediated delivery" Biochim. Biophys. Acta (1995) 1264:229-237.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Orum et al., "Locked nucleic acids: A promising molecular family for gene-function analysis and antisense drug development" Curr. Opinion Mol. Ther. (2001) 3:239-243.

Palazzolo et al., "The role of the polyglutamine tract in androgen receptor." J Steroid Biochem. Mol. Biol. (2008) 108(3-5): 245-253.

Persichetti et al., "Differential expression of normal and mutant Huntington's disease gene alleles." Neurobiol Dis. (1996) 3(3): 183-190.

Rajasekaran et al., "Human alpha B-crystallin mutation causes oxido-reductive stress and protein aggregation cardiomyopathy in mice." Cell (2007) 130(3): 427-439.

Robertson et al., "Localized mutations in the gene encoding the cytoskeletal protein filamin A cause diverse malformations in humans." Nat Genet (2003) 33(4): 487-491.

Saha et al., "5'-Methyl-DNA—A New Oligonucleotide Analog: Synthesis and Biochemical Properties" J. Org. Chem. (1995) 60(4): 788-789.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

Sanghvi, Chapter 15, Antisense Research and Applications, Crooke and Lebleu ed., CRC Press (1993).

Scholefield et al., "Design of RNAi hairpins for mutation-specific silencing of ataxin-7 and correction of a SCA7 phenotype." PLoS One (2009) 4: e7232.

Sen et al., "Role of histidine interruption in mitigating the pathological effects of long polyglutamine stretches in SCA1: A molecular approach." Protein Sci. (2003) 12(5): 953-962.

Seth et al., "Design, Synthesis and Evaluation of Constrained Methoxyethyl (cMOE) and Constrained Ethyl (cEt) Nucleoside Analogs" Nucleic Acids Symposium Series (2008) 52(1): 553-554.

Seth et al., "Synthesis and biophysical characterization of R-6'-Me-α-l-LNA modified oligonucleotides" Bioorg. Med. Chem. (2011) 21(4): 1122-1125.

Seth et al., "Synthesis and Biophysical Evaluation of 2',4'-Constrained 2'O-Methoxyethyl and 2',4'-Constrained 2'O-Ethyl Nucleic Acid Analogues" J. Org. Chem. (2010) 75(5): 1569-1581.

Shashidharan et al., "Torsin-A accumulation in Lewy bodies in sporadic Parkinson's disease brain." Brain Res. (2000) 877(2): 379-381.

Shea et al., "Synthesis, hybridization properties and antiviral activity of lipid-oligodeoxynucleotide conjugates" Nucl. Acids Res. (1990) 18(13):3777-3783.

Shiels et al., "CHMP4B, a novel gene for autosomal dominant cataracts linked to chromsome 20q" Am. J. Hum. Genet (2007) 81: 596-606.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75:49-54.

Swayze et al., The Medicinal Chemistry of Oligonucleotides in Antisense Drug Technology, Chapter 6, pp. 143-182, Crooke, S.T., ed., 2008.

Vezzoli et al., "R990G polymorphism of calcium-sensing receptor does produce a gain-of-function and predispose to primary hypercalciuria." Kidney Int. (2007) 71(11): 1155-1162.

Wahlestedt et al., "Potent and nontoxic antisense oligonucleotide containing locked nucleic acids" Proc. Natl. Acad. Sci. USA (2000) 97: 5633-5638.

Wang et al., "Biophysical and biochemical properties of oligodeoxynucleotides containing 4'-C- and 5'-C-substituted thymidines" Bioorganic & Medicinal Chemistry Letters (1999) 9(6): 885-890.

Wang et al., "Synthesis of Azole Nucleoside 5'-Monophosphate Mimics (P1Ms) and Their Inhibitory Properties of IMP Dehydrogenases" Nucleosides Nucleotides & Nucleic Acids (2004) 23 (1 & 2): 317-337.

Webster et al., "Mutation in the AChR ion channel gate underlies a fast channel congenital myasthenic syndrome" Neurology (2004) 62(7): 1090-1096.

Weinstein et al., "Genetic diseases associated with heterotrimeric G proteins" Trends Pharmacol Sci. (2006) 27(5): 260-266.

Wu et al., "Functionalization of the Sugar Moiety of Oligoribonucleotides on Solid Support" Bioconjugate Chem. (1999) 10(6): 921-924.

Wu et al., "Synthesis of 5'-C- and 2'-O-(Bromoalkyl)-Substituted Ribonucleoside Phosphoramidites for the Post-synthetic Functionalization of Oligonucleotides on Solid Support" Helvetica Chimica Acta (2000) 83: 1127-1144.

Yu et al., "Structure, inhibitor, and regulatory mechanism of Lyp, a lymphoid-specific tyrosine phosphatase implicated in autoimmune diseases" PNAS (2007) 104(50): 19767-19722.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

International Search Report for application PCT/US2012/049989 dated Dec. 5, 2012.

Ostergaard et al. "Rational design of antisense oligonucleotides targeting single nucleotide polymorphisms for potent and allele

(56) References Cited

OTHER PUBLICATIONS selective suppression of mutant Huntingtin in the CNS." Nucleic Acids Res. (2013) 41:9634-50.

GAPPED OLIGOMERIC COMPOUNDS COMPRISING 5'-MODIFIED DEOXYRIBONUCLEOSIDES IN THE GAP AND USES THEREOF

CROSS REFERENCED TO RELATED APPLICATIONS

This application is a U.S. National Phase filing under 35 U.S.C. §371 claiming priority to International Serial No. PCT/US2012/049989 filed Aug. 8, 2012, which claims priority to U.S. Provisional Application 61/522,659, filed Aug. 11, 2011, U. S. Provisional Application 61/596,723, filed Feb. 8, 2012, and U.S. Provisional Application 61/603, 196, filed Feb. 24, 2012, each of which is incorporated herein by reference in its entirety.

FIELD OF THE INVENTION

The present invention pertains generally to chemically-modified oligonucleotides for use in research, diagnostics, and/or therapeutics.

SEQUENCE LISTING

The present application is being filed along with a Sequence Listing in electronic format. The Sequence Listing is provided as a file entitled CHEM0087USASEQ_ST25.txt created on Jan. 29, 2014, which is 320 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

The synthesis of 5'-substituted DNA and RNA derivatives and their incorporation into oligomeric compounds has been reported in the literature (Saha et al., *J. Org. Chem.*, 1995, 60, 788-789; Wang et al., *Bioorganic & Medicinal Chemistry Letters*, 1999, 9, 885-890; and Mikhailov et al., *Nucleosides & Nucleotides*, 1991, 10(1-3), 339-343; Beigelman et al., 1995, 14(3-5), 901-905; and Eppacher et al., *Helvetica Chimica Acta*, 2004, 87, 3004-3020). The 5'-substituted monomers have also been made as the monophosphate with modified bases (Wang et al., *Nucleosides Nucleotides & Nucleic Acids*, 2004, 23 (1 & 2), 317-337).

A genus of modified nucleosides including optional modification at a plurality of positions including the 5'-position and the 2'-position of the sugar ring and oligomeric compounds incorporating these modified nucleosides therein has been reported (see International Application Number: PCT/US94/02993, Published on Oct. 13, 1994 as WO 94/22890).

The synthesis of 5'-substituted 2'-O-protected nucleosides and their incorporation into oligomers has been previously reported (see Wu et al., *Helvetica Chimica Acta*, 2000, 83, 1127-1143 and Wu et al. *Bioconjugate Chem.* 1999, 10, 921-924).

Amide linked nucleoside dimers have been prepared for incorporation into oligonucleotides wherein the 3' linked nucleoside in the dimer (5' to 3') comprises a 2'-OCH$_3$ and a 5'-(S)—CH$_3$ (Mesmaeker et al., *Synlett*, 1997, 1287-1290).

SUMMARY OF THE INVENTION

Provided herein are gapped oligomeric compounds comprising at least one 5'-substituted β-D-2'-deoxyribonucleosides having Formula I in the gap region. In certain embodiments, the oligomeric compounds provided herein hybridize to a portion of a target RNA resulting in loss of normal function of the target RNA. In certain embodiments, the oligomeric compounds provided herein have improved selectivity for a target RNA. In certain embodiments, the oligomeric compounds provided herein have improved potency for a target RNA. In certain embodiments, the oligomeric compounds provided herein have an improved proinflammatory profile. In certain embodiments, the oligomeric compounds provided herein have improved potency and selectivity for a target RNA. In certain embodiments, the oligomeric compounds provided herein have improved potency, selectivity and an improved proinflammatory profile.

The variables are defined individually in further detail herein. It is to be understood that the oligomeric compounds provided herein include all combinations of the embodiments disclosed and variables defined herein.

In certain embodiments, gapped oligomeric compounds are provided comprising a contiguous sequence of linked monomer subunits having a gap region located between a 5'-region and a 3'-region wherein the 5' and 3'-regions each, independently, have from 2 to 8 contiguous modified nucleosides wherein essentially each modified nucleoside in the 5' and 3'-regions is RNA-like and the gap region has from 6 to 14 contiguous monomer subunits selected from β-D-2'-deoxyribonucleosides and 5'-substituted β-D-2'-deoxyribonucleosides having Formula I:

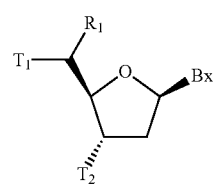

wherein independently for each 5'-substituted β-D-2'-deoxyribonucleoside having Formula I:

T$_1$ and T$_2$ are each, independently, an internucleoside linking group linking the 5'-substituted β-D-2'-deoxyribonucleoside having Formula I to the remainder of the gapped oligomeric compound;

Bx is a heterocyclic base moiety;

R$_1$ is C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl; and wherein said gap region comprises at least one 5'-substituted β-D-2'-deoxyribonucleoside having Formula I and a plurality of β-D-2'-deoxyribonucleosides.

In certain embodiments, gapped oligomeric compounds are provided wherein each substituted group comprises one or more optionally protected substituent groups independently selected from halogen, $OJ_1$, $NJ_1J_2$, $SJ_1$, $N_3$, CN, $OC(=L)J_1$, $OC(=L)NJ_1J_2$ and $NJ_3C(=L)NJ_1J_2$, wherein each $J_1$, $J_2$ and $J_3$ is, independently, H, $C_1$-$C_6$ alkyl or a protecting group, and L is O, S or $NJ_1$. In certain embodiments, gapped oligomeric compounds are provided wherein each substituted group comprises one or more substituent groups independently selected from F, OH, $NH_2$, =NH, SH, $N_3$ and CN. In certain embodiments, gapped oligomeric compounds are provided wherein each substituted group comprises one or more substituent groups independently selected from F, OH or $NH_2$.

In certain embodiments, each $R_1$ is independently selected from $C_1$-$C_6$ alkyl, substituted $C_1$-$C_6$ alkyl, $C_2$-$C_6$ alkenyl and $C_2$-$C_6$ alkynyl. In certain embodiments, each $R_1$ is independently selected from $CH_3$, $CH_2CH_3$, $CH_2CH_2OH$, $CH_2CHCH_2$ and $CHCH_2$. In certain embodiments, each $R_1$ is $CH_3$.

In certain embodiments, gapped oligomeric compounds are provided having one 5'-substituted β-D-2'-deoxyribonucleoside of Formula I. In certain embodiments, gapped oligomeric compounds are provided having two 5'-substituted β-D-2'-deoxyribonucleosides of Formula I. In certain embodiments, gapped oligomeric compounds are provided having three 5'-substituted β-D-T-deoxyribonucleosides of Formula I.

In certain embodiments, gapped oligomeric compounds are provided wherein the monomer subunit in the gap region that is adjacent to the 5'-region is a 5'-substituted β-D-2'-deoxyribonucleoside of Formula I. In certain embodiments, gapped oligomeric compounds are provided wherein the monomer subunit in the gap region that is adjacent to the 3'-region is a 5'-substituted β-D-2'-deoxyribonucleoside of Formula I. In certain embodiments, gapped oligomeric compounds are provided wherein the monomer subunit in the gap region that is adjacent to the 5'-region is a 5'-substituted β-D-2'-deoxyribonucleoside of Formula I and the monomer subunit in the gap region that is adjacent to the 3'-region is a 5'-substituted β-D-2'-deoxyribonucleoside of Formula I. In certain embodiments, gapped oligomeric compounds are provided wherein at least one 5'-substituted β-D-2'-deoxyribonucleoside of Formula I is located in the gap region at a position that is other than one that is adjacent to either of the 5'-region or 3'-region. In certain embodiments, gapped oligomeric compounds are provided wherein at least two 5'-substituted β-D-2'-deoxyribonucleosides of Formula I are located in the gap region at a positions that are other than ones that are adjacent to either of the 5'-region or 3'-region.

In certain embodiments, each 5'-substituted β-D-2'-deoxyribonucleoside has the configuration of Formula Ia:

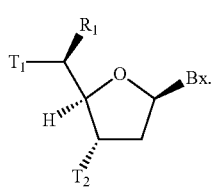

Ia

In certain embodiments, each 5'-substituted β-D-2'-deoxyribonucleoside has the configuration of Formula Ib:

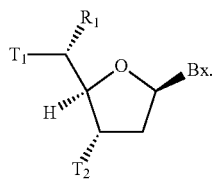

Ib

In certain embodiments, gapped oligomeric compounds are provided wherein each $R_1$ is a methyl group. In certain embodiments, gapped oligomeric compounds are provided wherein each $R_1$ is an (S)-methyl group. In certain embodiments, gapped oligomeric compounds are provided wherein each $R_1$ is an (R)-methyl group.

In certain embodiments, each internucleoside linking group that links adjacent monomer subunits is independently selected from a phosphodiester or phosphorothioate internucleoside linking group. In certain embodiments, each internucleoside linking group that links adjacent monomer subunits is a phosphorothioate internucleoside linking group. In certain embodiments, each internucleoside linking group that links adjacent monomer subunits is a phosphodiester internucleoside linking group.

In certain embodiments, each monomer subunit comprises a heterocyclic base moiety that is optionally protected and is independently selected from a purine, substituted purine, pyrimidine and substituted pyrimidine. In certain embodiments, each monomer subunit comprises a heterocyclic base moiety independently selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, each modified nucleoside in the 5' and 3'-regions provides enhanced hybridization affinity for an RNA target as compared to an unmodified β-D-2'-deoxyribonucleoside or β-D-ribonucleoside. In certain embodiments, each modified nucleoside in the 5' and 3'-regions comprises a modified sugar moiety. In certain embodiments, each modified nucleoside in the 5' and 3'-regions is independently selected from a bicyclic nucleoside comprising a bicyclic furanosyl sugar moiety and a modified nucleoside comprising a furanosyl sugar moiety having at least one substituent group.

In certain embodiments, gapped oligomeric compounds are provided comprising one or more 2'-modified nucleosides that each have a 2'-substituent group independently selected from halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_3)(R_4)$, $O(CH_2)_2$—ON$(R_3)(R_4)$, $O(CH_2)_2$—$O(CH_2)_2$—$N(R_3)(R_4)$, $OCH_2C(=O)$—$N(R_4)(R_4)$, $OCH_2C(=O)$—$N(R_5)$—$(CH_2)_2$—N$(R_3)(R_4)$ and $O(CH_2)_2$—$N(R_5)$—$C(=NR_6)[N(R_3)(R_4)]$ wherein $R_3$, $R_4$, $R_5$ and $R_6$ are each, independently, H or $C_1$-$C_6$ alkyl. In certain embodiments, each 2'-substituent group is independently selected from F, $OCH_3$, $OCF_3$, $OCH_2CH_3$, $OCH_2CF_3$, $OCH_2CH=CH_2$, $O(CH_2)_2OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ and $OCH_2$—N(H)—C(=NH)$NH_2$. In certain embodiments, each 2'-substituent group is independently selected from F, $OCH_3$, $O(CH_2)_2$—$OCH_3$ and $OCH_2C(=O)$—$N(H)CH_3$. In certain embodiments, each 2'-substituent group is $O(CH_2)_2$—$OCH_3$.

In certain embodiments, gapped oligomeric compounds are provided comprising one or more bicyclic nucleosides that each have a bridging group between the 4' and 2' carbon atoms of the furanosyl ring independently selected from 4'-(CH$_2$)—O-2',4'-(CH$_2$)—S-2',4'-(CH$_2$)$_2$—O-2',4'-CH(CH$_3$)—O-2',4'-CH(CH$_2$OCH$_3$)—O-2',4'-C(CH$_3$)$_2$—O-2', 4'-CH$_2$—N(OCH$_3$)-2',4'-CH$_2$—O—N(CH$_3$)-2', 4'-CH$_2$—NCH$_3$—O-2',4'-CH$_2$—C(H)(CH$_3$)-2' and 4'-CH$_2$—C(=CH$_2$)-2'. In certain embodiments, each of the bridging groups is independently selected from 4'-(CH$_2$)—O-2',4'-(CH$_2$)$_2$—O-2',4'-CH(CH$_3$)—O-2', 4'-CH$_2$—NCH$_3$—O-2', 4'-CH$_2$—C(H)(CH$_3$)-2' and 4'-CH$_2$—C(=CH$_2$)-2'. In certain embodiments, each bridging group is 4'-CH[(S)—(CH$_3$)]—O-2'.

In certain embodiments, gapped oligomeric compounds are provided wherein the modified nucleosides in the 5' and 3'-regions each have a modified sugar moiety. In certain embodiments, each modified nucleoside in the 5' and 3'-regions is independently selected from a bicyclic nucleoside comprising a bicyclic furanosyl sugar moiety or a modified nucleoside comprising a furanosyl sugar moiety having at least one substituent group.

In certain embodiments, gapped oligomeric compounds are provided comprising at least two different types of modified nucleosides in the 5' and 3'-regions. In certain embodiments, the two different types of modified nucleosides are selected from bicyclic nucleoside comprising a bicyclic furanosyl sugar moiety and modified nucleosides comprising a furanosyl sugar moiety having at least one substituent group. In certain embodiments, the 5' and 3'-regions include only 4'-CH[(S)—(CH$_3$)]—O-2' bicyclic nucleosides and 2'-O(CH$_2$)$_2$—OCH$_3$ substituted nucleosides.

In certain embodiments, gapped oligomeric compounds are provided wherein the modified nucleosides in the 5' and 3'-regions each have a modified sugar moiety and the modified sugar moieties of each modified nucleoside in the 5' and 3'-regions are the same. In certain embodiments, one or more modified nucleosides in the 5' and 3'-regions comprise a sugar surrogate.

In certain embodiments, gapped oligomeric compounds are provided wherein the 5' and 3'-regions each, independently, have from 2 to 8 monomer subunits. In certain embodiments, the 5' and 3'-regions each, independently, have from 3 to 6 monomer subunits. In certain embodiments, the gap region has from 8 to 14 monomer subunits. In certain embodiments, the gap region has from 8 to 12 monomer subunits. In certain embodiments, the gap region has from 8 to 10 monomer subunits. In certain embodiments, the 5' and 3'-regions each, independently, have from 3 to 6 monomer subunits and the gap region has from 8 to 14 monomer subunits. In certain embodiments, the 5' and 3'-regions each, independently, have from 3 to 6 monomer subunits and the gap region has from 6 to 10 monomer subunits. In certain embodiments, the 5' and 3'-regions each, independently, have from 3 to 6 monomer subunits and the gap region has from 6 to 8 monomer subunits. In certain embodiments, the 5' and 3'-regions each, independently, have from 4 to 5 monomer subunits and the gap region has from 7 to 8 monomer subunits.

In certain embodiments, the gapped oligomeric compounds provided herein are other than the gapped oligomeric compounds listed below:

| SEQ ID NO. ISIS # | Sequence | Gap Chemistry | wings 5'/3' | |
|---|---|---|---|---|
| 05/539558 | T$_e$A$_k$A$_k$ATTGT$_R$CATCA$_k$C$_k$C$_e$ | 5'-(R)-CH$_3$ | ekk | kke |
| 05/XXXX22 | T$_e$A$_k$A$_k$ATT$_b$GTCATCA$_k$C$_k$C$_e$ | 5'-CH$_3$ | ekk | kke |
| 05/XXXX23 | T$_e$A$_k$A$_k$AT$_b$TGTCATCA$_k$C$_k$C$_e$ | 5'-CH$_3$ | ekk | kke |
| 05/XXXX24 | T$_e$A$_k$A$_k$A$_b$TTGTCATCA$_k$C$_k$C$_e$ | 5'-CH$_3$ | ekk | kke |
| 09/XXXX30 | A$_e$T$_e$A$_e$A$_k$A$_k$TTGT$_b$CATC$_k$A$_k$C$_e$C$_e$A$_e$ | 5'-CH$_3$ | eeekk | kkeee |

Unless indicated otherwise each internucleoside linkage is a phosphorothioate. A subscript "R" indicates a 5'-(R)—CH$_3$ modified nucleoside. A subscript "b" indicates a 5'-CH$_3$ modified nucleoside. Nucleosides not followed by a subscript are β-D-2'-deoxyribonucleosides. Nucleosides followed by a subscript "e" are 2'-O-methoxyethyl (MOE) modified nucleosides. Nucleosides followed by a subscript "k" are 6'-(S)—CH$_3$ (cEt) bicyclic modified nucleosides.

In certain embodiments, the gapped oligomeric compounds provided herein are other than gapped oligomeric compounds complementary to at least a region of a nucleic acid that is a Huntingtin gene transcript. In certain embodiments, the gapped oligomeric compounds provided herein are other than gapped oligomeric compounds complementary to at least a region of a nucleic acid comprising a single-nucleotide polymorphism. In certain embodiments, the gapped oligomeric compounds provided herein are other than gapped oligomeric compounds complementary to at least a region of a nucleic acid comprising a single-nucleotide polymorphism-containing-target nucleic acid of a Huntingtin gene transcript. In certain embodiments, the gapped oligomeric compounds provided herein are other than gapped oligomeric compounds complementary to at least a region of a nucleic acid comprising a single-nucleotide polymorphism-containing-target nucleic acid of a gene transcript other than Huntingtin.

In certain embodiments, methods of inhibiting gene expression are provided comprising contacting one or more cells, a tissue or an animal with an oligomeric compound as provided herein wherein said oligomeric compound is complementary to a target RNA. In certain embodiments, the cells are in a human. In certain embodiments, the target RNA is human mRNA. In certain embodiments, the target RNA is cleaved thereby inhibiting its function.

In certain embodiments, in vitro methods of inhibiting gene expression are provided comprising contacting one or more cells or a tissue with an oligomeric compound as provided herein.

In certain embodiments, oligomeric compounds are provided for use in an in vivo method of inhibiting gene expression comprising contacting one or more cells, a tissue or an animal with an oligomeric compound as provided herein.

In certain embodiments, oligomeric compounds are provided for use in medical therapy.

DETAILED DESCRIPTION OF THE INVENTION

In certain embodiments, gapped oligomeric compounds are provided comprising a contiguous sequence of linked monomer subunits having a gap region located between a 5'-region and a 3'-region wherein the 5' and 3'-regions each, independently, have from 2 to 8 contiguous modified nucleosides wherein essentially each modified nucleoside in the 5' and 3'-regions is RNA-like and the gap region has from 6 to 14 contiguous monomer subunits selected from β-D-2'-deoxyribonucleosides and 5'-substituted β-D-2'-deoxyribonucleosides having Formula I:

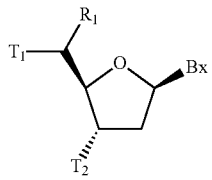

I wherein independently for each 5'-substituted β-D-2'-deoxyribonucleoside having Formula I:

$T_1$ and $T_2$ are each, independently, an internucleoside linking group linking the 5'-substituted β-D-2'-deoxyribonucleoside having Formula I to the remainder of the gapped oligomeric compound;

Bx is a heterocyclic base moiety;

$R_1$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and wherein said gap region comprises at least one 5'-substituted β-D-2'-deoxyribonucleoside having Formula I and a plurality of β-D-2'-deoxyribonucleosides.

The gapped oligomeric compounds provided herein have been shown to have improved properties. In certain embodiments, the activity of an otherwise unmodified gapped oligomeric compound against a target nucleic acid is enhanced by incorporation of at least one 5'-substituted β-D-2'-deoxyribonucleoside having Formula I into the gapped region. As indicated in the various in vitro data provided in the example section herein, such properties include selectivity, potency and or an improved proinflammatory profile.

In certain embodiments, a gapped oligomeric compound of interest is identified and then a series of identical oligomeric compounds are prepared with a single 5'-substituted β-D-2'-deoxyribonucleoside of Formula I walked across the gap region. If there are 8 monomer subunits in the gap then there will be 8 oligomeric compounds prepared which are subsequently assayed in one or more assays as illustrated herein to determine the lead from the series.

In certain embodiments, additional 5'-substituted β-D-2'-deoxyribonucleosides having Formula I are incorporated into the gap region of the lead oligomeric compound and assayed in one or more assays as illustrated herein. In certain embodiments, the lead compound is further functionalized with one or more terminal groups such as for example a conjugate group. In certain embodiments, a gapped oligomeric compound of interest is identified and then a series of identical oligomeric compounds are prepared with blocks of at least two 5'-substituted β-D-2'-deoxyribonucleoside of Formula I walked across the gap region.

In certain embodiments, gapped oligomeric compounds are provided having two or three 5'-(R)—$CH_3$ modified nucleosides in the gap without significant impact on Tm or potency. As shown using an in vitro hCRP assay (Example 22), oligomeric compounds comprising two or three 5'-(R)—$CH_3$ modified nucleosides in the gap that are linked by phosphodiester internucleoside linkages (other linkages in the oligomeric compounds are phosphorothioates) are well tolerated.

In certain embodiments, gapped oligomeric compounds are provided having a reduced proinflammatory response when compared to unmodified gapped oligomeric compounds. As shown using an in vitro hPBMC assay (Example 24), a gapped oligomeric compound having two 5'-(R)—$CH_3$ modified nucleosides that have phosphodiester internucleoside linkages (other linkages in the oligomeric compounds are phosphorothioates) in the gap reduced the proinflammatory response compared to the an identical oligomeric compound without the modified internucleoside linkages.

In certain embodiments, gapped oligomeric compounds are provided having a single 5'-(R)—$CH_3$ modified nucleoside walked in different positions in the gap as shown in an in vitro Huntingtin SNP assay (Example 26). The modified gapped oligomeric compounds for the most part showed comparable potency and selectivity when compared to the unmodified gapped oligomeric compound. One of the gapped oligomeric compounds showed slight improvements in both potency and selectivity for inhibition of the mutant type HTT mRNA expression over the wild type HTT mRNA expression.

In certain embodiments, a gapped oligomeric compound is provided having a single 5'-(R)—$CH_3$ modified nucleoside in the gap as shown in an in vitro Huntingtin SNP assay (Example 27). The modified gapped oligomeric compound provided comparable potency with improved selectivity for the mutant type HTT mRNA expression over the wild type HTT mRNA expression.

In certain embodiments, gapped oligomeric compounds are provided having one or two 5'-(R)—$CH_3$ or one or two 5'-(S)—$CH_3$ modified nucleosides that are walked in different positions in the gap of the oligomeric compounds as shown in an in vitro Huntingtin SNP assay (Example 28). Each of the 14 modified oligos tested showed significantly greater selectivity and potency for the mutant type HTT mRNA expression over the wild type HTT mRNA expression when compared to the otherwise unmodified oligomeric compound. Each of the modified oligomeric compounds except for one also showed a decreased potency for the wild type.

In certain embodiments, gapped oligomeric compounds are provided having a single 5'-(R)—$CH_2CH=CH_2$, 5'-(S)—$CH_2CH=CH_2$, 5'-(R)—$CH_2CH_2OH$ or 5'-(S)—$CH_2CH_2OH$ modified nucleoside walked in different positions in the gap of the oligomeric compounds as shown in an in vitro Huntingtin SNP assay (Example 29). Most of the 14 modified oligos tested showed greater selectivity for the mutant type HTT mRNA expression over the wild type HTT mRNA expression when compared to the otherwise unmodified oligomeric compound. Each of the modified oligomeric compounds showed a decreased potency for the wild type HTT mRNA expression when compared to an otherwise unmodified oligomeric compound.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a 2'-deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

As used herein the term "sugar surrogate" means a structure that does not comprise a furanosyl ring and that is capable of replacing the naturally occurring sugar moiety of a nucleoside, such that the resulting nucleoside sub-units or monomer subunits are capable of linking together and/or linking to other nucleosides or other monomer subunits to form an oligomeric compound which is capable of hybridizing to a complementary oligomeric compound such as a nucleic acid target. Such structures include rings comprising a different number of atoms than furanosyl (e.g., 4, 6, or 7-membered rings); replacement of the oxygen atom of a furanosyl with a non-oxygen atom (e.g., carbon, sulfur, or nitrogen, wherein replacement of the oxygen atom with sulfur in furanose is generally considered a modified nucleoside as opposed to a sugar surrogate but can be considered both); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein the term "nucleobase" generally refers to the nucleobase of a nucleoside or modified nucleoside. The term "heterocyclic base moiety" is broader than the term nucleobase in that it includes any heterocyclic base that can be attached to a sugar to prepare a nucleoside or modified nucleoside. Such heterocyclic base moieties include but are not limited to naturally occurring nucleobases (adenine, guanine, thymine, cytosine and uracil) and protected forms of unmodified nucleobases (4-N-benzoylcytosine, 6-N-benzoyladenine and 2-N-isobutyrylguanine) as well as modified (5-methyl cytosine) or non-naturally occurring heterocyclic base moieties and synthetic mimetics thereof (such as for example phenoxazines).

As used herein the term "modified nucleoside" refers to a nucleoside comprising a modified heterocyclic base and or a sugar moiety other than ribose and 2'-deoxyribose. In certain embodiments, a modified nucleoside comprises a modified heterocyclic base moiety. In certain embodiments, a modified nucleoside comprises a sugar moiety other than ribose and 2'-deoxyribose. In certain embodiments, a modified nucleoside comprises a modified heterocyclic base moiety and a sugar moiety other than ribose and 2'-deoxyribose. The term "modified nucleoside" is intended to include all manner of modified nucleosides that can be incorporated into an oligomeric compound using standard oligomer synthesis protocols. Modified nucleosides include abasic nucleosides but in general a heterocyclic base moiety is included for hybridization to a complementary nucleic acid target.

In certain embodiments, modified nucleosides include a furanose or modified furanose sugar group such as a 4'-S analog (4'-S-modified nucleoside and 4'-S-ribonucleoside refer to replacement of the furanose oxygen atom with S). Such modified nucleosides include without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as 2'-O—CH(CH$_3$)-4',2'-O—CH$_2$-4' or 2'-O—(CH$_2$)$_2$-4' bridged furanose analogs) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

In certain embodiments, modified nucleosides comprise a sugar surrogate wherein the furanose ring has been replaced with a mono or polycyclic ring system or a non-cyclic sugar surrogate such as that used in peptide nucleic acids. Illustrative examples of sugar moieties for such modified nucleosides includes without limitation morpholino, hexitol, cyclohexenyl, 2.2.2 and 3.2.1 cyclohexose and open non-cyclic groups.

In certain embodiments, modified nucleosides comprise a non-naturally occurring sugar moiety and a modified heterocyclic base moiety. Such modified nucleosides include without limitation modified nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a sugar surrogate group such as for example a morpholino, a cyclohexenyl or a bicyclo[3.1.0]hexyl.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2' bridge. In certain embodiments, the cEt comprises a comprising a 4'-CH((S)—CH$_3$)—O-2' bridge. In certain embodiments, the cEt comprises a comprising a 4'-CH((R)—CH$_3$)—O-2' bridge.

As used herein, "locked nucleic acid nucleoside" or "LNA" means a nucleoside comprising a bicyclic sugar moiety comprising a 4'-CH$_2$—O-2' bridge.

As used herein, "2'-substituted nucleoside" means a ribofuranosyl nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H(H) furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside other than a 13-D-ribose nucleoside that provides an A-form (northern) duplex when incorporated into an oligomeric compound and duplexed with a complementary RNA. RNA-like nucleosides are used as replacements for RNA nucleosides in oligomeric compounds to enhance one or more properties such as, for example, nuclease resistance and or hybridization affinity. RNA-like nucleosides include, but are not limited to modified furanosyl nucleosides that adopt a 3'-endo conformational geometry when put into an oligomeric compound. RNA-like nucleosides also include RNA surrogates such as F—HNA. RNA-like nucleosides include but are not limited to modified nucleosides comprising a 2'-substituent group selected from F, O(CH$_2$)$_2$OCH$_3$ (MOE) and OCH$_3$. RNA-like nucleosides also include but are not limited to modified nucleosides comprising bicyclic furanosyl sugar moiety comprising a 4'-CH$_2$—O-2',4'-(CH$_2$)$_2$—O-2', 4'-C(H)[(R)—CH$_3$]—O-2' or 4'-C(H)[(S)—CH$_3$]—O-2' bridging group.

As used herein, "DNA-like nucleoside" means a modified nucleoside other than a β-D-2'-deoxyribose nucleoside that provides a B-form (southern) duplex when incorporated into an oligomeric compound and duplexed with a complementary DNA. DNA-like nucleosides provide an intermediate duplex when incorporated into an oligomeric compound and duplexed with a complementary RNA that is between A-form and B-form. DNA-like nucleosides are used as replacements for DNA nucleosides in oligomeric compounds to enhance one or more properties. DNA-like nucleosides include, but are not limited to modified nucleosides that adopt a 2'-endo conformational geometry when put into an oligomeric compound.

As used herein, "RNA-surrogate nucleoside" means an RNA-like nucleoside that does not comprise a furanosyl. RNA-surrogate nucleosides include, but are not limited to hexitols and cyclopentanes.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein the term "monomer subunit" is meant to include all manner of monomers that are amenable to oligomer synthesis. In general a monomer subunit includes at least a sugar moiety having at least two reactive sites that can form linkages to further monomer subunits. Essentially all monomer subunits include a heterocyclic base moiety that is hybridizable to a complementary site on a nucleic acid target. Reactive sites on monomer subunits located on the termini of an oligomeric compound can be protected or unprotected (generally OH) or can form an attachment to a terminal group (conjugate or other group). Monomer subunits include, without limitation, nucleosides and modified nucleosides. In certain embodiments, monomer subunits include nucleosides such as β-D-ribonucleosides and β-D-2'-deoxyribonucleosides and modified nucleosides including but not limited to substituted nucleosides (such as 2', 5' and bis substituted nucleosides), 4'-S-modified nucleosides (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—CHR$_a$-4' bridging group, wherein R$_a$ is H, alkyl or substituted alkyl), other modified nucleosides and nucleosides having sugar surrogates.

As used herein, "conjugate" means an atom or group of atoms bound to an oligonucleotide or oligomeric compound. In general, conjugate groups modify one or more properties of the compound to which they are attached, including, but not limited to pharmacodymic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide or oligomeric compound wherein at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences. In certain embodiments, a microRNA has a nucleobase sequence as set forth in miRBase version 12.0 released September 2008, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "differentiating nucleobase" means a nucleobase that differs between two nucleic acids. In certain instances, a target region of a target nucleic acid differs by 1-4 nucleobases from a non-target nucleic acid. Each of those differences is referred to as a differentiating nucleobase. In certain instances, a differentiating nucleobase is a single-nucleotide polymorphism.

As used herein, "target-selective nucleoside" means a nucleoside of an antisense compound that corresponds to a differentiating nucleobase of a target nucleic acid.

As used herein, "allele" means one of a pair of copies of a gene existing at a particular locus or marker on a specific chromosome, or one member of a pair of nucleobases existing at a particular locus or marker on a specific chromosome, or one member of a pair of nucleobase sequences existing at a particular locus or marker on a specific chromosome. For a diploid organism or cell or for autosomal chromosomes, each allelic pair will normally occupy corresponding positions (loci) on a pair of homologous chromosomes, one inherited from the mother and one inherited from the father. If these alleles are identical, the organism or cell is said to be "homozygous" for that allele; if they differ, the organism or cell is said to be "heterozygous" for that allele. "Wild-type allele" refers to the genotype typically not associated with disease or dysfunction of the gene product. "Mutant allele" refers to the genotype associated with disease or dysfunction of the gene product.

As used herein, "allelic variant" means a particular identity of an allele, where more than one identity occurs. For example, an allelic variant may refer to either the mutant allele or the wild-type allele.

As used herein, "single nucleotide polymorphism" or "SNP" means a single nucleotide variation between the genomes of individuals of the same species. In some cases, a SNP may be a single nucleotide deletion or insertion. In general, SNPs occur relatively frequently in genomes and thus contribute to genetic diversity. The location of a SNP is generally flanked by highly conserved sequences. An individual may be homozygous or heterozygous for an allele at each SNP site.

As used herein, "single nucleotide polymorphism site" or "SNP site" refers to the nucleotides surrounding a SNP contained in a target nucleic acid to which an antisense compound is targeted.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic.

Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

B. Oligomeric Compounds

As used herein, the term "oligomeric compound" refers to a contiguous sequence of linked monomer subunits. Each linked monomer subunit normally includes a heterocyclic base moiety but monomer subunits also includes those without a heterocyclic base moiety such as abasic monomer subunits. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleosides having sugar surrogate groups.

In certain embodiments, oligomeric compounds comprise a plurality of monomer subunits independently selected from naturally occurring nucleosides, non-naturally occurring nucleosides, modified nucleosides and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups.

In certain embodiments, the oligomeric compounds as provided herein can be modified by covalent attachment of one or more terminal groups to the 5' or 3'-terminal groups. A terminal group can also be attached at any other position at one of the terminal ends of the oligomeric compound. As used herein the terms "5'-terminal group", "3'-terminal group", "terminal group" and combinations thereof are meant to include useful groups known to the art skilled that can be placed on one or both of the terminal ends, including but not limited to the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications of one or more nucleoside (including modifications to the sugar moiety and/or the nucleobase) and/or modifications to one or more internucleoside linkage.

a. Certain Modified Nucleosides

Provided herein are oligomeric compounds comprising modified nucleosides. Such modified nucleosides comprise a modified sugar moeity, a modified nucleobase, or both a modified sugar moiety and a modified nucleobase.

i. Certain Modified Sugar Moieties

In certain embodiments, compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituents, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position are selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$—O—(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$—O—(CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups (generally forming a 4 to 6 membered ring with the parent sugar moiety) independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) Ethylene(methoxy) (4'-(CH(CH$_2$OMe)-O-2') BNA (also referred to as constrained MOE or cMOE) as depicted below.

(A) 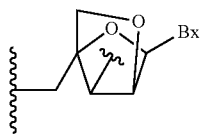

(B) 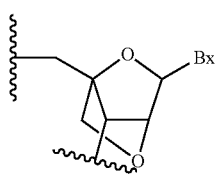

(C) 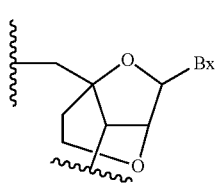

(D) 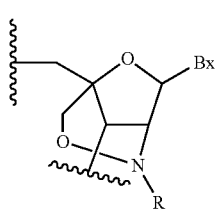

(E) 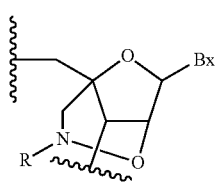

(F) 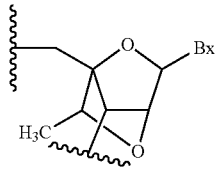

(G) 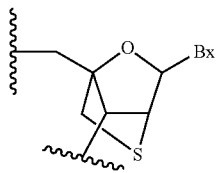

(H) 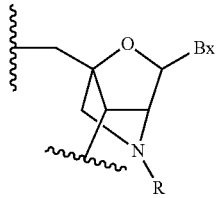

(I) 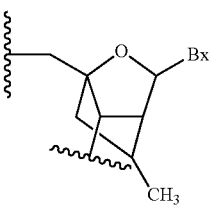

(J) 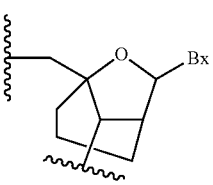

(K) 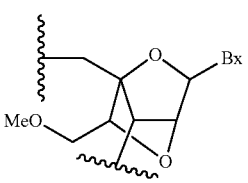

wherein Bx is a nucleobase moiety and R is, independently, H, a protecting group, or $C_1$-$C_{12}$ alkyl.

Additional bicyclic sugar moieties are known in the art, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., Nucleic Acids Research, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

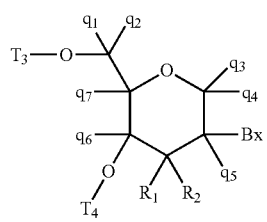

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_a$, $q_5$, $q_6$ and $q_7$ are each H. In certain embodiments, at least one of $q_1$, $q_2$, $q_3$, $q_a$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present invention provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleosides.

In certain embodiments, the oligomeric compounds provided herein include RNA-like nucleosides that have been modified to influence the sugar conformation to have predominantly 3'-endo conformational geometry. In certain embodiments, such modified nucleosides include synthetic modifications of the heterocyclic base moiety, the sugar moiety or both to induce a 3'-endo sugar conformation. In certain embodiments, RNA-like nucleosides are selected from RNA surrogates such as including, but not limited to, F-HNA or cyclohexenyl nucleic acid. RNA-like nucleosides are used to replace and mimic RNA nucleosides in an oligomeric compound so that particular properties of the oligomeric compound can be enhanced. Typically RNA-like nucleosides are used in the 5' and 3'-regions (wings) of gapped oligomeric compounds to improve stability in the presence of nucleases and also to increase the affinity for nucleic a nucleic acid target. Other properties that can also be enhanced by using RNA-like nucleosides include but aren't limited to modulation of pharmacokinetic properties through modification of protein binding, protein off-rate, absorption and clearance as well as chemical stability and specificity of the oligomeric compound (affinity and specificity for enzymes as well as for complementary sequences); and increasing efficacy of RNA cleavage.

In certain embodiments, RNA-like nucleosides include modified nucleosides comprising one or more 2', 3', 4' and 5' substituent groups, bicyclic nucleosides and RNA-surrogates. In certain embodiments, RNA-like nucleosides include, but are not limited to modified nucleosides comprising 2'-ribo-substituent groups selected from: F, $OCH_3$, O—$C_2$-$C_4$ alkyl, O—$CH_2CH=CH_2$, O—$(CH_2)_2$—O—$CH_3$ (MOE), O—$(CH_2)_3$—$NH_2$, O—$(CH_2)_2$—O—$N(R_1)_2$, O—$CH_2C(O)$—$N(R_1)_2$, O—$(CH_2)_2$—O—$(CH_2)_2$—$N(R_1)_2$, O—$(CH_2)_3$—$NHR_1$ and O—$CH_2$—$N(H)$—C($=NR_1$)[$N(R_1)_2$] wherein each $R_1$ is, typically H, $C_1$-$C_{12}$ alkyl or a protecting group. RNA-like nucleosides also include but are not limited to modified nucleosides having a bicyclic furanosyl sugar moiety (bicyclic nucleosides) comprising a bridging group between the 4' and 2'-carbon atoms. Such bicyclic nucleosides include, but are not limited to bridging groups consisting of from 1 to 3 linked biradical groups selected from O, S, $NR_a$, $C(R_b)(R_c)$, C=O, $C(R_b)$ =C(R$_c$) and C[=C(R$_b$)(R$_c$)] wherein C(R$_b$)=C(R$_c$) counts as 2 of said biradical groups wherein each R$_a$, R$_b$ and R$_c$ is, independently, H, C$_1$-C$_6$ alkyl, C$_1$-C$_6$ alkoxy, C$_2$-C$_6$ alkenyl or C$_2$-C$_6$ alkynyl. In certain embodiments, the bridging groups include, but are not limited to 4'-(CH$_2$)—O-2', 4'-(CH$_2$)—S-2', 4'-(CH$_2$)$_2$—O-2', 4'-CH(CH$_3$)—O-2', 4'-CH(CH$_2$OCH$_3$)—O-2', 4'-C(CH$_3$)$_2$—O-2', 4'-CH$_2$—N(OCH$_3$)-2', 4'-CH$_2$—O—N(CH$_3$)-2', 4'-CH$_2$—NCH$_3$—O-2', 4'-CH$_2$—C(H)(CH$_3$)-2' and 4'-CH$_2$—C(=CH$_2$)-2'. In certain embodiments, the bridging groups include, but are not limited to 4'-CH$_2$—O-2', 4'-(CH$_2$)$_2$—O-2', 4'-C(H)[(R)—CH$_3$]-O-2' and 4'-C(H)[(S)—CH$_3$]—O-2'.

In certain embodiments, the oligomeric compounds provided herein include DNA-like nucleosides that have been modified to influence the sugar conformation to have predominantly 2'-endo conformational geometry. Such modified nucleosides can include synthetic modifications of the heterocyclic base moiety, the sugar moiety or both to induce the desired 2'-endo sugar conformation. These modified nucleosides are used to mimic RNA nucleosides so that particular properties of an oligomeric compound can be enhanced while maintaining the desirable 2'-endo conformational geometry.

In certain embodiments, DNA-like nucleosides include, but are not limited to 2'-substituted furanosyl nucleosides comprising: 2'=CH$_2$, 2'-ara-CN, 2'-ara-F, 2'-ara-Br or 2'-ara-Cl, 2'-ara-N$_3$, 2'-ara-OH, 2'-ara-O—CH$_3$ or 2'-dehydro-2'-ara-CH$_3$.

The C3'-endo and C2'-endo conformational geometries are shown below:

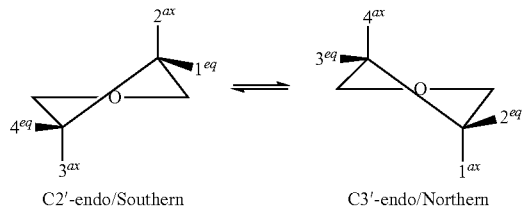

C2'-endo/Southern      C3'-endo/Northern ii. Certain Modified Nucleobases

In certain embodiments, nucleosides of the present invention comprise one or more unmodified nucleobases. In certain embodiments, nucleosides of the present invention comprise one or more modified nucleobases (heterocyclic base moieties).

In one embodiment, a heterocyclic base moiety is any heterocyclic system that contains one or more atoms or groups of atoms capable of hydrogen bonding to a heterocyclic base of a nucleic acid. In certain embodiments, nucleobase refers to purines, modified purines, pyrimidines and modified pyrimidines. In certain embodiments, nucleobase refers to unmodified or naturally occurring nucleobases which include, but are not limited to, the purine bases adenine (A) and guanine (G), and the pyrimidine bases thymine (T), cytosine (C) and uracil (U) and analogs thereof such as 5-methyl cytosine. The terms nucleobase and heterocyclic base moiety also include optional protection for any reactive functional groups such as 4-N-benzoylcytosine, 4-N-benzoyl-5-methylcytosine, 6-N-benzoyladenine or 2-N-isobutyrylguanine.

In certain embodiments, heterocyclic base moieties include without limitation modified nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

In certain embodiments, heterocyclic base moieties include without limitation tricyclic pyrimidines such as 1,3-diazaphenoxazine-2-one, 1,3-diazaphenothiazine-2-one and 9-(2-aminoethoxy)-1,3-diazaphenoxazine-2-one (G-clamp). Heterocyclic base moieties also include those in which the purine or pyrimidine base is replaced with other heterocycles, for example 7-deaza-adenine, 7-deazaguanosine, 2-aminopyridine and 2-pyridone. Further heterocyclic base moieties include without limitation those known to the art skilled (see for example: U.S. Pat. No. 3,687,808; Swayze et al., *The Medicinal Chemistry of Oligonucleotides* in Antisense a Drug Technology, Chapter 6, pages 143-182, Crooke, S. T., ed., 2008); *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-302).

Modified polycyclic heterocyclic compounds useful as heterocyclic base moieties are disclosed in the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,681,941; 5,750,692; 5,763,588; 5,830,653; 6,005,096; and U.S. Patent Application Publication 20030158403, each of which is incorporated herein by reference in its entirety.

b. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

c. Certain Motifs

In certain embodiments, oligomeric compounds comprise or consist of oligonucleotides. In certain embodiments, such oligonucleotides comprise one or more chemical modifications. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

i. Certain Sugar Motifs

In certain embodiments, oligonucleotides comprise one or more type of modified sugar moieties and/or naturally occurring sugar moieties arranged along an oligonucleotide or region thereof in a defined pattern or sugar motif. Such sugar motifs include but are not limited to any of the sugar modifications discussed herein.

In certain embodiments, the oligomeric compounds provided herein comprise a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar moieties of the two wings are the same as one another (symmetric sugar gapmer). In certain embodiments, the sugar moieties of the 5'-wing differs from the sugar moieties of the 3'-wing (asymmetric sugar gapmer). In certain embodiments, the sugar moieties in the two wings are selected from at least two different types that are different from the sugar moieties in the gap and at least one of each are in each wing.

In certain embodiments, the term "gapped oligomeric compound" refers to an oligomeric compound having two external regions or wings (also referred to as 5'-region and 3'-region) and an internal region or gap. The three regions form a contiguous sequence of monomer subunits with the sugar moieties of the external regions (wings) being different than the sugar moieties of the internal region (gap). In certain embodiments, the sugar moieties of each monomer subunit within a particular region is essentially the same. In certain embodiments, the sugar moieties of each monomer subunit within each wing region is selected independently from 2 different types of modified nucleosides. In certain embodiments, the sugar moieties of each monomer subunit within each wing region is selected independently from 3 different types of modified nucleosides. In certain embodiments, the sugar moieties of each monomer subunit within each wing region is selected independently from 4 different types of modified nucleosides. In certain embodiments, the sugar moiety of essentially each monomer subunit within the internal region is essentially the same. In certain embodiments, the sugar moiety of each monomer subunit within the internal region is a β-D-2'-deoxyribonucleoside, a nucleoside that is DNA-like or a nucleoside that supports RNaseH when in the gap region.

In certain embodiments, each monomer subunit within a particular region has the same sugar moiety. When the sugar moieties of the external regions are the same the gapmer is a symmetric gapmer and when the sugar moiety used in the 5'-external region is different from the sugar moiety used in the 3'-external region, the gapmer is an asymmetric gapmer. In certain embodiments, the external regions are small (each independently 2, 3, 4, 5 or about 6 monomer subunits) and the monomer subunits comprise non-naturally occurring sugar moieties with the internal region comprising β-D-2'-deoxyribonucleosides. In certain embodiments, the external regions each, independently, comprise from 2 to about 8 monomer subunits having non-naturally occurring sugar moieties and the internal region comprises from 6 to 14 unmodified nucleosides. The internal region or the gap generally comprises β-D-2'-deoxyribonucleosides but can comprise non-naturally occurring sugar moieties. The heterocyclic base and internucleoside linkage is independently variable at each position of a gapped oligomeric compound. A gapped oligomeric compound can further include one or more additional groups including but not limited to capping groups, conjugate groups and other 5' or 3'-terminal groups.

In certain embodiments, gapped oligomeric compounds comprise an internal region of β-D-2'-deoxyribonucleosides with a single 5'-substituted β-D-2'-deoxyribonucleoside having Formula I. In certain embodiments, gapped oligomeric compounds comprise an internal region of β-D-2'-deoxyribonucleosides having two 5'-substituted β-D-2'-deoxyribonucleosides having Formula I. In certain embodiments, gapped oligomeric compounds comprise an internal region of β-D-2'-deoxyribonucleosides having three 5'-substituted β-D-2'-deoxyribonucleosides having Formula I.

In certain embodiments, the 5' and 3'-wing regions of gapped oligomeric compounds comprise modified nucleosides wherein all the sugar moieties have the same type of modification such as cEt or MOE. In certain embodiments, the 5' and 3'-wing regions of gapped oligomeric compounds comprise two types of modified nucleosides having sugar moieties independently selected from 2'-substituted sugar moieties and furanosyl bicyclic sugar moieties. In certain embodiments, the 5' and 3'-wing regions of gapped oligomeric compounds comprise two types of modified nucleosides having sugar moieties independently selected from 2'-MOE substituted sugar moieties and furanosyl bicyclic sugar moieties each having a 4'-CH((S)—CH$_3$)—O-2' bridge.

In certain embodiments, gapped oligomeric compounds are provided that are from about 10 to about 30 monomer subunits in length. In certain embodiments, gapped oligomeric compounds are provided that are from about 12 to about 20 monomer subunits in length. In certain embodiments, gapped oligomeric compounds are provided that are from about 14 to about 20 monomer subunits in length. In certain embodiments, gapped oligomeric compounds are provided that are from about 14 to about 18 monomer subunits in length.

ii. Certain Nucleobase Modification Motifs

In certain embodiments, oligonucleotides comprise chemical modifications to nucleobases arranged along the oligonucleotide or region thereof in a defined pattern or nucleobases modification motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, oligonucleotides comprise one or more nucleosides comprising a modified nucleobase. In certain embodiments, oligonucleotides having a gapmer sugar motif comprise a nucleoside comprising a modified nucleobase. In certain such embodiments, one nucleoside comprising a modified nucleobases is in the central gap of an oligonucleotide having a gapmer sugar motif. In certain embodiments, the sugar is an unmodified 2' deoxynucleoside. In certain embodiments, the modified nucleobase is selected from: a 2-thio pyrimidine and a 5-propyne pyrimidine In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

iii. Certain Nucleoside Motifs

In certain embodiments, oligomeric compounds nucleosides comprising modified sugar moieties and/or nucleosides comprising modified nucleobases. Such motifs can be described by their sugar motif and their nucleobase motif separately or by their nucleoside motif, which provides positions or patterns of modified nucleosides (whether modified sugar, nucleobase, or both sugar and nucleobase) in an oligonucleotide.

In certain embodiments, the oligomeric compounds comprise or consist of a region having a gapmer nucleoside motif, which comprises two external regions or "wings" and a central or internal region or "gap." The three regions of a gapmer nucleoside motif (the 5'-wing, the gap, and the 3'-wing) form a contiguous sequence of nucleosides wherein at least some of the sugar moieties and/or nucleobases of the nucleosides of each of the wings differ from at least some of the sugar moieties and/or nucleobase of the nucleosides of the gap. Specifically, at least the nucleosides of each wing that are closest to the gap (the 3'-most nucleoside of the 5'-wing and the 5'-most nucleoside of the 3'-wing) differ from the neighboring gap nucleosides, thus defining the boundary between the wings and the gap. In certain embodiments, the nucleosides within the gap are the same as one another. In certain embodiments, the gap includes one or more nucleoside that differs from one or more other nucleosides of the gap. In certain embodiments, the nucleoside motifs of the two wings are the same as one another (symmetric gapmer). In certain embodiments, the nucleoside motifs of the 5'-wing differs from the nucleoside motif of the 3'-wing (asymmetric gapmer).

1. Certain 5'-Wings

In certain embodiments, the 5'-wing of a gapmer consists of 2 to 8 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides.

In certain embodiments, the 5'-wing of a gapmer consists of 2 to 8 linked nucleosides. In certain embodiments, the 5'-wing of a gapmer consists of 2 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 2 to 4 linked nucleosides. In certain embodiments, the 5'-wing of a gapmer consists of 2 to 3 linked nucleosides. In certain embodiments, the 5'-wing of a gapmer consists of 2 linked nucleosides. In certain embodiments, the 5'-wing of a gapmer consists of 3 or 4 linked nucleosides. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides. In certain embodiments, the 5'-wing of a gapmer consists of 7 linked nucleosides. In certain embodiments, the 5'-wing of a gapmer consists of 8 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2% substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2% substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside.

In certain embodiments, the 5'-wing of a gapmer has a nucleoside motif selected from among the following: ABBA; ABB; ABAA; AABAA; AAABAA; AAAABAA; AAAAABAA; AAABAA; AABAA; ABAB; AAABB; AAAAA; ABBC; AA; AAA; AAAA; AAAAB; AAAABAA; AAAAAAAA; ABBB; AB; ABAB; AAAAB; AABBB; AAAAB; and AABBB, wherein each A is a modified nucleoside of a first type, each B is a modified nucleoside of a second type and each C is a modified nucleoside of a third type. In certain embodiments, such an oligomeric compound is a gapmer. In certain such embodiments, the 3'-wing of the gapmer may comprise any nucleoside motif.

2. Certain 3'-Wings

In certain embodiments, the 3'-wing of a gapmer consists of 2 to 8 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides.

In certain embodiments, the 3'-wing of a gapmer consists of 2 to 8 linked nucleosides. In certain embodiments, the 3'-wing of a gapmer consists of 2 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 2 to 4 linked nucleosides. In certain embodiments, the 3'-wing of a gapmer consists of 2 to 3 linked nucleosides. In certain embodiments, the 3'-wing of a gapmer consists of 2 linked nucleosides. In certain embodiments, the 3'-wing of a gapmer consists of 3 or 4 linked nucleosides. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides. In certain embodiments, the 3'-wing of a gapmer consists of 7 linked nucleosides. In certain embodiments, the 3'-wing of a gapmer consists of 8 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside.

In certain embodiments, the 3'-wing of a gapmer has a nucleoside motif selected from among the following: ABB; ABAA; AAABAA, AAAAABAA; AABAA; AAAABAA; AAABAA; ABAB; AAAAA; AAABB; AAAAAAAA; AAAAAAA; AAAAAA; AAAAB; AAAA; AAA; AA; AB; ABBB; ABAB; AABBB; wherein each A is a modified nucleoside of a first type, each B is a modified nucleoside of a second type. In certain embodiments, an oligonucleotide comprises any 3'-wing motif provided herein. In certain such embodiments, the 5'-wing of the gapmer may comprise any nucleoside motif.

3. Certain Central Regions (Gap Regions)

In certain embodiments, the gap of a gapmer consists of 6 to 20 linked nucleosides. In certain embodiments, the gap of a gapmer consists of 6 to 14 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides. In certain embodiments, the gap of a gapmer consists of 13 linked nucleosides. In certain embodiments, the gap of a gapmer consists of 14 linked nucleosides.

In certain embodiments, each nucleoside of the gap of a gapmer is a 2'-deoxynucleoside provided that at least one nucleoside in the gap is a 5'-substituted β-D-2'-deoxyribonucleoside having Formula I. In certain embodiments, the gap comprises one or more modified nucleosides. In certain embodiments, each nucleoside of the gap of a gapmer is a 2'-deoxynucleoside or is a modified nucleoside that is "DNA-like" provided that at least one nucleoside in the gap is a 5'-substituted β-D-2'-deoxyribonucleosides having Formula I. In certain embodiments, "DNA-like" means that the nucleoside has similar characteristics to DNA, such that a duplex comprising the gapmer and an RNA molecule is capable of activating RNase H. In certain embodiments, modified nucleosides that are DNA-like have 2'-endo conformation geometry. For example, under certain conditions, 2'-(ara)-F have been shown to support RNase H activation, and thus is DNA-like and further has 2'-endo conformation geometry. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, the gap comprise a stretch of unmodified 2'-deoxynucleosides interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

4. Certain Gapmer Motifs

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing having features selected from among those listed in the following non-limiting table:

TABLE 1

Certain Gapmer Nucleoside Motifs

| 5'-wing region | Central gap region | 3'-wing region |
|---|---|---|
| AAAAAAA | DDDDDDDDD | AAA |
| AAAAABB | DDDDDDDD | BBAAAAA |
| ABB | DDDDDDDD | BBA |
| AABAA | DDDDDDDD | AABAA |
| ABB | DDDDDD | AABAA |
| AAABAA | DDDDDDDD | AAABAA |
| AAABAA | DDDDDDDD | AAB |
| ABAB | DDDDDDDD | ABAB |
| AAABB | DDDDDDD | BBA |
| ABAB | DDDDDDD | BBA |
| AA | DDDDDDDD | BBBBBBBB |
| ABB | DDDDDD | ABADB |
| AAAAB | DDDDDD | BAAAA |
| ABBB | DDDDDDDD | AB |
| AB | DDDDDDDD | BBBA |
| ABBB | DDDDDDDD | BBBA |
| AB | DDDDDDDD | ABA | wherein each A is a nucleoside of a first type, each B is a modified nucleoside of a second type and each D is a β-D-2'-deoxyribonucleoside wherein at least one D is a 5'-substituted β-D-2'-deoxyribonucleosides having Formula I.

In certain embodiments, each A comprises a modified sugar moiety. In certain embodiments, each A comprises a 2'-substituted sugar moiety. In certain embodiments, each A comprises a 2'-substituted sugar moiety selected from among F, $OCH_3$, $OCH_2$—C(=O)—N(H)($CH_3$) and O($CH_2$)$_2$—$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside.

In certain embodiments, each B comprises a modified sugar moiety. In certain embodiments, each B comprises a 2'-substituted sugar moiety. In certain embodiments, each B comprises a 2'-substituted sugar moiety selected from among F, $OCH_3$, $OCH_2$—C(=O)—N(H)($CH_3$) and O($CH_2$)$_2$—$OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne uridine nucleoside.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, each A and B is, independently, a modified nucleoside comprising a bicyclic sugar moiety comprising a 4'-CH($CH_3$)—O-2' bridge or a modified nucleoside comprising a 2'-$OCH_2CH_2OCH_3$ (MOE) substituent group. In certain embodiments, each A and B is, independently, a modified nucleoside comprising a bicyclic sugar moiety comprising a 4'-CH[(S)—($CH_3$)]—O-2' bridge or a modified nucleoside comprising a 2'-$OCH_2CH_2OCH_3$ (MOE) substituent group. In certain embodiments, each A and B is, independently, a modified nucleoside comprising a bicyclic sugar moiety comprising a 4'-CH[(R)—($CH_3$)]—O-2' bridge or a modified nucleoside comprising a 2'-$OCH_2CH_2OCH_3$ (MOE) substituent group. In certain embodiments, at least one modified nucleoside comprising a 2'-$OCH_2CH_2OCH_3$ (MOE) substituent group and at least one modified nucleoside comprising a 4'-CH($CH_3$)—O-2' bridge is located in each of the 3' and 5' wings. In certain embodiments, at least one modified nucleoside comprising a 2'-$OCH_2CH_2OCH_3$ (MOE) substituent group and at least one modified nucleoside comprising a 4'-CH[(S)—($CH_3$)]—O-2' bridge is located in each of the 3' and 5' wings. In certain embodiments, at least one modified nucleoside comprising a 2'-$OCH_2CH_2OCH_3$ (MOE) substituent group and at least one modified nucleoside comprising a 4'-CH[(R)—($CH_3$)]—O-2' bridge is located in each of the 3' and 5' wings.

iv. Certain Internucleoside Linkage Motifs

In certain embodiments, oligomeric compounds comprise modified internucleoside linkages arranged along the oligomeric compound or region thereof in a defined pattern or modified internucleoside linkage motif. In certain embodiments, internucleoside linkages are arranged in a gapped motif, as described above for nucleoside motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligomeric compounds having a gapped internucleoside linkage motif may or may not have a gapped nucleoside motif and if it does have a gapped nucleoside motif, the wing and gap lengths may or may not be the same.

In certain embodiments, oligomeric compounds comprise a region having an alternating internucleoside linkage motif. In certain embodiments, oligomeric compounds of the present invention comprise a region of uniformly modified internucleoside linkages. In certain such embodiments, the oligomeric compound comprises a region that is uniformly linked by phosphorothioate internucleoside linkages. In certain embodiments, the oligonucleotide is uniformly linked by phosphorothioate. In certain embodiments, each internucleoside linkage of the oligomeric compound is selected from phosphodiester and phosphorothioate. In certain embodiments, each internucleoside linkage of the oligomeric compound is selected from phosphodiester and phosphorothioate and at least one internucleoside linkage is phosphorothioate. In certain embodiments, at least one internucleoside linkage of the oligomeric compound is selected from other than phosphodiester and phosphorothioate.

In certain embodiments, the oligomeric compound comprises at least 6 phosphorothioate internucleoside linkages. In certain embodiments, the oligomeric compound comprises at least 8 phosphorothioate internucleoside linkages. In certain embodiments, the oligomeric compound comprises at least 10 phosphorothioate internucleoside linkages. In certain embodiments, the oligomeric compound comprises at least one block of at least 6 consecutive phosphorothioate internucleoside linkages. In certain embodiments, the oligomeric compound comprises at least one block of at least 8 consecutive phosphorothioate internucleoside linkages. In certain embodiments, the oligomeric compound comprises at least one block of at least 10 consecutive phosphorothioate internucleoside linkages. In certain embodiments, the oligomeric compound comprises at least one block of at least one 12 consecutive phosphorothioate internucleoside linkages. In certain such embodiments, at least one such block is located at the 3' end of the oligomeric compound. In certain such embodiments, at least one such block is located within 3 nucleosides of the 3' end of the oligomeric compound. In certain embodiments, each internucleoside linkage a phosphorothioate internucleoside linkage.

v. Certain Modification Motifs

Modification motifs define oligonucleotides by nucleoside motif (sugar motif and nucleobase motif) and linkage motif. For example, certain oligonucleotides have the following modification motif:

AAADDDDDDDDDBBB;

wherein each A is a modified nucleoside comprising a 2'-substituted sugar moiety; each D is a β-D-2'-deoxyribonucleoside wherein at least one D is a 5'-substituted β-D-2'-deoxyribonucleoside and each B is a modified nucleoside comprising a bicyclic sugar moiety. The following non-limiting Table further illustrates certain modification motifs:

TABLE 2

Certain Modification Motif

| 5'-wing region | Central gap region | 3'-wing region |
|---|---|---|
| BB | DDDDDDDD | AAAAAAAA |
| ABB | DDDDDDDD | BBA |
| ABB | DDDDDDDD | BBA |
| ABBB | DDDDDDDD | BBABB |
| ABB | DDDDDDDD | BBABB |
| BBABB | DDDDDDDD | BBA |
| ABB | DDDDDDDD | BBABBBB |
| AABAA | DDDDDDDD | BBA |
| AAABAA | DDDDDDDD | BBA |
| AABAA | DDDDDDDD | AABAA |
| AAABAA | DDDDDDDD | AABAAA |
| AAAABAA | DDDDDDDD | BBA |
| ABAB | DDDDDDDD | BABA |
| ABAB | DDDDDDDD | AABAA |
| ABB | DDDDDDDD | BABA |
| BBABBBB | DDDDDDDD | BABA |
| AAAAA | DDDDDDDD | AAAAA |
| AAAAA | DDDDDDD | AAAAA |
| AAAAA | DDDDDDDD | BBABBBB |
| AAABB | DDDDDDD | BBA |
| ABAB | DDDDDDDD | BBA |
| ABAB | DDDDDDD | AAABB |
| AAAAB | DDDDDDD | BAAAA |
| BB | DDDDDDD | AA |
| AA | DDDDDDD | AAAAAAAA |
| AAA | DDDDDDD | AAAAAAA |
| AAA | DDDDDDD | AAAAAA |
| AB | DDDDDDD | BBBA |
| ABBB | DDDDDDDD | BA |
| AB | DDDDDDDD | BBBA |
| AAABB | DDDDDDD | BBAAA |
| AAAAB | DDDDDDD | BAAAA |
| AABBB | DDDDDDD | BBBAA |
| AAAAB | DDDDDDD | AAAAA |
| AAABB | DDDDDDD | AAAAA |
| AABBB | DDDDDDD | AAAAA |
| AAAAA | DDDDDDD | BAAAA |
| AAAAA | DDDDDDD | BBAAA |
| AAAAA | DDDDDDD | BBBAA | wherein each A is a modified nucleoside comprising a 2'-substituted sugar moiety; each D is a β-D-2'-deoxyribonucleoside wherein at least one D is a 5'-substituted β-D-2'-deoxyribonucleoside and each B is a modified nucleoside comprising a bicyclic sugar moiety. The following non-limiting Table further illustrates certain modification motifs:

In certain embodiments, each A comprises a modified sugar moiety. In certain embodiments, each A comprises a 2'-substituted sugar moiety. In certain embodiments, each A comprises a 2'-substituted sugar moiety selected from among F, $OCH_3$, $OCH_2-C(=O)-N(H)(CH_3)$ and $O(CH_2)_2-OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside.

In certain embodiments, each B comprises a modified sugar moiety. In certain embodiments, each B comprises a 2'-substituted sugar moiety. In certain embodiments, each B comprises a 2'-substituted sugar moiety selected from among F, $OCH_3$, $OCH_2-C(=O)-N(H)(CH_3)$ and $O(CH_2)_2-OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne uridine nucleoside.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2% substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, each A and B is, independently, a modified nucleoside comprising a bicyclic sugar moiety comprising a 4'-CH(CH$_3$)—O-2' bridge or a modified nucleoside comprising a 2'-OCH$_2$CH$_2$OCH$_3$ (MOE) substituent group. In certain embodiments, each A and B is, independently, a modified nucleoside comprising a bicyclic sugar moiety comprising a 4'-CH[(S)—(CH$_3$)]—O-2' bridge or a modified nucleoside comprising a 2'-OCH$_2$CH$_2$OCH$_3$ (MOE) substituent group. In certain embodiments, each A and B is, independently, a modified nucleoside comprising a bicyclic sugar moiety comprising a 4'-CH[(R)—(CH$_3$)]—O-2' bridge or a modified nucleoside comprising a 2'-OCH$_2$CH$_2$OCH$_3$ (MOE) substituent group. In certain embodiments, at least one modified nucleoside comprising a T-OCH$_2$CH$_2$OCH$_3$ (MOE) substituent group and at least one modified nucleoside comprising a 4'-CH(CH$_3$)—O-2' bridge is located in each of the 3' and 5' wings. In certain embodiments, at least one modified nucleoside comprising a 2'-OCH$_2$CH$_2$OCH$_3$ (MOE) substituent group and at least one modified nucleoside comprising a 4'-CH[(S)—(CH$_3$)]—O-2' bridge is located in each of the 3' and 5' wings. In certain embodiments, at least one modified nucleoside comprising a 2'-OCH$_2$CH$_2$OCH$_3$ (MOE) substituent group and at least one modified nucleoside comprising a 4'-CH[(R)—(CH$_3$)]—O-2' bridge is located in each of the 3' and 5' wings.

d. Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 10, 11, 12, 13, 14, 15, 16, 17, 18, 19, 20, 21, 22, 23, 24, 25, 26, 27, 28, 29 and 30; provided that X≤Y. For example, in certain embodiments, the invention provides oligomeric compounds which comprise oligonucleotides consisting of 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

e. Certain Oligonucleotides

In certain embodiments, oligonucleotides of the present invention are characterized by their modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

f. Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

C. Antisense Compounds

In certain embodiments, oligomeric compounds provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Activities and Mechanisms

In certain antisense activities, hybridization of an antisense compound results in recruitment of a protein that cleaves a target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuranose sugar moieties in the nucleosides of the gap and modified sugar moieties in the nucleosides of the wings.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of potency divided by measure of toxicity).

b. Selective Antisense Compounds

In certain embodiments, antisense compounds provided herein are selective for a target relative to a non-target nucleic acid. In certain embodiments, the nucleobase sequences of the target and non-target nucleic acids differ by no more than 4 differentiating nucleobases in the targeted region. In certain embodiments, the nucleobase sequences of the target and non-target nucleic acids differ by no more than 3 differentiating nucleobases in the targeted region. In certain embodiments, the nucleobase sequences of the target and non-target nucleic acids differ by no more than 2 differentiating nucleobases in the targeted region. In certain embodiments, the nucleobase sequences of the target and non-target nucleic acids differ by a single differentiating nucleobase in the targeted region. In certain embodiments, the target and non-target nucleic acids are transcripts from different genes. In certain embodiments, the target and non-target nucleic acids are different alleles for the same gene.

Selectivity of antisense compounds is achieved, principally, by nucleobase complementarity. For example, if an antisense compound has no mismatches for a target nucleic acid and one or more mismatches for a non-target nucleic acid, some amount of selectivity for the target nucleic acid will result. In certain embodiments, provided herein are antisense compounds with enhanced selectivity (i.e. the ratio of activity for the target to the activity for non-target is greater). For example, in certain embodiments, a selective nucleoside comprises a particular feature or combination of features (e.g., chemical modification, motif, placement of selective nucleoside, and/or self-complementary region) that increases selectivity of an antisense compound compared to an antisense compound not having that feature or combination of features. In certain embodiments, such feature or combination of features increases antisense activity for the target. In certain embodiments, such feature or combination of features decreases activity for the target, but decreases activity for the non-target by a greater amount, thus resulting in an increase in selectivity.

Without being limited by mechanism, enhanced selectivity may result from a larger difference in the affinity of an antisense compound for its target compared to its affinity for the non-target and/or a larger difference in RNase H activity for the resulting duplexes. For example, in certain embodiments, a selective antisense compound comprises a modified nucleoside at that same position as a differentiating nucleobase (i.e., the selective nucleoside is modified). That modification may increase the difference in binding affinity of the antisense compound for the target relative to the non-target. In addition or in the alternative, the chemical modification may increase the difference in RNAse H activity for the duplex formed by the antisense compound and its target compared to the RNase activity for the duplex formed by the antisense compound and the non-target. For example, the modification may exaggerate a structure that is less compatible for RNase H to bind, cleave and/or release the non-target.

Antisense compounds having certain specified motifs have enhanced selectivity, including, but not limited to motifs described above. In certain embodiments, enhanced selectivity is achieved by oligonucleotides comprising any one or more of:

a modification motif comprising a long 5'-wing (longer than 5, 6, or 7 nucleosides);

a modification motif comprising a long 3'-wing (longer than 5, 6, or 7 nucleosides);

a modification motif comprising a short gap region (shorter than 8, 7, or 6 nucleosides); and a modification motif comprising an interrupted gap region (having no uninterrupted stretch of unmodified 2'-deoxynucleosides longer than 7, 6 or 5).

i. Certain Selective Nucleobase Sequence Elements

In certain embodiments, selective antisense compounds comprise nucleobase sequence elements. Such nucleobase sequence elements are independent of modification motifs. Accordingly, oligonucleotides having any of the motifs (modification motifs, nucleoside motifs, sugar motifs, nucleobase modification motifs, and/or linkage motifs) may also comprise one or more of the following nucleobase sequence elements.

1. Alignment of Differentiating Nucleobase/Target-Selective Nucleoside

In certain embodiments, a target region and a region of a non-target nucleic acid differ by 1-4 differentiating nucleobase. In such embodiments, selective antisense compounds have a nucleobase sequence that aligns with the non-target nucleic acid with 1-4 mismatches. A nucleoside of the antisense compound that corresponds to a differentiating nucleobase of the target nucleic acid is referred to herein as a target-selective nucleoside. In certain embodiments, selective antisense compounds having a gapmer motif align with a non-target nucleic acid, such that a target-selective nucleoside is positioned in the gap. In certain embodiments, a target-selective nucleoside is the $1^{st}$ nucleoside of the gap from the 5' end. In certain embodiments, a target-selective nucleoside is the $2^{nd}$ nucleoside of the gap from the 5' end. In certain embodiments, a target-selective nucleoside is the $3^{rd}$ nucleoside of the gap from the 5'-end. In certain embodiments, a target-selective nucleoside is the $4^{th}$ nucleoside of the gap from the 5'-end. In certain embodiments, a target-selective nucleoside is the $5^{th}$ nucleoside of the gap from the 5'-end. In certain embodiments, a target-selective nucleoside is the $6^{rd}$ nucleoside of the gap from the 5'-end. In certain embodiments, a target-selective nucleoside is the $8^{th}$ nucleoside of the gap from the 3'-end. In certain embodiments, a target-selective nucleoside is the $7^{th}$ nucleoside of the gap from the 3'-end. In certain embodiments, a target-selective nucleoside is the $6^{th}$ nucleoside of the gap from the 3'-end. In certain embodiments, a target-selective nucleoside is the $5^{th}$ nucleoside of the gap from the 3'-end. In certain embodiments, a target-selective nucleoside is the $4^{th}$ nucleoside of the gap from the 3'-end. In certain embodiments, a target-selective nucleoside is the $3^{rd}$ nucleoside of the gap from the 3'-end. In certain embodiments, a target-selective nucleoside is the $2^{nd}$ nucleoside of the gap from the 3'-end.

In certain embodiments, the target-selective nucleoside is 5'-substituted β-D-2'-deoxyribonucleosides having Formula I. In certain embodiments, a target-selective nucleoside comprises a 5'-substituted β-D-2'-deoxyribonucleoside having Formula I wherein the 5' substituent is selected from 5'-(S)-Me and 5'-(R)-Me.

2. Mismatches to the Target Nucleic Acid

In certain embodiments, selective antisense compounds comprise one or more mismatched nucleobases relative to the target nucleic acid. In certain such embodiments, antisense activity against the target is reduced by such mismatch, but activity against the non-target is reduced by a greater amount. Thus, in certain embodiments selectivity is improved. Any nucleobase other than the differentiating nucleobase is suitable for a mismatch. In certain embodiments, however, the mismatch is specifically positioned within the gap of an oligonucleotide having a gapmer motif. In certain embodiments, a mismatch relative to the target nucleic acid is at positions 1, 2, 3, 4, 5, 6, 7, or 8 from the 5'-end of the gap region. In certain embodiments, a mismatch relative to the target nucleic acid is at positions 9, 8, 7, 6, 5, 4, 3, 2, 1 of the antisense compounds from the 3'-end of the gap region. In certain embodiments, a mismatch relative to the target nucleic acid is at positions 1, 2, 3, or 4 of the antisense compounds from the 5'-end of the wing region. In certain embodiments, a mismatch relative to the target nucleic acid is at positions 4, 3, 2, or 1 of the antisense compounds from the 3'-end of the wing region.

3. Self Complementary Regions

In certain embodiments, selective antisense compounds comprise a region that is not complementary to the target. In certain embodiments, such region is complementary to another region of the antisense compound. Such regions are referred to herein as self-complementary regions. For example, in certain embodiments, an antisense compound has a first region at one end that is complementary to a second region at the other end. In certain embodiments, one of the first and second regions is complementary to the target nucleic acid. Unless the target nucleic acid also includes a self-complementary region, the other of the first and second region of the antisense compound will not be complementary to the target nucleic acid. For illustrative purposes, certain antisense compounds have the following nucleobase motif:

ABCXXXXXXXXXC'B'A';
ABCXXXXXXX(X/C')(X/B')(X/A');
(X/A)(X/B)(X/C)XXXXXXXXXC'B'A' where each of A, B, and C are any nucleobase; A', B', and C' are the complementary bases to A, B, and C, respectively; each X is a nucleobase complementary to the target nucleic acid; and two letters in parentheses (e.g., (X/C')) indicates that the nucleobase is complementary to the target nucleic acid and to the designated nucleoside within the antisense oligonucleotide.

Without being bound to any mechanism, in certain embodiments, such antisense compounds are expected to form self-structure, which is disrupted upon contact with a target nucleic acid. Contact with a non-target nucleic acid is expected to disrupt the self-structure to a lesser degree, thus increasing selectivity compared to the same antisense compound lacking the self-complementary regions.

4. Combinations of Features

Though it is clear to one of skill in the art, the above motifs and other elements for increasing selectivity may be used alone or in combination. For example, a single antisense compound may include any one, two, three, or more of: self-complementary regions, a mismatch relative to the target nucleic acid, a short nucleoside gap, an interrupted gap, and specific placement of the selective nucleoside.

D. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA). In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism. In certain such embodiments, the antisense compound is capable of modulating expression of one allele of the single-nucleotide polymorphism-containing-target nucleic acid to a greater or lesser extent than it modulates another allele. In certain embodiments an antisense compound hybridizes to a single-nucleotide polymorphism-containing-target nucleic acid at the single-nucleotide polymorphism site. In certain embodiments, the target nucleic acid is a Huntingtin gene transcript. In certain embodiments, the target nucleic acid is a single-nucleotide polymorphism-containing-target nucleic acid of a Huntingtin gene transcript. In certain embodiments, the target nucleic acid is not a Huntingtin gene transcript. In certain embodiments, the target nucleic acid is a single-nucleotide polymorphism-containing-target nucleic acid of a gene transcript other than Huntingtin. In certain embodiments, the target nucleic acid is any nucleic acid other than a Huntingtin gene transcript.

a. Single-Nucleotide Polymorphism

Embodiments of the present invention provide methods, compounds, and compositions for selectively inhibiting mRNA and protein expression of an allelic variant of a particular gene or DNA sequence. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

In certain embodiments, the expressed gene product of a mutant allele results in aggregation of the mutant proteins causing disease. In certain embodiments, the expressed gene product of a mutant allele results in gain of function causing disease. In certain embodiments, genes with an autosomal dominant mutation resulting in a toxic gain of function of the protein are the APP gene encoding amyloid precursor protein involved in Alzheimer's disease (Gene, 371: 68, 2006); the PrP gene encoding prion protein involved in Creutzfeldt-Jakob disease and in fatal familial insomnia (Nat. Med. 1997, 3: 1009); GFAP gene encoding glial fibrillary acidic protein involved in Alexander disease (J. Neurosci. 2006, 26:111623); alpha-synuclein gene encoding alpha-synuclein protein involved in Parkinson's disease (J. Clin. Invest. 2003, 111: 145); SOD-1 gene encoding the SOD-1 protein involved in amyotrophic lateral sclerosis (Science 1998, 281: 1851); atrophin-1 gene encoding atrophin-1 protein involved in dentato-rubral and pallido-luysian atrophy (DRPA) (Trends Mol. Med. 2001, 7: 479); SCA1 gene encoding ataxin-1 protein involved in spino-cerebellar ataxia-1 (SCA1) (Protein Sci. 2003, 12: 953); PLP gene encoding proteolipid protein involved in Pelizaeus-Merzbacher disease (NeuroMol Med. 2007, 4: 73); DYT1 gene encoding torsinA protein involved in Torsion dystonia (Brain Res. 2000, 877: 379); and alpha-B crystalline gene encoding alpha-B crystalline protein involved in protein aggregation diseases, including cardiomyopathy (Cell 2007, 130: 427); alpha1-antitrypsin gene encoding alpha1-antitrypsin protein involved in chronic obstructive pulmonary disease (COPD), liver disease and hepatocellular carcinoma (New Engl J Med. 2002, 346: 45); Ltk gene encoding leukocyte tyrosine kinase protein involved in systemic lupus erythematosus (Hum. Mol. Gen. 2004, 13: 171); PCSK9 gene encoding PCSK9 protein involved in hypercholesterolemia (Hum Mutat. 2009, 30: 520); prolactin receptor gene encoding prolactin receptor protein involved in breast tumors (Proc. Natl. Assoc. Sci. 2008, 105: 4533); CCL5 gene encoding the chemokine CCL5 involved in COPD and asthma (Eur. Respir. J. 2008, 32: 327); PTPN22 gene encoding PTPN22 protein involved in Type 1 diabetes, Rheumatoid arthritis, Graves disease, and SLE (Proc. Natl. Assoc. Sci. 2007, 104: 19767); androgen receptor gene encoding the androgen receptor protein involved in spinal and bulbar muscular atrophy or Kennedy's disease (J Steroid Biochem. Mol. Biol. 2008, 108: 245); CHMP4B gene encoding chromatin modifying protein-4B involved in progressive childhood posterior subcapsular cataracts (Am. J. Hum. Genet 2007, 81: 596); FXR/NR1H4 gene encoding Farnesoid X receptor protein involved in cholesterol gallstone disease, arthrosclerosis and diabetes (Mol. Endocrinol. 2007, 21: 1769); ABCA1 gene encoding ABCA1 protein involved in cardiovascular disease (Transl. Res. 2007, 149: 205); CaSR gene encoding the calcium sensing receptor protein involved in primary hypercalciuria (Kidney Int. 2007, 71: 1155); alpha-globin gene encoding alpha-globin protein involved in alpha-thallasemia (Science 2006, 312: 1215); httlpr gene encoding HTTLPR protein involved in obsessive compulsive disorder (Am. J. Hum. Genet. 2006, 78: 815); AVP gene encoding arginine vasopressin protein in stress-related disorders such as anxiety disorders and comorbid depression (CNS Neurol. Disord. Drug Targets 2006, 5: 167); GNAS gene encoding G proteins involved in congenital visual defects, hypertension, metabolic syndrome (Trends Pharmacol. Sci. 2006, 27: 260); APAF1 gene encoding APAF1 protein involved in a predisposition to major depression (Mol. Psychiatry 2006, 11: 76); TGF-beta1 gene encoding TGF-beta1 protein involved in breast cancer and prostate cancer (Cancer Epidemiol. Biomarkers Prev. 2004, 13: 759); AChR gene encoding acetylcholine receptor involved in congential myasthenic syndrome (Neurology 2004, 62: 1090); P2Y12 gene encoding adenosine diphosphate (ADP) receptor protein involved in risk of peripheral arterial disease (Circulation 2003, 108: 2971); LQT1 gene encoding LQT1 protein involved in atrial fibrillation (Cardiology 2003, 100: 109); RET protooncogene encoding RET protein involved in sporadic pheochromocytoma (J. Clin. Endocrinol. Metab. 2003, 88: 4911); filamin A gene encoding filamin A protein involved in various congenital malformations (Nat. Genet. 2003, 33: 487); TARDBP gene encoding TDP-43 protein involved in amyotrophic lateral sclerosis (Hum. Mol. Genet. 2010, 19: 671); SCA3 gene encoding ataxin-3 protein involved in Machado-Joseph disease (PLoS One 2008, 3: e3341); SCAT gene encoding ataxin-7 protein involved in spino-cerebellar ataxia-7 (PLoS One 2009, 4: e7232); and HTT gene encoding huntingtin protein involved in Huntington's disease (Neurobiol Dis. 1996, 3:183); and the CA4 gene encoding carbonic anhydrase 4 protein, CRX gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Adv Exp Med Biol. 2008, 613:203)

In certain embodiments, the mutant allele is associated with any disease from the group consisting of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congenital myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

i. Certain Huntingtin Targets

In certain embodiments, an allelic variant of huntingtin is selectively reduced. Nucleotide sequences that encode huntingtin include, without limitation, the following: GENBANK Accession No. NT_006081.18, truncated from nucleotides 1566000 to 1768000 (replaced by GENBANK Accession No. NT_006051), incorporated herein as SEQ ID NO: 8, and NM_002111.6, incorporated herein as SEQ ID NO: 10.

Table 3 provides SNPs found in the GM04022, GM04281, GM02171, and GM02173B cell lines. Also provided are the allelic variants found at each SNP position, the genotype for each of the cell lines, and the percentage of HD patients having a particular allelic variant. For example, the two allelic variants for SNP rs6446723 are T and C. The GM04022 cell line is heterozygous TC, the GM02171 cell line is homozygous CC, the GM02173 cell line is heterozygous TC, and the GM04281 cell line is homozygous TT. Fifty percent of HD patients have a T at SNP position rs6446723.

TABLE 3

Allelic Variations for SNPs Associated with HD

| SNP | Variation | GM04022 | GM02171 | GM02173 | GM04281 | TargetPOP | allele |
|---|---|---|---|---|---|---|---|
| rs6446723 | T/C | TC | CC | TC | TT | 0.50 | T |
| rs3856973 | A/G | AG | AA | AG | GG | 0.50 | G |
| rs2285086 | A/G | AG | GG | AG | AA | 0.50 | A |
| rs363092 | A/C | AC | AA | AC | CC | 0.49 | C |
| rs916171 | C/G | GC | GG | GC | CC | 0.49 | C |
| rs6844859 | T/C | TC | CC | TC | TT | 0.49 | T |
| rs7691627 | A/G | AG | AA | AG | GG | 0.49 | G |
| rs4690073 | A/G | AG | AA | AG | GG | 0.49 | G |
| rs2024115 | A/G | AG | GG | AG | AA | 0.48 | A |
| rs11731237 | T/C | CC | CC | TC | TT | 0.43 | T |
| rs362296 | A/C | CC | AC | AC | AC | 0.42 | C |
| rs10015979 | A/G | AA | AA | AG | GG | 0.42 | G |
| rs7659144 | C/G | CG | CG | CG | CC | 0.41 | C |
| rs363096 | T/C | CC | CC | TC | TT | 0.40 | T |
| rs362273 | A/G | AA | AG | AG | AA | 0.39 | A |
| rs16843804 | T/C | CC | TC | TC | CC | 0.38 | C |
| rs362271 | A/G | GG | AG | AG | GG | 0.38 | G |
| rs362275 | T/C | CC | TC | TC | CC | 0.38 | C |
| rs3121419 | T/C | CC | TC | TC | CC | 0.38 | C |
| rs362272 | A/G | GG | — | AG | GG | 0.38 | G |
| rs3775061 | A/G | AA | AG | AG | AA | 0.38 | A |
| rs34315806 | T/C | CC | TC | TC | CC | 0.38 | C |

TABLE 3-continued

Allelic Variations for SNPs Associated with HD

| SNP | Variation | GM04022 | GM02171 | GM02173 | GM04281 | TargetPOP | allele |
|---|---|---|---|---|---|---|---|
| rs363099 | T/C | CC | TC | TC | CC | 0.38 | C |
| rs2298967 | T/C | TT | TC | TC | TT | 0.38 | T |
| rs363088 | A/T | AA | TA | TA | AA | 0.38 | A |
| rs363064 | T/C | CC | TC | TC | CC | 0.35 | C |
| rs363102 | A/G | AG | AA | AA | AA | 0.23 | G |
| rs2798235 | A/G | AG | GG | GG | GG | 0.21 | A |
| rs363080 | T/C | TC | CC | CC | CC | 0.21 | T |
| rs363072 | A/T | TA | TA | AA | AA | 0.13 | A |
| rs363125 | A/C | AC | AC | CC | CC | 0.12 | C |
| rs362303 | T/C | TC | TC | CC | CC | 0.12 | C |
| rs362310 | T/C | TC | TC | CC | CC | 0.12 | C |
| rs10488840 | A/G | AG | AG | GG | GG | 0.12 | G |
| rs362325 | T/C | TC | TC | TT | TT | 0.11 | T |
| rs35892913 | A/G | GG | GG | GG | GG | 0.10 | A |
| rs363102 | A/G | AG | AA | AA | AA | 0.09 | A |
| rs363096 | T/C | CC | CC | TC | TT | 0.09 | C |
| rs11731237 | T/C | CC | CC | TC | TT | 0.09 | C |
| rs10015979 | A/G | AA | AA | AG | GG | 0.08 | A |
| rs363080 | T/C | TC | CC | CC | CC | 0.07 | C |
| rs2798235 | A/G | AG | GG | GG | GG | 0.07 | G |
| rs1936032 | C/G | GC | CC | CC | CC | 0.06 | C |
| rs2276881 | A/G | GG | GG | GG | GG | 0.06 | G |
| rs363070 | A/G | AA | AA | AA | AA | 0.06 | A |
| rs35892913 | A/G | GG | GG | GG | GG | 0.04 | G |
| rs12502045 | T/C | CC | CC | CC | CC | 0.04 | C |
| rs6446723 | T/C | TC | CC | TC | TT | 0.04 | C |
| rs7685686 | A/G | AG | GG | AG | AA | 0.04 | G |
| rs3733217 | T/C | CC | CC | CC | CC | 0.03 | C |
| rs6844859 | T/C | TC | CC | TC | TT | 0.03 | C |
| rs362331 | T/C | TC | CC | TC | TT | 0.03 | C |

E. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol.

Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32 +/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b. END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

Lipofectin™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus MgCl$_2$, 6.6 mM MgCl$_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/-extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al, *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation
Poly(A)+ mRNA Isolation

Poly(A)+ mRNA is isolated according to Miura et al., (Clin. Chem., 1996, 42, 1758-1764). Other methods for poly(A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.
Total RNA Isolation Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

Forward primer: AATGGCTAAGTGAAGATGACAAT-CAT (SEQ ID NO: 2)
Reverse primer: TGCACATATCATTACACCAGTTCGT (SEQ ID NO: 3)
And the PCR probe:
FAM-TTGCAGCAATTCACTGTAAAGCTG-GAAAGG-TAMRA (SEQ ID NO: 4), where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 5

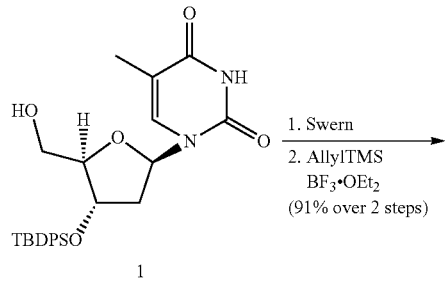

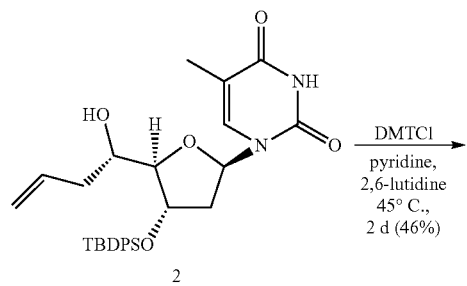

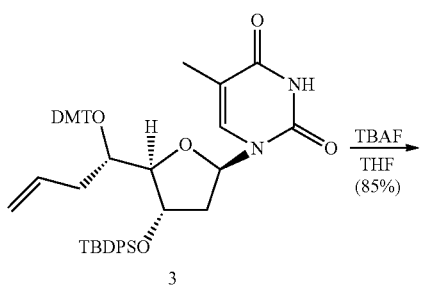

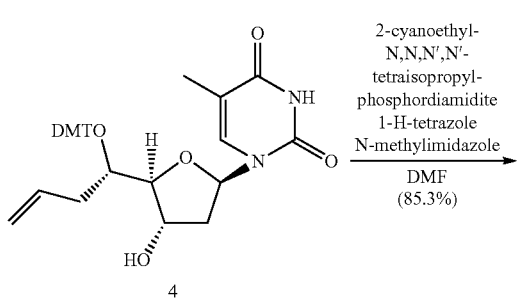

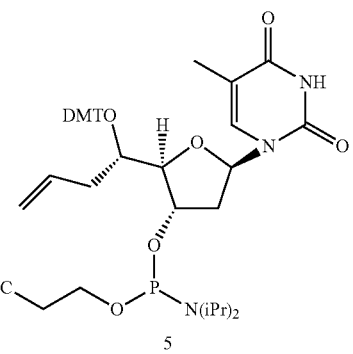

Compound 1 is commercially available from Chemexpress. The spectral analysis of Compound 5 was consistent with the structure.

Example 14

Preparation of Compound 10

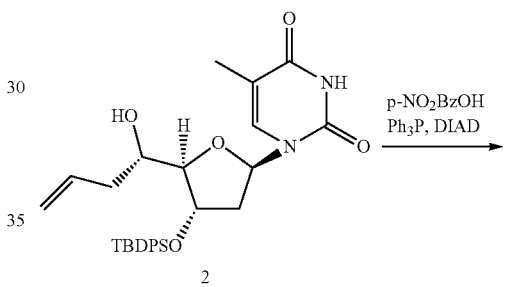

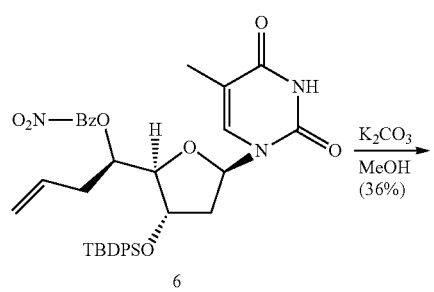

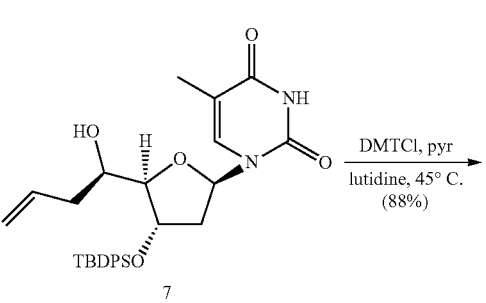

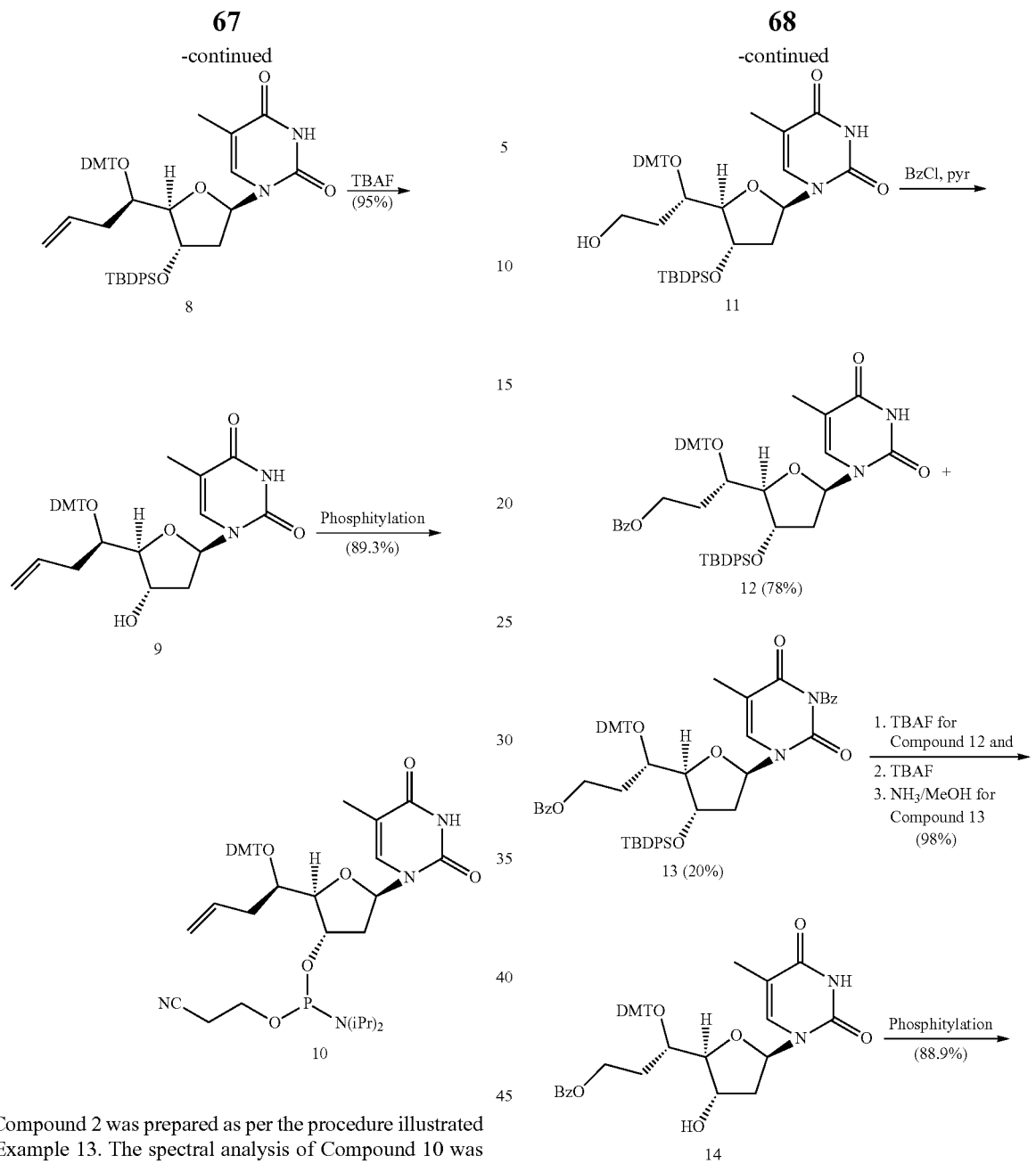

Compound 2 was prepared as per the procedure illustrated in Example 13. The spectral analysis of Compound 10 was consistent with the structure.

Example 15

Preparation of Compound 15

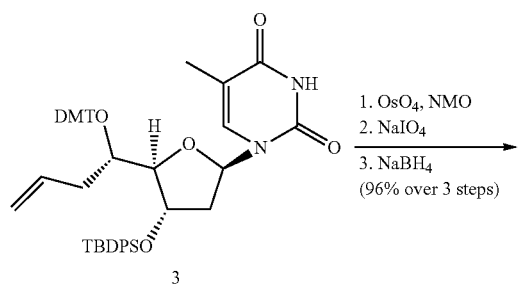

Compound 3 was prepared as per the procedure illustrated in Example 13. Compounds 12 and 13 were separated by column chromatography. The spectral analysis of Compound 15 was consistent with the structure.

Example 16
Preparation of Compound 19
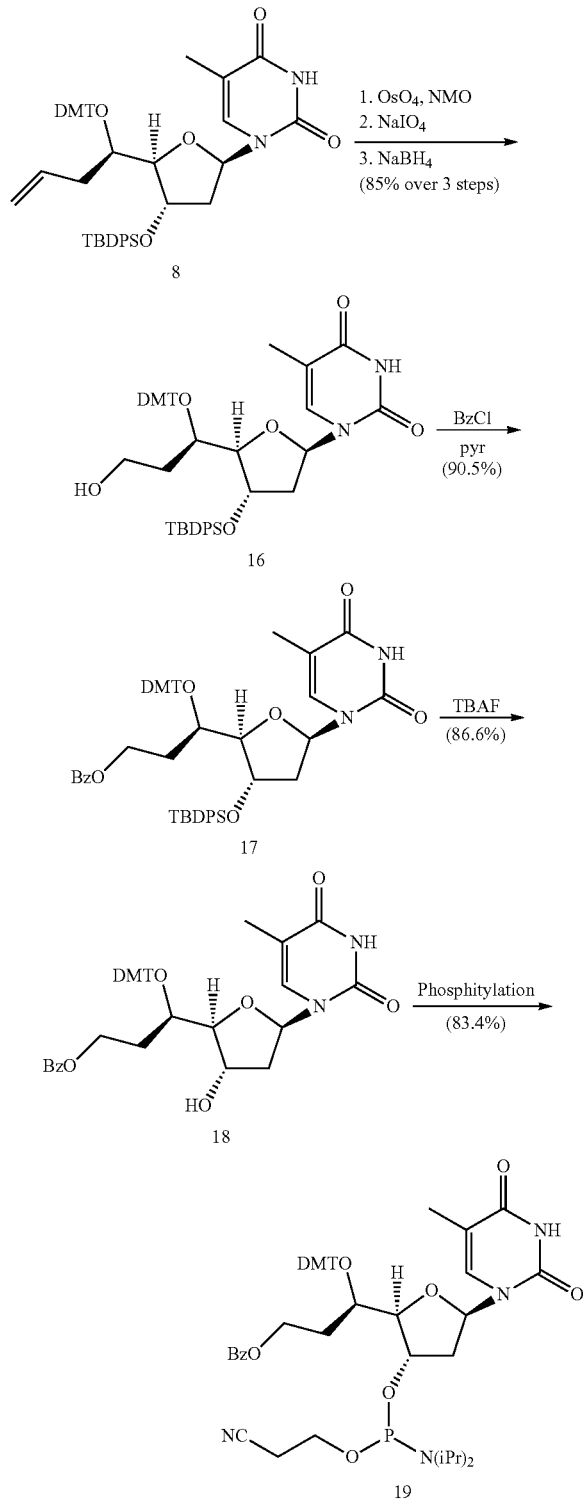
Compound 8 was prepared as per the procedure illustrated in Example 14. The spectral analysis of Compound 19 was consistent with the structure.
Example 17
Preparation of Compound 28
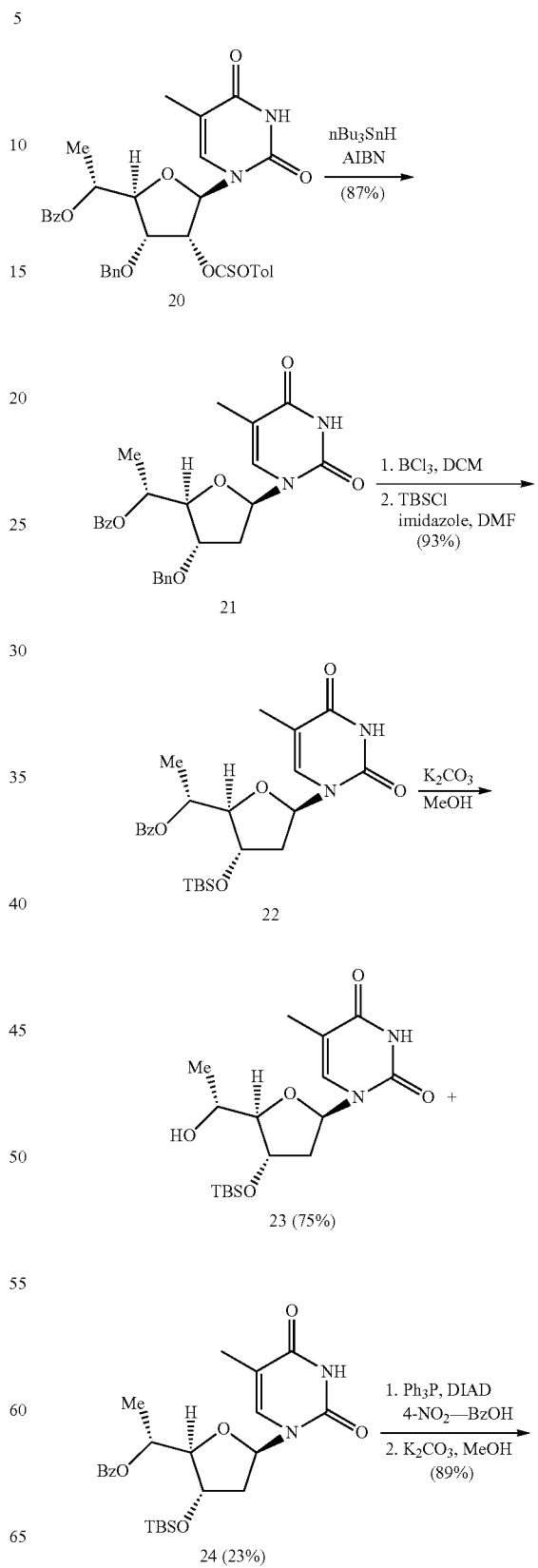

72

Example 18

Preparation of Compound 31

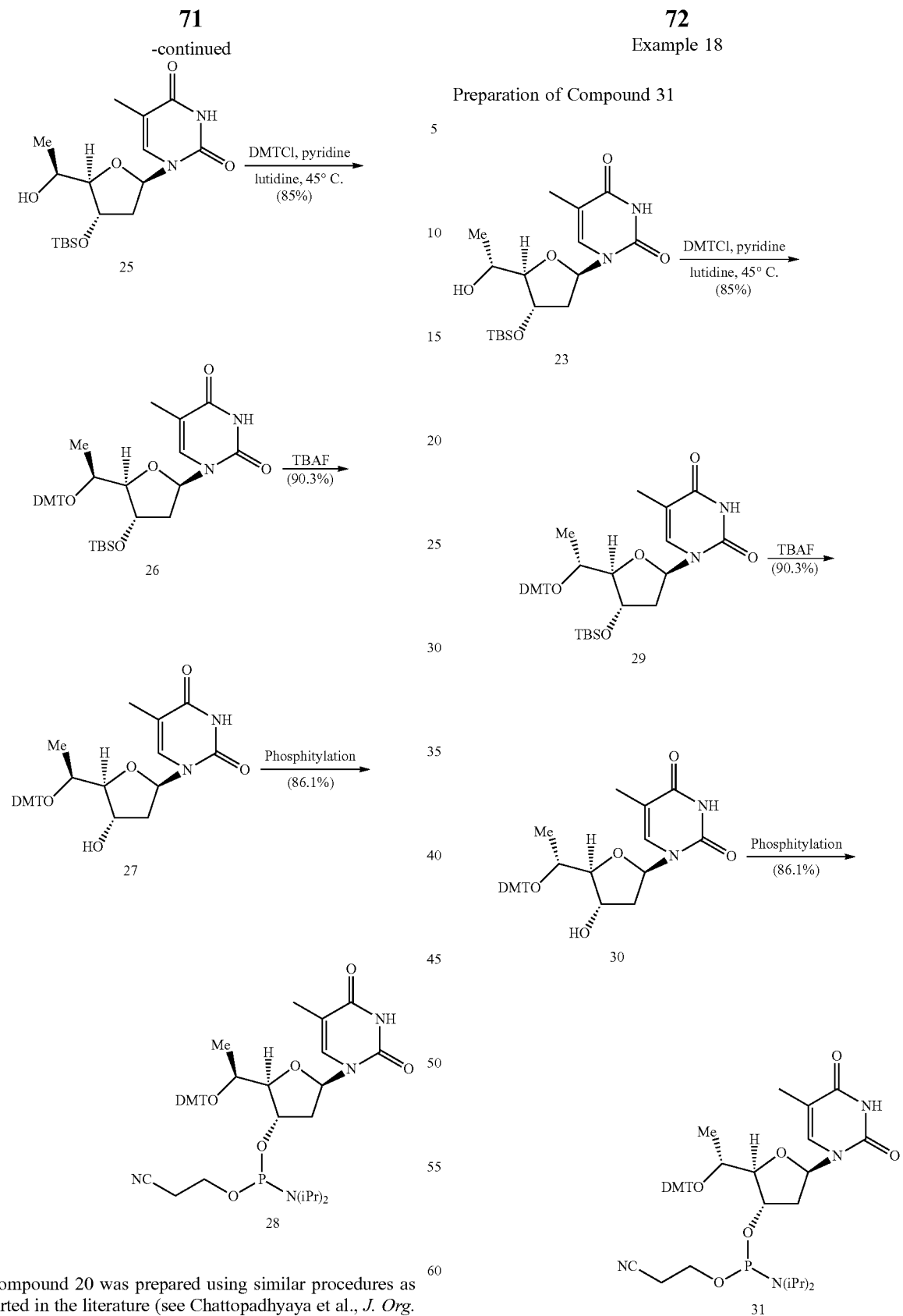

Compound 20 was prepared using similar procedures as reported in the literature (see Chattopadhyaya et al., *J. Org. Chem.*, 2009, 74(1), 118-134; Mesmaeker et al., *Synlett*, 1997, 1287-1290) and in published patent application WO 94/22890. Compounds 23 and 24 were separated by column chromatography. The spectral analysis of Compound 28 was consistent with the structure.

Compound 23 was prepared as per the procedure illustrated in Example 17. The spectral analysis of Compound 31 was consistent with the structure.

Example 19

General Method for the Preparation of Phosphoramidites, Compounds 32-34

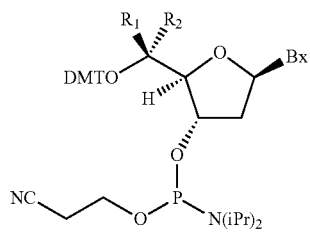

32

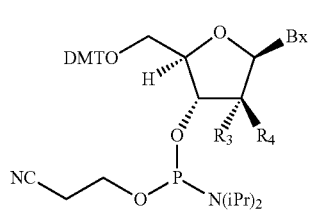

33

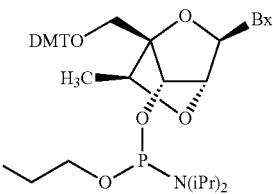

34

Bx is a heterocyclic base;
R₁ and R₂ are each independently H, alkyl, substituted alkyl, alkenyl, substituted alkenyl, alkynyl or substituted alkynyl; and
R₃ and R₄ are each independently H, OH, or a 2′-sugar substituent group Compound 32 is prepared using similar procedure as exemplified in Examples 13-18. Compounds 33 and 34 are prepared as per the procedures well known in the art as described in the specification herein (see Seth et al., *Bioorg. Med. Chem.*, 2011, 21(4), 1122-1125, *J. Org. Chem.*, 2010, 75(5), 1569-1581, *Nucleic Acids Symposium Series*, 2008, 52(1), 553-554); and also see published PCT International Applications (WO 2011/115818, WO 2010/077578, WO2010/036698, WO2009/143369, WO 2009/006478, and WO 2007/090071), and U.S. Pat. No. 7,569,686).

Example 20

General Method for the Preparation of Oligomeric Compound 38

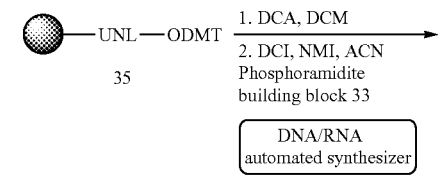

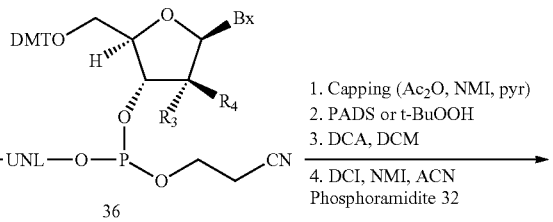

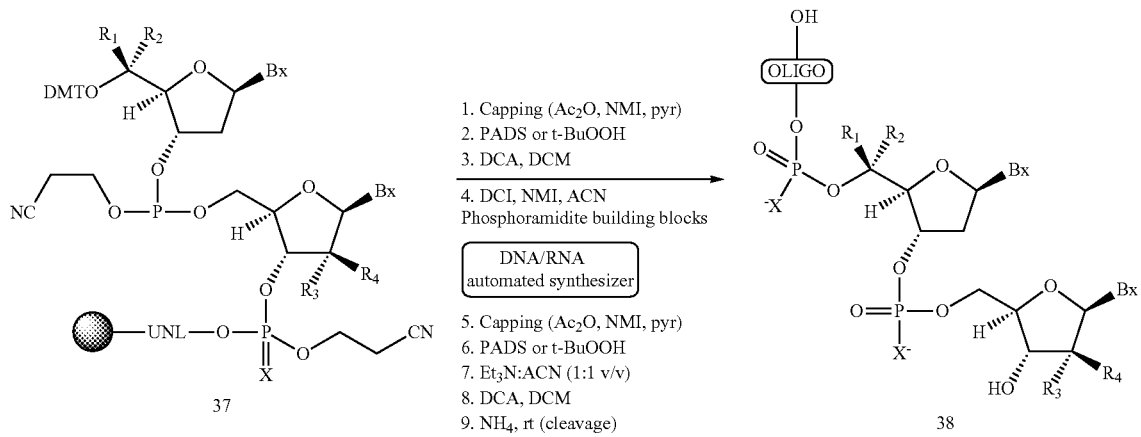

Bx is a heterocyclic base;
R₁ and R₂ are each independently H, alkyl, substituted alkyl, alkenyl, substituted alkenyl, alkynyl or substituted alkynyl;
R₃ and R₄ are each independently H, OH or a 2′-sugar substituent group; and X is O or S ● — UNL = Unylinker solid support The Unylinker™ 35 is commercially available. Oligomeric Compound 38 comprising a 5'-substituted DNA modification is prepared using standard procedures in automated DNA/RNA synthesis (see Dupouy et al., *Angew. Chem. Int. Ed*, 2006, 45, 3623-3627). Phosphoramidite building blocks, Compounds 32 and 33 are prepared as per the procedures illustrated in Example 19. The synthetic steps illustrated are meant to be representative and not intended to be limiting as other phosphoramidite building blocks which are disclosed in Examples 13 to 19 can be used in place of Compounds 32 and 33 to prepare an oligomeric compound having a predetermined sequence and composition. The order of addition to the solid support as exemplified can also be altered to provide a region or multiple regions of nucleotides containing 5'-substituted DNA modification.

The synthetic methods described herein (e.g. Examples 13-20) are versatile and allow for the incorporation of 5'-substituted DNA modification to be introduced at any position of the oligonucleotide.

Example 21

General Method for the Preparation of Oligomeric Compounds Comprising
5'-(R)-Me-Deoxyribonucleoside Via Solid Phase Techniques (Preparation of ISIS 460209 and 556848)

Unless otherwise stated, all reagents and solutions used for the synthesis of oligomeric compounds are purchased from commercial sources. Standard phosphoramidite building blocks and solid support are used for incorporation nucleoside residues which include for example T, A, U, G, C and $^m$C residues. A 0.1 M solution of phosphoramidite in anhydrous acetonitrile was used for β-D-2'-deoxyribonucleoside, and 5'-(R)-Me-deoxyribonucleoside. For 2'-O-MOE phosphoramidite, a 0.2 M solution in acetonitrile was used. For constrained ethyl (cEt) BNA phosphoramidite, a 0.2 M solution in a 1:1 (v/v) mixture of acetonitrile and toluene was used.

The oligomeric compound was synthesized on VIMAD UnyLinker™ solid support and the appropriate amounts of solid support were packed in the column for synthesis. Dichloroacetic acid (3%) in DCM was used as detritylating reagent. 4,5-Dicyanoimidazole in the presence of N-methylimidazole or 1H-tetrazole in CH$_3$CN was used as activator during the coupling step. The synthesis of oligomeric compounds was performed on an ABI394 synthesizer (Applied Biosystems) on a 2 μmol scale using the procedures set forth below.

A solid support preloaded with the Unylinker™ was loaded into a synthesis column after closing the column bottom outlet and CH$_3$CN was added to form a slurry. The swelled support-bound Unylinker™ was treated with a detritylating reagent containing 3% dichloroacetic acid in DCM to provide the free hydroxyl groups. During the coupling step, four to fourteen equivalents of phosphoramidite solutions were delivered with coupling for 6 minutes for unmodified deoxyribonucleoside phosphoramidites and 13 minutes for other modifications. All of the other steps followed standard protocols. Phosphodiester linkages were introduced by oxidation with 10% t-BuOOH solution in CH$_3$CN for a contact time of 10 minutes. Phosphorothioate linkages were introduced by sulfurization with PADS (0.2 M) in 1:1 pyridine/CH$_3$CN for a contact time of 5 minutes.

After the desired sequence was assembled, the cyanoethyl phosphate protecting groups were deprotected using a 1:1 (v/v) mixture of triethylamine and acetonitrile. The solid support bound oligomeric compound was washed with acetonitrile and dried under high vacuum. The solid-support bound oligomeric compound was then suspended in ammonia (28-30 wt %) at room temperature for 48 h to remove nucleobase protecting groups and to cleave from the solid support.

The unbound oligomeric compound was then filtered and the support was rinsed and filtered with water:ethanol (1:1) followed by water. The filtrate was combined and concentrated to dryness. The residue obtained was purified by cationic ion exchange HPLC (Source 30Q resin, A—50 mM sodium bicarbonate in CH$_3$CN:H$_2$O 3:7 (v/v), B—50 mM sodium bicarbonate, 1.5 M sodium bromide in CH$_3$CN:H$_2$O 3:7 (v/v), 0-30% in 110 min, flow 6 mL/min, λ=260 nm). Fractions containing full-length oligomeric compound were pooled together (assessed by LC/MS analysis >95%). The residue was desalted by HPLC on a reverse phase cartridge to yield the desired oligomeric compound.

| SEQ ID NO./ ISIS NO. | Composition (5' to 3') | Gap Chemistry (motif) |
|---|---|---|
| 05/460209 | T$_e$A$_k$A$_k$A$_d$T$_d$T$_d$G$_d$T$_d$$^m$C$_d$A$_d$T$_d$$^m$C$_d$A$_k$$^m$C$_k$$^m$C$_e$ | Positive control (3/9/3) |
| 05/556848 | T$_e$A$_k$A$_k$A$_z$T$_d$T$_d$G$_d$T$_d$$^m$C$_d$A$_d$T$_d$$^m$C$_d$A$_k$$^m$C$_k$$^m$C$_e$ | Single 5'-(R)-Me (3/9/3) |

Each internucleoside linkage is a phosphorothioate (P=S). Each nucleoside followed by a subscript "d" is a β-D-2'-deoxyribonucleoside. Each nucleoside followed by a subscript "e" indicates a 2'-O-methoxyethyl (MOE) modified nucleoside. Each nucleoside followed by a subscript "k" indicates a bicyclic nucleoside having a 4'-CH((S)—CH$_3$)—O-2' bridge also referred to as a (S)-cEt modified nucleoside. Each nucleoside followed by a subscript "z" indicates a 5'-(R)-Me DNA. Each "$^m$C" is a 5-methyl cytosine modified nucleoside. Nucleosides followed by subscripts "e", "k", or "z" are further illustrated below.

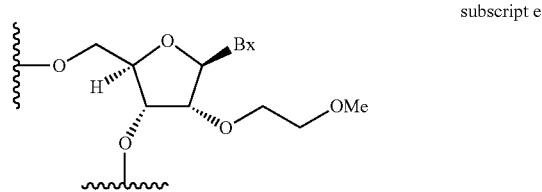

subscript e

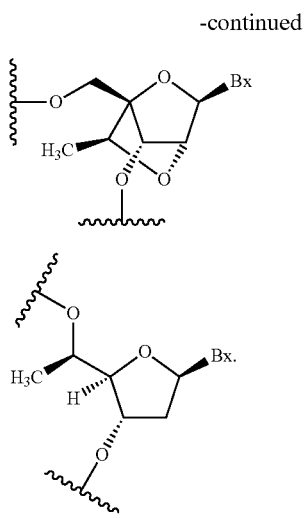

subscript k subscript z

Example 22

Modified Oligonucleotides Comprising 5'-(R)-Me DNA(s) Targeting Human C-Reactive Protein (hCRP)—In Vitro Study A series of modified oligonucleotides were designed based on ISIS 353512, wherein the central gap region contains fourteen β-D-2'-deoxyribonucleosides. These modified oligonucleotides were designed by replacement of two or three β-D-2'-deoxyribonucleosides in the 14 nucleoside gap region with 5'-(R)-Me DNAs. The thermal stability ($T_m$) and potency of these modified oligonucleotides targeting hCRP was evaluated.

Thermal Stability Assay

The modified oligonucleotides were evaluated in thermal stability ($T_m$) assay. The $T_m$'s were measured using the method described herein. A Cary 100 Bio spectrophotometer with the Cary Win UV Thermal program was used to measure absorbance vs. temperature. For the $T_m$ experiments, oligonucleotides were prepared at a concentration of 8 μM in a buffer of 100 mM Na+, 10 mM phosphate, 0.1 mM EDTA, pH 7. Concentration of the oligonucleotides were determined at 85° C. The oligonucleotide concentration was 4 μM with mixing of equal volumes of test oligonucleotide and complimentary RNA strand. Oligonucleotides were hybridized with the complimentary RNA strand by heating the duplex to 90° C. for 5 minutes followed by cooling to room temperature. Using the spectrophotometer, $T_m$ measurements were taken by heating the duplex solution at a rate of 0.5 C/min in cuvette starting @ 15° C. and heating to 85° C. $T_m$ values were determined using Vant Hoff calculations ($A_{260}$ vs temperature curve) using non self-complementary sequences where the minimum absorbance which relates to the duplex and the maximum absorbance which relates to the non-duplex single strand are manually integrated into the program. The results are presented below.

Cell Culture and Transfection

Hep3B cells were plated at a density of 40,000 cells per well and transfected using electroporation with 0.009 μM, 0.027 μM, 0.082 μM, 0.25 μM, 0.74 μM, 2.2 μM, 6.7 μM and 20 μM concentrations of the antisense oligonucleotides. After a treatment period of approximately 16 hours, RNA was isolated from the cells and hCRP mRNA levels were measured by quantitative real-time PCR. Human CRP primer probe set RTS1887 was used to measure mRNA levels. hCRP mRNA levels were adjusted according to total RNA content, as measured by RIBOGREEN®.

Analysis of $IC_{50}$'s

The half maximal inhibitory concentration ($IC_{50}$) of each oligonucleotide was calculated by plotting the concentrations of oligonucleotides used versus the percent inhibition of hCRP mRNA expression achieved at each concentration, and noting the concentration of oligonucleotide at which 50% inhibition of hCRP mRNA expression was achieved compared to the control. The results are presented below.

The 3-14-3 MOE gapmer, ISIS 353512 was included in the study as a control oligonucleotide against which the $T_m$ and potency of the modified oligonucleotides targeting hCRP is compared.

| SEQ ID NO./ ISIS NO. | Composition (5' to 3') |
|---|---|
| 06/353512 | $T_e{}^mC_e{}^mC_e{}^mC_dA_dT_dT_dT_d{}^mC_dA_dG_dG_dA_dG_dA_d{}^mC_d{}^mC_dT_eG_eG_e$ |
| 06/546127 | $T_e{}^mC_e{}^mC_e{}^mC_dA_dT_dT_dT_d{}^mC_{do}\underline{A_{zo}G_z}G_dA_dG_dA_d{}^mC_d{}^mC_dT_eG_eG_e$ |
| 06/544810 | $T_e{}^mC_e{}^mC_e{}^mC_dA_dT_dT_dT_d{}^mC_dA_dG_dG_dA_dG_dA_{do}\underline{{}^mC_{zo}{}^mC_z}T_eG_eG_e$ |
| 06/544806 | $T_e{}^mC_e{}^mC_{eo}\underline{{}^mC_{zo}A_{zo}T_z}T_dT_d{}^mC_dA_dG_dG_dA_dG_dA_d{}^mC_d{}^mC_dT_eG_eG_e$ |
| 06/544807 | $T_e{}^mC_e{}^mC_e{}^mC_dA_dT_{do}\underline{T_{zo}T_{zo}{}^mC_z}A_dG_dG_dA_dG_dA_d{}^mC_d{}^mC_dT_eG_eG_e$ |
| 06/544809 | $T_e{}^mC_e{}^mC_e{}^mC_dA_dT_dT_dT_d{}^mC_dA_dG_dG_d{}_{do}\underline{A_{zo}G_{zo}A_z}{}^mC_d{}^mC_dT_eG_eG_e$ |
| 06/330012 | $T_e{}^mC_e{}^mC_e{}^mC_eA_eT_dT_dT_d{}^mC_dA_dG_dG_dA_dG_dA_d{}^mC_e{}^mC_eT_eG_eG_e$ |

Each internucleoside linkage is a phosphorothioate (P=S) except for nucleosides followed by a subscript "o" which are phosphodiester internucleoside linkages (P=O). Each nucleoside followed by a subscript "d" is a β-D-2'-deoxyribonucleoside. Each nucleoside followed by a subscript "e" indicates a 2'-O-methoxyethyl (MOE) modified nucleoside. Each nucleoside followed by a subscript "z" indicates a 5'-(R)-Me DNA. Each "$^mC$" is a 5-methyl cytosine modified nucleoside. Nucleosides followed by subscripts "e" or "z" are further illustrated below. Underlined nucleosides indicate a region comprising 5'-(R)-Me DNA modification.

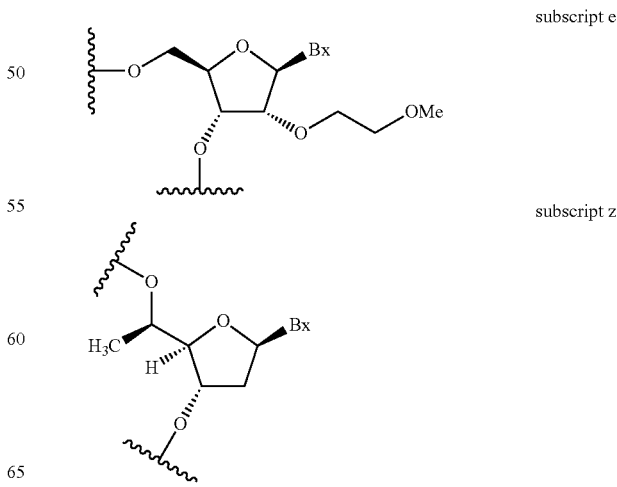

subscript e subscript z

| SEQ ID NO./ ISIS NO. | Tm (° C.) | IC$_{50}$ (μM) | | Gap Chemistry (motif) |
|---|---|---|---|---|
| 06/353512 | 66.7 | 1.1 | | Positive control (3/14/3) |
| 06/546127 | 65.9 | 2.5 | (pos 10, 11) | Two 5'-(R)-Me nts two PO linkages (3/14/3) |
| 06/544810 | 64.3 | 2.4 | (pos 15, 16) | Two 5'-(R)-Me nts two PO linkages (3/14/3) |
| 06/544806 | 62.8 | 2.8 | (pos 4, 5, 6) | Three 5'-(R)-Me nts three PO linkages (3/14/3) |
| 06/544807 | 65.1 | 2.7 | (pos 7, 8, 9) | Three 5'-(R)-Me nts three PO linkages (3/14/3) |
| 06/544809 | 64.2 | 5.0 | (pos 13, 14, 15) | Three 5'-(R)-Me nts three PO linkages (3/14/3) |
| 06/330012 | 71.7 | 0.6 | | Positive control/ different motif (5/10/5). |

Example 23

Human Peripheral Blood Mononuclear Cells (hPBMC) Assay Protocol—In Vitro

The hPBMC assay was performed using BD Vautainer CPT tube method. A sample of whole blood from volunteered donors with informed consent at US HealthWorks clinic (Faraday & El Camino Real, Carlsbad) was obtained and collected in 4-15 BD Vacutainer CPT 8 ml tubes (VWR Cat.#BD362753). The approximate starting total whole blood volume in the CPT tubes for each donor was recorded using the PBMC assay data sheet.

The blood sample was remixed immediately prior to centrifugation by gently inverting tubes 8-10 times. CPT tubes were centrifuged at rt (18-25° C.) in a horizontal (swing-out) rotor for 30 min. at 1500-1800 RCF with brake off (2700 RPM Beckman Allegra 6R). The cells were retrieved from the buffy coat interface (between Ficoll and polymer gel layers); transferred to a sterile 50 ml conical tube and pooled up to 5 CPT tubes/50 ml conical tube/donor. The cells were then washed twice with PBS (Ca$^{++}$, Mg$^{++}$ free; GIBCO). The tubes were topped up to 50 ml and mixed by inverting several times. The sample was then centrifuged at 330×g for 15 minutes at rt (1215 RPM in Beckman Allegra 6R) and aspirated as much supernatant as possible without disturbing pellet. The cell pellet was dislodged by gently swirling tube and resuspended cells in RPMI+10% FBS+pen/strep (~1 ml/10 ml starting whole blood volume). A 60 μl sample was pipette into a sample vial (Beckman Coulter) with 600 μl VersaLyse reagent (Beckman Coulter Cat#A09777) and was gently vortexed for 10-15 sec. The sample was allowed to incubate for 10 min. at rt and being mixed again before counting. The cell suspension was counted on Vicell XR cell viability analyzer (Beckman Coulter) using PBMC cell type (dilution factor of 1:11 was stored with other parameters). The live cell/ml and viability were recorded. The cell suspension was diluted to 1×10$^7$ live PBMC/ml in RPMI+10% FBS+pen/strep.

The cells were plated at 5×10$^5$ in 50 μl/well of 96-well tissue culture plate (Falcon Microtest). 50 μl/well of 2× concentration oligos/controls diluted in RPMI+10% FBS+ pen/strep. was added according to experiment template (100 μl/well total). Plates were placed on the shaker and allowed to mix for approx. 1 min. After being incubated for 24 hrs at 37° C.; 5% CO$_2$, the plates were centrifuged at 400×g for 10 minutes before removing the supernatant for MSD cytokine assay (i.e. human IL-6, IL-10, IL-8 and MCP-1).

Example 24

Evaluation of the Proinflammatory Effects in hPBMC Assay for 5'-(R)-Me DNA Containing Modified Oligonucleotides—In Vitro Study The modified oligonucleotides targeting hCRP from Example 22 were tested and evaluated for the proinflammatory response in hPBMC assay using methods described previously in Example 23. The hPBMCs were isolated from fresh, volunteered donors and were treated with modified oligonucleotides at 0, 0.0128, 0.064, 0.32, 1.6, 8, 40 and 200 μM concentrations using the hPBMC assay protocol described herein. After a 24 hr treatment, the cytokine levels were measured.

The levels of IL-6 were used as the primary readout and compared to the positive control, ISIS 353512 and the negative control, ISIS 104838. The results are presented below.

ISIS 104838 designated herein as SEQ ID NO: 07, is a 5-10-5 MOE gapmer with the following sequence, $G_e{}^mC_eT_e G_eA_eT_dT_dA_dG_dA_dG_dA_dG_dA_dG_dG_eT_e{}^mC_e{}^mC_e{}^mC_e$. Each internucleoside linkage is a phosphorothioate (P=S). Each nucleoside followed by a subscript "d" is a β-D-2'-deoxyribonucleoside. Each "$^mC$" is a 5-methyl cytosine modified nucleoside and each nucleoside followed by a subscript "e" is a 2'-O-methoxyethyl (MOE) modified nucleoside.

| SEQ ID NO./ ISIS NO. | Conc. (μM) | IL-6 (pg/mL) | Gap Chemistry (motif) |
|---|---|---|---|
| 06/353512 | 0 | 26.9 | Positive control (3/14/3) |
| | 0.0128 | 10.6 | |
| | 0.064 | 73.3 | |
| | 0.32 | 219.8 | |
| | 1.6 | 200.1 | |
| | 8 | 287.8 | |
| | 40 | 376.9 | |
| | 200 | 181.5 | |
| 06/546127 (pos 10, 11) | 0 | 11.5 | Two 5'-(R)-Me nts two PO linkages (3/14/3) |
| | 0.0128 | 15.1 | |
| | 0.064 | 19.0 | |
| | 0.32 | 37.3 | |
| | 1.6 | 67.5 | |
| | 8 | 86.3 | |
| | 40 | 111.2 | |
| | 200 | 83.1 | |
| 06/544810 (pos 15, 16) | 0 | 11.5 | Two 5'-(R)-Me nts two PO linkages (3/14/3) |
| | 0.0128 | 13.9 | |
| | 0.064 | 15.1 | |
| | 0.32 | 24.9 | |
| | 1.6 | 34.0 | |
| | 8 | 66.2 | |
| | 40 | 96.8 | |
| | 200 | 76.5 | |
| 06/544806 (pos 4, 5, 6) | 0 | 11.3 | Three 5'-(R)-Me nts three PO linkage (3/14/3) |
| | 0.0128 | 10.8 | |
| | 0.064 | 25.8 | |
| | 0.32 | 15.6 | |
| | 1.6 | 25.4 | |
| | 8 | 52.3 | |
| | 40 | 69.3 | |
| | 200 | 341.7 | |
| 06/544807 (pos 7, 8, 9) | 0 | 13.3 | Three 5'-(R)-Me nts three PO linkages (3/14/3) |
| | 0.0128 | 13.7 | |
| | 0.064 | 18.4 | |
| | 0.32 | 53.3 | |
| | 1.6 | 18.4 | |
| | 8 | 164.9 | |
| | 40 | 202.7 | |
| | 200 | 606.5 | |

| SEQ ID NO./ ISIS NO. | Conc. (μM) | IL-6 (pg/mL) | Gap Chemistry (motif) |
|---|---|---|---|
| 06/544809 | 0 | 10.8 | Three 5'-(R)-Me nts |
| (pos 13, 14, 15) | 0.0128 | 13.3 | three PO linkages (3/14/3) |
|  | 0.064 | 14.3 |  |
|  | 0.32 | 34.8 |  |
|  | 1.6 | 62.3 |  |
|  | 8 | 100.9 |  |
|  | 40 | 213.1 |  |
|  | 200 | 225.0 |  |
| 06/330012 | 0 | 10.9 | Positive control/ |
|  | 0.0128 | 12.9 | different motif (5/10/5) |
|  | 0.064 | 10.8 |  |
|  | 0.32 | 25.3 |  |
|  | 1.6 | 44.2 |  |
|  | 8 | 87.5 |  |
|  | 40 | 80.2 |  |
|  | 200 | 82.3 |  |
| 07/104838 | 0 | 9.3 | Negative control/ |
|  | 0.0128 | 10.4 | different motif (5/10/5) |
|  | 0.064 | 17.6 |  |
|  | 0.32 | 30.1 |  |
|  | 1.6 | 53.9 |  |
|  | 8 | 124.8 |  |
|  | 40 | 94.5 |  |
|  | 200 | 89.3. |  |

Example 25

Single Nucleotide Polymorphisms (SNPs) in the Huntingtin (HTT) Gene Sequence

SNP positions (identified by Hayden et al, WO/2009/135322) associated with the HTT gene were mapped to the HTT genomic sequence, designated herein as SEQ ID NO: 08 (NT_006081.18 truncated from nucleotides 1566000 to 1768000). The chart below provides SNP positions associated with the HTT gene and a reference SNP ID number from the Entrez SNP database at the National Center for Biotechnology Information (NCBI, http://www.ncbi.nlm.nih.gov/sites/-entrez?db=snp), incorporated herein by reference. The chart below furnishes further details on each SNP. The 'Reference SNP ID number' or 'RS number' is the number designated to each SNP from the Entrez SNP database at NCBI, incorporated herein by reference. 'SNP position' refers to the nucleotide position of the SNP on SEQ ID NO: 08. 'Polymorphism' indicates the nucleotide variants at that SNP position. 'Major allele' indicates the nucleotide associated with the major allele, or the nucleotide present in a statistically significant proportion of individuals in the human population. 'Minor allele' indicates the nucleotide associated with the minor allele, or the nucleotide present in a relatively small proportion of individuals in the human population.

Single Nuclear Polymorphisms (SNPs) and their Positions on SEQ ID NO: 08

| RS No. | SNP position | Polymorphism | Major allele | Minor allele |
|---|---|---|---|---|
| rs2857936 | 1963 | C/T | C | T |
| rs12506200 | 3707 | A/G | G | A |
| rs762855 | 14449 | A/G | G | A |
| rs3856973 | 19826 | G/A | G | A |
| rs2285086 | 28912 | G/A | A | G |
| rs7659144 | 37974 | C/G | C | G |
| rs16843804 | 44043 | C/T | C | T |
| rs2024115 | 44221 | G/A | A | G |
| rs10015979 | 49095 | A/G | A | G |
| rs7691627 | 51063 | A/G | G | A |
| rs2798235 | 54485 | G/A | G | A |
| rs4690072 | 62160 | G/T | T | G |
| rs6446723 | 66466 | C/T | T | C |
| rs363081 | 73280 | G/A | G | A |
| rs363080 | 73564 | T/C | C | T |
| rs363075 | 77327 | G/A | G | A |
| rs363064 | 81063 | T/C | C | T |
| rs3025849 | 83420 | A/G | A | G |
| rs6855981 | 87929 | A/G | G | A |
| rs363102 | 88669 | G/A | A | G |
| rs11731237 | 91466 | C/T | C | T |
| rs4690073 | 99803 | A/G | G | A |
| rs363144 | 100948 | T/G | T | G |
| rs3025838 | 101099 | C/T | C | T |
| rs34315806 | 101687 | A/G | G | A |
| rs363099 | 101709 | T/C | C | T |
| rs363096 | 119674 | T/C | T | C |
| rs2298967 | 125400 | C/T | T | C |
| rs2298969 | 125897 | A/G | G | A |
| rs6844859 | 130139 | C/T | T | C |
| rs363092 | 135682 | C/A | C | A |
| rs7685686 | 146795 | A/G | A | G |
| rs363088 | 149983 | A/T | A | T |
| rs362331 | 155488 | C/T | T | C |
| rs916171 | 156468 | G/C | C | G |
| rs362322 | 161018 | A/G | A | G |
| rs362275 | 164255 | T/C | C | T |
| rs362273 | 167080 | A/G | A | G |
| rs2276881 | 171314 | G/A | G | A |
| rs3121419 | 171910 | T/C | C | T |
| rs362272 | 174633 | G/A | G | A |
| rs362271 | 175171 | G/A | G | A |
| rs3775061 | 178407 | C/T | C | T |
| rs362310 | 179429 | A/G | G | A |
| rs362307 | 181498 | T/C | C | T |
| rs362306 | 181753 | G/A | G | A |
| rs362303 | 181960 | T/C | C | T |
| rs362296 | 186660 | C/A | C | A |
| rs1006798 | 198026 | A/G | A | G. |

Example 26

Modified Oligonucleotides Targeting Huntingtin (HTT) Single Nucleotide Polymorphism (SNP)—In Vitro Study A series of modified oligonucleotides was designed based on a parent gapmer, ISIS 460209, wherein the central gap region contains nine β-D-2'-deoxyribonucleosides. The modified oligonucleotides were designed by introducing a 5'-(R)-Me DNA modification within the central gap region. The 5'-(R)-Me DNA containing oligonucleotides were tested for their ability to selectively inhibit mutant (mut) HTT mRNA expression levels targeting rs7685686 while leaving the expression of the wild-type (wt) intact. The potency and selectivity of the modified oligonucleotides were evaluated and compared to ISIS 460209.

The position on the oligonucleotides opposite to the SNP position, as counted from the 5'-terminus is position 8.

Cell Culture and Transfection

The modified oligonucleotides were tested in vitro. Heterozygous fibroblast GM04022 cell line was used Cultured GM04022 cells at a density of 25,000 cells per well were transfected using electroporation with a single dose at 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT- PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented below.

Analysis of $IC_{50}$'s and Selectivity

The half maximal inhibitory concentration ($IC_{50}$) of each oligonucleotide is presented below and was calculated by plotting the concentrations of oligonucleotides used versus the percent inhibition of HTT mRNA expression achieved at each concentration, and noting the concentration of oligonucleotide at which 50% inhibition of HTT mRNA expression was achieved compared to the control. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity as expressed in "fold" was calculated by dividing the $IC_{50}$ for inhibition of the wild-type HTT versus the $IC_{50}$ for inhibiting expression of the mutant HTT mRNA and the results are presented below.

| SEQ ID NO./ ISIS NO. | Composition (5' to 3') |
| --- | --- |
| 05/460209 | $T_eA_kA_kA_dT_dT_dG_dT_d{}^mC_dA_dT_d{}^mC_dA_k{}^mC_k{}^mC_e$ |
| 05/556848 | $T_eA_kA_kA_zT_dT_dG_dT_d{}^mC_dA_dT_a{}^mC_dA_k{}^mC_k{}^mC_e$ |
| 05/556849 | $T_eA_kA_kA_dT_zT_dG_dT_d{}^mC_dA_dT_d{}^mC_dA_k{}^mC_k{}^mC_e$ |
| 05/556850 | $T_eA_kA_kA_dT_dT_zG_dT_d{}^mC_dA_dT_d{}^mC_dA_k{}^mC_k{}^mC_e$ |

Each internucleoside linkage is a phosphorothioate. Each nucleoside followed by a subscript "d" is a β-D-2'-deoxyribonucleoside. Each nucleoside followed by a subscript "e" indicates a 2'-O-methoxyethyl (MOE) modified nucleoside. Each nucleoside followed by a subscript "k" indicates a bicyclic nucleoside having a 4'-CH((S)—CH₃)—O-2' bridge also referred to as a (S)-cEt modified nucleoside. Each nucleoside followed by a subscript "z" indicates a 5'-(R)-Me DNA. Each "${}^mC$" is a 5-methyl cytosine modified nucleoside. Nucleosides followed by subscripts "e", "k", or "z" are further illustrated below.

subscript e
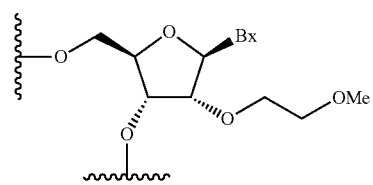

subscript k
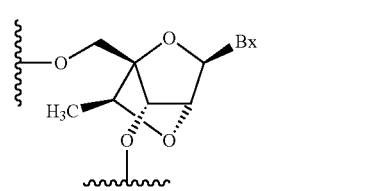

subscript z
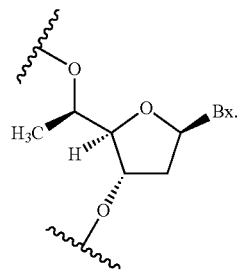

| SEQ ID NO./ ISIS NO. | $IC_{50}$ mut (μM) | $IC_{50}$ wt (μM) | Fold Selectivity (mut vs. wt) | Gap Chemistry (motif) |
| --- | --- | --- | --- | --- |
| 05/460209 | 0.30 | 0.99 | 3.3 | Positive control (3/9/3) |
| 05/556848 | 0.15 | 0.6 | 4.0 (pos 4) | Single 5'-(R)-Me nt (3/9/3) |
| 05/556849 | 0.16 | 0.46 | 2.9 (pos 5) | Single 5'-(R)-Me nt (3/9/3) |
| 05/556850 | 0.33 | 0.96 | 2.9 (pos 6) | Single 5'-(R)-Me nt (3/9/3). |

Example 27

Modified Oligonucleotides Targeting Huntingtin (HTT) Single Nucleotide Polymorphism (SNP), In Vitro Assay An additional modified oligonucleotide was designed based on a parent gapmer, ISIS 460209 wherein the central gap region contains nine β-D-2'-deoxyribonucleosides. The modified oligonucleotide was designed by introducing a 5'-(R)-Me DNA modification at the SNP site within the central gap region. The 5'-(R)-Me DNA containing oligonucleotide was tested for its ability to selectively inhibit mutant (mut) HTT mRNA expression levels targeting rs7685686 while leaving the expression of the wild-type (wt) intact. The potency and selectivity along with the thermal stability ($T_m$) of the modified oligonucleotides were evaluated and compared to ISIS 460209. The position on the oligonucleotide opposite to the SNP position, as counted from the 5'-terminus is position 8.

Heterozygous fibroblast GM04022 cell line was used Cultured GM04022 cells at a density of 25,000 cells per well were transfected using electroporation with a single dose at 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN. The results below are presented as percent of HTT mRNA expression, relative to untreated control levels and are denoted as "% UTC". Selectivity as expressed in "fold" was evaluated and measured by dividing the percent of wild-type HTT mRNA levels vs. the percent of mutant HTT mRNA levels. The $T_m$ was also measured using the method described in Example 22. The results are presented below.

| SEQ ID NO./ ISIS NO. | Composition (5' to 3') |
|---|---|
| 05/460209 | $T_eA_kA_kA_dT_dT_dG_dT_d{}^mC_dA_dT_d{}^mC_dA_k{}^mC_k{}^mC_e$ |
| 05/539558 | $T_eA_kA_kA_dT_dT_dG_dT_z{}^mC_dA_dT_d{}^mC_dA_k{}^mC_k{}^mC_e$ |

Each internucleoside linkage is a phosphorothioate. Each nucleoside followed by a subscript "d" is a β-D-2'-deoxyribonucleoside. Each nucleoside followed by a subscript "e" indicates a 2'-O-methoxyethyl (MOE) modified nucleoside. Each nucleoside followed by a subscript "k" indicates a bicyclic nucleoside having a 4'-CH((S)—CH$_3$)—O-2' bridge also referred to as a (S)-cEt modified nucleoside. Each nucleoside followed by a subscript "z" indicates a 5'-(R)-Me DNA. Each "$^m$C" is a 5-methyl cytosine modified nucleoside. Nucleosides followed by subscripts "e", "k", or "z" are further illustrated below.

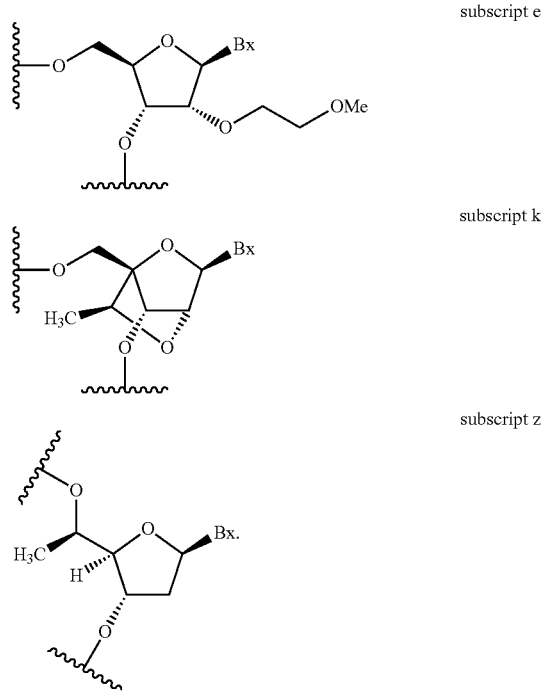

subscript e subscript k subscript z

| SEQ ID NO./ ISIS NO. | Tm mut (° C.) | Tm wt (° C.) | Gap Chemistry (motif) |
|---|---|---|---|
| 05/460209 | 53.7 | 52.2 | Positive control (3/9/3) |
| 05/539558 | 51.2 | 49.7 (pos 8) | Single 5'-(R)-Me nt (3/9/3) |

| SEQ ID NO./ ISIS NO. | % UTC mutant | % UTC wt | Fold Selectivity (mut vs. wt) | Gap Chemistry (motif) |
|---|---|---|---|---|
| 05/460209 | 23 | 57 | 2.4 | Positive control (3/9/3) |
| 05/539558 | 25 | 83 (pos 8) | 3.3 | Single 5'-(R)-Me nt (3/9/3). |

Example 28

Modified Oligonucleotides Comprising 5'-(R)— or 5'-(S)-Me DNA Modification Targeting HTT SNP—In Vitro Study A series of modified oligonucleotides was designed based on a parent gapmer, ISIS 460209, wherein the central gap region contains nine β-D-2'-deoxyribonucleosides. The modified oligonucleotides were designed by introducing 5'-(S)— or 5'-(R)-Me DNA modification slightly upstream or downstream (i.e. "microwalk") within the central gap region. The gapmers were created with a 3-9-3 motif and were tested for their ability to selectively inhibit mutant (mut) HTT mRNA expression. The potency and selectivity of the modified oligonucleotides were evaluated and compared to ISIS 460209.

The position on the oligonucleotides opposite to the SNP position, as counted from the 5'-terminus is position 8.

The modified oligonucleotides were tested in vitro. Heterozygous fibroblast GM04022 cell line was used Cultured GM04022 cells at a density of 25,000 cells per well were transfected using electroporation with 0.1, 0.4, 1.1, 3.3 and 10 μM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented below.

The IC$_{50}$s and selectivities as expressed in "fold" were measured and calculated using methods described previously in Example 26. The results are presented below.

| SEQ ID NO./ ISIS NO. | Composition (5' to 3') |
|---|---|
| 05/460209 | $T_eA_kA_kA_dT_dT_dG_dT_d{}^mC_dA_dT_d{}^mC_dA_k{}^mC_k{}^mC_e$ |
| 05/589429 | $T_eA_kA_kA_dT_vT_dG_dT_d{}^mC_dA_dT_d{}^mC_dA_k{}^mC_k{}^mC_e$ |
| 05/589430 | $T_eA_kA_kA_dT_dT_vG_dT_d{}^mC_dA_dT_d{}^mC_dA_k{}^mC_k{}^mC_e$ |
| 05/589431 | $T_eA_kA_kA_dT_dT_dG_dT_v{}^mC_dA_dT_d{}^mC_dA_k{}^mC_k{}^mC_e$ |
| 05/589432 | $T_eA_kA_kA_dT_dT_dG_dT_d{}^mC_dA_dT_v{}^mC_dA_k{}^mC_k{}^mC_e$ |
| 05/594588 | $T_eA_kA_kA_dT_vT_vG_dT_d{}^mC_dA_dT_d{}^mC_dA_k{}^mC_k{}^mC_e$ |
| 05/556848 | $T_eA_kA_kA_zT_dT_dG_dT_d{}^mC_dA_dT_d{}^mC_dA_k{}^mC_k{}^mC_e$ |
| 05/556849 | $T_eA_kA_kA_dT_zT_dG_dT_d{}^mC_dA_dT_d{}^mC_dA_k{}^mC_k{}^mC_e$ |
| 05/556850 | $T_eA_kA_kA_dT_dT_zG_dT_d{}^mC_dA_dT_d{}^mC_dA_k{}^mC_k{}^mC_e$ |
| 05/539558 | $T_eA_kA_kA_dT_dT_dG_dT_z{}^mC_dA_dT_d{}^mC_dA_k{}^mC_k{}^mC_e$ |
| 05/594160 | $T_eA_kA_kA_dT_dT_dG_dT_d{}^mC_zA_dT_d{}^mC_dA_k{}^mC_k{}^mC_e$ |
| 05/594161 | $T_eA_kA_kA_dT_dT_dG_dT_d{}^mC_dA_zT_d{}^mC_dA_k{}^mC_k{}^mC_e$ |
| 05/589433 | $T_eA_kA_kA_dT_dT_dG_dT_d{}^mC_dA_dT_z{}^mC_dA_k{}^mC_k{}^mC_e$ |

| SEQ ID NO./ ISIS NO. | Composition (5' to 3') |
|---|---|
| 05/594162 | $T_eA_kA_kA_dT_dT_dG_dT_d{}^mC_dA_dT_d{}^mC_zA_k{}^mC_k{}^mC_e$ |
| 05/594589 | $T_eA_kA_kA_dT_zT_zG_dT_d{}^mC_dA_dT_d{}^mC_dA_k{}^mC_k{}^mC_e$ |

Each internucleoside linkage is a phosphorothioate. Each nucleoside followed by a subscript "d" is a β-D-2'-deoxyribonucleoside. Each nucleoside followed by a subscript "e" indicates a 2'-O-methoxyethyl (MOE) modified nucleoside. Each nucleoside followed by a subscript "k" indicates a bicyclic nucleoside having a 4'-CH((S)—CH₃)—O-2' bridge also referred to as a (S)-cEt modified nucleoside. Each nucleoside followed by a subscript "v" indicates a 5'-(S)-Me DNA. Each nucleoside followed by a subscript "z" indicates a 5'-(R)-Me DNA. Each "$^mC$" is a 5-methyl cytosine modified nucleoside. Nucleosides followed by subscripts "e", "k", "v" or "z" are further illustrated below.

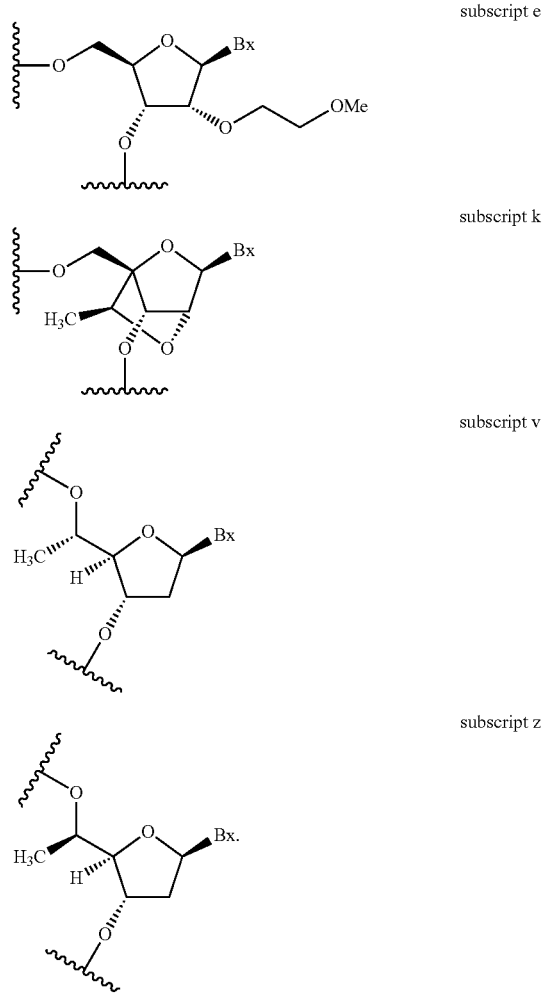

| SEQ ID NO./ ISIS NO. | IC$_{50}$ mut (μM) | IC$_{50}$ wt (μM) | Fold Selectivity (mut vs. wt) | | Gap Chemistry (motif) (3/9/3) |
|---|---|---|---|---|---|
| 05/460209 | 1.2 | 1.4 | 1.2 | | Positive control |
| 05/589429 | 0.22 | 3.3 | 15 | (pos 5) | Single 5'-(S)-Me nt |
| 05/589430 | 0.22 | >10 | >45.5 | (pos 6) | Single 5'-(S)-Me nt |
| 05/589431 | 0.16 | 1.9 | 11.9 | (pos 8) | Single 5'-(S)-Me nt |
| 05/589432 | 0.23 | >10 | >43.5 | (pos 11) | Single 5'-(S)-Me nt |
| 05/594588 | 0.81 | >10 | >12.3 | (pos 5, 6) | Two 5'-(S)-Me nts |
| 05/556848 | 0.16 | 1.8 | 11.3 | (pos 4) | Single 5'-(R)-Me nt |
| 05/556849 | 0.14 | 1.1 | 7.9 | (pos 5) | Single 5'-(R)-Me nt |
| 05/556850 | 0.22 | 1.7 | 7.7 | (pos 6) | Single 5'-(R)-Me nt |
| 05/539558 | 0.38 | 3.8 | 10 | (pos 8) | Single 5'-(R)-Me nt |
| 05/594160 | 0.28 | 3.3 | 11.8 | (pos 9) | Single 5'-(R)-Me nt |
| 05/594161 | 0.28 | >10 | >35.7 | (pos 10) | Single 5'-(R)-Me nt |
| 05/589433 | 0.27 | 4.4 | 16.3 | (pos 11) | Single 5'-(R)-Me nt |
| 05/594162 | 0.27 | 3.5 | 13.0 | (pos 12) | Single 5'-(R)-Me nt |
| 05/594589 | 0.48 | 4.4 | 9.2 | (pos 5, 6) | Two 5'-(R)-Me nts. |

Example 29

Inhibition of HTT mRNA Levels Targeting SNP by Modified Oligonucleotides, In Vitro Study Additional modified oligonucleotides were designed in a similar manner as the antisense oligonucleotides described in Example 28. Various chemical modifications were introduced slightly upstream or downstream (i.e. "microwalk") within the central gap region. The gapmers were created with a 3-9-3 motif and were tested for their ability to selectively inhibit mutant (mut) HTT mRNA expression. The position on the oligonucleotides opposite to the SNP position, as counted from the 5'-terminus is position 8. The potency and selectivity of the modified oligonucleotides were evaluated and compared to ISIS 460209.

The modified oligonucleotides were tested using heterozygous fibroblast GM04022 cell line. The transfection method and analysis of HTT mRNA levels adjusted according to total RNA content, as measured by RIBOGREEN were performed in the same manner as described in Example 28. The IC$_{50}$s and selectivities as expressed in "fold" were measured and calculated using methods described previously and the results are presented below.

| SEQ ID NO./ ISIS NO. | Composition (5' to 3') |
|---|---|
| 05/460209 | $T_eA_kA_kA_dT_dT_dG_dT_d{}^mC_dA_dT_d{}^mC_dA_k{}^mC_k{}^mC_e$ |
| 05/589414 | $T_eA_kA_kA_dT_bT_dG_dT_d{}^mC_dA_dT_d{}^mC_dA_k{}^mC_k{}^mC_e$ |
| 05/589415 | $T_eA_kA_kA_dT_dT_bG_dT_d{}^mC_dA_dT_d{}^mC_dA_k{}^mC_k{}^mC_e$ |
| 05/589416 | $T_eA_kA_kA_dT_dT_dG_dT_b{}^mC_dA_dT_d{}^mC_dA_k{}^mC_k{}^mC_e$ |
| 05/589417 | $T_eA_kA_kA_dT_dT_dG_dT_d{}^mC_dA_dT_b{}^mC_dA_k{}^mC_k{}^mC_e$ |
| 05/589418 | $T_eA_kA_kA_dT_cT_dG_dT_d{}^mC_dA_dT_d{}^mC_dA_k{}^mC_k{}^mC_e$ |
| 05/589419 | $T_eA_kA_kA_dT_dT_cG_dT_d{}^mC_dA_dT_d{}^mC_dA_k{}^mC_k{}^mC_e$ |
| 05/589420 | $T_eA_kA_kA_dT_dT_dG_dT_c{}^mC_dA_dT_d{}^mC_dA_k{}^mC_k{}^mC_e$ |
| 05/589421 | $T_eA_kA_kA_dT_dT_dG_dT_d{}^mC_dA_dT_c{}^mC_dA_k{}^mC_k{}^mC_e$ |
| 05/589422 | $T_eA_kA_kA_dT_gT_dG_dT_d{}^mC_dA_dT_d{}^mC_dA_k{}^mC_k{}^mC_e$ |
| 05/589423 | $T_eA_kA_kA_dT_dT_gG_dT_d{}^mC_dA_dT_d{}^mC_dA_k{}^mC_k{}^mC_e$ |
| 05/589424 | $T_eA_kA_kA_dT_dT_dG_dT_g{}^mC_dA_dT_d{}^mC_dA_k{}^mC_k{}^mC_e$ |
| 05/589437 | $T_eA_kA_kA_dT_dT_dG_dT_d{}^mC_dA_dT_g{}^mC_dA_k{}^mC_k{}^mC_e$ |

| SEQ ID NO./ ISIS NO. | Composition (5' to 3') |
|---|---|
| 05/589426 | $T_eA_kA_kA_dT_iT_dG_dT_d{}^mC_dA_dT_d{}^mC_dA_k{}^mC_k{}^mC_e$ |
| 05/589427 | $T_eA_kA_kA_dT_dT_iG_dT_d{}^mC_dA_dT_d{}^mC_dA_k{}^mC_k{}^mC_e$ |
| 05/589428 | $T_eA_kA_kA_dT_dT_dG_dT_i{}^mC_dA_dT_d{}^mC_dA_k{}^mC_k{}^mC_e$ |
| 05/589425 | $T_eA_kA_kA_dT_dT_dG_dT_d{}^mC_dA_dT_i{}^mC_dA_k{}^mC_k{}^mC_e$ |

Each internucleoside linkage is a phosphorothioate. Each nucleoside followed by a subscript "d" is a β-D-2'-deoxyribonucleoside. Each nucleoside followed by a subscript "e" indicates a 2'-O-methoxyethyl (MOE) modified nucleoside. Each nucleoside followed by a subscript "k" indicates a bicyclic nucleoside having a 4'-CH((S)—CH₃)—O-2' bridge also referred to as a (S)-cEt modified nucleoside. Each nucleoside followed by a subscript "b" indicates a 5'-(R)-allyl DNA. Each nucleoside followed by a subscript "c" indicates a 5'-(S)-allyl DNA. Each nucleoside followed by a subscript "g" indicates a 5'-(R)-hydroxyethyl DNA. Each nucleoside followed by a subscript "i" indicates a 5'-(S)-hydroxyethyl DNA. Each "$^mC$" is a 5-methyl cytosine modified nucleoside. Nucleosides followed by subscripts "e", "k", "b", "c", "g" or "i" are further illustrated below.

subscript e
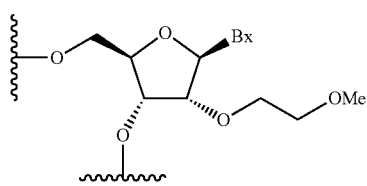

subscript k
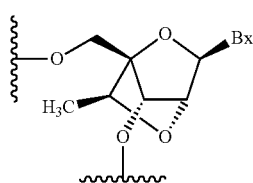

subscript b
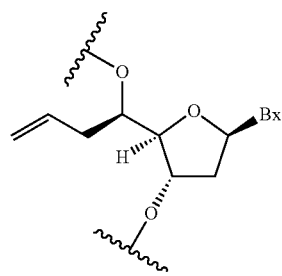

subscript c
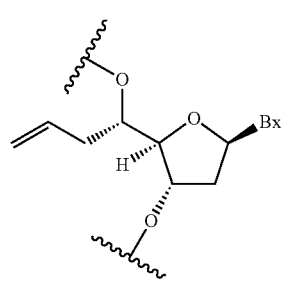

subscript g
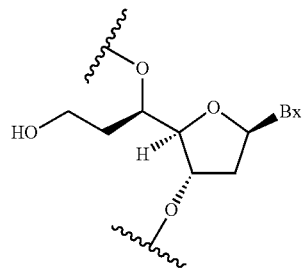

subscript i
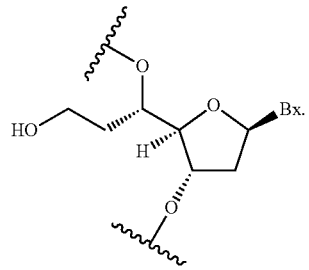

| SEQ ID NO./ ISIS NO. | IC$_{50}$ mut (μM) | IC$_{50}$ wt (μM) | Fold Selectivity (mut vs. wt) | Gap Chemistry (motif) |
|---|---|---|---|---|
| 05/460209 | 0.47 | 2.1 | 4.5 | Positive control (3/9/3) |
| 05/589414 | 1.0 | 7.6 | 7.6 (pos 5) | Single 5'-(R)-Allyl nt |
| 05/589415 | 1.4 | >10 | >7.1 (pos 6) | Single 5'-(R)-Allyl nt |
| 05/589416 | 2.7 | >10 | >3.7 (pos 8) | Single 5'-(R)-Allyl nt |
| 05/589417 | 5.4 | >10 | >1.9 (pos 11) | Single 5'-(R)-Allyl nt |
| 05/589418 | 1.2 | >10 | >8.3 (pos 5) | Single 5'-(S)-Allyl nt |
| 05/589419 | 1.1 | >10 | >9.1 (pos 6) | Single 5'-(S)-Allyl nt |
| 05/589420 | 3.2 | >10 | >3.1 (pos 8) | Single 5'-(S)-Allyl nt |
| 05/589421 | 2.0 | >10 | >5.0 (pos 11) | Single 5'-(S)-Allyl nt |
| 05/589422 | 0.73 | 3.2 | 4.4 (pos 5) | Single 5'-(R)-Hydroxyethyl nt |
| 05/589423 | 0.92 | 9.2 | 10 (pos 6) | Single 5'-(R)-Hydroxyethyl nt |
| 05/589424 | 0.21 | 4.4 | 21 (pos 8) | Single 5'-(R)-Hydroxyethyl nt |
| 05/589437 | 0.73 | >10.2 | >14 (pos 11) | Single 5'-(R)-Hydroxyethyl nt |
| 05/589426 | 0.91 | 5.1 | 5.6 (pos 5) | Single 5'-(S)-Hydroxyethyl nt |
| 05/589427 | 0.91 | >10 | >11 (pos 6) | Single 5'-(S)-Hydroxyethyl nt |
| 05/589428 | 1.1 | >11 | >10 (pos 8) | Single 5'-(S)-Hydroxyethyl nt |
| 05/589425 | 1.5 | >10.5 | >7 (pos 11) | Single 5'-(S)-Hydroxyethyl nt. |

Example 30

Modified Oligonucleotides Targeting Huntingtin (HTT) Single Nucleotide Polymorphism (SNP)

An additional gapmer is designed based on ISIS 540108 by introducing a modification at the SNP site at position 9 of the oligonucleotide, as counted from the 5' terminus (A01).

| SEQ ID NO./ ISIS NO. | Composition (5' to 3') | Gap Chemistry (motif) (5/7/5) |
|---|---|---|
| 09/540108 | $A_eT_eA_eA_kA_kT_dT_dG_dT_d{}^mC_dA_dT_d{}^mC_kA_k{}^mC_e{}^mC_eA_e$ | Positive control |
| 09/A01 | $A_eT_eA_eA_kA_kT_dT_dG_dT_z{}^mC_dA_dT_d{}^mC_kA_k{}^mC_e{}^mC_eA_e$ | Single 5'-(R)-Me nt |

Each internucleoside linkage is a phosphorothioate. Each nucleoside followed by a subscript "d" is a β-D-2'-deoxyribonucleoside. Each nucleoside followed by a subscript "e" indicates a 2'-O-methoxyethyl (MOE) modified nucleoside.

Each nucleoside followed by a subscript "k" indicates a bicyclic nucleoside having a 4'-CH((S)—CH$_3$)—O-2' bridge also referred to as a (S)-cEt modified nucleoside. Each nucleoside followed by a subscript "z" indicates a 5'-(R)-Me DNA. Each "$^m$C" is a 5-methyl cytosine modified nucleoside. Nucleosides followed by subscripts "e", "k", or "z" are further illustrated below.

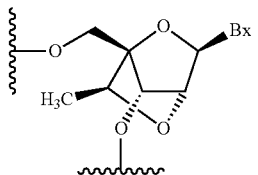

subscript k

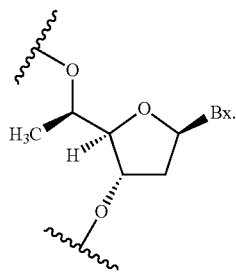

subscript z

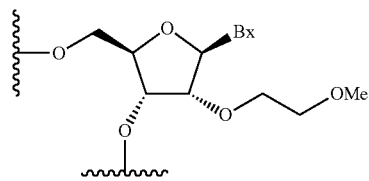

subscript e

SEQUENCE LISTING

<160> NUMBER OF SEQ ID NOS: 10

<210> SEQ ID NO 1
<211> LENGTH: 3160
<212> TYPE: DNA
<213> ORGANISM: Homo sapiens
<220> FEATURE:
<221> NAME/KEY: CDS
<222> LOCATION: (1035)..(2246)

<400> SEQUENCE: 1

```
cctcccctcg cccggcgcgg tcccgtccgc ctctcgctcg cctcccgcct ccccctcggtc      60 ttccgaggcg cccgggctcc cggcgcggcg gcggagggg cggcaggcc ggcgggcggt       120 gatgtggcag gactctttat gcgctgcggc aggatacgcg ctcggcgctg ggacgcgact     180
gcgctcagtt ctctcctctc ggaagctgca gccatgatgg aagtttgaga gttgagccgc     240
tgtgaggcga ggccgggctc aggcgaggga gatgagagac ggcggcggcc gcggcccgga    300
gcccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcggcggcgg cggcacctcc cgctcctgga gcgggggga gaagcggcgg    540 cggcggcggc cgcggcggct gcagctccag ggaggggtc tgagtcgcct gtcaccattt     600
ccagggctgg gaacgccgga gagttggtct ctcccccttct actgcctcca acacggcggc    660
ggcggcggcg gcacatccag ggacccgggc cggttttaaa cctcccgtcc gccgccgccg    720 cacccccgt ggcccgggct ccggaggccg ccggcggagg cagccgttcg gaggattatt      780
cgtcttctcc ccattccgct gccgccgctg ccaggcctct ggctgctgag gagaagcagg     840
cccagtcgct gcaaccatcc agcagccgcc gcagcagcca ttaccggct gcggtccaga      900 gccaagcggc ggcagagcga ggggcatcag ctaccgccaa gtccagagcc atttccatcc    960
tgcagaagaa gccccgccac cagcagcttc tgccatctct ctcctccttt ttcttcagcc   1020
acaggctccc agac atg aca gcc atc atc aaa gag atc gtt agc aga aac       1070
              Met Thr Ala Ile Ile Lys Glu Ile Val Ser Arg Asn
                1               5                   10 aaa agg aga tat caa gag gat gga ttc gac tta gac ttg acc tat att      1118
```

|  |  |  |  |  |  |  |  |  |  |  |  |  |
|---|---|---|---|---|---|---|---|---|---|---|---|---|
| Lys | Arg | Arg | Tyr | Gln | Glu | Asp | Gly | Phe | Asp | Leu | Asp | Leu | Thr | Tyr | Ile |
|  |  |  |  | 15 |  |  |  | 20 |  |  |  | 25 |

```
tat cca aac att att gct atg gga ttt cct gca gaa aga ctt gaa ggc     1166
Tyr Pro Asn Ile Ile Ala Met Gly Phe Pro Ala Glu Arg Leu Glu Gly
        30              35                  40 gta tac agg aac aat att gat gat gta gta agg ttt ttg gat tca aag     1214
Val Tyr Arg Asn Asn Ile Asp Asp Val Val Arg Phe Leu Asp Ser Lys
 45                  50                  55                  60 cat aaa aac cat tac aag ata tac aat ctt tgt gct gaa aga cat tat     1262
His Lys Asn His Tyr Lys Ile Tyr Asn Leu Cys Ala Glu Arg His Tyr
                 65                  70                  75 gac acc gcc aaa ttt aat tgc aga gtt gca caa tat cct ttt gaa gac     1310
Asp Thr Ala Lys Phe Asn Cys Arg Val Ala Gln Tyr Pro Phe Glu Asp
             80                  85                  90 cat aac cca cca cag cta gaa ctt atc aaa ccc ttt tgt gaa gat ctt     1358
His Asn Pro Pro Gln Leu Glu Leu Ile Lys Pro Phe Cys Glu Asp Leu
             95                 100                 105 gac caa tgg cta agt gaa gat gac aat cat gtt gca gca att cac tgt     1406
Asp Gln Trp Leu Ser Glu Asp Asp Asn His Val Ala Ala Ile His Cys
110                 115                 120 aaa gct gga aag gga cga act ggt gta atg ata tgt gca tat tta tta     1454
Lys Ala Gly Lys Gly Arg Thr Gly Val Met Ile Cys Ala Tyr Leu Leu
125                 130                 135                 140 cat cgg ggc aaa ttt tta aag gca caa gag gcc cta gat ttc tat ggg     1502
His Arg Gly Lys Phe Leu Lys Ala Gln Glu Ala Leu Asp Phe Tyr Gly
                145                 150                 155 gaa gta agg acc aga gac aaa aag gga gta act att ccc agt cag agg     1550
Glu Val Arg Thr Arg Asp Lys Lys Gly Val Thr Ile Pro Ser Gln Arg
            160                 165                 170 cgc tat gtg tat tat tat agc tac ctg tta aag aat cat ctg gat tat     1598
Arg Tyr Val Tyr Tyr Tyr Ser Tyr Leu Leu Lys Asn His Leu Asp Tyr
        175                 180                 185 aga cca gtg gca ctg ttg ttt cac aag atg atg ttt gaa act att cca     1646
Arg Pro Val Ala Leu Leu Phe His Lys Met Met Phe Glu Thr Ile Pro
190                 195                 200 atg ttc agt ggc gga act tgc aat cct cag ttt gtg gtc tgc cag cta     1694
Met Phe Ser Gly Gly Thr Cys Asn Pro Gln Phe Val Val Cys Gln Leu
205                 210                 215                 220 aag gtg aag ata tat tcc tcc aat tca gga ccc aca cga cgg gaa gac     1742
Lys Val Lys Ile Tyr Ser Ser Asn Ser Gly Pro Thr Arg Arg Glu Asp
                225                 230                 235 aag ttc atg tac ttt gag ttc cct cag ccg tta cct gtg tgt ggt gat     1790
Lys Phe Met Tyr Phe Glu Phe Pro Gln Pro Leu Pro Val Cys Gly Asp
            240                 245                 250 atc aaa gta gag ttc ttc cac aaa cag aac aag atg cta aaa aag gac     1838
Ile Lys Val Glu Phe Phe His Lys Gln Asn Lys Met Leu Lys Lys Asp
        255                 260                 265 aaa atg ttt cac ttt tgg gta aat aca ttc ttc ata cca gga cca gag     1886
Lys Met Phe His Phe Trp Val Asn Thr Phe Phe Ile Pro Gly Pro Glu
270                 275                 280 gaa acc tca gaa aaa gta gaa aat gga agt cta tgt gat caa gaa atc     1934
Glu Thr Ser Glu Lys Val Glu Asn Gly Ser Leu Cys Asp Gln Glu Ile
285                 290                 295                 300 gat agc att tgc agt ata gag cgt gca gat aat gac aag gaa tat cta     1982
Asp Ser Ile Cys Ser Ile Glu Arg Ala Asp Asn Asp Lys Glu Tyr Leu
                305                 310                 315 gta ctt act tta aca aaa aat gat ctt gac aaa gca aat aaa gac aaa     2030
Val Leu Thr Leu Thr Lys Asn Asp Leu Asp Lys Ala Asn Lys Asp Lys
            320                 325                 330
```

| | | |
|---|---|---|
| gcc aac cga tac ttt tct cca aat ttt aag gtg aag ctg tac ttc aca<br>Ala Asn Arg Tyr Phe Ser Pro Asn Phe Lys Val Lys Leu Tyr Phe Thr<br>335 340 345 | | 2078 |
| aaa aca gta gag gag ccg tca aat cca gag gct agc agt tca act tct<br>Lys Thr Val Glu Glu Pro Ser Asn Pro Glu Ala Ser Ser Ser Thr Ser<br>350 355 360 | | 2126 |
| gta aca cca gat gtt agt gac aat gaa cct gat cat tat aga tat tct<br>Val Thr Pro Asp Val Ser Asp Asn Glu Pro Asp His Tyr Arg Tyr Ser<br>365 370 375 380 | | 2174 |
| gac acc act gac tct gat cca gag aat gaa cct ttt gat gaa gat cag<br>Asp Thr Thr Asp Ser Asp Pro Glu Asn Glu Pro Phe Asp Glu Asp Gln<br>385 390 395 | | 2222 |
| cat aca caa att aca aaa gtc tga attttttttt atcaagaggg ataaaacacc<br>His Thr Gln Ile Thr Lys Val<br>400 | | 2276 |
| atgaaaataa acttgaataa actgaaaatg gaccttttt tttttaatgg caataggaca | | 2336 |
| ttgtgtcaga ttaccagtta taggaacaat tctcttttcc tgaccaatct tgttttaccc | | 2396 |
| tatacatcca cagggttttg acacttgttg tccagttgaa aaaaggttgt gtagctgtgt | | 2456 |
| catgtatata ccttttttgtg tcaaaaggac atttaaaatt caattaggat taataaagat | | 2516 |
| ggcactttcc cgttttattc cagttttata aaaagtggag acagactgat gtgtatacgt | | 2576 |
| aggaatttt tccttttgtg ttctgtcacc aactgaagtg gctaaagagc tttgtgatat | | 2636 |
| actggttcac atcctacccc tttgcacttg tggcaacaga taagtttgca gttggctaag | | 2696 |
| agaggtttcc gaaaggtttt gctaccattc taatgcatgt attcgggtta gggcaatgga | | 2756 |
| ggggaatgct cagaaaggaa ataattttat gctggactct ggaccatata ccatctccag | | 2816 |
| ctatttacac acacctttct ttagcatgct acagttatta atctggacat tcgaggaatt | | 2876 |
| ggccgctgtc actgcttgtt gtttgcgcat ttttttttaa agcatattgg tgctagaaaa | | 2936 |
| ggcagctaaa ggaagtgaat ctgtattggg gtacaggaat gaaccttctg caacatctta | | 2996 |
| agatccacaa atgaagggat ataaaataa tgtcataggt aagaaacaca gcaacaatga | | 3056 |
| cttaaccata taaatgtgga ggctatcaac aaagaatggg cttgaaacat tataaaaatt | | 3116 |
| gacaatgatt tattaaatat gttttctcaa ttgtaaaaaa aaaa | | 3160 |

<210> SEQ ID NO 2
<211> LENGTH: 26
<212> TYPE: DNA
<213> ORGANISM: Artificial sequence
<220> FEATURE:
<223> OTHER INFORMATION: Primer

<400> SEQUENCE: 2
aatggctaag tgaagatgac aatcat                                          26

<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3
tgcacatatc attacaccag ttcgt                                           25

<210> SEQ ID NO 4
<211> LENGTH: 30
<212> TYPE: DNA
<213> ORGANISM: Artificial sequence

```
<220> FEATURE:
<223> OTHER INFORMATION: Probe

<400> SEQUENCE: 4
ttgcagcaat tcactgtaaa gctggaaagg                                          30

<210> SEQ ID NO 5
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 5
taaattgtca tcacc                                                         15

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
tcccatttca ggagacctgg                                                    20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
gctgattaga gagaggtccc                                                    20

<210> SEQ ID NO 8
<211> LENGTH: 202001
<212> TYPE: DNA
<213> ORGANISM: Homo sapiens

<400> SEQUENCE: 8
gcccagcagg tgtcagcctc attttacccc gccctattc aagatgaagt tgttctggtt          60
ccaacgcctc tgacatatta gctgcatcat tttacatttc ttttttttt tccttttaa         120 atggggtctt gctctgtcac ccaggctgga gtgctgtggt atgatctcgg ctcactgcaa        180
tctccacctc cgaggttcca gcgattctct tgcctcagcc tcccgagtag ctgggactac        240
aggcacccac catcatactg gctaattttt gtgttttta gtagagatgg gtttcccca         300 tgttgcccag gctgatctca aactcctggg cttaagcaat acagccgcgt tggcctccca        360
aagtgttggg attacaagca tgagctaccc cacccagctc attttacatt tccacttgtt       420
aaactgaaaa ctggcccgag aaagcttctg tactgccatc cttgcgtcct tgcagatgaa       480
tcgtaaccta gcatagtagg taggcagact gaaaacctaa cttagcagta ggcttctgta        540
acaacagctg tgtctcagcc agttcctgca gccagacttc aaccactcac aggccgcaaa       600
ctgttcaaac tgtgttcgga gaaggcgaat tcatctggct gttaacgtgc ctcacttctg       660
ctttctgtgg ccactttccc ttttctgtcc ataaatttgc tttgaccaca cagcatccct       720
agagtctccc tgaatctgct gtgattctgg gacctgcacc atttgtgaat tgttttttt        780 ttccttgatc agctaaactc tgttcaattc aatttgttgg aagttttaa cataccaatg        840
```

```
gtgcaccaag gttccaattt ctccacttcc tcataaataa gtcattttaa atggcttttc    900
agtattccaa tatttggaag tattaatgtt tctaccaatt ttctatttt ggacattgag    960 gttgtttcat ttttttttc tttttttgag acagagtctc gctccgtcac ccaggctgga   1020
gtgcagtggc ctgatcccgg cccactgcaa cctccacctc cctcctcagc ctcctgagta   1080
gctgggatta caggtgcatg caccaccaca cccagctaat ttttgtattt ttagtagaga   1140
tggggtttca ccatgttggt caggctggtc tcaaactcct gacctcaggt ggtccacctg   1200
ccttggcctc ccaaaatgct gggattacag gcctgagcca ctgcgcctgg cctcatcttc   1260
ttgatattaa tgttgcttta acatctttgt ccctgtgttt tttgttttt ttttgagac    1320 ggagtctcat tcattctgtc acccaggctg gagttcagtg gcgtgatctc agctcactgc   1380
aacctctgtc tcctgggttc cagtgattct cctgcgtcgg tctcctgagt agctgtgttc   1440
ctgggtcttt cgatggttat ttaatacttc cctacagtaa tgccctgtgc gtacatgcta   1500
agtgtgatga atggttggc acagttaaat cttttgaaag acattgccaa gtcactcttc    1560
agaaaagtga taggaggtca tagcaatttt aagaagtcct catttctaca tttccttact   1620
aatctcggtt ggtgtctctt caatctttcc tcacactttt cttgggtttt tcctgaatca   1680
tgagtctact acatttacac attttaaagc atctttagaa acaggatctc attttgttgc   1740
ccaggctaga gtttggtggc atgattatag ctcctcatac tcctgggctc aagtgatcct   1800
tccacctctg aaaccccaaa atttgagaaa ggtctcattt aatttagaaa gtttatttg    1860 ccaaggttga gggtgcacac ctgtgatgat atacgagtta aaagaaaatt atttaggcag   1920
atactgaggg taagaaagtc ctcggtaagg ttttcttttc aatgaaaagc agccccaag    1980 cattttcttt tctaacaaag agcagcctgt aaaatcgagc tgcagacata cacaagcaag   2040
ctggaagctt gcacaggtga atgctggcag ctgtgccaat aagaaaaggc tacctggggc   2100
caggcagatc caacatggcg gctccatctt ccctttcctt gtcaaccatg tgcacagtaa   2160
ggagcaggca acatagtgtc ccccgagtag agaccaattt gcataataaa aggtgagggt   2220
agggtgggca gcttctttgc atgctatgta acattatgc ctggtccaac caatctttgg    2280
gccctgtgta aattagacac cacctcctca agcctgtcta taaaccctg tccattctgc    2340 cgcaggctgg aagacccact ggggcacccc tctctctcta taggagacag ctattcattt   2400
ttctcttcct ttcacctatt aaagctccac tcttaacccc actccgtgtg tatctatgtt   2460
cttgatttcc ttggcatgag gcaatgaacc ttgggtatta ccccagaacc ttgggtatta   2520
tgccacttca gtgacacagc ctcaggaaat cctgatgaca tgttcccaag atggtcgggg   2580
cacagcttgg ttttatacat tttagggaga catgagacgt caattcatat atgtaagaag   2640
tacattggtt ccgtccagaa aggcggggac aacttgaggc agggagagag cttctaggtc   2700
acaggtagac aaatggttgc attcttttga atctccgata agccttttcca aaggaggcaa   2760 tcagaatatg cgtctattga ctgggcgcag tggctcatgc ctgtaatgcc agcactttgg   2820
gaggcggagg tgggtggatc acctgaggtc aggagtttga gagcagcccg ccaacatgg    2880 tgaaaccctg tctctactaa aaatacaaaa aattagctgg gcgtggtggc gggcgcctgt   2940
aatcccagct actcgggagg ctgaggcagg agaatagctt gaacccagaa ggaagaggtt   3000
gcagtgagct gagatggtgc cattgcactc cagcctgggc aacaagagtg aaactccatc   3060
tcagaaaaaa aaaaaaaagg cctgggcaaa gtggctcacg cctgtaatcc cagcactttg   3120
ggaagccgag gcgggcaggt cacaaagtca ggagattgag accatcctgg ctaacatgat   3180 gaaacccat ctctactaaa aaatacaaaa aactagctgg gtgtggtggc gagcacctgt    3240
```

```
agtcccagct actcggcagg ctgaggcagg agaatggcgt gaaccgggga ggcggagctt    3300
gcagtgagcc gagatcacac cactgcactc cagcccggac gacagggcaa gactctatct    3360
caaattaaaa aaaaaaaaaa aaaaaaaaaa aagagagag agaatatgca tctatctcag     3420
tgagcagaag gatgactttg aatggaatgg gagcagttcc tagcttgaac ttccccttta    3480
gcttcagtga tttgggggct caaggtatgt tcctttcaca tacctcagcc tcccaagtag    3540
ctgggaccac aagtgcatgc caccacacgt ggctaatgtt ttatttttt tgtaggaata     3600
gggtctcact atgtgtccag gctggtctaa aacccctgag ctcaaatggt cctcccgcct    3660
cagcctcccg aaatgctggg attacaggca tgagccagca tgcccggcct agtctacatt    3720
tttataaatt gctaattcaa agttccctct ccaaaacctc atggttttcc ctgttctcat    3780
cccctgcacc ctcccttccc ctggagtact cacctggcct tggaggtctg gtgtgagccc    3840
ggacttcgat tctaggcaca gcatgtgatg agcgccccca ggtcaaacac ctcccctctg    3900
cggcctgtgc ttcaccgcct tgacagtgag aaaggtctcc cttcggctca ttctcgaagt    3960
ctcaaacttc acttctcctg tgcgctgatt ctgaattcag ccccgtcca aggtcctggc     4020
ccctttctct tctgcttggc gtgttgttca tcaccactgt gcactgctga gggtaagtgc    4080
ggttctctgg acctctgctt tatcattaga acagactctt gcggtttccc acgacattcc    4140
tttcacttct cacttggaag atgagccgtg aggaaatcct gtgttgtgtg gtatgtgggc    4200
tgtgcttctg cttgacttga gggccaagca gcattgcaag ccatggtttt aaataagaaa    4260
gaacatttct aaccttcatc ttctagtaag gaaacaagtg ggctttagag ttcttgctca    4320
ggaaagacct atgtcccagt ccaaccggac cttttactaa agagatcttc ctgatcctcc    4380
tccccaggcc aggggagggg tcctccctgg ggttggagcc tttagtaggg ggtcggagac    4440
acgacgtagc cttcatgaca ttcatagtct agttacacga tccctgtaag ggtcagttga    4500
agtaagtgct acaaaggaag ggaggtgctc agtggagagg gctctctttt atgtattata    4560
tttcttcat ggggagggat atggatcagg gatcagcaga ggtgtttcag tcccgaggga    4620
aagaaagtca gcgtggcttg ggagttggga gcagcaagac agtggctcaa gatatcttaa    4680
gactagtgga gtacaccttg catgttaaaa gccttgctca gggctgcctg gttcttgtag    4740
gacgacagag atggcctagc tctgcatact gcaccccccag gggctcagaa cagtgcaaat    4800
gtcagtctat ctgtcagtgg cagagccagc cttggagcag gggtgcaagg aggtctctgc    4860
actggccagg catgcagaac attctgttca gtagcactgg acagaaggcc ccatctagat    4920
gagacagagc tggtggggca ggacaaagac tcctggcagc tcaaacgcc tggcagatgc     4980
ttggagagag ggggcttctt gagacagcac catttctggg aagagagtca cctgggaggg    5040
atgaggccac gctccggctt ggaggtgaag agaggggctg ctgcaagaaa gaattagaga    5100
catgccagcc tttgctgtgt tgcccaggct ggtcatgaac tcttggcctc aagcaatctt    5160
cccacctcag cctccccaag cgctgggatt atagacatga gccccatgc tggccaataa     5220
aagatgattt tatggagggg atggtggtga aggttgtggg tggtatgaaa tagtaagaaa    5280
tatatattgg tctgcaccca gttcctgcca cagagctcct aaaatcctga gaacttcctg    5340
ggtgagcatc ttttgttcta atgaggtgac tcttggtggc tcctggatag gagtgaatca    5400
ccagaaagat caagccagag ttagaagcag aaagtgctgg ctataacaca ggaaagctgt    5460
aacacaaata ataagttttt ttttttttt tttgagatgg agcctcactc tgttgcccag    5520
gctggagtgc aatggtgcaa tctcagctca ctacaagctc tgcctccag gttcaagtga     5580
```

```
ttctcctgcc tcagcctcct gagcagttgg gactacaggt gtgtgccacc acatctggct    5640
aattttttgta ttttttagcag agacggggtt tcaccatatt aaccaggctg gcctcaaact   5700
ccttaccttg tgatccgcct gcctcagcct cccaaagtgc tgggattaca ggcatgagcc    5760
accgtgcctg gccaaaagac attgttctta aagaatcaa ctaactaacc aaataaataa     5820
aaatctaacc taattaagaa actaaaaata cacaaaaatt aatttcaagg ggagaaaaat    5880
catgtaaaga gagaaagata atgaatactt tgcagaaatt tatgaacata aacataaaac   5940
ttggatgaaa tgcatttcta ggaaaacata atttatcaaa actaaccaca agtaaaatag   6000
aagcctaaat aggatatttt caagagaaga agtaaagttg tcaaagtgct acccttcaaa    6060
aaaacaccag gctcaaacaa tctgacatgg gaatgttagc acaccttaga gagcaaataa   6120
aactttgaat gggcttgaaa tattccagac tctagaaaaa caaaacttcc caattctttt    6180
tataaagcaa gtataaattg ataccaaaat cttataaaga ccttatacaa aacttcatac   6240
caatctcttt tatgaataca aaaccccttaa taaagtatta ccagacagaa cccaacaata   6300
cataaaaatg tcacatcata acatagtggg gtttatttca ataatgcatg gatggttcaa    6360
tacaaggaaa ttcagtaaca caatataata gatcatgtga atatacccaa agaaaaaata   6420
gattattttc atagatgctg taaaggcatt tgaccaaatt caacacctac tttttaggtg   6480
gtcaataaaa taaattagtt actccttctt tagcatgata aaatatattt atcagcccag    6540
aaggcatcat tttacccgat aagggcacac gctggaggga ataatgttaa aattaggaat   6600
aagaggatag ctagtttctt tcttcttttt tttttttgag acggagtctt gctctgttgc    6660
caggctggag tgcagtggtg caatgttggc tcactgcacg ccccccgcct cccaggttca    6720
agcgattctc ctgcctcagc ctcccgagta gctgggacta caggcgcgca ccaccatgcc    6780
cggctaatttt ttttttgtat tttagtagag atggggtttc accatgttgg tcaggctggt    6840
cttgaactcc caacctcacg tactgggatt accggtgtga gccaccacgc cagcccaact   6900
actttcaaca ttatccttaa tactgatgct tattgactta ctatgggggtt acctctagat   6960
aaatccataa taagttgaaa atataagtaa aaaatgccct taatacacct aacctaccaa   7020
acatcatagc tgagcccagc ctgccttagc tatgctcaga cactgacgtc agcctacaat    7080
tggcaaaatc acacagcagc acagtctact gcagagcatc tgctgtttgc ccttgtgact   7140
gcgtggctgc ctgggagctt cccagcttca caagacagta ttacgtagca catcactagc    7200
ctggggaaag atcaaagttg aaaatttgaa gtgtggtttc cattgaatgt gtactgcttt    7260
tgcaccatca tcaagtcaaa aaattttagt tgaaccagcc taagtttggg accatcttta    7320
ttttcaggag gaacttccat gtacattgat gacggacgat agaatccgtt tctatcatcc     7380
taatgaacat aatgaataaa tccagacaaa cataaacatt aacagagtaa gcagctttcg   7440
gggctggaag ccagaagagg gtgggagcgc agagagagag gccaaacacc agggctgctt    7500
ctgctttgcg ggtatttgct gatctggaca aggtatctgg aaggctgagc taagcctcct   7560
tttttttttga ggtggcgtct cactctgttg ccaggctgga gtgcaatggt gcgatctcag    7620
ctcactgcaa cctccacctc cctggttcaa gcgattctcc tgcctcagcc tcccgagtag    7680
ctgggattac aggctcccgc cactacaccc agctgatttt tgtaatttta gtagagacgg     7740
ggtttcacca tgttggccag gatggtctcg atctcttgac gtcatgatct gtccacctcg     7800
gcctcccaaa gtgctgggat tataggcgtg acccaccgtg cccgtctga gctaagcctc    7860
ttgagcatag gggactaaaa atgaaatcta gcgcatgcca agtttagggt cccaggcaat    7920
tccttttccac tttggggtcc actttgggt ccaccccacc caagaagaag gatgacttgg    7980
```

```
aagtaaaacca gctctgaaat atggatggtc ctctgggacc ataccaatcc cttcatatca   8040
accacatcca gttcctcaaa actggaactt ggattaagat ggcctaggac ttctagtgtc   8100
ccaggagcct ggcattgcaa acaaaaatcc tctccggaag aagataatac cttaagcttc   8160
aaatgactct ctaataaatt tcaaatacaa tgtccagcac acaaacacaa attaccagga   8220
acgtgatatg aggcctgatg gatgggaatt agcagaaact tcaggcatga gaaacatacc   8280
ctcagaggcc tagaatctat ctagtgtcta gataatggag atatgaaata cagacactta   8340
aacaactatg tttcccatgt tcaaagagga aatttgcaaa acttgaaagt gttggcagga   8400
aatcagaaac tataaaatgt gacaacagca tactttagag tcagtataaa ttacggtccc   8460
gaaaactgca gaattccaga acttaatggt aaagcaaggg tttaacagca gaatagaaat   8520
agccagagag aactaggaag taagtcagat gacactaccc agaataaggc actgagaggc   8580
caaggaatgg aaaatgcaga agaaaggata tggtgagagg atctaatata catttatttg   8640
gagtaccagg agagagagaa aggagaagaa cagaagccgt gtttcaagga cggtgactga   8700
gaggcttcga aactgatgaa agccatcagt tcacaaattc aaagcccagt gaattccaag   8760
gagaaaaaaa gaaatccata ctgtgaaagc aagtccagac aatgacaaac accatcaaca   8820
atacacagga caggcataag atgcatttaa tggggacact cagaggcaga gggttatcag   8880
aaggaggcac ttctctccca agttctcatc atcccagggc cagggacagc tggtcacacc   8940
ttagggagtt cactaggaga gggatctggc ttcttgtcat tctgggtatt tgtagggaaa   9000
ttggaaggga accagagagca cctagccaat cgcatagcaa tgggagattt caggctgtgg   9060
ggaatgtctt tgctggtgaa aagaacatcc tgaccttaga aatctttcac cgagggggat   9120
ctgcgttcca gaacttctgg agctggtata ggtaaggctt tgagcttttcc tactgagcca   9180
gcctgttgct aggttaccaa aggggacctc gagggccatc tggccaacaa gcagacttgt   9240
ctctccttac acccccagac gtatcactgc aaaactacag aaaaccaaag acagagaaaa   9300
tcttaaaagc agccagattt aaaaaatggc atattagttt caaagcagca gccatgaaat   9360
tgacagctga tgtctcaaca gcaagaatga aaagtggaag acaggccagg tgtggtggct   9420
caggcctgta atcccagcac tttgggaggc cgaggcgggt ggatcacgag gtcaggagac   9480
caagaccatc ctggctaaca tggtgaaacc ccgtctctac taaaaataca aaaaattag   9540
tcgggcatgg tggtgggtgc ctgtagtccc agctactcgg gaggctgagg caggagaatg   9600
gcgtgaaccc gggaggcgga gcttgcagtg agccgagatt gtgccactgc actccagcct   9660
gggtgacaga gcaagactct gtctcaaaaa aaaaaaaaa aaaaaaaaa aaagggtgac   9720
gaagcttcaa tctcctgaaa ggaagcaact gccgcctttg attcgatacc caccaaaatc   9780
cgtgaagaag gaaggcaaaa taaaacacact tcctgattga actggaaaga tttccgcaat   9840
agaagaccca ctgtccaagg aattctaaag gatgctttcc aggcagaaga aaatgacccc   9900
agaggaagat cagagattca ggaaagaaat ggagagtgat aaaaatggaa aattcggggg   9960
ccaatttaaa caaaagctga ctgctctaca actgttgtgt ctctatcttt tgtaacatat  10020
atgtgtgtgt agcttttttt ttttttttg tcaagatgga ttctcactct gtcgcccagg  10080
ctacagtgaa atggcacggt ctcggctcac tgcaacctct gccccttggg ctcaaatgat  10140
tctcttgcct cagcctcctg agtagctgag attacaggtg cctggcacaa tgcctggcta  10200
attttttgtat ttttactaga gatgggattt ctccatgttg gccaggctgg tcttgaacac  10260
ctgacctcag gtgatccacc tgcctggggcc tcccaaagtg ctaggattac aggcgcgagc  10320
```

```
cactgcatct ggcctatgtg tgtgtttata tggaattaaa acacatggca ataatccct    10380 ccaaattggg agaaaccaaa aatagcattt aaatgttgta agctccctgc ataatcaaga   10440
agagaataga tttacgttag attttgatac ctggaggatg aatgttgtaa tttctagggt   10500
gaccatgaaa agaggagaca acggtgtatg ttttttttt tttgagatgg agtctcactt    10560
tgtcacccag gctggagtgt tgtggtgtga tcttggctca ctgcaacctc ctcctcttgg   10620
gttcaggcca tcctcccacc taggcctcca gagtaggtgg gatcacaggc acctgccacc   10680
acacctggct aatttttttt tttttttaaa tatttagtag agatggggtt tcaccatgtt   10740
ggccaggctg gtcttgaact cctgacctca ggcgatctgc ctacctctgc ctctcaaagt   10800
gctgggatta caggtgtgag ccatcgcgcc cggccaacag tgatcacttt caaactaaca   10860
gaggttcaaa aataaaatca gacttaacca aaaaccaggt aacagagctg gtaggatata   10920
cagaaagact gacctcacgt atatcaacga ttacagttaa tattaatgaa ggaaatgctc   10980
tagtttaaaa acgagggttg tcaaagaccc cacataagaa gctccttacc agcggtgcac   11040
ctagaaccta aggaaacagg acagatgaag gaggacgcgc ccccgccgct gtcctgcgcc   11100
tcagccatcc tatgagacgg gaaaggtttc tgtctgcagc tgggcccgtg ctctttacca   11160
gctcctggct ttcttctctg gaaggttcct gcctgttttg ccctcacacc tgctcctctc   11220
tcagccctct caggggtggg gctggaggcc accaaagagc ctcctctgct ctccagttgc   11280
tcgactgctc ctcatttccc cctggggtct gcgtcagggt ttccttcttt tccagcccca   11340
ccccgcgtgc atcccacctg gtctcgggtc ggggctgctc ccgcttactg cccccctgccc  11400 aggctggtgt gcacccccte tggctgcttt caaggcctct tctctcttct cggcaggaca   11460
ggcacaggca ggtggccagg tgtcatgctt agctccccgc ccagtgagat tctttcattt   11520
aacaatcttc ccctgaatag ttcatgttca ttgctgaaaa tttgaaaaat atggaaaagc   11580
acaaagatta agatataaac cgccctcaat tcccctgccc agagagagtc actgctatga   11640
cttggtgact aggaacctta tttctctctc gctctttttt ttttttttga cagagagtct  11700
tgctctgtca cccaggctgg agtgcagtgg ctcgatctca gctcactgca acctccgcct   11760
cctgggttca gcgattctc ctgcctcagc ctcttgagta gctgggatta caggcacctg    11820
ccaccatgcc cggctaattt ttgtatttt agttgagaga gggtttcatc ttgttggtca    11880
ggcggacttg aactcctgac ctcaggtgat cagcccacct cggcctccca aagtgctggg   11940
attacaggtg tgagccactg cgccttcatc tctcttctgt gtatgtgtac gctgttttt    12000 ctttagaatg ggggacgtta tcaggctcta catggtgtgt agtcggctag catgttgtaa   12060 gcctttcct gtgtcacaag tgctcatctg gaacaggatt ctaatgactg cctgtggcta    12120
tgttgggatt cctttaactc agctccttct gcccagcatc tatctttttt ccatctttg    12180 tcctaagtgt tgctataata aatcattgat cacacatgcc tgactgtttg cataggataa   12240
attacgggaa atgttttgc tgttcaggga ctgtgcccat ttttaggcct cagagacacc     12300
atgccagact gcccagtatt gatctttact cttttagat gatgccaaac ttttctgtga     12360
actttaaaaa cctgtgtctt gacagtccat ttctgtaagt ctttcacatt agatttcctg   12420
tcaggatgat agtcaattct aggcagatga tgttttctca gccatggctg aagcagttgt   12480
gatttgttgt ggccatgtaa agtcccgatg atccattgcc tccctggatg ggttggaata   12540
atttggtttg ggagcatata acagaatgac ctggagtcac agcagctcag acggaagtgt   12600
atttctccct tacagatgaa agaattccag gccaggctgg aatgacaact gcacacagtc   12660
atctgggccc cctccttcca gctcccatca ccccaggatg tggctttat gcagatgatc    12720
```

```
caaaatggct gctcaagtcc cagccaacac atcccattcc agggagcagg aaaaaggtgt    12780
gtctttccct tcattttatg tgattccttt ctagaagtac tactcattac ttctgcttgc    12840
atctccctgg ctagcactta cttagttata tggccatagc tagctgaagg aaggacaggg    12900
actgtcatac actagctaag aggcaaactg cttagataaa aaggtctcta agaaggtca     12960 gagcggctgc tagggtgcaa ctctattact tattgttatg ggacgaactg tgtccctcat    13020
tcaggttgat gtcctaagcc ccagaacctc agaatgggat tgtatttgga gacaggttct    13080
ttaaggaggt aaggaggcta aaatgagatc attagggtgg gccataatcc gactgatgtc    13140
ttacaagaag agattaggac acggacatgc tcagagggac ggccacgtga ggacaccaag    13200
aaaggcagct gtctgcaagt caaggacagg gctcagggga aaccaacctt gccaacacct    13260
tcatctcgga cttctagcct ctaggaccat gagaagatac atttctgttg tttaagctgc    13320
ccggtctgtg gtactttgtt atggcagccc aagtaaacaa atacagtcat ctgctgctgg    13380
aacaaatcac cccagcactg tggcttggca gcacacatgt ctagtcatag agttatatgt    13440
agttacgtgt agagccatat gtatcgtcac acgttctgtg ggtcaggaat ttggacccag    13500
cttaaccagc tccacttctc gccagggttc agtcaaatac cagctgcctc ccacctgaga    13560
gctcagccgg ggaagggtcc ctttccaatc tcacgtggtg ttggcaggat ccagttcctc    13620
atggcctgct ggactgagaa cctcagttct cactgcctgt tggccagagg ccgcctttat    13680
gtcctcgcca tgtgggcctc tccaacatgg cagctgactt catcagagca tccatgccaa    13740
gaaggcaaca gagagggcca gggagactga agtcataccc ttttgcgacc tagtcatggg    13800
gtgacattcc atcacctttg cccattggtt agaagcaggc caccaggtac agcccaagct    13860
cacggggagg ggtcatacaa gggtgtcaat accaggaggt gaggggtgct ggggccatct    13920
tatgagtctg cccactgagg taactaacaa ccttgaggcc tgacacagtg gacaaaggcc    13980
cttattaaca gcagagaact gggaactta tttatttatt tattttttgag acagagtctc   14040 actcttgtca cccaggctgg agtgcaatgg catgatcttg gctcactgca acctccacct    14100
cccaggttca gcaattctg cctcagcctc cggaatagct gggactacag gcatgcacca     14160
ctacacccgg ctaatttttg tattttagt agagacaggt ttcgccatg ttggccaggc      14220 tggtctcgaa ctcctgacct ctggtgatct gcctgccttg gcctcccaaa gtgctgggat    14280
tacaggcgtg agccaccgca cctcgctgga acttaatttt tttagagaca gtgtcgctct    14340
atcacccaag ctggagtgca gtggtgcaat cctagctcac ttgcagcctc aaattcctgg    14400
gttcaggtga tcctcccaca tcagcctccc aagaactggg aactaacagc tgtttctctg    14460
ctgtccttct caagaaaagg gaggctactg ctaccccact ggggacaatg ctgggtttcc    14520
ctttaggaca ggctctgaga caaggcgag gtgctgtttg tggccacaga gcagggact      14580 ctgggttgca ggtgtggcct ggctaaagta ggctttactg ggctcctctc tgcctgcatc    14640
accccccggc tgggcggttg tctctgaggc caaccttact ccctgctggg caggctggac    14700
agctgccctc tccgtttgcc cctctaccac ccaaaaggca ggaggctctg agaccagga     14760 ccctgcccgc cacggcctgt gtcccaggcg tgagggggtg ccccacagac ctctgctgag    14820
ctgctgctga atgacgcccc ttgggggtcc tgccggaagg tcagagcagg ggtgcactcc    14880
cataaagaaa cgccccagg tcgggactca ttcctgtggg cggcatcttg tggccatagc     14940
tgcttctcgc tgcactaatc acagtgcctc tgtgggcagc aggcgctgac cacccaggcc    15000
tgccccagac cctctcctcc cttccggggc gctgcgctgg gaccgatggg gggcgccagg    15060
```

```
cctgtggaca ccgccctgca ggggcctctc cagctcactg ggggtgggt ggggtcaca      15120 cttggggtcc tcaggtcgtg ccgaccacgc gcattctctg cgctctgcgc aggagctcgc      15180
ccaccctctc cccgtgcaga gagccccgca gctggctccc cgcagggctg tccgggtgag      15240
tatggctctg gccacgggcc agtgtggcgg gagggcaaac cccaaggcca cctcggctca      15300
gagtccacgg ccggctgtcg ccccgctcca ggcgtcggcg ggggatcctt tccgcatggg      15360
cctgcgcccg cgctcggcgc cccctccacg gccccgcccc gtccatggcc ccgtccttca      15420
tgggcgagcc cctccatggc cctgcccctc cgcgcccac ccctccctcg ccccacctct      15480
caccttcctg ccccgccccc agcctcccca ccctcaccg gccagtcccc tccctatcc      15540 cgctccgccc ctcagccgcc ccgcccctca gccggcctgc ctaatgtccc cgtccccagc      15600
atcgccccgc cccgccccg tctcgccccg ccctcaggc ggcctccctg ctgtgccccg      15660
ccccggcctc gccacgcccc tacctcacca cgccccccgc atcgccacgc ccccgcatc      15720 gccacgcctc ccttaccatg cagtcccgcc ccgtccctcc tcgtccgc ctcgccgcga      15780 cacttcacac acagcttcgc ctcaccccat tacagtctca ccacgccccg tccctctcc      15840 gttgagcccc gcgccttcgc ccgggtgggg cgctgcgctg tcagcggcct tgctgtgtga      15900
ggcagaacct gcggggcag gggcgggctg gttccctggc cagccattgg cagagtccgc      15960
aggctagggc tgtcaatcat gctggccggc gtggccccgc ctccgccggc gcggccccgc      16020
ctccgccggc gcagcgtctg ggacgcaagg cgccgtgggg gctgccggga cgggtccaag      16080
atggacggcc gctcaggttc tgcttttacc tgcggcccag agcccatttc attgccccgg      16140
tgctgagcgg cgccgcgagt cggcccgagg cctccgggga ctgccgtgcc gggcgggaga      16200
ccgccatggc gaccctggaa aagctgatga aggccttcga gtccctcaag tccttccagc      16260
agcagcagca gcagcagcag cagcagcagc agcagcagca gcagcagcag cagcaacagc      16320
cgccaccgcc gccgccgccg ccgccgcctc ctcagcttcc tcagccgccg ccgcaggcac      16380
agccgctgct gcctcagccg cagccgcccc cgccgccgcc ccgccgcca ccggccccgg      16440 ctgtggctga ggagccgctg caccgaccgt gagtttgggc ccgctgcagc tccctgtccc      16500
ggcgggtccc aggctacggc ggggatggcg gtaaccctgc agcctgcggg ccggcgacac      16560 gaaccccccgg ccccgcagag acagagtgac ccagcaaccc agagcccatg agggacaccc      16620 gcccctcct ggggcgaggc cttccccac ttcagcccg ctccctcact tgggtcttcc      16680
cttgtcctct cgcgagggga ggcagagcct tgttggggcc tgtcctgaat tcaccgaggg      16740
gagtcacggc ctcagccctc tcgcccttcg caggatgcga agagttgggg cgagaacttg      16800
tttcttttta tttgcgagaa accagggcgg gggttctttt aactgcgttg tgaagagaac      16860
ttggaggagc cgagatttgc tcagtgccac ttccctcttc tagtctgaga gggaagaggg      16920 ctggggggcgc gggacacttc gagaggaggc ggggtttgga gctggagaga tgtggggca      16980 gtggatgaca taatgctttt aggacgcctc ggcgggagtg gcggggcagg gggggggcgg      17040
ggagtgaggg cgcgtccaat gggagatttc ttttcctagt ggcacttaaa acagcctgag      17100
atttgaggct cttcctacat tgtcaggaca tttcatttag ttcatgatca cggtggtagt      17160
aacacgattt taagcaccac ctaagagatc tgctcatcta agcctaagtt ggtctgcagg      17220
cgtttgaatg agttgtggtt gccaagtaaa gtggtgaact tacgtggtga ttaatgaaat      17280
tatcttaaat attaggaaga gttgattgaa gttttttgcc tatgtgtgtt gggaataaaa      17340
ccaacacgtt gctgatgggg aggttaattg ccgagggatg aatgaggtgt acatttttacc      17400 agtattccag tcaggcttgc cagaatacgg ggggtccgca gactccgtgg gcatctcaga      17460
```

```
tgtgccagtg aaagggtttc tgtttgcttc attgctgaca gcttgttact ttttggaagc   17520
taggggtttc tgttgcttgt tcttggggag aattttttgaa acaggaaaag agagaccatt  17580
aaaacatcta gcggaacccc aggactttcc ctggaagtct gtgtgtcgag tgtacagtag   17640
gagttaggaa gtactctggt gcagttcagg cctttctctt acctctcagt attctatttc   17700
cgatctggat gtgtcccaga tggcatttgg taagaatatc tctgttaaga ctgattaatt   17760
tttagtaata tttcttgttc tttgtttctg ttatgatcct tgtctcgtct tcaaagttta   17820
attagaaaat gattcggaga gcagtgttag cttatttgtt ggaataaaat ttaggaataa   17880
attattctaa aggatggaaa aacttttttgg atatttggag aaattttaaa acaatttggc  17940
ttatctcttc agtaagtaat ttctcatcca gaaatttact gtagtgcttt tctaggaggt   18000
aggtgtcata aaagttcaca cattgcatgt atcttgtgta aacactaaac agggctcctg   18060
atgggaagga agacctttct gctgggctgc ttcagacact tgatcattct aaaaatatgc   18120
cttctctttc ttatgctgat ttgacagaac ctgcatttgc ttatcttcaa aatatgggta   18180
tcaagaaatt tcctttgctg ccttgacaaa ggagatagat tttgtttcat tactttaagg   18240
taatatatga ttaccttatt taaaaaattt aatcaggact ggcaaggtgg cttacacctt   18300
taatccgagc actttgggag gcctaggtgg acgaatcacc tgaggtcagg agtttgagac   18360
cagcctggct aacatggtga aaccctgtct ctactaaaaa tacaaaaatt agctggtcat   18420
ggtggcacgt gcctgtaatc caagctacct gggaggctga ggcaggaaaa tcgcttgaac   18480 ccggaggca gagtctgcag tgagttgaga tcacgccact gcactccagc ctgggtgaca   18540
gagcgagact ctatctcaaa aaaattttt tttaatgtat tatttttgca taagtaatac    18600
attgacatga tacaaattct gtaattacaa aagggcaata attaaaatat cttccttcca   18660
cccctttcct ctgagtacct aactttgtcc ccaagaacaa gcactatttc agttcctcat   18720
gtatcctgcc agatataacc tgttcatatt gtaagataga tttaaaatgc tctaaaaaca   18780
aaagtagttt agaataatat atatctatat atttttttgag atgtagtctc acattgtcac   18840
ccaggctgga gtgcagtgat acaatctcgg ctcactgcag tctctgcctc ccaggttcaa   18900
atgcttctcc tgcctcagcc ttctgagtag ctgggattac aggcgcccac caccatgtcc   18960
agctaatttt tgtatttttta gtagagatgg ggtttcacca tgttggccag ctggtcttg   19020 aactcctgac cttgtgatct gtccacctcg gcctcccaaa gtgctgggat tacaggtgtg   19080
agccaccatg cctggctaga ataataactt ttaaaggttc ttagcatgct ctgaaatcaa   19140
ctgcattagg tttattttata gttttatagt tattttaaat aaaatgcata tttgtcatat   19200
ttctctgtat tttgctgttg agaaaggagg tattcactaa ttttgagtaa caaacactgc   19260
tcacaaagtt tggattttgg cagttctgtt cacgtgcttc agccaaaaaa tcctcttctc   19320
aaagtaagat tgatgaaagc aatttagaaa gtatctgttc tgtttttatg gctcttgctc   19380
tttggtgtgg aactgtggtg tcacgccatg catgggcctc agtttatgag tgtttgtgct   19440
ctgctcagca tacaggatgc aggagttcct tatggggctg gctgcaggct cagcaaatct   19500
agcatgcttg ggagggtcct cacagtaatt aggaggcaat taatacttgc ttctggcagt   19560
ttcttattct ccttcagatt cctatctggt gtttccctga ctttattcat tcatcagtaa   19620
atatttacta aacatgtact atgtgcctgg cactgttata ggtgcagggc tcagcagtga   19680
gcagacaaag ctctgcccte gtgaagcttt cattctaatg aaggacatag acagtaagca   19740
agatagataa gtaaaatata cagtacgtta atacgtggag gaacttcaaa gcagggaagg   19800
```

```
ggatagggaa atgtcagggt taatcgagtg ttaacttatt tttattttta aaaaaattgt   19860
taagggcttt ccagcaaaac ccagaaagcc tgctagacaa attccaaaag agctgtagca   19920
ctaagtgttg acatttttat tttatttgt tttgttttgt ttttttgag acagttcttg    19980
ctctatcagc caggctggag tgcactagtg tgatcttggc tcactgcaac ctctgcctct   20040
tgggttcaag tgattctcat gcctcagcct cctgtttagc tgggattata gacatgcact   20100
gccatgcctg gtaattttt tttttttccc ccgagacgga gtcttgctct gtcgcccagg    20160
ctggagtgca gtggcgcgat ctcagctcac tgcaagctcc gcttcccgag ttcacgccat    20220
tctcctgcct cagtctccca gtagctggga actacaggcg cctgccacca cgtccagcta    20280
atttttttgt attttaata gagacggggt ttcaccgtgt tagccaggat gatcttgatc    20340
tcctgacctc gtcatccgcc gaccttgtga tccgcccacc tcggcctccc aaagtgctgg    20400
gattacaggc atgagccact gtgcccggcc acgcctgggt aatttttgta tttttagtag    20460
agatggggtt ttgccatgat gagcaggctg gtctcgaact cccggcctca tgtgatctgc    20520
ctgccttggc ctcccaaagt gctaggatta caggcatgag ccaccatacc tggccagtgt    20580
tgatattta atacggtgt tcagggaagg tccactgaga agacagcttt ttttttttt     20640
tttttgggg ttgggggca aggtcttgct ctttaaccca ggctggaatg cagtatcact      20700
atcgtagctc acttcagcct tgaactcctg ggctcaagtg atcctcccac ctcaacctca    20760
caatgtgttg gactatagg tgtgagccat cacacctggc cagatgatgg cttttgagta    20820
aagacctcaa gcgagttaag agtctagtgt aagggtgtat gaagtagtgg tattccagat    20880
gggggaaca ggtccaaaat cttcctgttt caggaatagc aaggatgtca ttttagttgg     20940
gtgaattgag tgaggggac atttgtagta agaagtaagg tccaagaggt caaggagtg     21000
ccatatcaga ccaatactac ttgccttgta gatggaataa agatattggc atttatgtga    21060
gtgagatggg atgtcactgg aggattagag cagaggagta gcatgatctg aatttcaatc    21120
ttaagtgaac tctggctgac aacagagtga aggggaacac cggcaaaagc agaaaccagt    21180
taggaagcca ctgcagtgct cagataagca tggtgggttc tgtcagggta ccggctgtcg    21240
gctgtgggca gtgtgaggaa tgactgactg gattttgaat gcggaaccaa ctgcacttgt    21300
tgaactctgc taagtataac aatttagcag tagcttgcgt tatcaggttt gtattcagct    21360
gcaagtaaca gaaaatcctg ctgcaatagc ttaaactggt aacaagcaag agcttatcag    21420
aagacaaaaa taagtctggg gaaattcaac aataagttaa ggaacccagg ctctttcttt    21480
ttttttttt tgaaacggag tttcgctctt gtcacccggg ctggagtgca atgatgtgat    21540
ctcagctcac taaaacctct acctcctggg ttcaagtgat tcttctgcct cagcctccca    21600
agtaactggg attacaggcg tataccacca tgcccagcta attttgtgt tttagtaga     21660
gatggggttt caccatgttg gccaggctgg tctcgaactt ctgacctcag gtgatccact    21720
cgcctcagcc tgccaaagtg ctgggattac aggtttgggc cactgcaccc ggtcagaacc    21780
caggctcttt cttatactta ccttgcaaac ccttgttctc attttttccc tttgtatttt    21840
tattgttgaa ttgtaatagt tctttatata ttctggatac tggattctta tcagatagat    21900
gatttgtaaa aactctccct tccttttggat tgtcttttta ctttcttgat agtgtctttt   21960
gaagtgtaaa agttttaat tttgatgaag tcgagtttat ctattttgtc tttggttgct    22020
gtgcttcaag tgtcatatct aagaaatcat tgtctaatcc aaagtcaaaa aggtttactc    22080
ctatgttttc ttctaagaat tttagagttt tacatttaag tctgatccat tttgagttaa    22140
tttttatata tggttcaggt agaagtccaa ctttattctt ttccatgtgg ttattcagtt    22200
```

```
gtcccagcac tgtttgttga agagactatt ctttccccat ggaattatct tagtacccct   22260
gttgaaaatt aatcgtcctt aattgtataa atttatttct agactgtcag ttctacctgt   22320
tggtctttat gtcgatcctg tgccagtacc atacagtctt gattactgaa gtttgtgtca   22380
cagtttaaat tcatgaaatg tgagttctcc aactttgttc cttttcaaga ttgatttggc   22440
catgctgggt cccttgcatt tccgtacgaa ttgtaggatc agcttgtcag tttcaacaaa   22500
gaagccaagt aggattctga gagggattgt gttgaatctg tagatcaact tggggagtat   22560
tcgcatctta acaatattgt cttccaccta tgaacatggg caaactttgt gtaaatggtc   22620
agattgtaag tatttcgggc tgtgtgggca cagtgtctct gtcacagcta cgcggctctg   22680
ccattgtagc atgaaagtag ccataagcaa tatgtatgag tgtctgtgtt ccaatagaat   22740
tttattaatg acaaggaagt ttgaatttca tataattttc acctgtcatg agatagtatt   22800
tgattatttt ggtcaaccat ttaaaaatgt aaaaacattt cttagcttgt gaactagcca   22860
aaaatatgca ggttatagtt ttcccactcc taggttaaaa tatgatagga ccacatttgg   22920
aaagcatttc tttttttttt tttttttttt tttttgagac ggagtttcac tcttgttgcc   22980
caggctggag tgcagtggcg cgatctcggc tcactgcaac ctctgcctcc caggttcaag   23040
acattctcct gcacggcctc cctagtagct gggattacag gcatgcgcca ccacacccag   23100
ctaattttgt atttttagta gagacggggt ttctccatgt tggtcaggct ggtcttgaac   23160
tcctgacctc aggtgatcca cccgcctcag cctcccaaag tgctgggatt acagggtgtg   23220
agccaccaca ccctgctgga aagcattcct ttttttggctg ttttttgtttt tttttaaac   23280 tagttttgaa aattataaaa gttacacata tacattataa aaatatcttc aagcagcaca   23340
gatgaaaaac aaagcccttc ttgcaagtct gtcatctttg tctaacttcc taagaacaaa   23400
agtgtttctt gtgtcttctt cccagatttt aatatgcata tacaagcatt taaatgtgtc   23460 atttttttgtt tgcttgactg agatcacatt acatatgtat ttttttactt aacaatgtgt   23520
catagatatt gttccatagc agtacctgta attcttatta attgctatgt aatatttttag   23580 aatttctttt taaaagagga cttttggaga tgtaaaggca aagtctcac attttttgtgg   23640 ctgtagaatg tgctggtgac atattctctc taccttgaga agtccccatc cccatcacct   23700
ccatttcctg taaataagtc aaccacttga taaactacct ttgaatggat ccacactcaa   23760
aacatttagt cttattcaga caacaaggag gaaaaataaa ataccttata aagcactgtt   23820
taatattgta ttaaattgga tcaatttggg ggctagaatg tatgttagag acatgatatg   23880
tccataggtc cttgctatca cagtgaggtc tcagggacga tcgtttggta tcatttggga   23940
tctcataagc agactctctc tgcttgacct gacaaatcag agtctgtgtt ttaacaggtt   24000
cagtgagtga cttacatgca cattggagtt tgggaagctc cactgtaggt gcttagacct   24060
tacctttgtt gttgctaata acaatgcaag catttgggag gaagacctgt gttgctcata   24120
tgtgtccagg tgtagctgag gtggccttgc ttatctgctg tagggccgtt gagcatttct   24180
gtagctgtga tgagtgagct gaggtgagcc tgcggagagc tcccagccat ggtagtggg   24240 actcgcttag atgaactgga aggaccctt catctgagca gccactatgg agaaaaacaa   24300
ccgaatgagg ggagagacaa tgtgcaattt tatttagggc acaaaggaga gctgtggtta   24360
gaaggtgaca tttgagtgga aagggggcaa gccatgtgta tagcgggaga agagaggtcc   24420
aggcagagtt aacagaaggc agaaatgctt tccatgtttg agaaccagta aggaggccag   24480
tggctgaagt aaggtgaagg gcagaaataa ggatgaggct gcgagagatg agaggttaga   24540
```

```
gacgagcgtc ttgtgcacca agataagctt gtgtggtcaa aacaagtagt ttaatttatg   24600 ttttaaaag atcattttgg ctgggcacaa tggttcatgc ctgtaatacc agtagtttga    24660
gacggtgtgg tgggaggatt gcctgaggcc agacgaccag catagccaac atagcagcac   24720
ctataaggtc tctacaaaaa actttaaaaa attagctggg catagtggtg tgtgcctgta   24780
gtcccagcta ctcaggaggc tgaggaggct ggaggattgc ttgagtccag gagtttgagg   24840
ctgcagtgag ctatgattat gccactacac tacaacctgg gcaagagagt gagaccctgt   24900
ctctaaatat acacacacac acacacacac acacacacac acacacacac acacacacac   24960
acacacatat atatgtatat atatgcattt agatgaaaag atcactttga caataccaca   25020
tgctggtgag gatttagaaa aactaggtca cttattgctg gtgggaatat aatatagtac   25080
ggccactctg gaaacagtt tggcagtttg tcataaaact gaacataccg ttagtataca    25140
gcccagcagc aactacaatc ctgggcatta atcctagaga aatgaaacct taatgttcac   25200
ataaaaacct atactcaagt atgcatagca gctttaccca taatatctaa gaactggaat   25260
cagctcagat gtccttcaac aggtgaatgg ttaaactact cagtaataaa aaggaatgag   25320
ctactgatag catgcaacag tttaggtgaa gttatgctaa tgaaaaaagc caatcccaaa   25380
aggttataca tactgtatga ttctatgttt ttttgcaatg gcacagtttt agggatggag   25440
aatagattag tggttgcctg gggttagaga tggggtagta gagtaggtta gtggtggcag   25500
aggagagaaa agagagggag gtgaatgtgg ttataaaagg acaacacagg gaatacttg    25560 taatggaaat gctttgtctt tttttttttt ttttttttt tggcgacaga gtcttgctct    25620
gttgcccagg ctggagtgca gtggcatgat cttttctcac tgcaacctct gcctcctggg   25680
ttcaagtgat acttgtgtct cagtctccca tgttcagagt gaaacaaacc agaggtaatg   25740
ttcatccaaa taatccaaca cacatgacat taaaacatca agatcaggtc ggacgtggtg   25800
gctcatgcct gtaatcccag cacttttggg aggccaaggt gggcagatca cttgaggtca   25860
ggagttcgag accagccggg ccaacatgat gaaaccccat cttgactaaa aatcaaaaaa   25920
ttagccgggc atggtggtgt gcacctgtag tcccagctac ttgggaggct gaggcaagag   25980
aactgcttga acccgagggg cagaggttgc agtgagctga gagtgcgcca ttgcacttca   26040
gcctgtgtga cagagtaaga ctccatctcc aaaaaaaaaa aaccaagatc aattaaaata   26100
cagcattact gggccgggtg tggtggctca cacctgtaat cccagcactt tgggaggccg   26160
agatgggcag atcacgaggt caggagatcc agaccatccc ggctaacacg gtgaaacccc   26220
gtctctacta aaaatacaa aaaattagcc gggtatagtg gtgggtgcct gtagtcccag    26280
ctacttggga ggctgaagca ggagaatggt gtgaacccgg gaggcagagc tggcagtgag   26340
ctgagatcgc gccactgcac tccagcctgg gcgacagagc aagactccgt ctcggggaa    26400 aaaaaaaat aaataaatag aatgctgtag tgtccttgag tttacatgcc cctccttacg    26460
cttgtgtgcc cgtgcagatt gcttgattac acaattagag gaggctggcg gaggattgtt   26520 ttaattttt ttttttgag acagtctggc tctgttcccc aggctagagt gcaatggcgc     26580
aatcttggtg cactgcaacc tctgcctcct gggttcaagc agttcttctg ccgcagcctc   26640
ccgagtagct gggattatag gcgcccgcca ccacgcccaa ctattttttg tatttttagt   26700
agagcagcgt ttcaccatgc tggccaggct ggtctcgaac tcctgacctc agatgatctg   26760
ctgccccagc ctcccaaagt gctgggatta caggcgtgag ccacacctgg ccgtttgttt   26820
taattttgaa ggtgaagtga aagtgactac atttaccaaa agtgattgaa aagccaggac   26880
tgttcttacc ctgttttttcc agttcttgct cagagcaagg tggtttcttt ttcacttaat   26940
```

```
caccatactt actttcatg tagaacaagt cagtttgagt tatcagttca tcatcttaac  27000
taaattccat gggggaagga attagtttta gtttcttaaa cttccaggtt tgcttattgg  27060
acaaaatgag atagcaaggc agtgttttta agttagattt tttatttctt tggtaataca  27120
attttctcag aaacttagta gtcttttagt ttagttgttt ttagttggtc ctatgttttg  27180
gatcacccct ctctacttta ttttgatagt gccaactgtg aagacatctg aagccatagg  27240
tttggatggg aaggaggcat ctttagcctg atcatcttcg ccaggctgtt tatctccttt  27300
tgcttggctg agaagtctta ataggaggct tattcccagc tatttgggga catagaagca  27360
gttagccatt gcttatattt tactgaggtc tgtgtggtat gttgattgta gtcagttaac  27420
gattttgaga actgaaggca gcctggtata tatagagtag gtattagact gtgtttcttc  27480
taattgaatt tccatctct tgtaatctat gccatcatct tctgtactgc tgagaaagaa  27540
agaaagtttc taatcaaact ataccactgg ttgtaagatg cagtttggct ttagtgatgt  27600
taacacatga ttcaaacgtg aaattgattg agtattggtg aaatacagag gagatttaaa  27660
gccagaagac ctgggtttaa atgctggctg tatgacttca tatctgtgtg atcttgggca  27720
tgtcatggtt ggcacttcaa tttcttctct ctataatggg ggaagtgagg ccagtcatgg  27780
tggctcatac ctataatccc agtgctttgg gaggccaaga tgggaagatc gcttgaggcc  27840
aggagtttga gcaattgggc aacatcgtga ggccccgtct ctacaaaata ttttgaaaaa  27900
attagccagg cccagtggtg cgtgcctgtg gtccgcgcca ctcaggaggc tgagacggga  27960
ggatcctttc agcctaggag tttaaggcta aagtgagcca tgattgtgct atcgtactcc  28020
agcctgggca gcagagcaag atcctgactc taaaaaaaag taaaataaag taaaatgggg  28080
gaaatgaact gctttagtaa catcatctgt tttttctgtg agcagcgtag cttgacagcc  28140
attggtgaac tcgtgccctg tgcttccctg tccagatccc cattctgccc gcaacatgga  28200
gtataacggt ttattcatag tagtcgagaa acactcactg aatgaatgaa tgaggtgtag  28260
aactaagtgg agtgggtaat tcaacacata ttaatttcct tcttttttttt attttagaa  28320 agaaagaact ttcagctacc aagaaagacc gtgtgaatca ttgtctgaca atatgtgaaa  28380
acatagtggc acagtctgtc aggtaattgc actttgaact gtctagagaa aataagaact  28440
ttgtatattt tcagtcttaa tgggctagaa tattctttgt gtcccagcta ttttaaatgg  28500
attcagaaat ccatttaaga tgaagaagga cccttttccc atatttctgg ctatatacaa  28560
ggatatccag acactgaaat gaataatgtt ccctttttgt aatctttat gcaaaaatta  28620 aaaccattat ggtaattgaa caacatgttt atgtttagtt aacaccccta gcaactatag  28680 ttatttttaaa accatctatg gtttgatatt tttgcatttg ttgcaatagt aggaacagca  28740
caagacagtt cagtttgtct ctcttatttg ctttttcttg gcagtttgct gtcctattgt  28800
acctctgctc ctagcagtgg ctggagccca ctcctctgtg cttcgggatt agtggggatc  28860
gtggggcatt gactgtaggt cagctttcct tgcttgatct ttctcactgg gatgaactag  28920
cagcaccttc ttttgtagct gctttgcttt tgactatctt tctgaccgtt gttcctagta  28980
gctgtagatg gtaaatatat ttaggcctgt ttccaatggc tcagtaggag acatattcac  29040
ctatgatatc tgaattctgt tacccacatg ggcatgcgtg aaatagttgc cttgccttac  29100
tttcccttgg aataaataat tcatgttatt ctcctggtag aagctagaaa aagccttat  29160 agtcagtcag aaaaaaattt ttagacaaat aatcttgatt ttagtactga caaaaacgtg  29220
tggtgattct tttttttaatt tttttttgag acggagtttc actcttgttg cccaggctgg  29280
```

```
agtgcaatgg cgtgatctcg gctcactgca acctctgcct cctgggttca agtgattctc    29340
ctgcctcagc ctcccaagta gctggagtta caggcatgtg ctactgtgcc cagctaattt    29400
tgtatttta gtagagatgt tggtcaggct gatctcgaac tcccaacctt aggtgatctg    29460
cccgcctcag cctcccaaag tgctgggatt acaggcgtga gccagggcgc ccggtgattc    29520
atttgttttt tcaaaaaatt tcctcttggc cattgctttt cactttttgtt ttttttttt    29580
ttttgagacg gagtcacgat ctgtcaccca ggctggagtg cagtggcatg atcttggctt    29640
actgcaagct ctgcctccca ggttcacgcc attctcctgc ttcagcctgg cgagtagctg    29700
ggactacagg tgctcgccac cacacccggc taattttttg tatttttagt agagatgggg    29760
tttcaccgtg gtcttgatct cctgacctca tgacccgctc aactcagcct cccaaagtgc    29820
tgggattaca ggcgtgagcc accgcgcccg gccctctctt gtctttttat tgtggtaaaa    29880
tgcacataaa attgactgtc ttaaccattt ttaggggtac agttcagtat atatattcgt    29940
aatgttgtac agccatcact gccatctact tcataagttt ttcttctgtc aaaactgaac    30000
atctgtcttc attaaactcc ctatcatcca ttctttcctg tagtcccttt ctactttctg    30060
tctgtatgag tgtaactgct ctggagacct catgtaagtg gattcctaca ggatttgtgt    30120
ttttttttttg gtgatctgct tatttttaat gcctctgtgc atttgtatta tatactttca    30180
aagtgatttc acaaaaccgt tcattttag gttaactcat ttctgttgtt tgtgaaatac    30240
tgtgtatgat tctgttctgt ttctgtctaa tttgtggaaa tgttgtggga agaaaatgaa    30300
ataacaaatg agcatatgtc ctgaaaataa aaatataaaa attctaagtt agcatgctat    30360
tgtagaatac aacgctatga taaaagtagg aaaaaaaaag gtttgaattc tatctctgct    30420
acctgtgtaa gctgggtgac tttagataag ctgtaacgtg tttgagcctt actggctcat    30480
ttttgaaatg taatccctag ttacacagtt cttgtgggat cagatggtac atgtgaaaca    30540
ctgtgaaaaa gcaactgcat agatatgttc attagccacc tgagcgggaa gcgtatccca    30600
ttgcgatgcc catcatccaa agctatatgt tatctttact tttttttttt tgagacagag    30660
tcttgctctg ttgcccaggc tagagtgcag tggtgcaatc tcagctcact gcaagctcca    30720
cctcccgggt tcacgctatt ctcctgcccc agcctcccaa gtagctggga ctacaggcac    30780
ccgccaccat gcctggctaa attttgtat ttttagtaga gatggggttt caccgtgtta    30840
gccaggatgg tcttgatctc ctgacctcgt gatccgcccg cctcggcctc ccaaagtgct    30900
gggattacag gcgtgagcca ctgcccctgg ccatctttac ttttttttgtg aaatgacttt    30960
aaatacttgg caaacatttg gtcattgttc atctgatctc caccatccag gtctcagaga    31020
acataatttc tctctgaaag cttattgacc caggaaataa gatctctttc aatctgagtg    31080
cgtcaggctt tattcttgtc attttgtctt tgataatttt tcaaatggaa ttcatggaat    31140
gttggcttat attcatatat tagtaaagta tgttgagaca tcttaagatt gatttgtggt    31200
tctatatgcc atattaaatc aaaataatag ctgttaatgg ttttcacatt agtctgtctc    31260
ttgttttttat ggagtaatgc tgagagttca ttatgcttgt tctacagaag agcatgttaa    31320
aaggagtttt tggagtcaga gaggttattc ttggtttcat aggatacact ctatactttt    31380
tagggatttc agagtatata gctgaaggtg atattttatg taaatatgtt ttatggaaac    31440
ttattgctca tcgctgtttc ctgttaactc tcctaaaata taattaaact tttggaactt    31500
ttttatagct tttgtgctag actaattttt gtctctaatg aggttatata aatggcagct    31560
tctgacgttt tcaatgtagg aagtcattta aaacttcatg tatattgtga aaatgtagtc    31620
tgctttaagc tctctaaagt ggtctaagtt actggttcct aagtatggat gagcatcaaa    31680
```

```
atcatctgga aaatttgtta aaaatacagt aatgaaggca cctcactgtc cttttttccca    31740 aacatacttc tgcattctgt ttgagtaggt agggactaca cattttttcac aagtatcctc    31800 ttgggaatac ccaggaatgc ttacttgagc aacctcttac taatatgtac cttgataagg    31860
tggctaggta aacataaata tacaaaaatc catagatctc ccatatatta gcataaatca    31920
gctagaaaat ataacgttta aagatctagt tcacagtagc accaatatat cgaactctaa    31980
ggaatcgata aatatgcaaa aactttataa aaacttctgt taatgtttct gaaagatata    32040
ggtgaccact ttctagatag gaagatttta tattactaag ttgaattttc tctaaattaa    32100
cacagaaatt taaaataatc ttgatcaaaa ttctagtaga ggtattttttg aacttgttca    32160 ctgcaagaat aaatacataa ttgcaaagaa tatctcaaaa tcatcaccag gcctggtgtg    32220
gtggcccatg cctgtaatcc cagcactttg ggaggctgag gcaggcagat cacctgaggt    32280
caagagtttg agaccagctg gaccagtgcg gtgaaacact gcctctacta aaaatacaaa    32340
aattagctgg gtgtggtggt gcatgcctgt agtcccagct acttgggagg ctgaggcagg    32400
agaattgctt gaacccagga ggtacaggtt gcggtgagcc tagatcgcac cactgcattc    32460
cagcctgggc gacaagagca aaattctgtc tcaagaaaaa agagaaaaaa gaaaagaaaa    32520
tcaacactaa tatggtgaga cttaatgtat gtgacattaa aatagtgatt ggatgttaaa    32580
acaggtatag aacagaaaga agagtgtatg tgtgtatctg tatgaattta tgatgggtgt    32640
aacatatatg tattagggaa atgagggaaa tgatacattt ctctgacttt gggagaacat    32700
tatatctcta cctcatattg caaacaaaca taaagttcag attaattacc taaatgtgaa    32760
aaaatgaaat aatttctttta aaaatgtaa tcttagtttg aggaaggtta acattataaa     32820
ggaaaaaact gttttgagtg gaatatagtt caatatgtca aaatccacct tcaacaaaat    32880
tgaaagtaaa ttgaacttgg ggaaagtatt gacagcatat agatcaaagg ttactagcct    32940
gtgtaaagag cagttataaa tatcgttaag aaaaacactg tcgacctgtc ggcaccttgt    33000
tctccgactc ccagcctcca gaactgtgac gagtaagtgc ttattgttta aaccacccag    33060
tctgtatgtg gtattttgtt atagaaactc aagctgatta ggacactagt aatcagtaga    33120
ctgaaactga aacaaaaata agaacctttt ttacctgtca aattggcaaa cattaagaat    33180
attcagattt ttgtcagagg tgatacaacc ttctaagaag gcaatttggg aaaatataaa    33240
gctttagatt attatatgtc tgacctagca gttttacctc tagggtgctt accccctagga    33300 aagtgtgtaa tgatattggt gcagtgccct tcatcccatt agaaaattaa aaataacctt    33360
aatggcctac cactaaaagg ggattgaaaa tttaagatat atttatttat gtgtttattg    33420
agatggagtc ttgcactgtc cgcctgggcc agagtgcaat ggtgcgatct cggctcactg    33480
caacctctgc ttcccgggtt catgtgattc tcctgcctca gcctcctgag tagctgggat    33540
tacaggctca caccaccgca cccggctaat ttttttgtatt tttagtagag atggggtttc    33600
actgtgttgg ccagactggt ctcgaactcc tgacctcatg atccgcgccc ctcggcctcc    33660
cagtgttggg attacaggtg tgagccactg cgcctggcca gatacattta tacaagagaa    33720
tgttagttaa cattcataga tatttatatt ttgtttactt tttattaaaa aaatttttttt    33780 tagagacagg atcttactct gtcacccagg caggatgcag ttgcacaatc atagcccact    33840
gcagcctgaa ctcctgggct taagtgatcc ttctgcctca gccttttgag tacctgggg    33900 actttaggca gtgctactat acctggctaa tttttaaatg ttttatagat gagatcttgc    33960
tgtattgccc aggctggtct agaattcctg ggcccaagtg atcctcccac cttggcctcc    34020
```

```
caaagcgctg agattacagg catgagccac cacttctgac caatagatat ttatatttgt    34080
gactggaaaa tatattaaca atgtgttaaa aaattcagtt aaaaaataat gaaagatttt    34140
tgcttctggc taagatagaa taacaaggac agcatttatc ttcttgcctt gaaatagttg    34200
aaaacgaagg aaatatatgt aacagtggtt ttcaagttat tgggcatcag gcaaagaaga    34260
atagttatcc caggaaaatg aatgtggaga gccctacaat ttccttacat tactgcctgg    34320
tcatggcaag aggaaaaact gagaggagac tgaggctgag ccagtggttt gctgggttga    34380
ggaggcagag ctgggagtgc agagatgcaa ggtggtgaga gcccatatgg aagaatacca    34440
gggaagagag ctgcagaggg agctccggag acctgcaccc tgccctctca gtaccctgtc    34500
atgtgtgtag ctgagtactg acgagcactt gcttgtgcgg aaatgaccca gggctggagg    34560
tagagccacc tgaaaggatt agaaggaaca gttgctgaaa gtcacacagg gccaggaaga    34620
atttctaatc acaccagttg gagtggaaaa cctcagctct catagagcag gtagggtact    34680
cagaagggtt tgcccaccta gccccagact aagtttcgtt actctgaccc tacctaatat    34740
taaaagagag ttaattaaat tgttcgcaac aaaaataata tatttcagtg tttgtaacac    34800
gtagaagtga attgtatgac aatagcataa aggctggaag agcagaaatt gacatgtatt    34860
tgcgctgggc agaataatgc tcccctcttt ccccaaaaga tatcaagtcc taatccctgg    34920
agcctgtaaa tattacttta tatgaaaaat tgttttatga tgtgattaaa ttcaggatct    34980
tgagatgagg gggctatctt ggatgatctg ggtaggcact aaatgcaatc acatatatat    35040
aaaaaggagg cagagggaga ttttacacac agagagaagg ccctgtgaag atggaacaga    35100
aagatttgaa ggtgctggcc ttgaaaattg gagtgatgaa gctataagcc aaggaatgca    35160
gcagccacca aagctggaag aggcacggag cagttctcat ttagagccta ctccagaggg    35220
aatgtgtgtc tgccaattcc ttttttttt ttttttttaa gatatcattt accccttaa    35280 gttggttttt tttttttttt ttttttttta gtatttattg atcattcttg ggtgtttctt    35340
ggagaggggg atttggcagg gtcataggac aatagtggag ggaaggtcag cagataaaca    35400
tgtaaacaaa ggtctctggt tttcctaggc agagggccct gccacgttct gcagtgtttg    35460
tgtccctggg tacttgagat tagggagtgg tgatgactct taacgagtat gctgccttca    35520
agcatctgtt taacaaagca catcttgcac cgcccttaat ccatttaacc cttagtggac    35580
acagcacatg tttcagagag cacggggttg ggggtaaggt tatagattaa cagcatccca    35640
aggcagaaga attttctta gtacagaaca aaatggagtg tcctatgtct acttctttct    35700
acgcagacac agtaacaatc tgatctctct ttcttttccc acatttcctc cttttctatt    35760
cgacaaaact gccaccgtca tcatggactg ttctcaatga gctattgggt acacctccca    35820 gatgggtgg cggccgggca gagggctcc tcacttccca gatggggcgg ccgggcagag    35880
gcgcccccca acctcccaga cggggcggcg gctgggcggg ggctgccccc cacctcccgg    35940
acggggcggg tggccgggcg ggggctgccc accacctccc ggacggggcg gctgccggg    36000 cgggggctgc ccccacctc ccggacgggg cgggtggccg gcgggggct gcccccacc    36060 tcccggacgg ggcggctggc cgggcggggg ctgccccca cctcccggac ggagcggctg    36120
ccgggcggag gggctcctca cttcccggac ggggcggctg ctgggcggag gggctcctca    36180
cttctcagac ggggcggctg gtcagagacg ctcctcacct cccagacggg gtggcagtgg    36240
ggcagagaca ttcttaagtt cccagacgga gtcacggccg ggcagaggtg ctcttcacat    36300
ctcagacggg gcggcgggc agaggtgctc cccacttccc agacgatggg cggccgggca    36360
gagatgctcc tcacttccta gatgggatga cagccgggaa gaggcgctcc tcacttccca    36420
```

```
gactgggcag ccaggcagag gggctcctca catcccagac gatgggcggc caggcagaaa    36480
cgctcctcac ttcctagacg gggtggcggc tgggcagagg ccgcaatctt ggcactttgg    36540
gaggccaagg caggcggctg ggaggtgaag gttgtagtga cccgagatca cgccactgca    36600
ctccagcctg ggcaacactg agcactgagt gagcgagact ccgtctgcaa tcccggcacc    36660
tcgggaggcc gaggctggca gatcacttgc agtcaggagc tggagaccag cccggccaac    36720
acggcgaaac cccgtctcca ccaaaaaaca cgaaaccagt cagacatgg cggtgcgtgc     36780
ctgcaatccc aggcacttgg caggctgagg caggagaatc aggtagggag gttgcagtga    36840
gtagagatgg tggcagtaca gtccagcctt ggctcggcat cagagggaga ctgtgcgagg    36900
gcgagggcga gggcgaggga attccttaat ttcagtttag tgatactaat tttggactct    36960
ggcctctaaa actgtgaaag aaaaaatttt ttgtttgttt gtttctttta agccacatag    37020
tttgtggtaa tttgttacag cagctgcagg aaactaattt atgctgcatg tgaaatggtg    37080
taataaggta gattgtgatg aagatacata gtataaacaa ttaagcaaca actaaaagca    37140
caacaaggaa ttatagctaa tgaaccaaaa aaggagatta gaataataaa aatggtgaat    37200
cccaaagaag ccagaaatag gggaagaggc aaataaagga aagaaagagc ttgatggtag    37260
atttcaacct aactatgtca aaaaggacat tacatgtaaa aggcagcgat ttttcagatt    37320
gaatggaaaa gtaagactcg gtatatgctg ctgcctgcaa gaaacacatt ctaaatataa    37380
aggcaaaaat aacctacagg taacagaacg gaaagaagtt cactgtgctt acaagaatta    37440
gatgcaagct agactggttc tgttaatatc agacaaagtg gatttcaaag caaaggctct    37500
tgcccaggat gagatggtca tttcataatg atgaagggga ttcgttcatc agcctggcat    37560
agcaagctga aatgtttatg caccggacta cagagctaaa atacatgaag caaagcctga    37620
cagaactaca agtagaaaca gacaaatcca cagtgataga gatttcagta gccgctctca    37680
atgatttgta gaacacgtag ccataatatc tggatctaga acacttgacc aacactgtcc    37740
cctgtgcaac ctcattggca tttacaggac actccaccca gcaccagcag aagagacact    37800
ctctcaagtg ctcacagaat gtttgccaag atagagcaga tgctgggcca taaacaagt    37860
ctctaaatta aaagcattca aattattcag agtatgtttt ctgacctcag tatcattaag    37920
ttggaatata ttataggaag ataacctgga aaagcctcag atatgtggaa aaacccatt    37980
ccacatggcc catgggtcag aagtgaagtc aaaagggaaa tttgaaagtc ttttggattg    38040
actgatataa aaacaataga tttctaaact tgtggggtgc tgttacagca tagtaaatgg    38100
aaatttctag cattaaatgc ctgttttagg aaagaaagat ttcaaatcaa tgacctcagc    38160
ttctaccttt ggaaacttga aaatgacaag caaatggaat ccagagttac cagaagggcc    38220
aggtacggtg gcttatgcct gcagttctgc cactttggga ggccgaggca ggtggattgt    38280
ttgagactgg cagttgaaga ccagcctggg cagcctaggg agaccccata tctacaaaaa    38340
acaaaaaaat tagccaggtg tggtggcatg tgcctgtagt cccagctaac caggagtcta    38400
aggtgggagg attgcttgag tctgggaggt tgaggctgca gtgaactgtg attgtgccac    38460
tgtgttccat cctgggcaac agaatgagac cctgtctcaa aaacaaaaac agttactaga    38520
agaatggaca tcataaagat aggagcagaa gtcagtaaaa tagaaaacaa aaatacatag    38580
gaaatcaata aaaccaaaag ctggttcatc aagaacatca ataaattggt aaagctgata    38640
ggaaaaacag tgaagtcaca aattagcaat atcaggaatg agggagatga cagtagtata    38700
gattatatag atattaaaag gactgtatga ggcaggtgtg gtggttcacg cctgtaatcc    38760
```

```
cagcaccttg ggaggccgag gtggacagat cacctgaggt caggagtttg ggaccagcct    38820
ggccaacatg gtgaaactct gtctctacta aaaatacaaa aattagttgg tcgtggtgct    38880
gtgtgcctgt aatcccagct acttgggagg ctgaggcagg agaattgctt gaacctggga    38940
ggcggaggtt gcagtgagct gagattgtgc cgttgcactc cagcctgggt gacagagcaa    39000
gactccatct caaaacaaat aaataaataa aaaggactat atggtaatat tatgaacaac    39060
tttatgccaa taaatttgac aacttataga tgaaatggat gagttccttg aaagacacag    39120
aaactattaa agctctctca agaagatata gataagctga ttagccctat atctatttta    39180
ttgaatttaa atgtaaaaat caatatttag ttactggaaa acttttaagt gtggttggaa    39240
atggtatacg aacttttttca actgaatttt atgaagtcta atcacaggta aaggttttct    39300
gatgaaaatt tagtgtctga attgagatat actgtaaaaa atgttatata tcttaattat    39360
ttcttcacat taattacatg ttgaaataat actttgggtg tattgggtta aattaaatat    39420
tatgaaaatc ttgcctgttt tctttttact tttgatgcgt cagctaggaa atataaaagt    39480
gtagctcaca ttctgtttct gttgacagta ctgcttggaa gcacagtgtt tgaatgatct    39540
atcatttcaa agacctttcc tcagttcgtt attcatggct gtctgtattc cacatagata    39600
aggtctgaaa tactgctaag tggcatgttt tgttttatgc ttttataagt ttgttgatca    39660
ttactgatgt ggacttttgg tgcctcttag gctcattgct atcttccaac cattgtttgc    39720
aattttttacc tagagataaa gagaaagaga catttggttt cagagtagtt agattgggat    39780
catgaaagag caacctcatt ttgatgcttc aaaaatagca catccccgt attactggga     39840
tttgctattc ttgggattac ttcaagaaca tccttgtgtt actggtttgg atgcttctga    39900
atgctgtgaa gtcagtttca tgtacatggc tcatcagttt agctctctct tggctttgtt    39960
tagacagttg gagcatgatg gcctaaacag cttctttcaa ttaaacattt taaaatagtt    40020
tacaaatagt aaacaaactc cagttttttgt gactctttgt ctcgcacaac aaaaacacaa    40080
tctgaccatg atcatctggc atcttagggt gaaatatggt tatactttgg cccataccga    40140
aagcaagatt aaaaaggggc aggagagata gactgctgaa ctgattttca aggttccaag    40200
aatattgtag gttaagagta aaagtaaaact tttggtagaa agcagtgggt tgtctaggat    40260
tgaagtatct gaagttttta aacgaaaatt taaaagaaa aatgagaatt gccttacaag    40320
tacaatctct tctttttttaa aaaataaact ttattttgaa atagttttag atttatagaa    40380
aaaaattaga tagggtagga agttttcata taccctacat ccagttaccc cagttattat    40440
catcctaatt tagtgtgaga catttttcatg tttaatgaat caatattgat atgctattaa    40500
cttaagtcca gactttattc agattttctt aatttctatg taatgtcctt tttctgttcc    40560
agaattccat gcaggacacc ggatacctca ttacatttca ttgtcatgtc accttaggct    40620
cctcttgaca gtttctcttc tttttttgct tagaaattct ccagaattttc agaaacttct    40680
gggcatcgct atggaacttt ttctgctgtg cagtgatgac gcagagtcag atgtcaggat    40740
ggtggctgac gaatgcctca acaaagttat caaagtaaga accgtgtgga tgatgttctc    40800
ctcagagcta tcattgttgt aggctgagag aagaagcgat cattgagtgt tcttctgttt    40860
tgagtccctg aggatgtctg cacttttttc ctttctgatg tatggtttgg aggtgctctg    40920
ttgtatggtt tggaggtgct ctgttgtatg gtttggaggt gctctattgt atggtttgga    40980
ggtgctctgt tgtatggttt ggaggtgctc ttgtatggtt tggaggtgct cttgtatggt    41040
ttggaggtgc tctgttgtat ggtttggagg tggtcttgta tggttgcag gtgctctatt    41100
gcatggtttg caggtgctct attgtatggt ttggaagtgc tcttgtatgg tttggaggtg    41160
```

```
ctcttgtatg gtttggagat gctctattgt atggtttgca ggtgctctat tgtatggttt    41220
ggaagtgctc ttgtatggtt tggaggtgct cttgtatggt ttggaggtgc tctgttgtat    41280
ggtttggagg tgctctgttg tatggtttgg aggtgctctt gtatggtttg gaggtgctct    41340
attgtatggt ttggagatgc tctggtatct gcctgcattg cttgccacac ctgcccggtc    41400
agaaggcgct atgttgacaa ttgtgcctgc acggtgccta ggtcaatgaa gggaaccgat    41460
ggtagccact ggatgctcct gggaaaatgt cactacaggc accagagaag ccagagctat    41520
gcccaaattt ctatgagtct cagttttctt aaccataaaa tgggatcaat gttttgtgg     41580 catgtgtatg agtgtgtgtc tgtgtatgtg tgaggattaa attgtgtatg tgtgaggact    41640
aattgccact actggatcct caaagtggta agaagtgttc ttattaataa tgacatcctt    41700
acactcttac ccagcaagat tgatgggtgt ggcactgctt ctcttttttcc atcacatggt    41760 ttccatggta tccttttgcc cagggaatct ttgctttgtg gctagcactt tgttgtttgg    41820
ctaatcacgc tttctgtggt caggacgctg gcttctctgg agccatggga ttctagctcc    41880
ctgtcttgtc cctagagtgg tcactgtctt ctctctccgc ttgcaattcc tgctttgctc    41940
gcatctcact tatgcagtga cgtatatcag tttcaccttg ttctccgtgc ctgctgatca    42000
ttggcaccac ttgcatggtg ccatttaggg cctgcttcca gttaagcttg cttctccaca    42060
ggcctaaata tccttgcttg cttcttttat tctcactggc aggaccaggg cggtctgtct    42120
ttgcatgaga cagggtctcg ctcagtcacc caggctggag tgcagtggct gatcacggct    42180
cattgcagcc ttgagctacc gggctcaagc tatcctcctg gcttggcccc ttgagtagct    42240
gggactacag gcgtgcacca ccatgcccag ctaatttta aaattatttg tagagatggg    42300
atctcgccag gttgcccagg ctggtcttga acgcctgggc tcaagtgatc ctccctcctt    42360
ggtttcccaa agtgctggga tcacaggtgt gagccactgt gcctggccct tgatgtttca    42420
gttcttgata tttgatcctc agagtcagaa aatctaaaaa gagggctatc ccaggttgcc    42480
ttggttcatg gcaaatggga cgttaagagg gcagagagaa tatgaacaga aactgttcta    42540
atattggtca tttaatgtgt aagtattgtt cttttttaaa cctccttcat ttttttttcca    42600 ggaattgctg gacacagtgg cttggtgtgt gtctgaggac tgtaggccat ggccctaggt    42660
tgtggtttta ggtctcaggt gctcttcctg gctgtctcct tgcttctttc ccatgtcctc    42720
ttctttgttt ccagccattt ctcccttatg cttaagtttg gtgcagcagg gtttggctgc    42780
tctcagattc ctgcttcctc agatgctgta gttgtcaggc ccagcgggct ggcagcggga    42840
tcaggatctg gctaggtttg ctctcactgt ggcagagtag ggggaggcgt gggagagcac    42900
gtgtgacccc aggccagctg tagggagcat aggcatggtc acgtagcctt caggtcctag    42960
actttgtctt ctcatgagta tggctgtgtg tgtatggtga aaactaggtt ctacttagcc    43020
caagaaaatg ggcacatttt gcatgtggtt tctgtagaga aatgcactgg gtatctgaca    43080
tagcctggca gcatgcctcc ctcaggtagg ttagtctcag gcggtgaagc acgtgtgtcc    43140
agcaagaact tcatatgtgg cataaagtct ccgttctgtg aggtgctggc aaatcaccac    43200
caccgtcaag aggctgaagt gattttttgtc tagggaggca ggaaaggctt cctggagtca    43260
gcagccagta ggtgaaagag tagattggag accttcttaa tcatcaccgc ctcttgtctc    43320
aaggggtgcc aggaagctgt ggaggctgaa cccatcttat gctgccagag agtgggacac    43380
catgagggtc aggtcaaggg gttgtacctt gtttggtaga gaattagggg ctcttgaaga    43440
ctttggatgt ggtcagggga gtgtatcatt taggaagagt gacccggtga ggacgtgggg    43500
```

```
tagaggagga caggtgggag ggagtccagg tgggagtgag tagacccagc aggagtgcag    43560
ggcctcgagc caggatggtg gcagggctgt gaggagaggc agccacctgt gtgtctgcgg    43620 aagcagggc aagagggaag aggccagcag cgtgctgcca tcacccagcg actggcgtag    43680
attgtgagag accattccct gctcttagga ggggctgagt tttagttttc tcttgttata    43740
caataagctt ggtatttgtt tacaaaacat ttgtaaagct aaatcaaggt ttgataaggc    43800
ttctagtttt atttaagaag taatgttgaa ataaatgttt gtccaattcg ctttgctcat    43860
ttaaggactt tcagtacaaa ctgcaacaac aggattagga tttaaacgtt tctgagatgt    43920
ttttactcct cagaatttcc cagaatgtga tctggttttg attttcaagc ttgctgaccc    43980
aataggttaa cccacaagtt ttacgaagac catctcagtc cacttacatc aactgcccat    44040
gccacggtta aagagatcat cgactgatgt ttggcacagc ttcctccctc ttgggtgggc    44100
aagcatttgg aagagaaggc tcctatgggt gagagtgggg caccaaagtc ttccctgtcc    44160
catcccctag cttgagaagc ccttctctaa tgtggacttt gtgccgttag catcgttact    44220
agcttgaagt tgaccatctg gacgtacttt ctggtttagc ctcacaagtg agcaaggagg    44280
gttgagagat gtgctgtgag gaatgtgggg ccccagctgg cagcaggctc tgggtcaggg    44340
gggcagggac cacgggcata cctgacagtg aggaggggcc acacctgcag aaaaggatgc    44400
aggactccgc cttgggaagt gttctaggcc agagcgaggg tctgtggttt ataagtacac    44460
ccacagtgct cgggaccctg cagatgtcca gggtgccgtc tgagcccgta tcatccaaca    44520
gaatgttctg ctagtgaaga ttaaagattt actccagggg ctttaggatt tattatatat    44580
atataaatcc tatatatata attttttttt ttttttttt tgagatggag tttcgctctt    44640
gttgcccagg ctggagtgca atggcgtgat cttggctcac tgcaacctcc gcctcccggg    44700
ttcaaactat tctcctgcct cagcctctcg agtagctggg attacaggcg cccaccacca    44760
cacccggcta attttgtat tttttagtag agacggagtt tctccatgtt ggtcaggctg    44820
gtcttgaact cctgacctca ggtgatctgc ccgccttggc ctcccaaagt gctgggatta    44880
caggcatgag ccacccccacc tggccaggat ttattgtatt tgaaccatct accattttaa    44940
ttttgatgtt atgtagtatt tgatgataat gaaagttaaa ttgttttttct ttccattttt    45000 ctgtttaagt gaatgacctg tatctagttt attcagtaac ttcctgcata tatttgtttc    45060
tttcattctt aatgaatata ttcttaattt agttgctatt atgttttgct ttgccccaaa    45120
attgaaatct tagttcctt ttagctcgtt ttagaactag tgatgggatg tgtcttccat    45180
aaatctcttg tgatttgttg taggctttga tggattctaa tcttccaagg ttacagctcg    45240
agctctataa ggaaattaaa aaggtgggcc ttgcttttct tttttaaaaa tgttttaaat    45300
tttaaatttt tataggtaca cgtatttgt aggtacatgt aaatgtatat atttatgggg    45360
tacatgagat attttgatac aggtatacaa tacataataa tcacaccatg gaaagttgga    45420
tatccatgcc ctcaagcatt tatccttttgt gttacaaaca atccagttac atgctttact    45480
tattttattt tatttttgag acagagtctt gctttcaccc atgctagagt acagtggcat    45540
gaccttggct cactgcaacc tccgcctccc gggttcaacc gaactttggg ctggtctcaa    45600
actcctgacc tcaggtgatc cgcccgcctc ggcctcccaa agtgttggga ttacaggcgt    45660
gagccactgt gccgggcctg attgtacatt ttaaaataac taaaacagtc agggcacagt    45720
ggctcatgcc tgtaatccca gcatttggg aggctgaggc aggtgatcac ctgagatcag    45780
gagttcgaga ccagcctggc caacatggag aaaccctgtc tctactaaaa atacaaaaat    45840
tagccaagtg tggtggcggg cgcctgtaat cctggctact cgggaggctg aggtagggga    45900
```

```
atcgcttgaa cctggggtg gaggttgcag tgagccgaga tcacgccact gcattccagc   45960
ctgagcgaca gagtgagact ttgtctcaaa aaataaaaat gaaataaaat tgggccgggt   46020
gtggtggctc acaccttagt cccagcactt tgggaacctg aggcaggtgg atgcttgaga   46080
ccaggagttt gagaccagca tgggcaacat ggcaaaacgc tgtctgtaca gaaattagct   46140
gggtgtggtg gtgcacaact atagtctcag ctacttggga gattgaggtg ggaggattaa   46200
ttgagcctgg aaggttgaat ctataggtag ctgagattgt gccactgccc ttcagcctgg   46260
gcgaccaagt gagaccctgt ctcaaaagaa aaacaaaaaa acaaaaaaca aaccactatt   46320
atcgactata tattattgtc tatgatccct ctgctgtgct gtcgaatacc aggtcttggg   46380
cccttatttc catcactgag caaacttcac tctgttaagc agcaggtgtg ggatttcatc   46440
gttattcagt aattcacaat gttagaagga aatgctgttt ggtagacgat tgctttactt   46500
ttcttcaaaa ggttactctt tattagatga gatgagaatt aaaaatggta acttacttta   46560
tatctttata attgaagccc actagacctt aaagtagtta ccagatgttt tatgcattta   46620
aatggccttt tctctaaaat tagaaagtaa caaggaaaga aaatgcttcg tttctatgca   46680
accctcttgg tgactagtat gtgactctta atgcaaccct cattgcaccc cctcagaatg   46740
gtgcccctcg gagtttgcgt gctgccctgt ggaggtttgc tgagctggct cacctggttc   46800
ggcctcagaa atgcaggtaa gttgtacact ctggatgttg gtttttgtcg ggggccagct   46860
gctactgatc ctttatgtct cagctcagat gtcatttcaa aagtctgctc tgccctctcc   46920
aaattgcagt cgaccttgcc ctgtttatgt ttccctcata gcactaatcc atgtcagaaa   46980
ttgtcacgta cagtctatct gtgtgcttgt ttattttcta tcccacccct ccgcaagaga   47040
cttatgggat gtgtgcccca ggacagcagg ggtcttactg tcttatgctc tgttgcagcc   47100
cagcagcgat aacagtgtct gcacatagta cttgcttaaa agatacttgc caaattgttg   47160
aaggttgagg taccaatttc attattgctg actataggag ttatagcaaa atatccattt   47220
gtctgttaca tgagttaaaa atatggttgt tgcactgtga atagtttggt ttagtcaaaa   47280
cagttgtatc ttaacggatt gagaaacaaa agcaggacca cttttcatca gctccctcct   47340
tctccttaac cagcaataca tgctgatgct gatatcccat agaccctcag ctccatcctg   47400
agtcactggg aatgtggtct aaaccctcac tattaatatg aactgagttt caataagaat   47460
cttatatggg tcgggcatag tggctcatac ctttgatccc agcacttcag gaggccaagg   47520
caggtggatt gcttgaccca gactaggcaa catggtgaaa cgccgcctct acaaaaaata   47580
caaaacttag ccaggcatgg tggtgcgtgc ctgtggtcac agccactcga gaggctgagg   47640
tgggaggatc acttgagcct gggaggtgga ggtcgtgttg agccaagatc gcaccactgc   47700
actccagcct gggcaacaga gtgagacctg tctcaaaaaa accaaaatcc agaaaagaac   47760
ttatatggct gcagaggtat aatcactaag gaaatttcct tttgtataat cttttttctt   47820
ttactatcat ttaaaaaaat gtgttatatt tctgaagcaa cacatccagg ttctgcacat   47880
agcagccaaa gtgaccttaa agaatataac tgggtcttgt cattccctta tttaaactct   47940
tgtacccatt tcccagtgcc gtttagatag agattccaga ctcgtcaatg gctctgtcac   48000
ctcagacacc ctgcattgac tcattagtct gattagagtc aggttttct tcctcctgat    48060
ggttttttt tccccttag ttctcagcgg aacagtcact tccttaggga ggtttcccca    48120
gccaccctct gaggccgtgc ttgttgccag actctgccac tagagggcag ggctgcacca   48180
ctcctggcac ctcgcacccg gcctgccctg tcactctgtg tgttgggtga attcctgtga   48240
```

```
tctgtgactc actgctctgt gtcctacaca ttcggctttt cttctctccc cacaacccca   48300
ttttataatt ctccttttc aggaaagctt tattcccatt taaaaatttt tgttttaaa     48360 atggtatttt cttacactta ttttctaatt aaaaatgagt gttttaagaa gtattatgat   48420
ttactgcaaa taattttaa acccagcctt ttagatcctc tgtgatcata agagaaatga    48480
aggatgtctc ccaacacttg agcttcatcc acatttcatc ctcctgttct ttcagctgag   48540
ttttccccat cccattaggg actgttggaa tataaaactg gcttttccct aacagggaat   48600
gaattgcttc tgtttctcct gaaggagagc tggaagaatg acttgcgttc ttttgcatac   48660
acaggcctta cctggtgaac cttctgccgt gcctgactcg aacaagcaag agacccgaag   48720
aatcagtcca ggagaccttg gctgcagctg ttcccaaaat tatggcttct tttggcaatt   48780
ttgcaaatga caatgaaatt aaggtatgat tgttgcctca ggtcacaaac atgcgagtga   48840
tgctgtgagt gagtctgtgg agggtgaggg cttctgaaca gggagtcctg tgggagtgct   48900
tcttggggta tgttgtatgt cgtaatttag actaccatca tttgtgttat ttttgaggca   48960
cctaaggact tctttccact tctcatttct tactgtgggg tgaagagttg aattgggaga   49020
tggtttctag atgcaaattg aaaaggcatt tttccagagc agatttgttt tcggcgtact   49080
agagtgactc tttaacctag ctgcgggaag atgactgtgc caagactgca ggtaggaaa    49140 agctcactga cgaggccttg tgggtctgaa cgtcctgcag ctatcagagc ctgttggctt   49200
cctgttgtgc attccaacaa atcatcttca aacccacttt agtgttttgt ttataatgtc   49260
cagaaatagt gaccctgtca catgctctac agattacagg attcttagcc tcttccttt    49320 tggtaggtca gtcctgggtt tgagcccaag tgaccctcct gggaggtgat gatacacact   49380
gggtagagtg gaatcagatg gacttggatt agaattctgt cctctttact agttatttc    49440 ctctaggcaa actgcccaac agctctaagc tatttccttc gtattctgaa aaataagcct   49500
taatgggacc catatagggc aactctgaga gtaaaataaa ggaatatgtg ttagagtgta   49560
gcatagtcac ccacgggaag ggcttagatg ttagctgcta ctgctcttat tagctgaatg   49620
atttggaata aactgttagc ctctctcatg tttttttctct tgagcttcga agttttcttg   49680
ttaatactaa ggagatattc aaactagtca tggggttttg gaatgacgaa gggagatgat   49740
gaatctaaag aatttagtgt aatatttctt catgctcagt aaatggtagt ttctgctgct   49800
gttattttta ttaccatctc tttggaatgg gagtaggtgc tcctttgtgg tcagaggctg   49860
tgagagctcc acagcgccag tttgcccatc tgtacactgg ggtctgttga aggcagtccc   49920
ctctgtgata tctctggctg tcagagctca gatgatagat ggtattttg tactcttagt   49980 tctcatcatt ttcatgattt cgatcaccat ttgagtatga tgatgctaac actttgttga   50040
acgtagaatc cgttaattac ttccttcctg aacctttggc attaaaaaaa atctattctg   50100
ctacctctct gctcatttat ggttattcaa atttattatc aagagcctgg tacagtggct   50160
tgtgcctata attgtagcta cttgggaggc tgaggtagga ggattgcttg aggcaggag    50220 tttgagacca gcctgggcaa gatagtgaga ccctatctct aaaaaactg aaaaaaaatt    50280 agctggacat gatggcatgt gcctgtggtc ctagctactc aggaggctga acaggaggc    50340 tcggttgagc ccaggagttg gagttcgagg ctacactgag ctgtgattgt gccaccacac   50400
tccagcatgg gtggtaaaac aagatgccat ttcttaaaaa aaaaaatat atatatat      50460 attatcaatg aaattcagta gtaccaacag gattataaac aaagatagta gttccttcc    50520 tacttttct cttaatcctt gtgtctcaca ggcaaacata actcttagta tttcttccaa    50580
tatttacttt catgtttctt tctttctttc tttttttttc tttgagatgg agttttgctc   50640
```

```
ttgttgccaa ggctggagtg caatgacgca atcttggctc accacaacct ctgtctcccg   50700
ggttcaagcg attctcctgc ctcagcctcc tagtagctgg gattacaggc atgcatcacc   50760
acgctcggct aattttgtac ttttagtaga gatggggttt ctccggggttg gtcaggctgg   50820
tctcgaactc ctgacctcag gtgatcctcc cacctcagcc tcccaaagtg ctgggattac   50880
aggcgtgagc cactgcgccc agcaacttcc acatttctaa ataacatgct tctactgcta   50940
tttttttttt caattttaga catttttta ctttcactat agttctatca gaattcagtg   51000
tgtacgttat tatgcctaag taaatagtca tggttgctta cgtattatat ttctttgatt   51060
gtgtttctta tttgatgaga aagctgtgtt ttttgctctg ggttgaaact ggagagagga   51120
cctggggagg aggaggagga cagatgaagt tggtgactgt accttcatgg ccatagctgg   51180
gttctcagca cccggggatc tgctgatcac ctactcatag gccaggcccc tatcgaagtt   51240
ctaggtgacc cagtgctggg gacggggggg ccacctgcaa ggtctaatca tggaggtggg   51300
ggctacagtg ttggcttgtg ctggggccag catccttagg aaggcatctt ggaggtggag   51360
gagacagccg cccacttctt gattgggggcc ttcagcagca ccagcttctt gggcaggctg   51420
gtgctggctt tcatcaccat gtcgtgttca atcttcttcc agatcctgac ttctaggttc   51480
agctttcctc agaccctggt tcctttcaga ggccattgct gctgccttgc tcttctgctgg  51540
cttgtgcctt gattatatgt cttttgtacaa cttttgttt tcctggagtt aatcttcaca   51600
tctgttttct tggagttaat cgttacctct atatcgcttg cttattattc tttggccttt   51660
ttgtcttctc acaccttcca acttctttgt aatatgtgtt tagtacaatt tttcatgaca   51720
ggtagtttac tgaatcagtt ttttccccagt gtggtcatcc aacttgagtt atccagctct   51780
ctgccccagt ctgggcaggt tgatcttcag gtctgtagta cacttgtatc ctaggacttc   51840
tctttgccat tagcctggaa tttcctttgc agttctcccg ttggatgccc agttcctaga   51900
tgccatatgt ttttctatcg tctagtagct tcctgagaga agatgaatgg gagggaaatt   51960
gtatgaggtt ttgcattcat aaaaatgcca ttttttttcc tgtacacttg gctgggtatg   52020
gtgttctggg gtagaaatca ttttccctca gaaatgcaaa gtctttgccc tgttgtctta   52080
aaatctccaa cgtgacccga ttccttaacc tatgaatgta cttttctttg gaagctttcc   52140
atttttgggg aggtgaagtg ctaggtactt agtaggcctt ttaatttgga aacttacatc   52200
ccttcagttc tgggaaaatt ttcttaacat ttctctgaga agttcttgcc tttttatttc   52260
tgtgttctct cctgaaattg gttagttgga tgttggtcct cctagattga ctcacatctt   52320
accttttttct tttctttttc tggtactttt tagatatcca tctcaaactc ttctattcat   52380
tgttatgttt ttaacttctt tcttttctttt gtctcttgat ggggtcttgc cctgttgccc   52440
aggttgtggt gcagtggtgc gatcatagct cactgcagcc tcaaattcct gggctcaagc   52500
agctgttctg cctcacccctc ccaagtagtt gggactacag gtatgcacca ccacgtccag   52560
ctattttctt tacttttttt tttttttttt tgagatggag tcctactctg tcgcccaggc   52620
tagagtgcgg tggtgggatt ttggctcact aagcctctg cctcccaggt tcaagcagtt   52680
ctcctgcctc agcctctcaa gtagctggga ttacaggtgt gcaccaccat gcccggctaa   52740
ttttttgtatt tttagtagag ccagagtttc accatgttgg ccaggctggt ctcgaacgcc   52800
tgacctcagg tgatccgcct gccttggcct ccgaaagtgc cgggattaca ggcgtgagcc   52860
catcattaga tctttaaata ccagtatcta taagtctttt cctcttgagt cagctagtat   52920
ccctggaagg aaattactca ttttcctgct tggaggctat aagcttggct atgtttatcc   52980
```

```
tgcaaccggg gactggaagg gaggggactg acagtgttgc tggtcagggt gccctcttac   53040 ttttttgtttt ctgtgtgcat ctcacgtctg tcctcagcct atgtaaacac ctcttgagat   53100
tatccctctc aatctttgcc ggaggtgggg gaggggctgc ttcctgggct gccttggatt   53160
ggagggaaga cctcaggtga gtgggtggga atttgcccaa ggagccatga gaccagccac   53220
tatttcaccc tctccatccc tccactttca gatgtatgtg gcgcctccaa agcccgagct   53280
cttcttggcg tctgtggctt caataagctt gcttttttgct ggtatccctc ctaccctccc   53340
ctgtccccag caaagcttgc atttgaactt cttcctacgg gctaacaaat cagtcagtta   53400
tgtagctctt gttacttttt agcttccgaa gttttgttga cacccgtagt ctgctaatgt   53460
ccctgttctg ttctttctgt tcgtgtaaat atatgcttta tacaacttct ttacatgatt   53520 tttgtgggggt ttctgggtag cagagcttca caagttcaat ccagcgtgtt ggattagaaa   53580
tctcccaccc tctggtttat tcttattctc aaaattacct gccaaacact gatactccct   53640 tgttttttcct tttcctgaca ggaaatgtac ataccataca ggacagaaat cattagtgta   53700
tcccttggtg aataaccaca aagtgaactt aaccccttgta accgccaccc aggtcaagac   53760
agaatattac caagcactca gaagcctctc ccctattccc ccgtcactgc tcctgccttc   53820
ctccccaagg tcatgactgc tggcttctaa ttccagagtc tgttttttaaa ttctgtgtac   53880 atagaccatg gattaagtgt tcttttttgtc tggtttattt tggtcgacat taagttcatg   53940
agagtcttct atattatcgt gtgtattagt attcctgtag ttttaggagc ttcatagcat   54000
tccattgtag ggatatacca cagtttattc attgtattat cactgggttg tttctagttc   54060
ttggctattg cgagcagtgc tactgtgacc actcttaggt gtgtcttttg gagtacatgt   54120 gcaggttttcc atcttgcaca gctagaggtg gagttgttgg gtgatagggt gtgtgcatct   54180
cagctgcagt agaaactgcc aaatagcttt ccttgagtgc ttgtaccagc tcacccttt   54240 gccactgtgt atggggattc caggagctct ggtcctcgct agcacttgga attgctgatg   54300
cttttactct tagccttcct gatgggtgtt ttctggaatc acattatgat tttaattccc   54360
attccttaaa gtaccccttgg ctctgaagtt taatgattca tgcatctctt cccttttgaa   54420
gtactcttac aggtatgttg tgcatgtgtt gaaaagtggc actatctatt ctaaaataca   54480
gtatgcctcc tctgtgtttg aacagttgta gcgtggcctt ggggcctcct gttagctggc   54540
ttggagaagg gattctttggg attgtagaga ttagacctga ggaggcccct tggagctctc   54600
tgactaaatt ttattctttta ttattccaaa ctatttaagc tcaccgtgtg ctgactcatc   54660
ataataatga gtagctctca ttgtgcttgt ctatttggac tcatacaatg atttttttttt   54720 tttctttgag acagagtctt gctctgttgc ctaggctgga gtgcagtggc acaatctcgg   54780
ctcactgcag cctccacctc ccaggttcaa gtgattcttg tgcctcagct tctcaagtag   54840
ctgagactgc aggtgcgtac caccatgcct ggctaatgtt tgtattttta gtagagacgg   54900
ggtttcacca tgttggccag gttggtctca aactcctgac ctcaagtgat ctgccttctt   54960
cagcctccca aagtgctggg attacaggtg tgagccactg agcttggcca aagtagtttt   55020
ttaagatgtt agtatctttt cttgcagcta aaaaagtttg tcagagatga ttctactttg   55080
ttctccaggt gttttctcag ggagaaattg gaggcagtaa gccactgggg gagtcctgtg   55140 gctgggggt ggggtagtcc tgtggctcct tgtcagggag tcctgtggct ggcaaggaga   55200
gaagtcctgt ggctggggttg ggagggagtc ctgtggctgg ggtctcatcc tgtgcctaac   55260
agtgtccaga ggtgccgaga ccagctcagt cggggagacc ctaacccagc agcgctagag   55320
gaattaaaga cacacacaca gaaatataga ggtgtgaagt gggaaatcag gggtctcaca   55380
```

```
gcctttagag ctgagagccc tgaacagaga tttacccaca tatttattaa tagcaaacca   55440
gtcattagca ttgtttctat agatgttaaa ttaactaaaa gtatcccctta tgggaaacga  55500
ggggatgggc cgaattaaaa gaagaggttg ggctagttaa ccgcagcagg agcatgtcct   55560
taaggcacag atcgctcatg ctattgtttg tggcttaaga atgcctttaa gcggttttcc   55620
accctgggtg ggccaggtgt tccttgccct cattcctgtc aacccacaac cttccagtgt   55680
gggcattagg gccattatga acatgttaca gtgcttcaga gattttgttt atggccagtt   55740
ttggggccag tttatggcca gattttgggg ggcctgctcc caatacagag gtctcgtgta   55800
aattccctgg gaggcgataa gcctctgaga aacagactat gctaaccacg ccatgaaaga   55860
gaaacttatt tataaatcag atgccagtta ctagtttact gcttatttgc ccaggcgtag   55920
ctctgacaga gtccccgact catagtgctt gctcagtgca tgctgaacaa tgattggaat   55980
caagtcatgg ctcagagcat agttttgaat aatgggaaat ggatgttctt aagtaacata   56040
gtcaccaaga taatgcgact agctgggtca cccctttca atttaggat atttttatca    56100
agatttaaat ggccatcatt agagttatag cactttctcc tttggattgt cctagaggcc   56160
catgagaaag tattccctaa tttcttagga gaacagtttg tgggtagtat gcggtcatgt   56220
ccagttaaat tgcagatatt tccgatcgaa gatgttccag tcctgagaac ttcgtgacat   56280
tagcaggact tctacaagcc atctcttagg gtgggcatt tactgcagtt ggctagtact    56340
cttttctcct taactttgtc atttgttgat ttttttttaa ctgtccccaa atactgtggg   56400
cagagtgtat ctagaattga ggcctccacc attgcggaga ggacatggat gctgagcagt   56460
cccctgagtg aaggttataa agaagcaaat agactacaca tgtctgtaaa ctgctcttga   56520
gtgtcccaaa tttggggtac ttcagttcag ctgtaggaaa agcctcaaac tgtttatact   56580
ttgcaagaat tggaaacttc taattcacgt taagttttat gtaatacatg ataagcttca   56640
taggagcttc atctttatc tacttggact tttgcttccg taggttttgt taaaggcctt    56700
catagcgaac ctgaagtcaa gctcccccac cattcggcgg acagcggctg gatcagcagt   56760
gagcatctgc cagcactcaa gaaggacaca atatttctat agttggctac taaatgtgct   56820
cttaggtaag gtggaggcat atgagtggaa gagtctccag catgtactca agatagacct   56880
ttgaaataaa taaaaccaga tgatccctca gcttctagac caggctattt ggcactggtt   56940
gattgaatgt gaactgcact ggggctgctg tgagcccgca tgggtctctg tgaccctgca   57000
gatgcagccg tgcccaggga ctgggcagtg ggtgtgggct ggtgtgagcc ctgtctgcca   57060
cccagggcct ggccctctgt ctgtgtcggc catgactatg gtgagtcttg taggcttgag   57120
actgtgcctc gggttcctgc gggttctctg taggtcagtt gacagtttct cctgttgttt   57180
gggtaactgt ggaaacgaac actggcaagt gctgaagcga gcatgtggac gtgcgatatg   57240
aaataacgac ctggctttca aaggcagtga ggctctctgg aaaggacctt gctgagctag   57300
ggatgtgggt gtgtagccat tcccagtggg cctcatggcg tactcgttca tgatcatgtt   57360
tgtgccatct tgatctctca ggatctcttc ttttttaaca gattaagccg ggaatctcca   57420
aacagtgagt cagatgttaa gatgtcttgc ttccacccccc acaggcttac tcgttcctgt   57480
cgaggatgaa cactccactc tgctgattct tggcgtgctg ctcaccctga ggtatttggt   57540
gcccttgctg cagcagcagg tcaaggacac aagcctgaaa ggcagcttcg gagtgacaag   57600
gaaagaaatg gaagtctctc cttctgcaga gcagcttgtc caggtaggag cacagggttt   57660
actctaggcc ctgcatgtga atgactgaca ttcaaagaac cgattaattt ggaagagaag   57720
```

```
cggcagaacc gagagttaga ggtgtggact ctggagctgc gctgctcgtt tccaaccta    57780 ggtgctgacc tctagctgtc ttccctctgt atgtccctgt caccgtgagt caaatgcggg    57840
tgatgcctcc tcaggtgccg tgttacctaa gcctctcaga gaccactgct accctgtttc    57900
taaaaccaga ggtcacgata tgtgttcatc cacccagtaa atactgattg agcacccact    57960
gtgtgctagg ctctgggata ggggctgggt atacaatggt gagtatttca gctgcagctt    58020
ctgccccgtg gaggctgtgg cctagcacac tggtctaggc acggtggtat atgctcactc    58080
aaggagatag ggacgtggtc gtttggggtg tcggaacaaa atgtcggaac ttctctttcc    58140
aatgcagaga aaccttgcag taattctaat gtactgtgat tggcagttga cttcagttct    58200
ttgtagcacg cttactcagg ttatttcact aactatgtaa ccatgcagcc tcattttaag    58260
caattggatt ttttgaactt tacttaaaat gttatgtcag gttttttatt gtgcttaatg    58320
tgtgccattt agctaagttt tgtaggatac gaaattgtaa gtggcttaaa atgattctta    58380
atagaatcat gaattgaaga taatgctaat aatttaagca ctgagttagg tagtgtttgt    58440
aaaatgctta gaatgcttcc tggcacatgt taaggccatg taagtgctgc gtgttgataa    58500
acagctgagc aaaagtggac tcttaagaaa gtattggggc tgagagttct gttccaacca    58560
gctgcccttt ggttattttt cagaataaaa gcagagtctc atgggatatg acatttatat    58620
ttccttcaca aaaacactg ctgagtgttt tgttgagtaa aaagggtgta gccatggtaa    58680
taatacattt aaaatatagt ttatttcatc tttaccttgc cttgtttttt ttttaagcta    58740 gcttttatt gagaattcca cacatacaaa agtatcaact catgaccagt tatatttcat    58800
ttataatcct acttctccct tttttttatta tttgaaagca aaccccaatt atcctcttat    58860
ttcatctata agtatttcag tatctctata gatgaggact cttcttatt tttaaaactt    58920 tatttttaaa atgatggtca gatgcagtgt tcatgcctgt aatcccagaa ctttgggagg    58980
ccaagctggg cggatcactt gaacctggga gtttgagacc agcccgggaa acatggcgaa    59040
accccatgtc ttaaagaaaa aaatcagcca agtgtggtga tgcatgcctg tagtcccagc    59100
tacttgggag gctgagatgg gagggtcaca tgagcctgga agatcaaggc tgcagtgatc    59160
catgattgta ccactgcact ccatcctggg tgatggagca agattctgtc tcaaaaaaac    59220
aaaactgcaa acaacgtca caaaacagtg ccattgttag acctgaaaat attaaacatt    59280
tcctacatca aatacccacc aactcattat caattttct ctctactctt ttggaatcag    59340
catctaaata aaattggtcg ataaggattg taaatctctt tgatgaactg gttcccctcc    59400
atcccagttt ttttcccta gagttcattt attgagaaac cagattgttt gtcttctaag    59460
ttttcctgtg gtctgatata ctgcttccat ctccactgtg taaattaaca cctttttctc    59520
ttctctgtat ttcctgtaaa tcaataattg gaggaaagc cttgtcagat ttagtgtata    59580
ttttatatct gagtccagta tttcttatat aatattttaa gataagtgta ctcttttaaa    59640
aagtattgaa actatatgct caattttttt taactgatgc ttttaagaag gctgcttgat    59700
cataaaagtt tagagatcat tggtctgatg ggaaaagcaa ataattacta aaccgtttag    59760
caaggttgag gtgcacatgg tggggcctgg agaagttcag tcatgagccg tcacttatgg    59820
gcacgtggaa tctgacccgg cacagagttg ggagaagaca ggagctttat agacagaaaa    59880
tgtggtcttt gctaagtccc aggagtgaaa gggtgagaca gtgctcacag cacacgagtg    59940
tgggtgcgta gacagagcaa gggtgggtcc tgaaaaggcc tgcaggcttt ctcatagatt    60000
agcaagagtg ctggttacgg aggtttctaa catttgtgaa cagatcgaaa ctgtgttaaa    60060
ttgggattgc agtaatcctg gaaggacagg gatagagggt gaaggggaaa aagggtatg    60120
```

```
gatgtgagac ttaattgctg attttcttaa gacctttctc caaagtaaat aaatgatgtg   60180
gcacattttt gaactggcaa attctaaact ctagatatga ttatctctat aacatatctt   60240
actccatctt cttttgacta aaaactgttc ttaattaaat taccatgaga cgttcaattc   60300
agcaaatgta gtttggctaa ccatatttaa ttagaattta atataatcct aggcctggcc   60360
aaactattaa gcaagtgtgg gcaaaatatt gataatttta gatatgcagg aacttagttt   60420
gctttccatg tgtgcttttc gaaaaaggaa taaattgaaa aatagaggaa gccctgaaat   60480
ccaagaagca aactctctca cctaggcatg cagtaaaagc aattctagga tgattgctgt   60540
ttggcgcgta gttcgtatta gaaaccattc ttcttgaata aatagtatgt ttaagaagct   60600
gggcagaggg aaggcatatg catatattat caacaaggag ggagaaaaag gcaattagta   60660
accatccata ggagggtcag caagatttat aaaggaaatt tgtgatccaa gtatgaagca   60720
aaataaggtg cagaataaat tttaagcaag taatagatta gagtaagaga acccatttga   60780
ccattaacct tgggacattc tctttcaaat gacatggagt agtactgaaa tctttctttc   60840
tttctgagtc taggttattg tgactggact cagaagaaaa tatttcatta ttgcagtgaa   60900
taacatttgt gaacattatt gttcataaat tatgcagtga ataacattta tgaacacgtg   60960
atgtgtaaga tacatactgt ttattttag ttaagttttt tggctcaact tctaggcaga   61020
gaacattaaa tgtaaatagt gttacctagg agcatgtaaa tggaaatctc catagtatga   61080
aagcagtgct gttgctaaca gaatttagga gggggcagat gaggtgaagg aaatgtgggt   61140
gctgatttcc ttattacatt gagaggagcc aggagattct ttgttcaaaa tggatggctt   61200
aagaagtcaa agtataagct gattacgtag agcaggtacc caaaaatgtt ttgtgtaagg   61260
ggccagatag taaatatttt cagtcttgca ggccatccca agtctgtggc agctactcaa   61320
cactaccttt gtagcatgaa agcagccaca ggcagcccat aaatgtggct ctgttccggt   61380
gaaactttag gtacaaaagc aggtgcaggc cagacctgac ctgtgcactg tggtttgctg   61440
acctgggatt caggggtata gaagttacca tcagaagagc taaaagtgag acttttttact   61500 ttatactctt ctacactgtc tgattttgaa aaaaagaaac atgtatttta taatattaaa   61560
gatagggttg gcaaatagca aataaaaata cagaatacca gtgaaatttg aacttcagat   61620
acattatgag taattttatg gtgtaagtat attccaaatc atgtgggaca tacttacact   61680
acaaaattat ttgttgtttg tttacagttt aaatttgagt gccttgtatt ttatctggca   61740
actgtaatta aagggaaaaa gaataaattc attatgttca tataatgtga tatagcaggg   61800
gtccccaacc cccaggctgc agagtggtac tggtccatgg gtccccaacc cccaggctgc   61860
agagcggtat tggtccatgg cctgttagga accaggctgc ccagcaggaa gtgagcagca   61920
ggtgagctgg cattcccacc tgagcaccgc ctcctgtcag atcagtggca gcattagatt   61980
cccataggag tgcaaaccct attgtgaact gcacatgtga ggggtctagg ttgtgcgctc   62040
cttatgagaa tctaatgcct gatgatctga ggtggaacag tctcgtcttg aaaccatccc   62100
ctggccctgt ggaaaaattg tctcccatga aaccagtctc tggtgccaga aaggttgggt   62160
agcactgtga tatagtatta aaagtgctaa taaatatggc atactgcctt taaaatgtct   62220
ggtagctctt tctcagtggc actcataata gtgttttttg attttttaaat gtgtgtcaag   62280 ctgactctcc cctccgtgta tgctgggctt tattttccct ttcctagtca ccagttttgg   62340
gaaatagaga tcttcattct catgctgctc ctctagtgca agtgctccat ttattttaa   62400 ggaattaata taacaaaaaa tcatgggaat ttagaaaaca acatgaaagc taatgatcac   62460
```

```
attggtggaa gtgatagggt aatatttagg gggagaagtt aaggtataaa ctttgtcaat    62520
gaagtcctat taaaaacaac aaaaaagtga agcttaggat gcattttata aactctgacc    62580
agaacacctg tgtttctctg tttctaggtt tatgaactga cgttacatca tacacagcac    62640
caagaccaca atgttgtgac cggagccctg gagctgttgc agcagctctt cagaacgcct    62700
ccacccgagc ttctgcaaac cctgaccgca gtcgggggca ttgggcagct caccgctgct    62760
aaggaggagt ctggtggccg aagccgtagt gggagtattg tggaacttat aggcaagtta    62820
ttagcaaggt ctactcttac aattaacttt gcagtaatac tagttacact ctattgatta    62880
tgggcctgcc ctgtgctaag cagtctgcat tccatcttcc ttgccaaaac ttataataca    62940
aatttcatct ttatttata aatagggag ttgggctggg tgtggtggct cacgcctgta    63000
atttcagcac tttggaagga tcgcttcagc ccaggagttt gagacaacct ggccaagtga    63060
gaccctgtct ctacaaaaaa aaaaaaaaaa aaaaaattag ctgggcatgg tggcacatgc    63120
ctgtagtccc agctgctttg gaggctgagg tggtaggatt gcttaagccc aagaggttga    63180
ggctgcagtg aatcttgatg gcagctgcac tgagcctggt gacagagcaa gatgctgtct    63240
caaaataaat ttaaaaataa aataagagaa ttaaagttta gcaggttggg tggcaaaatg    63300
aggccacaca tttaaagccc ctcctcctga ttcttttctc tgccttggct gcctcctgtg    63360 gcatttagg tgctgagaaa tgaaaacagt agggaaaata gttccaggat cctcatgtta    63420
atttgccaga atggcatct tcaagtcgtc agagggatct gagagttcct tcctggcctg    63480
acttgagaaa atccgtctgt ccccagctct gcgtctgcct ccactgccca gtcacctcct    63540
ctccatgctc ttggggctgg gccctacccc accatgcagt gctgccctgg agcagtgagc    63600
ttggtgggtc ctgtctggca tgagagctgc cttgggagc tggatcccag cctctaccac    63660
tgggtctggt gcctagcagg ctatggataa acttctgctg actccggcct ctcctaagcc    63720
actgcaacgt ggtcggtgta gtgcacagtg tgtgtgcagc gtggccttac tcacagcctc    63780
cacattagag agaatctgac tgaagtctta ctgctgcctc gtgtgaacat aaatgtttgc    63840
cagaaccatg agcaggaaat gttaatctgc cttgtttcct gtcctttaca cggaagaatt    63900
tttttctgta tggaatgcgt gccttacaaa taatgagtgg aaatacccat cgctaatgaa    63960
aagttatact tgactgttag tcagctaaat aatctgagat ttctaatact tttaatttgg    64020
cttttacaat gcaatttatc ttagcttttt tgatttctta ggtcatatct ttagaactat    64080
atatttgaat gttaatgtaa ttttcatatt gaaattaaaa tgttgaactg cgatgttaag    64140
tgtttcctgt ggaaaaacgt tcacattttc tctagtttta aagttgaatc aagctgtttg    64200
aagattttca catttcttct agattttatc agcttgttac tttatctgtc actttctgtg    64260
atttgcagct ggaggggtt cctcatgcag ccctgtcctt tcaagaaaac aaaaaggtga    64320
ttatttcaga aatcagagtc ttgtgttgaa tcttactgat tttcttgtat ttctgtaatg    64380
taatgtatct tgtatttctt gtaatactgt attggactct gtgtatatct cttctcagat    64440
gagtgattat atgtgtgaat gttgctggaa tctgataacc aggcctgaat agttttgtag    64500
ggtggctttt aaaaattact ttcatatcag aattgctttg tcataaattt tgaacgcatc    64560
ataaatttct aatgttcggg gtcagcagac ttttttttgta aagggacaga gtgtaaacat    64620
cttagcttta tgggccatat ggtctctttt gcaacattca gctctgccct gtgacaggaa    64680
tgcagttgta aagacatgag ctactggcca gctatgttcc agtagaactt tacttacaga    64740
aacagacagg ctgtagtttg ccaatacctg ccttagggaa tgtgttgtta tattttgtga    64800
gttaccttct cagtaaattt tatttagtat tagtcaggaa tattattaag tagcttcttt    64860
```

```
tccagcctgg tcaacatagt gagacccggt ctctaccaaa acaaaacaaa acaaaaaaac   64920
agccacgcat gtggcatgtg cctgtagcct cagctgctgc tcagggggct gaggcaagag   64980
gattgtttga gcccaggagt ttgaggtcac agtgagctgt agtcatgcca ctgcactcca   65040
gcctaggcaa cagaatgaga ccttgtgtct taaaaaaaaa aagtttcctt tgttgggtta   65100
ttttaatttg gacctggtta tcattttca gccatattta actttgtaca tatcagaatg   65160
ttctgataaa acttaacttt tattaaagtg tttgtgatat aatctgctag ttttggtaca   65220
cattatcttt tgcaatgcca gttattttct tttccagtgt gggtttgcat aggaaaagaa   65280
ttgctgtcac tttctatttt gaaatcttaa aagactgatc ctttttgtg tcatgatttg   65340 agtatttaat tgagagccta atgcctaata ttatttgcag tattaaatgg gatcttaaca   65400
ggaatagcat tctagccttc attgaattaa gtaaacattt cttaagagaa cttgaatct    65460 ataatatttg cgtcatcata gtatgagata cttaatcaag tttgagattt tagtgaaaca   65520
ttgtttagaa gccaaaagga ttctaggaaa aattaatgtc tatattcttg aattaggaga   65580
gattttggga cgtgtgacta agttacgctg acacttgttt gtttcttagt cgcttttcc    65640 agtggcggtg agaacgaaga tgactgattc acattgctca gatgagttta tcctcttctg   65700
gctgggacat gggatatatc ctgtctcttt taagccttt tggtattttt cccccattga    65760
gagctgtgtc ttcaaactct tctgttatag ctggaaaatc ctttttaagt gaaatctgcc   65820
caaattataa gacagatgaa ggtagagttg tgttggatat aggattaggg tgaaagtagt   65880
gggggtgtcc tggagcctct cttctggtgg cagcctagct cttgtgcctt tgaggaaatt   65940
accctgggga cggctctgtg gaacatattt gcaaccact gatttggaag atagagatgg    66000
cttttgttaa gatctgaatt caccttttg gcatttatt tgatttctca aggtaaagaa     66060
cttattttgt aataaagttt cctattattt agtagatagg ccaagttgct gtgttaattc   66120
catgtagatt ttgggtttcc tttgctcatt ttttcactct taatctcaca tcattgtaag   66180
tttatggaag ttatcatact tctgactttt tctttgaaga gcagaaatta gaaattccca   66240
ataattattt tgatagtgtc atttaatgac actcacatgt gatgtagcca caaagattta   66300
atgagttcag ttttaaatca tattaagact gttggtttca tttgttctca ttaatgtaat   66360
tctgaagatg aacaataaaa tgtatttta gaactttcaa atgaaatatt atttcatcct    66420
tccagatcat ataatgctta agttctgatt gttaatcata aagtctagaa aattaaaga    66480 taataaaatg aaagtgactt ttaggtatta gagttttatt ataaattctg gtgtgtcatt   66540
ggagctatga catgaatatt tcaaaggcca atagcattgg atctttacag ttataactta   66600
ccatttttaa gtttaagtag taatatagat tatttaataa tcaaaatcaa taaatattaa   66660
ttattaaaat gttttgtggt atagtttgag aatcattgct tttaactttt tccatatagg   66720
tttattgact ttaatagcat tctaaacata acatctctac attctttgtg tttaatactg   66780
tggaggtata aaaatactta tatatgatga taaactatat tagagtaaat taaatattct   66840
tatgagtttc atttagagt gcatttactt aattttgaag tccttatttt tagcaaacta    66900
aaaggaatgt tggtacatta tttactaggc aaagtgctct taggagaaga agaagccttg   66960
gaggatgact ctgaatcgag atcggatgtc agcagctctg ccttaacagg tagttctcac   67020
tagttagccg ctggtgtgga ccttcactgt ctgccttcca cccttgccc ttcctgctcg    67080 tccccctgca cctggtggac agcacgactg ggggcagcag tggagccagg ttgcttaaat   67140
ggggcatatt cgggcttctt ttataatact tactctgaag cttgtgtgtc tgtggtgttt   67200
```

```
gcatcatata tttgttgttt tccatggttt aggctgtttt aaaattaggt ttatggcttg    67260
agcatagggc tttgtgagta ggggatggca ggtcgaaaca tctcatgagt tggatgggtt    67320
atgctggggg ttgggaaatg ggatgaaaaa ttatgggatg aaaaattgcc tatggatagt    67380
ttaacttgaa agaatctgcc tttgtttaca gatagttatc tttttctttt tttgagatag    67440
agtctcacac tgtcacccag tgcagatacc cagtgtcact ggagtgcagt ggtgtgctct    67500
tggtgcactg cagcctccgc cttctgggtt ccagcgattc tcctgcctca gcctcccaag    67560
tagctgggac tacaggtgcc cgccaccacg cttggctaat ttttgtattt ttttgtggag    67620
acgggttttt gccatgttgg tcaggctggt cttgaactcc tgacctcaag tgatctgcct    67680
gcctcagcct cccacagtgc cgggattaca ggagtgagcc actgtgcccg ccagttaca     67740 gatacttatc taatgaaatt ctctgtgtac tttataaaag atgaggatta actgaaggta    67800
ctaataactg gattatatga gggtggtttt ggttgtataa tcctatctaa aagaatattt    67860
tagctataac tgaaagtaag acttaaatat ttagagagga aaatctgaat aattctagta    67920
gtaattattt atttacaaaa taaaatagat tttttttttg attacacaaa ttaaacaaca    67980
ataaaacatc acagcaatcc ggatactata aagctcacat gcttaccgac ccaactgccc    68040
caggagtgac cactgccaac agcttcatgt cgaccttttt gccataattt ttatatagcc    68100 tttttttgttt ttaaatggta atttagaaag tcaactagga aaatgtgtta caggtttatc    68160
ttccaggaga ataggactgg agtcgagatc ttgaatgtgg cttggaagaa ggcaagccca    68220
ccccagagag atgagttgac agttgttttct gaccactgct tgcttagagg gcctgcgtgt    68280
ctgtgaccgc ctagctttgc gccctgact aggctgcccc ttaattacaa atgtctttat     68340
atattgctcc agctaaggct tggagtagtc ggttaagaac ttgaacttcg gtttttgcag    68400
tgaaacagca tttgagaata tcaccttctg ataagcctta ttttataagg tgggtactgt    68460
agtgggaggc agtgtgagag atgcttgaag gatgcactgc tgtcctgcat ttcagcatct    68520
tcaggatgct gtgcagctga acatttgat aacggtggaa ctgttcgtta ttttgcaagc     68580
ctgtgattcc ctattgaatg ttttctctcg ccatttgaca aatgagtgtt tctctgtctt    68640
cagcctcagt gaaggatgag atcagtggag agctggctgc ttcttcaggg gtttccactc    68700
cagggtcagc aggtcatgac atcatcacag aacagccacg gtcacagcac acactgcagg    68760
cggactcagt ggatctggcc agctgtgact tgacaagctc tgccactgat ggggatgagg    68820
aggatatctt gagccacagc tccagccagg tcagcgccgt cccatctgac cctgccatgg    68880
acctgaatga tgggacccag gcctcgtcgc ccatcagcga cagctcccag accaccaccg    68940
aagggcctga ttcagctgtt acccottcag acagttctga aattgtaagt gggcagaggg    69000
gcctgacatc tttttttttta tttttatttt gagacagagt ctcactccat agtgcagtgg    69060
aggccgggca caggggctca tgcctgtaat cccagcactt gggagactg aggcaggcgg     69120 atcacttgag gtcaggagtt cgagaccagc ctggccaaca tggtgaaacc ctgtctctac    69180
taaaaataca aaaattagtt gggcgtggtg gcacatgtct gtagtcccag ctgttaggga    69240
ggctgaggca ggagaattgc ttgagcctgg gaggcagagg ttgcaatgag ccgagatcgt    69300
gacactgcac tccagcccgg gcaacagagc aagactccat ttcaaaaaaa ataaaaaaat    69360
aaagtgcagt ggctcgttct cagcccactg caacttctgc ctcccaggct cgagcgattc    69420
tcccgcctca gcctcctgag taggtgggat tacaggtggg caccaccaca ctcagctaat    69480
gtttgtattt tcagtagaga cagggtttca ccatgttggc caggctggtc tcaaactcct    69540
gaccttagat gatccaccca ccttggcctc ctaaagtatt gggattatag ttgtgagcca    69600
```

```
ccatgcccgg ccctgccacc tgccatcttt tgagttcttc cctggagacc tagacctgaa    69660
ccctcctgct tgttctcttg ttatctaata ccoctattga cagcgcagct tagatcatta    69720
atggagagct tgacctcatc tgataccttc actgaaggaa acaacttagt gtcttttgtg    69780
ttgaacactg aggtaaaaaa ttggaatagt tgattatatg aactctgcta aaattgagtg    69840
cattttacat ttttttaaggc cttgttgggc cctggttaaa taattatttt taaaaatcct    69900
taaggagcct attataaaca gatctgtggt cttaatgaaa tgtgattaat actgtgcatt    69960 atttttaagaa cttttgactt ttcaaaaaac ttttacaaca tttcccattt gatagcggca    70020
taggtttaag cacttctcat ctctaagtta gtggacaaaa aaccctcatg atagtctaa     70080 taatgtttgc tacaagtcca tgttgagttt tatactccat tttattttca gttttaaaaa    70140
ctgtggttaa atatgtgtaa cataaaattt atgttcttaa ccattttttg cgtatacagt    70200
tcgctggtat taaatacatt taaataatgt catggaatca ttgctaccac ccatctctgt    70260
aaccttttga tcatgtaaca ctgaagctct gttcccattg aactctattc ctcctttccc    70320
gccaagtccc tggcaaccac gattcttctt tctgtcttct gaatttgact actttgggtt    70380
ctcatatact ttaggagtca cacagtattt gttttactta gcataatgtc cccaaagctc    70440
atgcatgttg tagcctatgt tagaacttcc taatgtttca ggccaaatac tattccattg    70500
tatggatagg ccacattttg cttttccatt cctctgtcca tggacacttg tattgcttca    70560
tgttttagcc attgtgaatc atgctgttat gaacgtgggt gtacagatag ctcctggaga    70620
ctctgctttc cattttttttg gctaaatacc cagaaatgga gttgcttta cattccaatt    70680 ttaatttaaa acattcatat cattgagtgt tttacttaat agtatagtag ttaacaaact    70740
taataaaata gtattttggt aataatttgc tggtagtcca ttgttcagtt tttttaggta    70800
aattacacag gacatttcaa gtggacatga aacatcttgt gatgtggaat catgccccaa    70860
gctgatggct aaacatatga aataccatac cctaaattta gtagatttag tctttgcaat    70920
ttaggagata acctgttata ttgttaggtt tttgtcgaaa agctttgtcc tcatatttcc    70980
aacttgctgt aaaatttgtt tgtgaagaca aatattttg tatgggtttt ttcttttttca    71040 tattaaaaag aaatgtccac attggaattt ttttggagtt tttagagcta atagagcttt    71100
tcataatgta gtgggaatga gtgatcagta agctcttagc agtttccatg cgtgcatttc    71160
tgtgccttga aataaatgac agatgagtac atttgtgttc tgtgtgtaaa atgtgctctt    71220
tcctcattgc acttccatgt tggagggctt gtctcttggt gatcacactt caaaattctc    71280 acagccccc ttgaaccgtt taggtgttag acggtaccga caaccagtat ttgggcctgc    71340
agattggaca gccccaggat gaagatgagg aagccacagg tattcttcct gatgaagcct    71400
cggaggcctt caggaactct tccatgggta tgtggactac aggtgatgcg ctacaaagtg    71460
gtttgtattc agacctggac atcttaatta tatctttgct tccaagaaga agtcctttga    71520
tactgttttc tgagttctga atagctgatg aaaatgacca attgaggaat aatcatactt    71580
tttcttgatc taaatcttat actttgagt tatcttagca taaatgtata attgtatttt    71640
aagtggaaat ttgtcactta atcttgattt ctctgttttt aaagcccttc aacaggcaca    71700
tttattgaaa aacatgagtc actgcaggca gccttctgac agcagtgttg ataaatttgt    71760
gttgagagat gaagctactg aaccgggtga tcaagaaaac aaggtgaggg acataggctt    71820
gagacgactt ggtgtttctg agcttgtgtg aggatttaaa atcgccctgg ctactgtcta    71880
ctttattgct ttcccatccc tgggccttta aatttcccct ttaaataccca gctcttccca    71940
```

```
ggcctgttgt tttctgcctt tccaggtact acccacagcc ttgagaattg cctgagttct   72000
gcctcctttg agagtgtgcc ccagacaaat ctattctgta ctgaatgttt ccttgtctga   72060
tttcttggat cattcatttg atggttgcgt atggcctgca acgtttcttg ttttggttct   72120
actgaactgt tctaaaagtc tctcttcata ttatcttttt acatgtaaat gtaactgtct   72180
tcacttttaa ttcctcaagg acaaggaata gcgtttcaca gttcgtccca tcaatcagaa   72240
ttatagcctt tggcatctcc ctatctacca ggcccacttc ctcttagatt tgggcttccc   72300
caggctgttg cctttcccca gtagcttct gcttgtcctg tagaagacct ttcatgcttt   72360
gcttctgcag cagccgttcc tgaatgccta gtgtcaactg ccttcttacc acgcccaccc   72420
tccctgcatg ctgcatttat cccctgccac agccctgtga ccctgtgtcc tgctgcctct   72480
gacttgtctg tttctgcttg gccatggtct ctgtgaggtc aggtgtgcat atgggcacaa   72540
accagggcat ctctttatcc ccagcacctg gcttaagtgc tgctctggaa ctatctgttg   72600
aatgaactaa tgcatgaatg tattgttgag tatgagacaa acaagtgtca ttgtctcctt   72660
tctagccttg ccgcatcaaa ggtgacattg gacagtccac tgatgatgac tctgcacctc   72720
ttgtccattg tgtccgcctt ttatctgctt cgttttgct aacaggggga aaaatggtg   72780 agtacaaaag gggatgtgca cagttgaagg aaataactag gtttcagagg tcagcttggt   72840
ggcctgtttt tgccttgcgt gcagcagagg aagtagaatc tgaggatgag tttggttttc   72900
actagccgag gggagggagg aaatgatggg agcaggtagg ttattgggtc tggttttgtt   72960
catttgaaaa caatctgttg tttgaggctg aaggtggctt gggtgatttc ttggcagtgc   73020
tggttccgga cagggatgtg agggtcagcg tgaaggccct ggccctcagc tgtgtgggag   73080
cagctgtggc cctccacccg gaatctttct tcagcaaact ctataaagtt cctcttgaca   73140
ccacggaata ccctggtatg ttaaaagttc acatcttatt ttctcagatt taatcattat   73200
tgtaaaaact atttcagtat tgactatttt agttttagag cagtaagtgt tttgagttca   73260
tttgggatat ttgacctgcg ttgtagctct tcagaaaaca catgaatagt gaagttcttt   73320
gtttcatggg ttcccttag atgaaaccca tagaggagaa aagtagaaac ctcagcacgt   73380
aagagccaac atatatacac atcggattta aacctaaagc acaaattgtg cctggtcgca   73440
gtggcgctga gtcgcactca gccaggccag gcattcacac tcagggtgag tgggaaccag   73500
gactggctga ggcagcagtg gacccaagtc tccatcgcgc ccatgcttac tatggagcct   73560
tctcgttctc tcttttttctt tgggtgagag ggtacacttg tgttttgaa tttatatgag   73620 gtaagtgtgt aataggtttt tttctaatct ttttaagtg gaatctggaa ttttaatcag   73680
atttattatc tgacaaccta gaattataat ccagaaagtc tgtggtattg aggacatatt   73740
ggcaatatga tgaatctcta attcttaaat cctgaaactt ttttttttt aatcacttag   73800 ggttattata gtgaagtcat ttctgaattt ggatcttctc ttcacacctc tttttctctt   73860
tcctgagaat taagcttttg tttcgagtta gaaagttgat agtagggaat tgttccatgg   73920
ctgagcaatt tatctccaca gaggaacagt atgtctcaga catcttgaac tacatcgatc   73980
atggagaccc acaggttcga ggagccactg ccattctctg tgggaccctc atctgctcca   74040
tcctcagcag gtcccgcttc cacgtgggag attggatggg caccattaga accctcacag   74100
gtaacggcca gttttcagc tgtgtttttt ctagttatgc ttactaaggt ttaagtttag   74160
atgatgatgt ttgttgcttg ttcttctggt taggaaatac attttctttg gcggattgca   74220
ttcctttgct gcggaaaaca ctgaaggatg agtcttctgt tacttgcaag ttagcttgta   74280
cagctgtgag ggtgagcata atcttctgtg gaaccatttc ttcacttagt ggacatttta   74340
```

```
tcattgctac aattaaaatt ggagcttaat aggaaatatt tccatgcact ctaaagctgt    74400
aaccagtaat acccaccatg tatccatctc tcagctttag aaagaaaacg ttgccagtaa    74460
agttaatgct tcataaactt cagtttaagt tctaattctc agaatatttg tttgaaatag    74520
acctcttcct aaaggatata tttagaaata acctatcatt aagtgtaaag tctgttgaat    74580
atgctgggca cggtgactca cacctgtaat ctgaccactt tgggaggcca aggtggaagg    74640
attgcttgag cccaggagtt caagactatg ggcaacatag ttgaccctgt ccctacagaa    74700
aattaaaaaa aaaaaaaaaa aaagtagctg ggtatggtgg tgcatacctg tagtctcagc    74760
tactcgggaa gctgaggtgg aggggggatt gcttgagccc cagagatcaa ggctgcagta    74820
aggcgtggtt acaccactgc cctctagcct gggcaacaga gtgagactgt ctcaaaaata    74880
atagtaataa taatcagttg aattaaaaaa aaaaaaaaaa aaaccactgt gctaggccca    74940
tagtatggta agagttaaag tgagccttag ggattattta ctcaacctct gtttctgtat    75000
aaagtggaat aggctcaatt ctttaagtga tagcatgttg aacctttcca taccaactgg    75060
ctcataagtc acaactggcc agtcaacaag agtaaaaatt aactggtaaa aatcaaagca    75120
aaaaacctac aattgtcaaa tttgtgggat aactccccct tttaaaatgt catgcctgac    75180
agtaatttct ctctagtttc caggttttca gtcagttgtg tctttttga gcagaaggaa    75240 gcatgctaag agctcaatct tgtggctagc tgggggtctt tgtgtcagcc atgcatgtga    75300
tggtgcccct gggtgcttgg ggctgcaggg gaggggtaca gcagtagggg cctgttctgt    75360
tctctcgtgc tgtggagtac atagtgacat agtggggtgg tccttggtgt aggtcccttg    75420
ttcctacccc tgggtctgag atttatttag aagtggtgtt ggggctgtgc ggcaggcccc    75480
tctgtaactg atcaatgttt gtgaagttgc tgtttgagag ttgaaaccat gacataagca    75540
gaaatggaag gaagaaagaa ccagttatgt gaaagggaca catttacttt taagcttgta    75600
tttactgaga taaagtattc ttaatcaatg ttcttgagag gtgtgggaaa aatgcaacat    75660
cctggttgca gttaaaccca gaacattgtg tgttgaagag tgacggttct caaaccgtca    75720
agacgcgggt actgagtggg actaacctgc tgtcctcttg ccttggacct tgtgttccag    75780
aactgtgtca tgagtctctg cagcagcagc tacagtgagt taggactgca gctgatcatc    75840
gatgtgctga ctctgaggaa cagttcctat tggctggtga ggacagagct tctggaaacc    75900
cttgcagaga ttgacttcag gtaagtgagt cacatccatt agatttcatg aactaagctc    75960
aattgaaagt tctgggatca cttgatgcaa ggaatgatgt tatcaagtac cctgtccatc    76020
agaaatccga gtggtttagg tagatgacag tgattttctc ctcccagtgg cttttttgctg    76080 aactttgccc tatgcttgga attttatttt attttattat ttatttagag acaagatctt    76140
gctctgtcgc ccaggcttga atgcagtagc acaatcatag ctcactgaag ctttgaactc    76200
taggactcaa gtggtcctcc tgcctcagcc tcccgattag ctaggagaat aggtgtgtgc    76260
cgtcacactg gctaatattt tttgtagaaa tggggtcttg ctatgttgcc caggctggtc    76320
tcaaactcct gggcttgatt gatcctccat cttggcctcc caaagtgctg ggattacagg    76380
catgagccac tgtgcctggc ctagaatttt aaaatataag tagaagagta gatttttttt    76440
tttggtagtc ctcgtcattt aagtattctg gatagtggga ataaaagagc ttagaatttt    76500
tcatctttgt cttaaacttt taaaaaatg tagcttatat taattctgct gtttaaaaa     76560 gaatatactc ttcattatac tgaacctagg taagacagct ggtttatatt ttgttgcaat    76620
taaaaaacgt gagctgtggt tgcagtgagc caagattgtg gccattgcac ttcagcctgg    76680
```

```
caacagagtg agacttggcc tcaaaaaaaa aaaaataaca tgagctgtgt tggcactttc    76740
attttctaag agtagttttg gctggagaag ttttctttca gtactttctt ttagaaggga    76800
aattttcctt tataatttag ggtttgtttt ttttttttcc aagccacctt ttatagagcc    76860
cttgtgggtt atttcattta atccttagaa tgtttataaa tctgggcttg ttctcggctc    76920
cacccacaga tagggacgct gagcgtgcat gagtgggcag caagatagca ggttatggag    76980
ggcccagctc accccttctg tggcttgagc caatttttata gggcacttac agagtctttt    77040
gaaatagtat ttattttgaa gaaaagaaa aacagtttac tgagtactgt cttattgagt     77100
ctggaattgt gagaggaatg ccacctctat ttatttaaag ccattggcct ttttttgttgt   77160
tttgagtaag tgctgcccaa ggtccttcca gggcacctgg atgagcctgc tctggagcaa    77220
gctggcggta agtgtttact gagtaactaa atgattcat tgttaaatgt gctcttttgt     77280
taggctggtg agcttttttgg aggcaaaagc agaaaactta cacagagggg ctcatcatta   77340
tacaggggta agcggtttat ttttgtgaga tgctgttta ccttcaagaa ggtgaaagtg     77400
aggctttcct tgtggaattt ctctaaatgc attcgtcatg ttttagatgt ttatttcaca    77460
gtttatatca tgaaagttat aatcttgtca tatggattta agtctagtaa tgttgagttc    77520
tttctcacta gctttccaaa atatcttacc taaaatttag tcaaatacaa gattatgttt    77580
attttttatta tccttctctc taaagctttt aaaactgcaa gaacgagtgc tcaataatgt   77640
tgtcatccat ttgcttggag atgaagaccc cagggtgcga catgttgccg cagcatcact    77700
aattaggtat ttaccaatat tttatctctt ttcctttttt ggttgaagta ctaaaagata    77760
cgagaatgga aagagaggga agaattcaaa ggatgtagag cagtattcct gaatctgagc    77820
tcatttcagc cattctattc ttaaactata atgaaaaaaa aatccaaaaa agtctaaaat    77880
tataattaaa aaaacaacaa aatactaact gtccattgta aaaagtaatg cactttcatt    77940
gtaaaaattt tggactatag agaatagtac taagaagaaa aaaaaaatca ccttcaattc    78000
tgctgccacc tggaggtaat cactgttaat attttgctat atactctatg agtttcttgt    78060
tcaaaatcag gtcaaaatta catgcaattt tgtaatctga caatttccac ttaatatttt    78120
attagcattt tcctgttatg aaacagtaat tttagttatg ggtcgttgtt ttgctatgcg    78180
gttgggataa aattttatat actttttttg gcaattactt attatacata aatgtttgtg    78240
tatagttttc ttttttctgag aattcctgga agttgagtta ccaggcccgg cttttgaattt  78300
tttttttttat ttttttttttg agacagagtc ctgctctatt gtccaggtgc tatctcggct  78360
cactgcaacc tctgtctccc tggttcaagc gattctcctg cctcagcctc ccgagtagct    78420
gggattacag gggcacacca ccacgcccaa ttaattttg tattttagt agagacaggg      78480
tttcacgata ttggccaggc tggtctcgaa cttctgaccc cgtgatccac ctgcattggc    78540
ctcccaaagt gctgggatta caggcgtgag ccatggcgcc tggccaggct ttaaatttaa    78600
aacaaatctt ctaatagctt tatggaggtt ataatttaca tttcttgaaa tgtactcact    78660
ttgagtgtat agtaaactcc aatttttatca catttctgtc accccaaatg tatccttgtg   78720
cccatttgct gtaacctccg gttcctgccc caactcctag gcagccactc atctattttc    78780
tgtcccttaa gatttgtgtt ttcgccaggc gctcatgcct gtaatcccag cactttggga    78840
ggccgaggtt ggtggatcac ttgaggtcag gagttcgaga ccagcctggc caacatggtg    78900
aaaccttgtc tctactaaaa atacaaaaat tagtcggatg tggtggcaca cgcctgtaat    78960
cccagctact cgggaggctg aggcaggaga atcacttgaa cctgggaggc ggaggttgca    79020
gtgagcagag atcgcgccac tgccttccaa cctgggcaac agagagagac tgtctcaaaa    79080
```

```
caaacaaaga tttgtatttt ctggacattt tatagtactg gggtcatagt atagatggac   79140
ttttgcattt ggcttctttt acttaattgt gagattggtt cttgttgtag catgtatcag   79200
tagtttgttc attttattg gcgaaagtat tctattatat gaataatacc atattttatc    79260
tatccatcag atggatatta tagagttcat gttttggcta atttatgaat tatggtactg   79320
tgaacatttg cctgcaagat tttgtgtaga catgtcttca tttctcttga gtagatcacc   79380
tagaagtgga tttttaaata attttggtac ttactgtgaa actgctcttc aaaaacatac   79440
cattgttcct tccttccttc cttccttcct tccttccttc tttccttcct cccttcctcc   79500
ctcccttccc tacttccctc tccctttccc tttcccttcc ccttttccct tcccttccc    79560
gcctgcctgc ctgcctgcct tccttccttc cttccttcgt ttctttctac atatacacat   79620
tttttttaaat ttcaatggtt tttggggtac aagtggtttt tggttacatg gctgaatttt  79680
ggttacatgg tgaagtctga gattttagta cacctgtcac ccgagtagtg taccttgtac   79740
ccaatatgta gttttttgtc cctcaccttc cagccttccg ccttgtgagt ctccaatgtc   79800
cattataccaa cactgtatgc ccttgcgtac ccacagctca gctcccactt ctgagaacat  79860
atagcagaaa catgccaaag tatactccca ctaccagaat gtgattgtgc ctgattcttc   79920
tcaccagtac aaatatttca aaaaagtta aatatgtatc agttttttgg gcagaagttg    79980
atacttctct ttatttattt attttttttg agatagggtc tcattctatg atgcccaggc   80040
tggagtgtgg tggtgcgatc tcggctcact gcagtctctg cctcccaggt tcaagtgatt   80100
cccacgtcag cctcccagga agctggaatt acaggcgagg gccaccactg ccagctaatt   80160
tttgtatttt ttggtagaga tggggtttca ccatgttggc cagactggtc tcaagctcct   80220
gacctcaagt gatccacctg ccttggcctt ccaaagtgct gggattacag gcgtgagcta   80280
ccacacccgg ctgatatttc tttttaaaat aacttacctt cttttgaaag taatacatgt   80340
ttaatgaaca gaatttaagg aaaatataaa aaaacgaaat aatctttgta atcaaactac   80400
tgaaaagaaa accaaagtta cattttggtg catattcttt ttcattttca tcattgtaat   80460
ttgcatttct ttgattactt gtgagacact ccttttcattt acttaatagg tttatatgac  80520
ttgcctattc agagattttg cagctttacc attttctgca aatgatagca acttcttttt   80580
gtttgtttgt ttgtggagac agagtctcgc tctgtcactc aggcaggaat gcagtggtgg   80640
aatcttggct cattgcaact attgcctcct gggttcaagc gattttcctg cctcagcctc   80700
ccaagtagct gggattacag gagtgtgcca ccatgcccgg ctaattttg tatctttagt    80760
agagatgggg ttttgccatg ttggccgggc tgatcttgaa ctcctggcct caagcggtcc   80820
ccctgtctcg gcctcccaaa gtgctgggat tacaggcgtg agccaccgta cccagccagt   80880
agttacttct tatattctag aaaaaattct actcatgatc aagtctccat gaggaaagag   80940
actttaattg aagatcatgg ggcttgcaga ccaatatgat aaaatagttc attgtttcta   81000
aaagtattac tgagtgttga tggcagatat gaaccctttt gttttgtag aaaatgtta     81060
cccgtattct ccatttgaat tcagtttaga tttgttagga atcgcagctt aagctttgcc   81120
atctgggagt gttttgggaca gttttgcaga caaaattgca aaagtgccta aggaatgcag  81180
ctggcattca gacctgctct gtgctcagta ctctgtggac agacactgtt cagcacttgt   81240
tgatcagaag gtttagaaag agaactttca aagttggttt ttaattaaag catttaatag   81300
tgtaaataga aagggattaa attttatgac agacaaaaga aagtacagca cccagctggg   81360
cgtgggggct cacgcctgta atcccagcact atggggggct gaggtgggtg gatcacgagg  81420
```

```
tcaggagttc aagagttcaa gaacagcctg gccaaggtga tgaaaccctg tctctactaa    81480
aactacaaaa attagccggg cgcggtggca ggcgcctgta atcccagcta ctcaggaggc    81540
tgaggcagga gaatcacttg aacctggacg gcagaggttg cagtgagcca agattgcacc    81600
attgtactcc ggcctgggcc acagagtgac attctgtctc aaaaaaaaaa aaaaaagaaa    81660 aaagaaagt acagcaccca gttatgtccg agtgggtgca tgagagtgac cctgagattg     81720
gagacaacgc tgtcacgtgc ttgaagaacg ccacctgaga aaggggggcga gaagtggtgt   81780 ccgctggtaa ccagaggtgt tggcttagcc atctgcaggg aggagggtgg tctatcacag    81840
gtgagtttca tctactttct taagcaaatt aaccttactt ttgtgttagg cttgtcccaa    81900
agctgtttta taaatgtgac caaggacaag ctgatccagt agtggccgtg gcaagagatc    81960
aaagcagtgt ttacctgaaa cttctcatgc atgagacgca gcctccatct catttctccg    82020
tcagcacaat aaccaggtat gctgacccag tggcatcttc acattgtcgg gaaaatgccc    82080
tttcctgatg cctttcttta ggctttaatt gaaaacattt tatttttctag aaaaaagctt   82140 cagctcagga tgtttgagtg taggtcagtc ctttgatagg atattatcat tttgaggatt    82200
gaccacacca cctctgtatt taagctctgc cacaatcact cagctgtgac actgtaaatc    82260
tcttaatagt ttattacatt ccatgtgctg acagttgtat ttttgtttgt gacacttacg    82320
tattatctgt taaaacattt tcactttagt tgtgttacct ttaaagagga ttgtattcta    82380
tcatgcctgt tgatttttg gtgagcgggc tattaaagtc agtgttattt agggttatcc     82440
actagttcag tgatttgcga gattatcatt cacatttatt gtggagcttt tgaatatcgt    82500
gtcaaatggc cacatatatc ccattcttat ctgcttctta ggtgagtggg acacagtgct    82560
ttaatgaagc tataatcttc agaattctag cttgcagaga agattgcaga agtgataaga    82620
cttgtgcttt ttaattttgt cttttaaatg ttattttaaa aattggcttt atatgatact    82680 cttttttttct gctgagtaac agtgttttac aaaacttgga ctaaatgact tctaagctta   82740
aatgatcact tgatgctttt tttctgaatt aggaactcag cttatcaaat atcaaagtca    82800
taattcctga ataaataacg tcttttttca tgtaaagact gctttaaaaa acacatggaa    82860
ggctgggtgc ggtggctcac gcctgtaatc ctaacacttt gggaggccca ggtgggcagg    82920
tcgcttgagc tcaggggttc aagaccaccc agggcaacat ggcaaaaccc acctctactc    82980
aaatacaaaa aattagccag gcgtggtggc gggcccctgt aatcccagct actcgggagg    83040
ctgagggatg agaatcactt gagccccgga ggcagaggtt gcagtgagcc aagattgtgc    83100
cattgcactc ccagcttggg ctacagagtg agactctgtc tcaaaaaaag acacacacac    83160
aaacaaaaaa aacatggaga cattttttttg gccaccttaa tatttcccct cagataattt    83220
cctttgttta aactcagaac tggcattttc tctcttggag aagattcagg acaaatactc    83280
ctttaagata agtagaagca gtgaaagagg atttgattat caggaatttg ataagcttag    83340
aataaattgt tgcttcttaa tgtcatttca gaagatgaat atttattaat agatgccaac    83400
tgagatatca ttaaaattga ttactaacta ctacttggaa aagtctccca gttccaaact    83460
tcagcaggcc tcttgacaat tcagctgtgg tcaattgggt cttgcgtgat agatacaatg    83520
accaattgtg cagcagagtg tgctgcttag ctgcctattc tgttagcatt catgtgttaa    83580
cttaaaatca taatctcctt agttttgttg agtgtctccg tggacaagac actgtgaggg    83640
atacaaaatc agattggctt tattcaaacc actggggtat tataattcat ttataattta    83700
ttttattttt tgccttttttt ccatgtgttc taaaggaatt agagtttgta tataactata   83760 atggggata gaaattgaca tgtgccatga agggaatgca aaaaagtgcc gtgggagatg      83820
```

```
agaagtggag aaaggaattt ctttttctt ggaagcagga ataacttcat gaagcatgta    83880
tttcaactta aacagatagt aggcaacgct gtaaggggga tatggctgca gcaaaagtgt    83940
tcggggcaga ctgggaggaa gggagggaat aaattcagcc attgttatgg aataatgatc    84000
aaaatttatt ttcagcccgt ttcacttaaa agttgagact gcttaacttt ttttaatctt    84060
taatcttaaa cttttaaatg ccatttgatc tttaaaaata tatgttttaa tagtgtattt    84120
taagtctcta tattttgtt attagaatat atagaggcta taacctacta ccaagcataa    84180
cagacgtcac tatggaaaat aacctttcaa gagttattgc agcagtttct catgaactaa    84240
tcacatcaac caccagagca ctcacagtaa gtctctttct tgatcggtct tactgacatt    84300
gtaatagttt ttggtagctt gtatggccag ttagttgtat ggtcatctta cggtgaggtg    84360
cttgtcttac agctcttact tatccatgag gcttgctaag aaattgtgct tctgtgaaaa    84420
gaatctcagc ttactccagg aatgtaaatg actatgtttt ttctgattat taaagtaata    84480
cacgcccaaa ataaaaaaat tcagccaatt taggaagaca caacaattaa aataagccag    84540
gcatggtggc tcatgcctgt aatcccagca ctttgggagg ccaaggttgg gggctcactt    84600
gaggtcagga gtcggatacc agcctggcca acgtggtgaa accccatctc tactaaaaat    84660
acaaaaatta gctgggcgtg gtggcgggcg cctgtaatcc cagctactca ggaggctgag    84720
gcaggagaat cgcttgaacc tgggaggtag aggttgcagt gagctgaggt caagccactg    84780
cactccagcc tgtgcaatag agcgagactc tgtctcaaaa aaaaaaaaa aaaagaaaa    84840 gaaaaaagta aactactgtc acctgcattg gtaatgtatc agaagtttaa aatgtctaga    84900
ttataattaa ctcagtgacc tggtaatata tactaaggga aaaatattta taatttacat    84960
ttttacattt ttattttttt aattttatta ttttttttt gagacagagt tttgctcttg    85020
ttgcccaggc tggagtgcaa tggcatgatc tcagctcacc acaacctcca cctcccgggt    85080
tcaagcaatt ctcctgcctc agcctcctga gtagctggga ttacaggcat gcaccaccat    85140
gcccggctaa ttttgtattt ttagtagaga cagggtttct ccatgttggt caggctggtc    85200
tcaaactccc aacctcaggt gatccgcccct cctcgacccc ccaaagtgct gggattacag    85260
gtgtgagcca ccatgcctgg ccttacattt ttataataag aatttatgtt gctgacatta    85320
gaaaagaacc ataatatcca agaatccaag ataattaaa ttatgtacat atgctagtat    85380
atagtgtgat gctttggaga attttaaca atatggagat gtataatctg gattgtaata    85440
ttgagtgaaa aaaggcagaa tacaaacctg gtggggtat agtcggattt cagttaagaa    85500
aaataatatt tacatatata catttctcac actggcagat aatcaccaag ataaatttg    85560 ggattgtgga tgattttttt cttctttata tttttcagat attctcaaat tttctaaaat    85620
gagcaagtat aactttgtt atcagaaaaa aataatatac aaaagtaatg ttaatttgct    85680
ggtgaccagg ttaaaccttt ttatttttat tttttgagat ggaatctcac tctgttgccc    85740
aggctagagc acagtggcat gatcttggct cactgcagcc tccgcttcct gggttcaaat    85800
gattctctgg ccccagcctc ctgagtggct ggaattacag gcgtgtggca ccacacctgg    85860 ctaattttg tattttagt agaggtaggg tttcaccagg ttggtcaggc tggtctcgaa    85920
ctcctgacct cgtgatccac ccacctcggc ctcccaaagt gctgggatta caggcgtgag    85980
ctactgcgcc cagccagacc ttttattttt atttgacaaa agaaatactt ccatgttata    86040
gaagactaaa tattgtttgg gctgtctgca gtatggtctt cccttgattt gttcaaaata    86100
tcgtaaactt tgcttatta ttttattgt ggccgactgt gtcgggcact gttgtaggct    86160
```

```
tgggatggaa aaacaggatt cctgcccttta gggtttctgc aggctggtca gggagacgat    86220
gtggtaagct ggagctcagc tcctaaggat gtgcaggggc agttgagagg cggaagggtg    86280
ggagatcatt ccagggtgtg ggcagcacag gaacctctct tcattgggat ataattgcca    86340
ttctgataac acgtgtttga ggtgtctaaa gtaggaagtt gtaccatggt gggacagata    86400
tcctgtggtt atcatacaca gatctcagtt ttcttctcat tgtttgtact ttttataaag    86460
ggtaacagga gatataattc aataaacctt tgtggtgttt gggtgtgatt ttattgtttc    86520
tttcttctca gtttggatgc tgtgaagctt tgtgtcttct ttccactgcc ttcccagttt    86580
gcatttggag tttaggttgg cactgtgggt atgtattttc ctcagtatat attaatagtt    86640
gtctacaaca gtatgacata aacatagtta ttaggatgcc ctttttcttt cttttttaagt    86700 cttttatcaa tttggctttt tggaaaaata tctgatggaa tacttgtttc tgctatatta    86760
gctgtgtgag actagtgaca ggagctgtgg gaaatgaatg ccaaatgttc ttaggcattg    86820
atgggaattt cagggtgtgg tcttcaagtt catttaaggg aattttcata tgctggcaaa    86880
aggcttttct cattagcttg actctttcca aaattatttg ctgtgaatta gaagtttagg    86940
aacctttttt cacttaattg tgacctagca tacgaaatgg tgatgattta ggaactactg    87000
ttcttgtatt aacagctttt atttaaaaat gattttcctc cagtagatgg ccctactagc    87060
atctgggaaa taatttcaag tcttctccag cattcaggaa taggcttttca ttttgtgtat    87120 caattactga gaatgatttt ggtgactcac atcacatttg agaagtaaac ctgcagattt    87180
cttgtgtgtg tcagcaaatg accaactgat atttgcttga agtggattac attatctgct    87240
ctagaatgat tgctttccca ccttcctcac atacagactg agcagctacg gtttctaatc    87300
ataggtctgg cactagactt cacttctggg caactttggc attggagtaa aatgtattaa    87360 tttaagaaa gttaaaaatc cgttcaagta aacatacagt tctaatactt tttacaattt    87420
aaaatataga tttaaatgat aaaataaaaa agaaaatatg ggtagacacc ataatcctcg    87480
tttctgcatc tgttcacaag gggttgatat ttatgagttc tattctccat atccattcta    87540
tgttctctta atgctcagtc agcacctcag gtggttggag ttcaatgctt ggtagtttga    87600
cttacactgt cttttctagg ggattgagcc ctgggtagtc ctgcttattt gaggttgcaa    87660
tttgtctttc aataactttt actacaagat atggcgtgtt aaaggatacc attggggaac    87720
caacataata atatcaggaa aactaaccac gtcagacctg ccccattgtg tatcaagtac    87780
actatttttc catagtaata aagagttcac cccagccaat tctcttttat tttgtgcctg    87840
tttactcaat ggcattaaca tgcccaaatg tctgggtagc tgtctcatct ccagttcagc    87900
agaaccattg tcatatgccc tagtaaaagc attccttcat tggacactta ggccccaata    87960
ctttcattca gatctactac ctgatttcat ttctcaaatg attttttatgg agctctgatt    88020 tataggaaag atgttagttg attaaaaata aaacaatttc tgagctggta taaaatgtat    88080
tgtgacatgc cttcctcttg gaattgcaag agaaaggaag actgttgttt gcttaaaaat    88140
tgtctataat ttgactttgc aaatgtctgc ttccagagtg cctccactga gtgcctcaga    88200
tgagtctagg aagagctgta ccgttgggat ggccacaatg attctgaccc tgctctcgtc    88260
agcttggttc ccattggatc tctcagccca tcaagatgct ttgattttgg ccggaaactt    88320
gcttgcaggt actggtactg agttgaaaca gggactccag gacttggatt ttgatttcct    88380
tagggggaat gggggtggtg agcatatgag gggaaaatac tataaggtca ttgccagtga    88440
tggcttgtcc ctttagtcaa atttcagatg ttacctatat gcataaacac atgcagttgg    88500
cagctgttct gtgctgagta ttttaaagta gcctcttccc aatatagccc ctcagttaac    88560
```

```
tacaagtaaa ctcattttga atttcattt  aatgggcacc atatgccagt actccctcgg  88620
gcactgggat gttaagaaag tataatgtat ggacttcatt ctcaagttag ttttagatta  88680
gaggggata  cacgtaaaca aaagtgcagt ggtcacacag agtggccta  atcactctcc  88740
ttgggcagat ttatgggctg gtaggaaaga gcacaacacg gagagggtgt agcaccttgg  88800
cgatgataat ggaggatgtg gccagcaagg aagacggagt ccattgaaat tgattttggg  88860
agaagttgcc aatctccatg aaagaattgg ggcctgtgct atttgcttca ggggctata   88920
ggagagtttc gtgaaaggga ctaaagatg  agtattttaa taagatcatt catccaactt  88980
gaacatgggc tggaggagaa ggtagggaga ctcaggagat taatgttgat gctaaggcaa  89040
gataatggct ttgggactgt agggaagaca ctgattgtaa gagaatgaag gaggcagaat  89100
tgccaggcct ggttcaccaa ctgaacttcg gttgtgaaga caaagaaacc tgggatgact  89160
tcacatcctg ggcaggtgtg tggtggtgac agtcatggaa attgggaaca cagatttgtg  89220
cgggaaacat cagtttcagt ttgagtttgg cttatcagtt gaatatcagg cacagatgtc  89280
tggccaactc tcaacatagg gtcttaaatg acttcagttc cccaagcaat ttgtccttcc  89340
catgctattg gggtggagag gtaatgtctg tgcccatatc acagccagtg ctcccaaatc  89400
tctgagaagt tcatgggcct ctgaagaaga agccaaccca gcagccacca agcaagagga  89460
ggtctggcca gccctggggg accgggccct ggtgccatg  gtggagcagc tcttctctca  89520
cctgctgaag gtgattaaca tttgtgccca cgtcctggat gacgtggctc ctggacccgc  89580
aataaaggta atgtcccact tgggtgctgg attcatacag ccttaatgac tatgggtttc  89640
cagactacct ttgtttagta atctgtccct tctttattct cttttgctt  taaatgaaca  89700
aaattgctca gattgtgaca ctaaatttaa catcaaaatg tgaccatgtg gatgggtgca  89760
gtggctcgtg cctgttattc cagcactttg ggagactgag gcaagtggat cacttgaggc  89820
caagagttcg agaccagcct gggcaacatc acgaaacccc ctctctacta aaaatacaaa  89880
aaattagatg ggttgggccg ggcgtggtgg ctcaagcctg taatcccagc actttgggag  89940
gccgaggtgg gcggatcacg aggtcaagag atcaagacca tcctggctaa cacagtgaaa  90000
ccccgtctct actaaaaata caaaaaaatt atctgagcat ggtggcgggc gcctgtagtc  90060
ccagctgctc gggaggctga ggcaggagaa tggcgtgaat ccgggaggcg gagcttgcag  90120
tgagccgaga tcgtgccact gcactccagc ctgggtgaca gagcgagact ccgtctcaaa  90180
aaaaaaatta gatgggcatg gtggtgcgtg cctgtaatcc cagctacttg ggaggctgag  90240
gcaagagagt tgcttgaacc tgggaggcgg agtttgcagt aagccttgat tgtgccgctg  90300
cactccagcc tgggtgacag agtcagactc tttccaaaag aagaaaaaaa tgtgaccatg  90360
tgttttatag ctctttagt  atcatcagtc actgttatcc ctaagaggga aatacctagc  90420
tttagtttta ggtttccagc attagccaag aaagctcaga attgatgttc ctggccaagt  90480
acctcattgc tgtctcctta aatcttggtt aatggctact gtcctggcta gcatagttat  90540
ggagcatttc catggttgta gaatgttctg ccaatctcag ggacagtttt gcttttctgt  90600
gaagcaataa aatcaacttc aaaacaaatg ttaactattt gtacaatgga tttaagatag  90660
accagttcac atacttttt  ttttttttt  ttttgagatg gagtttcatt cttgttgcct  90720
gggctggagt gcaatggtgt gatctcagct cactgcaact tctgcctcct gggttcaaac  90780
gattcttctg cctcagcctc tcgaggcaga ttacagctgg gattacaggc atgcaccacc  90840
acacccagct aatttttttg tagttttagt agagacgggg tttcaccatg ttggtcaggt  90900
```

```
tggtctcaaa ctcctgacct gaagtgatct atccgcttcg gcctcccaaa gtgttgggat    90960
tacgggcatg agccaccacg cccagcctaa gatagaccag ttcacttact gtttatatct    91020
gattactctc tctttgcctt gtcttctacc tttaaaaatc tccctactaa cttcccattc    91080
tcctttagct gccatcagtc ttctcccttc tctgcaaaca tctctggaga gtcccagcct    91140
cagcccacag agcttcccac tgctctgagg tggaccttgt ttgcaaggct tctttggctc    91200
tcttggcctg gaccctgtct actacttcag ccatccttcc ttaaccctg  ctggtggttt    91260 ctgttgccac actccatagc agcgtttccc gcccagatca tgtctttaca tctctgggca    91320
ctgctctggt cctgcctgcc tttccctctt tgtatcctgc aggctgctac ccccatcttg    91380
agtgtcctct tcagttggct ttcagagggc ctcctgggtg ttcccttacc cacttgccac    91440
tccccagtca ctgggttcag tccttcctgc ccaccagcac atgctttcta ggctctgtcc    91500
taggccgtct tctctctttg tagtctctgg gccagtgctg ttctagagag tggcagaatt    91560
ttctataacc atggcagtgc tccatagcta tgccaggcaa gacagtagcc actaaacaca    91620
tatagctgtt gagcccttga aatgcagcta gtgtgactga agaactgaac cccgattcgg    91680
tttaattttc attaaattta aatttaaata accttatgtg ggtagtggct ccagtattgg    91740
gcagggcagc ctgagagtcg gggctgttct cctgtcttca gtgtctagat gagggacctc    91800
agaggacctg tctctggagc tgcagttcaa tgtagccagc tgccccgtga cacttacata    91860
tagctgattt gtggatatgt cagacacggt gtgatgagct cagctttctg tcctcctccc    91920
cacatctgcc cctgccccat ttaccccact ttgtgtctta tcaagctaga aacaggtcac    91980
cacaagtctt catttccact caccaagtct tttgtttccc ctactaaata ttttgcgaga    92040
agaaagtgtg tacctttgta ttcacataca tgtacatgca catatacatg cacatatgca    92100
ggggtcccca acctctgtta aaaaccggac tgcaggccgt gcgtggtggc tcacgcctgt    92160
aattccagaa ctttgggagg ccgagaccag tgcatcacaa ggtcaggaga tcgagaccat    92220
tccggctcac acggtgaaac cccgtctcta ctaaaaatac aaaaaaaaat tagccgggtg    92280
tggtggcggg cgcccatagt cccagctacc tgggaggctg atgcaggaga acggcgtgaa    92340 cctggggaggc ggagcttgca gtgagccgag attgtgccat tgcactccag cctgggcgac    92400
agagcgagac tctgtctcaa aaacaaaaca aaacaaaaaa aaaaaaaacc aggctgcaca    92460
ggaagaagtg agcaagcatt accatctgag ctctatctcc tctcaggcca gtggtggcat    92520
tagattctca taggagcgtg tatgagttcg ttctcacact tctgtaaaga catacctgag    92580
acatataaag aaaagaggtt taattggctc acagttctgc aggctgtaca ggcttctgtt    92640
tctgggaagg cctcaggaaa cttgcagtca tggcagaagg tgaaggggaa gtaggcacat    92700
cttcacatgg cccacaggaa aaagagagaa ggagagagag agagagacag agagagagag    92760
agaaaaagaa agattgagag ggagagagga gggagaaagg agagtgcctg tagggggagt    92820
tgctacacaa aggagcacca gggggatggt gctcaaccat tagaaactac ccccatgatc    92880
caatcacctc ccaccaggcc ccacctccga cactggagat tacaattcag catgagattt    92940
gggtggggac acagagccaa accatatcag agcatgaacc ctattgtgaa ctgcacattt    93000
gagggatcta ggttgcatgc tccttatgag aatctaatgc ctgatgatga tttgaggtgg    93060
aacagtttca tcccgaaacc atccccgcc  aaccctggtt tgtggaaaaa ttgtcttcca    93120
cagaaccggt ccctggtgcc aaaaagtttg gggacctctg cacatatgca tgcacctgta    93180
catgacacac taatacatgt acatatgcat actttatatt ctctgccact tctggtccag    93240
actgatatac tatctcattt ggattactgc actagccttt tgttttggaa acagcatttt    93300
```

```
ttaaaaaatt taatttaatt tttttgagat agggtgtcat tctgttgccc agcttggagt   93360
gcagtgtcat gatcatagct cactgcggcc tcgatctccc aggctcaagt gatccttctg   93420
cctcagcctt ctcagtagtt gggactacag gcatacccac catgcccagc taatttttg    93480 attttttttt tttttgaga  cagagtctca gcctgtcgcc caggctggag tgggttggcg   93540
cgatctcagc tcactgcaac ttctgcctcc caggttcaag tgattctcct gcctcagcct   93600
cccgagtagt tgggattaca ggcgcctgcc accacaccca gctaactttt tgtatttta    93660 gtagagacgg ggtttcacca tgttggccag gctggtctcg aacttgtgac ctcgtgatta   93720
gcccgcctcg gcctcccaaa gtgctgggat tacaggcgtg agctaccgct cccagccagg   93780
aaacagcatt cttgagataa ttcatataat tcacccattt aaagtatata attcattctc   93840
tttagtatgc ccacagagtt gtacagccat caccagaatc agttttagaa cccataaagg   93900
aactctgtac tctttaccca aaacctccat gcctccagct gcaggcagcc actaacctgc   93960
cttctgtctc tgtgactcta cgtcttctgg acattactgt ggatgggctc atacagtcag   94020
tgagcttgtg actggtgcct tctaccaagc agggttttca gtgtagcagc ctctctgttt   94080 ttctttttt  tttaaattgt gacggaactt ctgcctcccg ggttcaagcg attctcctgc   94140
ctcagcctcc cgagtggctg ggactacagg cccatgtcac catgcctggc taattttttt   94200
tttttttttt tttagtagag atgggttttca acatgttagc cagggtggtc tcgatctcct   94260
gacttcatga tccgcctgcc tcggcctccc aaagtgctgg gattacaggc gtgagccacc   94320
atgcccggct aacctttcat ttactgtctg catttcttcc ctgatgcctt ccagtccatg   94380
cacccgattg tagccattca tcctattatg gtttaaggtg actgtcttag tcagcatggg   94440
ttgccataac aaaataccat agcctgggtg gcttcaacaa cagaatttac ttctcacact   94500
tctggaggtt gggaagtcca agatccagga ctttcgcctt gccctcatgt ggtgaggggg   94560
tgaggaagct ctgtggggcc tcttatatat ggatgctaat ctcattcatg aggggtctgc   94620
cctcatgacc cagtcacctc ccaaaggccc cacctcctaa taccatcacc ctggtaatta   94680
agtttcagtg tataaatttg ggggactata gacattgaaa ccataacaag cacttttcta   94740
agatcaggga gtgagtaagt agcagagcta ggacctcaat tccacatgtc agtcatcttg   94800
ccttcactct gctccatgat ggctgcctcc tagagcattg ggagtctcga tgttctatat   94860
gctctcatgt gttgtgtatt ggagatagtt gaggctttat gaatacatct ggatttgttg   94920
acttctagct ttgctggtaa ccagctgtga ccttgaataa gttacttcat ctctgagcct   94980
gtttcctctt ttagaaacag gagtttaaaa tgctgctttg ggttgggcac ggtggctcat   95040
gcctgtaatt ccagcacttt gggaggctga gatgggagga tcactggagc ttggagttcg   95100
agaccagcct gggcatcata gtgtgagatc ctgtctcctc aagaaattaa aaaattagct   95160
gggtgatgtg gcgtgtgcct gtggtcccat ctactctgga ggctgaggtg ggaggattgc   95220
ttgagcccag gaggttgagg ctacaatgaa atatgattgc accccatcct gggtgacgag   95280
tgagaccctg tctcaaaaaa gaaaaaaaaa atgctgcttt gtacccccttt catgtcatgg   95340 cgtcatggcc aacatagaat gccctggttg tttgctgttg gagggcatgg gcctgggggc   95400
tccctgaggg ctccttccat cttcaactca ttctctgtgc acctgttagg aagttgtggg   95460
ccagtcccta ccatgtatca ttgtgtgggt aaaagtaaat aaaatgtgta cagtgtctga   95520
actgtacata tcagggtcca agaacaaaat gagtgacatg ggttagctct ttttaataaa   95580
tggtaaaacc aaatattcta atttcagtt  ttgttatact tccatcacat gttttgtttt   95640
```

-continued

```
ttttgttttt tgtttttgtt tttctatttt aggcagcctt gccttctcta acaaaccccc    95700
cttctctaag tcccatccga cgaaagggga aggagaaaga accaggagaa caagcatctg    95760
taccgttgag tcccaagaaa ggcagtgagg ccagtgcagg taggaaacag cgtggggaag    95820
ggagggacat gagtgcagca tctgtcatgt agaaacatag gatttaagta acttggtgtt    95880
ttagagaaat aaatataata cacatcagta aagtgagaga aagtttctcc aggtgcggtt    95940
caagatatta gaaactaatg actgatgtac acagaccacc ttttggtctg aagcatttct    96000
aagtgccact ggctgacatg cagcccctac agcctccagg cttccagccc tagcatggag    96060
catcactctc ctatgcttcc ctggttgcag gtgatggctg gagaggcctc ctgattttca    96120
gtaagggaag tggtgtagat gcttaggaat agatgtagtg agtgaaaaaa ctgattctga    96180
tatgtcaaaa attctgattg gaaatggaat atttacattt ggaagagcta aaggcgagag    96240
aaagtgggga taaagtcatc tgagttggag gagcttaaac cattcacaag tttggaggac    96300 cttttttttac ccatgaaaag gtcagaacag aaggggctag gatttaggtg tgactgcagt    96360
ttattgaatt cccatccata ctgctctcgg tgggcagtgg caggggcagg agaggagcct    96420
ggcaaagcat gaagtgactg ctgctgcctc tgctatctgg gacgcctggc cacctgtctg    96480
tacagtctcc ctccagaccc attctcacgc tgtctcttgg cacccagggg ccagtgatgg    96540
ttctcccatt tgttttgtgt atatagcatt tatatcaagg ctatttattt atttatttat    96600
tttatttatt tattttttttg agacagagtc tcactctgtc acccaggctg gagtgcagtg    96660
gtgcaatctc ggctcagtgc aagctctgcc tcctgggttc aagcaattct cctgcctcag    96720
cctcctgagt agctgggact acaggtgtgc accaccacac ctggctaatt ttttgtattt    96780
tttattagtg gagacggggt ttcaccttgt tggccaggat ggtcttgatc tcctgacctc    96840
gtgatccgtc cacctcagcc tctcaaagtg ctgggattac aggcatgagt cactgtaccc    96900
ggcctattta tttattttta attgacaaaa ttgtatatat ctgtaatata caacatgatg    96960
tttgaaatat gtgtacattg gccaggcgtg gtggctcaca cctgtaatcc cagcactttg    97020
ggaggctgag gtgggcggat cacgaggtcg ggagttcaag accaaactgg ccagcatggt    97080
gaaatcctgt ctctactaaa aataccacaa aaaaaaaaa aaaaaaaaa agccgggcat    97140 ggtggctcgc gccagtcgtc ccagctactt gggaggctga ggcaggagaa ttgcttgaat    97200
ctggcaggtg gaggttgcag tgagctgagt tcatgccact gcactctagc ctgggcgata    97260
gagcgagact ccgtctcaaa aaaaaaaaa aaagaagaaa tacatatgca ttgtggaatg    97320
gctaattaac ctgtgcatca cctcacgtat cattgttttg tggtgagaac acttaaaatc    97380
tactctttca gtgattttct tgcatatggt acattgctat taactgcagt caccatgcta    97440
tacagtagat ctcttgaact cattcctcct gtctataaat gaaattttgt atccttgacc    97500
aacacattca aggtttttt tgagatggag tcttcttcac ccaggctgga gtaccatggc    97560
acgatctcat ctcactgcaa cctccgcctc ccaggttcaa gcaattctcc tgcctcagcc    97620
tcctgagtag ctgggattac aggcacatgc tactgcacct ggctaatttt tgtatttta    97680 gtagaagtgg agtttcacca tgttggccag gctggtctcg aactcctgac ctcaagtgat    97740
ccgcctgcct tggcctgcca aagtgctggg attacaggtg tgagccactg cacccggcct    97800
caagcgtttt aaaagatgct cttttctaag gattgactgt agtacaggag gaagattgac    97860
ctgttgaaaa gcctcagcct ttacaagtgt aaaattatca gtatattact atcatctttc    97920
tgatgaatta aataaactaa ggactccaag tcaaagtctt caaactgaa gtagaatagt    97980 tgtatatagt gcttggcact ttaatattta gtatcggttt aatgataatg tttgtgcctt    98040
```

```
tgccgtcttt aaaacatttt tacatcatcc ctgtttgatt acttggtgtg ctcatgaagt   98100
tgttggccac taaggaatct taggctcaga gaggttctgg aattggccag tggtccttga   98160
atcagctgct cctatgattc tctaactgat ttctcacaaa gcaaacaagc aatcataaca   98220
aaacaactgt gcacactgct cttcttattt tgttatttaa aaagtactta ggctctactt   98280
atgtttgtta gtcaatttct cattacttct agttaatcaa aaggtcagag gaaatacttg   98340
aatattttca tactagaata ctttaaaaaa tcatgatttc cagtaatctc tttaaaactt   98400
ggcaagttat tttgatctaa aagtttatct tttgtgtgca tatttttaaa gcttctagac   98460
aatctgatac ctcaggtcct gttacaacaa gtaaatcctc atcactgggg agtttctatc   98520
atcttccttc atacctcaaa ctgcatgatg tcctgaaagc tacacacgct aactacaagg   98580
tatgggcctc tgcatctttt aaaaatatat atgcacacat acttacgtct aatggatagt   98640
tgatgttttt cttatgattt gtaggatgta taagcccttt gagatatgag ttacatttag   98700
ttttttcaag tttgtttgtc tttcagcttt gtttatgata gcttctatca tacaggtgtt   98760
ttggattttc atattgtttg tactcacagc taagattgat tacagtgaca gagctaggat   98820
gtgcagccag gttataggggg gaagtggccc tggtggagtc tggagggatc cgtgtacagg   98880
cttccttccc tcccgtgagg ctcacacaaa aatacagcaa catgctggtc ctgcaggtac   98940
cctctgccta acatgagcca caattccaga ctcacagaag aaaagcaggt gttcggcata   99000
aaccatgtgt ttcaaatagt ctgggcatgg tgagccactt gttatcagct agggaaagtt   99060
tatgtcagcg taagaaactg ttcaccagat accccaaga gccagccttt ctgtctaggg   99120
atgttttagt ttttagttc attttttttt ttaactttaa aattttctgt tcatctgcaa   99180
tttgttagat atgaagtatg tgtctaattt aattttttgtt tttggttgtc cccaataatg   99240
tttacagaag aattttttctg cactaattgg cttgagttac ttacattctc atagttctct   99300
agtttcagta gtttcatttta ttattttgtt atatcaatct atctgtctgc tcatctatta   99360
gaagcatcct tgttttttt ttttctttt tagacagagt cttgctctgt ccccaggttg   99420
gagtgcagtg gtgcaaccat gcctccctgc agtctcaggg ctcaagtgat cctcccacct   99480
cagctcctga gtacctggga ctaccggcat gtgccaccac acccagctaa ttttacatt   99540
ttttgtagag acagggtctc cctaagttgc ctgggctggt ctcaagctcc tggcttaagt   99600
aatcctccct ccttggcctc ccaaagtgct gggattacag gtgtgagcaa ctgcacccgg   99660
ctacaagtat acttcttaat tattgtagct taatggtatt tatgagggga tcagttcccc   99720
tgttgttctt tagaattttc tggatattct tctttattga ttttgggatg tgaacaatag   99780
aatcaacttc tacttgtaga ttgatttagg gagaacttat acctcagatg ttaagtcacc   99840
ctgtccagaa tgtgggatgc tttcctattt gttcagaact ttttaaatta cctcagaagc   99900
acatgaaatt taaaggattt taaaaaaaac ttaaagatta tttcacatag ctcttgcaca   99960
tttcttgata aatgaatcct caggtattcc tctgtttttg ttactaatag ttacttctta  100020
tgggtttttt ttcccctgaa aatcatttat caaacgtatg tggcttattt tctgaaggat  100080
gtttgataat tttggaagat atgaaagtct tcatatttta caaggtttga ggtctcttta  100140
agctgcatgg ttctcatgtc agctcccaaa gcagaagacg gcatgttgaa aaatgccgta  100200
gagaagatac ttcttttcca cctgttttca actcatatca tcttgaattt cagggcacct  100260
ttccatgctc ctagtgcttg ctatctgttt attattttcc ttcctgaata ccctgaactc  100320
cagcatgttc tgctgtaatt ctggcctccc tggcatcttg gactcctgtt tcctttgctc  100380
```

```
tgtcatcccc gcggtcagct cctgctgcgc agcttctcag ctgaagtgcg tttggagtgc   100440
ctggcgtgtc ttgctggatc tttgagtatt gcctctggtt tccttggttc cttctgctga   100500
gttgctcagc gtctccactc cccatttctt gtgtggccct tcctgcactc ctctgattcc   100560
ttttgtcttc cctggtttct tgctttggtt tcgagtctcc acagaacttt tgcagctctt   100620
ctgaagacct ggaagctttt tcatcttaat tctcatctca tgacctcttt tcccttcttt   100680
gagagctaga acttcccatg gtgaacttct cttccagaa ttccatgcct tcttttccct   100740
cccacttacc tgttgtccag gagaggtcag attgctgtgc atattggagg agaacccttt   100800
cttccctggg ctcttcatct cacatgacat caccacatca cctcgttcct tggaccctca   100860
gtggtgtcac tgctggattt ttcttccctt tggctggcct tagggcacac ccaggttgac   100920
tagcgtagtc atggtattta gatccactca cattttcagt ttctgtgtct gtctcttgcc   100980
tgcttctgac ttcgcccaga gaaagcttct cttcacaag ggttcttaga tttatgttca    101040
ctgagcacct tctttctga ggcagtgttt taccaatatt tattttccta gtcagtctcg    101100
ccttaccttt cttgttatgc atgtctttgg tcctgaccca ttctctgagt ctgtaaaata   101160
gaattgctgt ataatttaat tacatgaaat cctttagaat cttaacacat cttacacctg   101220
atttaatatt ttattgtatc caaattgaac caacccctatg tgaatttgac agtgattct    101280 cccagggatc ctagtgtata aggaatagga cttagtattt tctattttt gataaccac     101340 ataccagata ctgattatga tggacattta acccttttt ctcattatga aagaaagtta    101400
ggaattattt cttccagtag cgccagtgta acctgaaagc ctttgaaaga gtagttttg    101460 tatagctatc tgaaaggaat ttcttttccaa aatattttc cagtgctgac aacaaacacg   101520
cagacacacc ctgcaaggtg agtgtacggc gccgcacagt ggaggcatct gctgcagccg   101580
tcgatgtttg tgtctttggt tgtacattat gagatcgtga cagggccagt aaccgtgtgt   101640
tctctccttc accttcccaa ggtcacgctg gatcttcaga acagcacgga aaagtttgga   101700
gggtttctcc gctcagcctt ggatgttctt tctcagatac tagagctggc cacactgcag   101760
gacattggga aggtttgtgt cttgtttttt ctccttgggt tgtggctggc acacttgatg   101820
tgcgtcttct gggctgagtt catctaggat ggagcctggt tctccagggt gcctccggga   101880
gactcctccc tgccccacgt gcttgcgtca caggacccaa gtctgactct gccttagcca   101940
tgaagtttag ggggaagttt ctatttgtat tctatttttg tctgttatca tgtattagct   102000
tagacccagt ttagtttgga aaatcagtgg gttcaaaat gtgtttgtag agtcctttat    102060
ttcttaactt gaccttttca agtggaaagg ggcaaaacag acgggtaagg gggcggggcg   102120
ggaggtgtga cttgctcttt tgtgcctgag gaagtaacag agctggggtt gacagtcata   102180
ttctctgaca cagatagtct ctgacttatc tcacagaaag tcagcggcag agcctgagtt   102240
aaaagtctcg tagattttct ttttctttt tttggtggct aatttcagtt ttatttatat    102300
ttgtttattt atttattata ctttaagttc tgggttacat gtgcagaatg tgcagttttg   102360
ttacataggt atacacgtgc catgatggtt tgctgcaccc atcaacccat cacctacatt   102420
aggtatttct cctaatgtta tccctccccc agtcccctca ctcccatgg gccccggtgt    102480 gtgatgttcc cctccctgtg cccatgtgtt ctcattgttc aatttccact tgtgagtgag   102540
aacatgcggt gtttggtttt ctgatcttgt gatagtttgc tgagaatgat ggtttccagc   102600
atcatccatg tgcctgcaaa ggacatgaac tcatccttt ttatggctgt atagtattcc    102660
atggtgtata tgtgccacat tttcttaatc cagtctatca ttgatggaca ttcgggttgg   102720
ttccaagtct ttgctattgt gactagtgcc acaataaaca tacatgtgca tgtgtcttta   102780
```

```
tcgtagaatg atttataatc ctttgggtat atgcccagta atgggattgc tgggtcaaat 102840
ggtatttcta gttctagacc tttgaggaat cgccagactg tcttccacaa tagttgaact 102900
aatttacact cccaccaaca gtgtaaaagt gttcctattt ttccacaacc tctccagcat 102960
ctgttgtttc gtgacttttt aacgatcgcc atcctaactg gcgtgagatg gtatctcatt 103020
gtgattttga tctgcatttc tctaatgacc agtggtgatg agcatttttt cgtatgtctg 103080
ttggctgcat aaatgtcttc ttttgcgaag tgtctgttca tatcctttgt ccatttttg 103140 atggggttgt ttgcttttt ttcgtaaatt tgtttaagtt ctttgtagat tctggatgtt 103200
aatcttttgt cagatgggta gattgcaaaa attttatccc attctgtagg ttgcctgttc 103260
actctgatga tagtttcttt tgctatgcag aagctcttta gtttaattag atcccgtttg 103320 tcaatttttgg cttttgttgc cattgctttt ggtgttttag acatgaagtc tttgcctatg 103380
cctatgtcct gaatgttatg gcccaggttt tcttctagga ttttatggt cctaggtctt 103440 atgtttaagt ctttgatcca tcttgagttg attttgtgt aaggtataag gaaggggtcc 103500
agtttcagtt ttctgcatgt ggctagccag ttttcccaac accatttatt aaatagggaa 103560
tcttttcccc attgcttatg tgtgtcaggt tgtcaaaga tcagatgatt gtagatgtgt 103620
ggtggtattt ctgaggcctc tgttctgttc cattggtcta tatatctgtt ttggtaccag 103680
taccatgcag ttttggttac tgtagtgttg tagtatagtt tgaagtcagg tagtgtgatg 103740
cctccagctt tgttcttcta gcccaggatt gtcttggcta tgcaggctct tttttggttc 103800
catatgaagt ttaaaatagt tttttccaat tctgtgaaga aagtcagtga tagcttgatg 103860
gggggatagc attgaatcta taaattactt tgggcagcaa ggccatttc acgatattga 103920 ttcgtcctat ccatgaacat ggaatgtttt tctatttgtt tgtgtcctct cttatttcct 103980
tgagcagtgg tttgtagttc tccttgaaga ggtccttcac atcccttgta agttgtcttc 104040
ctaggtgttt cattcccta gtagcatttg tgaatgggag ttcactcatg atttggctct 104100
ctgtttgtct gttattggtg tataggaatg cttgtgattt ttgcacattg attttgtatc 104160
ctgagacttt gctgaagttg ctaatcagct taaggagatt ttgagctgaa ccaatagggt 104220
tttctaaata tacaatcatg tcatctgcaa acagggacag ttttacttcc tctcttccta 104280
tttgaatacc ctttattgct ttctcttgcc tgattgcgct ggccagaact tccaatacta 104340
tgttgaatag gagtggtgag agagggcatc cttgtcttgt gccggttttc gaagggaatg 104400
cttccagttt ttgcccattc agtatgatat tagctgtggg tttgtcataa atagctctta 104460
ctatgttgag atacgttcca tcgatacctc gtttattgag agttttttagc atgaaaggct 104520 gttgaatttt gtcaaaggcc ttttctgcat ctgttgagat aatcatatgg tttttgttgt 104580
tggttctgtt tatgtgatgg attacgttta ttgatttgcg tatgttgaac cagccttgca 104640
ttccagggat gaagctgact tgattgtggt ggataagctt tttgatgtgc tgctggattc 104700
agtttgccag tattttattg aggattttca catcgatgtt catcagggat attggcctaa 104760
aattctcttt ttttgttgtg tctctgccag gctttggtat caggatgatg ctggcctcat 104820
aaaatgagtt agggaggatt ctctcttttt ctattgattg aaatagtttc agaaggaatg 104880
gtaccatctc ctctttgtac ctctggtaga attcggctgt gaatccatcc tggacttttt 104940
ttggttagta ggctattaac tattgcctca gtttagaaac ctgttatcag tctattcaga 105000
gattcagctt ttttctggtt tagtcttggg agggtgtatg tgtccaggaa tttatccatt 105060
tcttctagat tttctagttt atttgggtag agatgtttat agtattctct gatggtagtt 105120
```

```
tgtatttctg tgggatcggt ggtgatatcc cctttatcgt ttttattgag tctatttgat    105180
tcttctctct tttcttcttt attagtcttg ctagcggtct acctattta ttgatctttt     105240 caaaaaacca gcacctggat tcattgattt tttttggagg gttttttttc gtgtctctat    105300
ctccttcagt tctgctctga tcttagttat ttttgtctt ctgctagctt ttgaatttgt     105360
ttgctcttgc ttttctagtt cttttaattg tgatgttagg gtgttaattt tagatctttt    105420
ctgctttctc ttgtgggcat ttagtgctat aaatttccct ctacacactg ctttaaatgt    105480
gtcccagaga ttctggtatg ttgtgtcttc gttctcattg gtttccaaga aaatttttat    105540
ttctgccttc atttcgttat ttacccagta gtcattcaag agcaggttgt tcagtttcca    105600
tgtagttgtg tggttttgag tgagattctc aatcctgagt tctaatttga ttgcactgtg    105660
gtctgacaga cagtttgttg tgatttctgt tcttttacat ttgctgagga gtgttttact    105720
tccaactatg tggtcagttt tagaataagt gcaatgtggt gctgagaaga atgtatgttc    105780
tgttgatttg gggtgcagag ttctgtagat gtctattagg tccgcttggt ccagtgctga    105840
gttcaagtcc tggatatcct tgttaatttt ctggctcatt gatctgccta atattgacag    105900
tggggtgtta aagtctccca ctattaccgg gtgggagtct ctttgtaggt ctctaagaac    105960
ttgcttcatg aatctgggtg ctcctgtatt ggggcgtgt atatttagga tagttagctc     106020
ttcttgttga attgatccct ttaccattat gtaatggcct tctttgtctc ctttgaactt    106080
tgttgattta aagtctgttt tatcagagac taggattgca atccctgctt ttttttgct     106140 ttccatttgc ttgttagatc ttcctccatc cctttatttt gagccaatga gtgtctttgc    106200
atgtgagatg ggtctcctga atacagcaca ccaatgggtc ttgactcttt atccaatttg    106260
ccagtctgtg tcttttaatt ggggcattta gcccatttac atttaaggtt aatattgcta    106320
tgtgtgaatt tgatcctgtc attatgatcc tagttggtta ttttgcccgt taactgatgc    106380
agtttcttca tagcgtcagt agtctttaca atttggcatg ttttgcagt ggctggtact     106440 ggttgttcct ttccatgttt agtgcttcct tcaggagctc ttgtaaggca ggcctggtgg    106500
tgacaaaatc tctgcatttg cttgtctgta aaggatttta tttctcgttc acttatgaag    106560
cttagtttgg ctggatatga aattctgggt tgaaaatact ttttttaaag aatgttgaat    106620
attggctccc actctttcct ggcttgtagg atttctgcag agagatctgc tgttagtctg    106680
atgggcttcc ctttgtgggt aacccgacct ttctctctgg ctgcccttc cttcatttca     106740 atcttggtgg atctgatgat tatgtgtctt ggggttgctc ttctcgagga gtatctttgt    106800
ggtgttctct gtatttcctg aatttgaatg ttggtctgcc ttgctaggtt ggggaagttc    106860
tcctggataa tatcctgaag agtgttttct aacttggttc tattctcccc atcactttca    106920
ggtacaccaa tcaaacgtag atttggtctt ttcacatagt cccatatttc ttggaggctt    106980
ggttcatttc ttttcactct tttttctcta atcttgtctt ctcgctttat ttcattaatt    107040
tgatcttcaa tcactgatat cctttcttct gcttgattga atcggctgtc gaagcttgtg    107100
tatacttcac aaaattctcg ttctgtggtt tttagctcca tcaggtcatt taagctcttc    107160
tctacactgg ttattctagc cattagtcta acatttttt caaggttttt agcttccttg     107220
tgatgggtta aacatgctc ctttagctcg gagaagtttg ttattaccga ccttctgaag     107280
cctacttctg tcaattcatc aaactcattc tccatccagt tttgttccct tgctggtgag    107340
gagttgtgat cctttggagg agaagaggtg ttctggtttt tggaattttc agcctttctg    107400
ctatggtttc tccccatcat tgtggtttta tctacctttg gtcttgatg ttggtgacct     107460 acggatgggg ttttggtgtg ggtgtccttt ttgttgatgt tgatgctatt cctttctgtt    107520
```

```
tgttagtttt ccttctaaca gacaggcccc tcagctgcag gtctgttgga gtttgctgga 107580
ggtccactcc aggccctgtt tgcctgggca tcaccagcag aggctgcaga acagcaaata 107640
ttgctgcctg atccttcctc tggaaacatc gtcccagagc acgaaggtgt ctgcctgtat 107700
gaggtgtttg ttggcccta ctgggaggtg tctcccagtc aggctacatg ggggtcaggg 107760
acccacttga ggcagtctgt tcattatcgg agcttgaatg ccgtaccggg agaaccactg 107820
ctctcttcag agctgtcagg cacgtatgtt taaatctgga gaagctgtct gctgcctttt 107880
gttcagatgt gcccttcccc cagaggtgga atctagagag gcagtaggcc ttgctgagct 107940
gcagtgggct ctgcccagtt cgagcttccc tgctgctttg tttacactgt gagcatagaa 108000
ccacctactc tagcctcagc agtggtggac acccctcccc cagccaagct cctgcatccc 108060
aggtcgattt cagagtgctg cgctagcagt gagcaaggcc ccatgggcgt gggacccgct 108120
gagccaggca caggagagaa tctcctggtc tgctggttgt gaagactgtg gaaaagtgc 108180
agtatttggg caggagtgta ctgctccttc aggtacagtc actcatggct tcctttggct 108240
tggaaaggga agtcccccga ccccttgtgc ttcccaggtg aggcaacacc ccgccctgct 108300
tcggcttgcc ctccgtgggc tgcacccact gtccagcaag tcccagtgag atgaactagg 108360
tacctcagtt ggaaatgcag aaatcacctg tcttctgtgt cgatctcact gggagctgta 108420
gactggagct gttcctattc ggccattttg gaagcatccc ttgttttttg aggtggagtc 108480
ttgctctgtc gcccaggctg acgtgcatcg gcacaatctc ggcccactgc aacctttgcc 108540
tcctggtttc aagcgattct cctacctcag cctccggagt agctgggatt acaggcacct 108600
gccaccatgc ctggctaatt ttttgtattt ttagtggaga tggggtttca ccacattggc 108660
caggctagtc tcgaactcct gaccttgtga tccacccacc tcagcctcct agagtgctgg 108720
gatcacaggt gtcagccacc acgcccagcc atatttcag atctccctct ctttgcccta 108780
aaccactgtg cttaataagt agttttttagt ggccagcagt ctccatgtat aacacatttt 108840
agcaaaatgg aaaatactat atgttttaaa tttgaacgtg agattatact gaaataaaaa 108900
tcatctaact gggattcttt aaatagtaag attttcttttt ttgtatgtgg gttttttttt 108960
aaccttatta ttatgactgt catatataga aatggctgtt tttcagttac agtcagtgaa 109020
tgtatcaaat gctgccttat ccaaataata aaagtaaatt attaataagt cacaatttaa 109080
tgaagattga tgttagttga tctttatatt cttgaaatca gccatatggt tgtgtgtgta 109140
tgtatatatt tttaaaggta cataaagata ataagctcat ctctgaaaat ttttacattt 109200
ggcataagaa taactggata attaagcatc ttattctctg gcctgtgtct ttacagttaa 109260
aggtagattt actcacctct ccttttttgt ttttctaagt tcatctttttt tgctgtttca 109320
agacagaggc ccatttttagc tttctcgcat atccttttgt ttgtactttg gaagcctcac 109380
ctgcttaatt gttgagtttt tatccgtggt cttttagagg gggatatgta gggtagaagc 109440
tttcacaggt tcttgtttgc acttggcccc tgactgtttt gaggaatctc cctcactgac 109500
tcacagcatg gcaaggtttc agatctcttt ctgccacaca gcagttctga ggcagctgga 109560
aagatatcca gatgcttaga ttgtcaggcc aggcttgaga tatacaaact attgagcctt 109620
atctgtgacc ttgcttaggt gaaggcatca gagcccctgc accaacatgc ataggcctct 109680
gcatgtgtgc ggggctgggt gttgaggtct gagcacaagt gtagctggag aggtgagctt 109740
gatgtggcga cgggtatgag caggttttct tcagacttct gtgagtttac ctagttccag 109800
gatttaaagg cacagagact ttagaattaa aatagaatca ttttctttttt ctaaatagca 109860
```

```
acactaggaa taaaaaataa taattccaca ttcttgacag gtaatgtttt ttcttgtctt   109920
ctaatcctta tttattccat actcattttt atacataatt gaaatgtatt atgcattgga   109980
tttttctttt gcattatatt atagacgatt tttcatgtaa ctccttactg ttccatttta   110040
tatgttttgt ctggtttaag actttatctg caaaccggga aactgtctct acaaaaagaa   110100
aaacaaaaat agttggccgc agtggcatgc gtctgtggtc ccagctactc ggggctgagg   110160
tgggaggatt gcttgagcct tgggaggttg aggctgcaaa gagccatgat catgccattg   110220
cactccagca tgggtgacag actttatact gtctgttttg ggtgatttga taatgatatg   110280
ccctgatgta gttttttttat atcttgtgtt tcttgtgcct gggtttattg aggttgggtc   110340
tgtggcttca tagtatttttt aaagtttgga aaattttagg ccattctttc tttctttctt   110400
tcttttttttt tttttttgaga cagtgtctcg ctctgtcgcc tgcgttggag tgcagtgaca   110460
ctatcttggc tcactgcaag ctctgcctcc tgggttcacg ccattctcct gcctcagcct   110520
cctgagtagc tgggactaca ggcgcctgcc accacgcctg gctaattttt tgtatttttta   110580
gtagagacga ggtttcactg tgttagccag gatggtctca atctcctgac ctcgtgatct   110640
gcccgcctgg gcctcccaaa gtgctgggat tacaggcgtg agccactgca cccagctagg   110700
ccattatttc ttcaaagatt tttttttctgc cctgcctccc tccttttttc cctctcttaa   110760
aggggctgtg atttcctgaa tgattgctta gtgttgtccc atagcttact gatgctcttt   110820
tcagtgtttg attgttttat gtgttttctg ttttgtatag tttctattat tgtgtttttca   110880
agttctctga tcttttcttc tacagtgtct actctgttgt taatctgtta atctgttgtt   110940
aatcctgtcc agcgtatttt tttttttgtt tttgaaacag tctcactctg ttgcccaggc   111000
tggagtttag tggtgcgata tcagctcact gcaacctcca cctcccaggc tcaagcaatt   111060
cttctgcctc agcctcccga gtagctggga ctataggcac gtgccaccac acctggctaa   111120
tttgtgtatt tttattagag atgggggtttc accatgttgg ccaaactggc cttgaactcc   111180
tgacctcagg tgattcatcc gcctcggtct cccaaagtgt tgggattata ggcatgagcc   111240
accgtgtctg gcccctgttc agtgtatatc actaattttg tttttatctc tagaagtttg   111300
atttaggtct tttaaaaatg tctccctgtg tttctgttta gctttgtgaa cacaattgta   111360
ataactgttt taatatcctt ctctgctagt tctaagatct tctaataact tcccagttct   111420
tggtgtttct cattggttga ttgatactcc tcgtttttggg ttgtatttttc ctgcctcttt   111480
gtatggctgc caatttttta ttggatgccc aaccttgtga atttttacttt gttggatgct   111540
atatattttt gtgttcccat agatcttctt gagctttgtt ctgaggttag ttgagttaca   111600
tatagatggt ttactctttt gggtcttgct ttataaattttg tcagatgggt tggagcagtg   111660
cttagtttag gactaatttt tttttttggac taattattcc tctttaggaa taattaggta   111720
ccatgcttag gaggcaagac catcctgagt actctaccta atgaaccaga aagtttgggt   111780
tttccagtcc gcctgctgag aacagtgact ttctagccct gtgtgagcgc tgagctctgc   111840
tccttctaat cctttccaat gcttctttcc ctggcctcag ggagttttct cacacacata   111900
tctctgctga gtactcgaga gggaccttcc ccagatctcc agagctctct ctgtcttgtt   111960
ttctcttctc tggtgctctg tcttatgaac tgtggctgtc ttggtctcct tagattctca   112020
gcacctcttc aattcagagg gttgcctgtc cctcctcctt gtgccacagc ctaggaactc   112080
tctcaaagca gcgagtttggg gcagccatag ggctgactta gtctctcgtc tcccagggat   112140
cactgtcctt cattgctcat gtccagtgtc ttgaggactc tgggttttgt ctgttttgtt   112200
ttttggtttg ctttggttgt ctcaggcagg agggtaaacc cagtccctca ccctcattgt   112260
```

```
gctcagtagt ggaagtctca ctctattaca ttagatatta gtatttgtag cagagccctg   112320
gttccctggt acttggggag ctcttgaaag gccagaaaca gcatgctttc tcaccttttc   112380
cagggcttca gtttctggtg cacatcaagc attccataca catttgttaa agtcctttgt   112440
tagacaagta gtgattcaca ggttctattt gtaattttt cagttaacat gtattgggta    112500
tctgctggga gctagtaaaa acaaaaagtg gtgtgtgaca aattcaattc tgacaagaac   112560
aaccttaaac acttagaata tactttgagc atatcagaat tttaaaaatg tgtggccctt   112620
gagtatttga aaccaacaag aatctattgc ttattagtag aggatatttt gttaaacaag   112680
tggagagaga ggcattttca gtctaattgg tgttggcttt tagcagctga tggaaaccag   112740
ttcgtgatta gccaggcagt ggtgaaacag gctgtgcatt ctgaatgcct aggtatctag   112800
gcattcagaa tggtggcgct cttttgagtta gcatcttctt cttctctgat tcttttttt    112860 ttttttttga gatggacttt cgctcttgtt gcccaggtaa caactccagt gcaatggcgc   112920
catctcggct cactgtaacc tctgcctccc tggttcaagc gattctcctg cctcagcctc   112980
tcaagtagct gggattacag gtgtgcgcca ccacgcctgg ctaattttgt attttggta    113040 gagatggggt ttcactatat tggtcaggct ggtcttgaac tcctgacctc aagtgatgca   113100
cctgcctcga tctcccaaaa tgctgggatt acaggcgtga gccaccactc ccagccctt    113160 cttgattctt gaaaaggaca ttgggtgctg tacatctcgt tatagatgtt gataaaatg    113220 cttgtgagaa gagtaacatt aaggtagtta tttggtcatt tttgcagatt attttaagac   113280
aattctagga ctgatttgtg gtaaatcaca cattgctgta tcatagttgt gttcactgaa   113340
catattcagg ggctctacag atgcagggct cttagctgct ttgcacactt ctgaattcct   113400
gccctgcgaa caggactgga tacctaatag acaacaggta cttgataaca gtttattgaa   113460
ttaatgagtg aatgaacaga tacataaatg catgaaagaa tggttgtaat gtatataact   113520
tggatttcaa gacttttttac tgactgttca aaataagaaa ttgaaaactt tcctctgatt   113580
ttcctctact atttacacaa tttaaatgga agttatcttg taccttcaat ttctgtctag   113640
gattcgtaca ataacgggtc atctctgagt cgcttaatgt ctcacttgtc tttctacagt   113700
gtgttgaaga gatcctagga tacctgaaat cctgctttag tcgagaacca atgatggcaa   113760
ctgtttgtgt tcaacaagta agagcttcat tcttttcctc ttctgttaag acgttcgggt   113820
atgacagcaa aacgctgcta ctccttaaga ggcaggcgct gttggcataa tcagctggga   113880
ggattgtggg gtccagcgca gcacttttg gctcagtcca tgattgagcc aagaggccat    113940
ccttcccttc actccccagg aggacgaggt ctgtcactgt ggagggcaga ggacaccaga   114000
agctcctctg caacctcgct agttaacttc cagtccctcg gagtttctgt ttagaatgct   114060
caatctcatt tagaattgca aggaaaccca aaacgcctat ttaaggtaca aacagcactt   114120
catacaatat ctcatgaggt attaatagtg attcacagga agaatttcac gctgtgagtc   114180
tttgctaaca tatccagtta tttacagatg gatttgatat ttgtgtggga gattcttaaa   114240
agtgttgttc acgccacatt gttgatgcct catttttttc actgtagttg ttgaagactc   114300
tctttggcac aaacttggcc tcccagtttg atggcttatc ttccaacccc agcaagtcac   114360
aaggccgagc acagcgcctt ggctcctcca gtgtgaggcc aggcttgtac cactactgct   114420
tcatggcccc gtacacccac ttcacccagg ccctcgctga cgccagcctg aggaacatgg   114480
tgcaggcgga gcaggagaac gacacctcgg ggtaacagtt gtggcaagaa tgctgtcgtt   114540
ggtggaagca cgaaagagca agcaggaaat actttgtaaa agaataaaaa cgaaaaatgt   114600
```

```
tagcgaacat cttctaatag tctgctgtat tcagagaact ctaggagata tatatggttg   114660
atgcaaagat gatttaaggc atagcccggc cttccaagaa gtgtgtggcc agtgagtgag   114720
atgggcttgg gacttacaca tctcagaggt gggggtagag gaggaggaac actgagtggg   114780
ctgagaagca gccagctctc attgccaaag tgtgtcagca aaccagaatg cagttcataa   114840
tgtccccacc cattcaaagc acaggacctg tagagtggtg tggcatgtgt tggtggcact   114900
tttcaggcct gtaacaagga tgaaagaaca gcttcatagc agcacagtag tgctggtgtt   114960
cagaggtgtg tgaaggccat agaagcatct tggatatatt accttgtgtt ttgtcagctt   115020
tatgactaga agtctctttt cacttaaatt tgtttttttt tttttgaga cggagtcttg   115080 ctctgtcgcc caggctggag tgcagtggtg caatctcagc tcactgcaag ctctgcatcc   115140
tgggttcatg ccattctcct gcctcagcct cccgagtagc tgggactaca ggcgcctgcc   115200
atcacgcctg gctaactttt ttttgtattt ttagtagaga cggggtttca ccatgttagc   115260
caggatggtc tcgatctcct gacctcgtga tctgcccgtc ccggcctccc aaagtgctgg   115320
gattacaggc gtgagccacc gcgcccggcc tcttttcact taaatttatg tttgtgtttt   115380
taatgcctag tatacaggac ttcttaaatt gccttaagta tgaacaggta tttgagttgc   115440
taatctgtat agtagcaata atagaatccc ttgttttttcc ttttataaat ttagcgatta   115500
aatagctaca attaaaacac tagagtcagg agtcaaggaa aatacccatg ttccaggctg   115560
tatgttagtg atgtacttac tatatattgg agtttcagga gtaagtctgt ttcaatgctt   115620
tctgtaacca tttggggtat taataagcat gtgagtgtgt gcatgtttgg gttaatttca   115680
tatatgtttc ttagaaggga tatcattgat gtaaatattt taaaggcttg tcctccaaaa   115740
aaatcatgta atttcttcta aattactgat cttttaaatg accttcacct ttctctcaaa   115800
tctcacttaa gactgggctg agtagtcagt ttcctgtagc agaaaaaagc tcagacttga   115860
gtagccttct gcgagtgagg agacttgatg gctgtcaggc agctgtaaac tctaaataga   115920
gtgtcattat ctgaagaggg cgatgctgcc acactgagtg gcctttcaag ttgtttctca   115980
atctgacacg ttctgatcgt gtgaatgtga aattggtttg agcaggagta tatctgagtg   116040
cagaggagat tatttaaaga tattctcatt ctctgcttcc cttttattcc catttggcag   116100
atggtttgat gtcctccaga aagtgtctac ccagttgaag acaaacctca cgagtgtcac   116160
aaagaaccgt gcagataagg taaatggtgc cgtttgtggc atgtgaactc aggcgtgtca   116220
gtgctagaga ggaaactgga gctgagactt tccaggtatt ttgcttgaag cttttagttg   116280
aaggcttact tatggattct ttctttcttt ttttctttt tatagaatgc tattcataat   116340
cacattcgtt tgtttgaacc tcttgttata aaagctttaa aacagtacac gactacaaca   116400
tgtgtgcagt tacagaagca ggttttagat ttgctggcgc agctggttca gttacgggtt   116460
aattactgtc ttctggattc agatcaggtt tgtcactttt atctttcatc catcatacct   116520
gttcctaatt tagtacaaat taccctaaaa gacactgaaa tctactttaa agaaatgtgg   116580
tctgcatgtt tccctcatca gttgctgctg cttatctttt tcatgcacct agctggtgca   116640
gaaggcctgg ggcatagcca gcctcagcaa gtcagcatcc ttgccccagc tcctggact   116700 caaggctaac ctggggttgg ctgttaggga ttttccaaagg tttgtcccat ccacttgcct   116760
cccctccaaa ataagtttga atttaaattg tgagatacaa ttaagattta ttgtttgggg   116820 aacattttg caaaatctag agttagttta aacagattat caattattac cataattgat   116880
catctgcagt ttcaagctat ctaacaggtt cacttacctc tttaaaaagg aatgaatttt   116940
agcaggacag taactgagac ccgtgctcct ggagtccatg tgggagctgt gtggctctgc   117000
```

```
acaagcattt gcacgcttcc cctcttgact gcattacctt cctcctatag ttgctgtggg    117060
caccagattc tggctagtcc tgtcccttca tgatgcacat tttcctcaag attcgtccca    117120
gttaaatcac tgcagatgaa actgcctttt catcgtcaaa atttaactgt cattttgag     117180
ccgtgatctt gggctacttt cttatgtggg gtaggaatat ttgtgagtta gaaatattac    117240
acttctctat ttccttctag acgtaaatct gttaatcctg tcagcactgt tactcacctg    117300
aaagggtctg tttccctagg agaactgagg gcactcggtc aacactgatt ttccacagtg    117360
ggtattgggg tggtatctgc ttgtttttt tgttgttgtt gtttgttttt tttgttttt      117420
ttttgagat ggagtctcgc tctgtcaccc aggctggagt gcagggtgc gatctcggct      117480
cactgccagc tccgcctcag aggttcacgc cattctcctg cctcagcctc ccgagtagct    117540
gggactacag gcacccacca ctacgccagg ctaatttttt gtattttag tagagacgag     117600
gtttcactgt gttagccagg atggtctcca tctcctgacc tcgtgatctg cccgcctcgg    117660
cctcccaaag tgctgggatg acaggcgtga gccaccgcgc ccggcctggg gtctgctttt    117720
aatgaaggag gcatcaaggg gtgggctttg cgttggcctg atgctttcat cttcttttca    117780
caaaacctgt ccgaagaaaa tccgtctaaa tgggccattg ctctcctcag gaaatagtca    117840
ttgggaactt cttttccttt cctttgacac taggaggctg actggggaga gccctggtc    117900
tatggctgtg ggcagcaggg gctgagagga gcaggctctc agggggcac gggtacccca     117960
agggaagcca gagccctgat tgttccatt ctagtaagaa caaagactgc tctggtttca     118020
tgtttgttct gattgccttt catcaaccgg tccccttct cccagttctt aagattcagt     118080
acagtgacag ttttatgaac aagaatagaa cactagaaca gacaaaccat tgaactctat    118140
gctgataaag atttattgag ctcctgctgt atgtttgcat tctgcccaga ggctctgaga    118200
aaaccaggcc atatgctcca tgctttatcc atggaagctc cccgtcaggt tgggaaagct    118260
gacagctgca gggaatacag tgtgacacaa aactggctcc catgcagccc ttacgtgtcg    118320
cctctcagat ggttggggga cgaaggtcga ctcctttggg tatcttatta ctaaaccagt    118380
ttcagggaat ctgtgccacc ctatctgcca ttaacgtgaa cagatgagtc cccaaggtgt    118440
aattttgggt attgtctgat gtctcttgga atttattatt tgttttttcca atgagatttc   118500
acctcagggt atagtaaagt tgttgagggg attcctggat gtgttctgca attatctagg    118560
ctgatttcag aatagagtta tgcttatagt caaatttatc agctgtcaag aattttattt    118620
aaaatttatg cagataagca ggaggaaaag aagcctggtt tttacatttt aatcctatta    118680
ttgatgtgaa atttatttt ccttcctgta ggtgtttatt ggctttgtat tgaaacagtt     118740
tgaatacatt gaagtgggcc agttcaggta atagcatttt attatttag atttttttct     118800
tcttcttgtg tacttacatg taatttaggt tattaagtga atgtttaaac tactgttagg    118860
cattttgct gttttctta aatggaaatc tgactaacat actgtgcatt tttgcttctc      118920
ttaaaaatta atgtatatct caagacttgt ttggaagtag ttatgtatct gaaaattcca    118980
tatgttgtca gtattcattg cacatttcaa agcatttaat tgtgttgaca gatggtggaa    119040
tgaaatcttg tggtggagca ctagttttta aatcttctta gagaaagcag ttttatataa    119100
tgttgtcttt agtaattatt atgcatttgt attctctgca gcttttttctt gctagatgtt   119160
gaggttttaa tacttcttgc tagtccatta caggtttata attattaaaa gttaaaattc    119220
ttttagtacc taaaatgctt aataaacatt gtaattagga aaatttagtg cagaaggaaa    119280
gtgttcccag attccctggg gtctggaaac atagtgttta ttctaattac atgacacctc    119340
```

```
cactgtgttt tggggcaagt tactgtttct cttttgagtt tcaatttctt caagagcaaa    119400
gaggcagagg agagctagga agatcgtagc tgctgtgccc ctgtgccgtc gggtgccttc    119460
tacctgctgc ctccgaacct ttacacatgt ccctgctctg cgcgagggca cagatgggat    119520
gcactgtggc aggggtgggg ttagagtaga tcacggacac ctgttagctt gatgtgtgct    119580
tgctgtcaag gttaatcat gaattatttt atgttgctta tattgatatg tatcttaatt    119640
ttaaaagaaa ggtctaaatg gatgttttg ttttaggga atcagaggca atcattccaa      119700
acatcttttt cttcttggta ttactatctt atgaacgcta tcattcaaaa cagatcattg    119760
gaattcctaa aatcattcag ctctgtgatg gcatcatggc cagtggaagg aaggctgtga    119820
cacatggtaa cgggacacac ctttcactgt cgtcttcggt gtcgtgatgt gcttggcagt    119880
gttcgttttc atatcccac tttgaacgtt gtcagtggca gccatgtgct tctcaggctc      119940
tgcatgtgtg tctgtgtatg tgaaggtact ggttagagac gtttcaaaag agaagagagc    120000
atattcttta ctctcagcaa tttgtaatct tctcagggaa aaaaattcaa gaaacagtaa    120060
gataacctaa ggtacagata gattctgaat ataaagttcc tgttcattca catgaaacgc    120120
taaaagttct tcacttgatc ttagccaaaa ggccaagaag cgatgcaaca ctaaaaattc    120180
ttaaatcgaa cttgccgtga attaaatttt gatctctcat ccagtggtat tggagatata    120240
gtttgacttg ggttcagggc tttctgtttt gcctgatgat tttgctggag cttaataag     120300 gaacccagga gatggccagc tgtgcaagcc cccagcctgt ggaaggagct agtgtggttt    120360
tatgaatgag ttgcaaatct ttcttttgagc ttttttgaact gatcttccag cattgcccta  120420 ttgaccccctc cctgactcct ttgctggaat ctgtaggctt tgaactttg acagggacac    120480 atcctaagac ccttgcaaac tcccagatgt gagaatggca ctactactta gagtcttttc   120540
gactcagcgt gtgtgcagaa gagcatcaac cgggctgtgt tgcgaggcag ggccttggct    120600
gacctctcag tgtttacata gctaagccag ttagtgtttg ccacggcctc acaagggctt    120660
cagattcaca cagccaaagt atagattatt aaaggcatag gtgtttggtt tcctggactt    120720
ggagggtctt tggacagaaa atcagtaggc aaccacaccc agtactttgt gctgggaagc    120780
ttggtcatct gtgagagggt cagagagtat acccatgcgt gcatgccacc gaagggtcag   120840
tgagtattcc tgtgtgtgca tgtctcaggg ccggagagag tatgtgtcac tgagaggtca    120900
gagtgtttgt gtgtgtgtca aagagggttg cattgtgccc ttcactgagg ggtcagaggg    120960
tgcctcgcgt gtgtgtgtgt gtacgtgtgt gtgtgtcact gaggggtcag agtgtgcctg    121020
tgtgtgtgct tgtgtgtgcg tacatgtcac tgaggggtca gagtgtgcct ctgtgtgtgt    121080
gctcatgtgt gtgcatacgt gtcactgagg ggtcagagtg tgcctctgtg tgtgctcatt    121140
tgtgagcgta tgtgtcactg agggggtcag agtgtgcctc tgtgtgtgtg ctcatgtgtg    121200
agcgtatgtg tcactgaggg ggtcagagtg tgcctctgtg tgtgctca tgtgtgagcg      121260 tatgtgtcac tgagggggtca gtgttcctat gtgctcatga cattgagggt cagagtgtgc   121320
ctgtgtgcca atgaaaggca tttcttatat tttttatat gtggtcatag tagaccagtt     121380
aatttatttt gactcctgtg ttagaccaaa ataagacttg ggggaaagtc ccttatctat    121440
ctaatgacag agtgagttta cttaaaaaag cataataatc cagtggcttt gactaaatgt    121500
attatgtgga agtctttatt gtcttttcag atgaatcaag tagattattc ttgagaccag    121560
gaatgttgct gttttggtta tttggaaagt tttatcattt tcaaattgac ttttgaattt    121620
gagtcacctt ttttcagaag tggtgttaaa ttataggagc cctaggtttt ttttcttttt    121680
ttagaagtca tcacaaaatg atcagtgttc agaggaagag ctttgacctt ccacatggta    121740
```

```
taatgattga taaccttaat tcatctctta ccataaacca agtatgtgta agggttttct   121800
ttatttcttg aaagcatttt gtagatgttg agagcagttt tccaaatgta atttccatga   121860
aatgcctgat aagggtaccc ttttgtcccc acagccatac cggctctgca gcccatagtc   121920
cacgacctct ttgtattaag aggaacaaat aaagctgatg caggaaaaga gcttgaaacc   121980
caaaaagagg tggtggtgtc aatgttactg agactcatcc agtaccatca ggtaagagga   122040
atgtatgttg gaactgtcgt ggatacttta ttgacccgtg cagatggaag gaagtgccat   122100
gtggtaacgc tcactgttaa ctgtgttact ttgaaccagg tttgggcttt ctgggcctg    122160
ggtagatgcc ggtgcagggg gatggggagg gaggcggggg gtgggggggt gtggtggagt   122220
tggggaggtg cagtggcagg aggtgttgtt ggtgtgtatc cttttttttt ttttgagatg   122280
gagtctctct ccgtcgccca ggctggagtg tggtggcacg atcttggctc attgcaagct   122340
ccacctcccg ggtttaagca attctcctgc ctccacctcc cgagtagctg ggattacagg   122400
catgcaccac catgcccagc aaattttttt ttttgtattt ttagtagaga tggggtttca   122460
ccatgatggc caagctgttt cgaactcctg acctcaagtg atcctcctgc cttggcctcc   122520
caaagtgcta ggattacagg cgtgagccac catgcccagc ctggtgttta tctttaaagt   122580
gggcacagcc acaggagttc acctgactcc tggtctgaga gtcacgagat cgttcaagat   122640
agtgaggccc tcttttccaa aacgaggacc aaaaatcaat tgacagtgtt ggtcaagatg   122700
gtagaaacct taaaatgata gaaatctcaa ctctgaaata aaaactttat ttgtatattt   122760
atttaccact attttgacat agggctaagg tcttttttctt tgagctgatt tctggttttg   122820
ttttcttaaa gtggcataag aattcaaaga cattttgagg aaggctgagt gcagaaatct   122880
ctcttttttaa atgacttctc ctttcttttta acttgcactg ttgtctagcc ctcacttatt   122940
ttgtcaattc tttttagctg tttgtctttg aatcttcata aagccatagc ttttctcata   123000
agaagcagca ctttctttgt tcattcatat tttaatgaac ccctgtagta tttaattaaa   123060
tacttaatgc ctaattaaat cacataattg caatgcaaaa gtacatgtat cataaagagg   123120
tctgaaaatg agcaactggc aagcaggtgg tggcaggcag agctgcttgg gtgggtgggt   123180
gtcatggaga ggagttcatc agccacatgt tcagtgagct ctggatatgt ctgtttagaa   123240
atgatcacta ataaacttgt gctcaaccat gtatacctct gggaagcagg tgctcttcag   123300
tagattgcct ctgcagagaa cacagaattg aagtgaatgt ccacaaaggc aatgagccac   123360
ctgcagaata gtttagtcaa ggctgtgttt gaagtttgcc aaagattaat atacatttga   123420
ttttcatgtt gtgccttttc tctgattgtg aaatattaca aattctatac aaataacaat   123480
gatggcaaat cctcctgagc aaagtgtgca ccttgtatgt gccctagagg aacttgtgtt   123540
tcgttctgat tccctacat ttctcatgtc atagagtggg ggttgcatta gtgtccccct    123600
gtcctcgctg ggatcacatc tgtttggatc ctagagtctt ccagctgaac tgggacaagt   123660
ataacagacg gacacgtagg ggtggaaagg cgtctcttgg cagcagactt tctaattgtg   123720
cacgctctta taggtgttgg agatgttcat tcttgtcctg cagcagtgcc acaaggagaa   123780
tgaagacaag tggaagcgac tgtctcgaca gatagctgac atcatcctcc caatgttagc   123840
caaacagcag gtttgtcccc gcagccttgg cttgttgttg catagtgatg gtagcttaag   123900
gtccttgtga aggtgggtg gctggaatca gctcttcctt cagtcctaat ctgtgccttg    123960
atagcagttc tccgtgctag tcatgggaca gctgacttca tttcttctca caatgccatc   124020
tcaggttggt attgcccacc tactttacag ggggatccc cacagctccga gaggttatgg   124080
```

```
aggtgatcag gcagcacaca gctttagagt gctggggtga gggcgggcca aggctaactc   124140
taaagcccga acccttacct cctacactgc ctcctgcatt ctggtcaacc cagtgtttta   124200
tttggtggtt agattttttgt ttttgttacc ttactgcttg taatttagca gttttccttt   124260
cctttcccttt cctttccttt ccgacagggt ctcactctgt cacccaggct agagtgcagt   124320
cgtgtaatct cactgcaaca acctctgcct cccaggttca accaattctc ccacctcagc   124380
ctcctgagta gcaaggacca caggtgtgca ccactacgcc tggctagttt tttgtatttt   124440
tagtagagat gaggtctcgc tgtgttgccc aggctggttt taaactcctg ggcgcaagtg   124500
atccaccaac cttggcctgc caaagtgctg gcattacagg tgtgagccac ctcgcctggc   124560
ctattcatca ctaatcagaa tttctatgat caaatgacat gaatcattgt ttccacaact   124620
gcagtggaag gaaatggcct ggcagtgcca gtttcagaag cagcctgccc ccagtcaggc   124680
acaggccact gtgcccccag tgtagcagca cctctgtagc tcacagagaa gggtggtggg   124740
gacctccttg aggcagctct gccagaaaat ctcatgagct gcctggcaca gcttgaggtt   124800
gccttttaag tggactcagc aaatacatgt ttgttcatct tgattataca caataaacaa   124860
ctactctgta tagtacgagt agtccgtggt ttttggcatt tgatttaaac ttagaggcat   124920
gtgatattga tgttactgcc ttcatgactg caccccatt ctgatttcat aatgaatgt   124980
tatcttgaga ccagttagac aacaggacag ggatcttggc ttctggtgag attgacagca   125040
gttttagtgt ggtcagggtc tccctgccta cagatggttt tagaatgtg ccctggaagc   125100
tttatcccat tcttttctgt gcgtaatctg agtagagtgg agatcgaagg cctgaataca   125160
tagtaaatac ctgacttaat atctgccgca atggaaattg tgtgatacaa catttatgaa   125220
acgcttagtg cagcacctgc caggtagctc accacaggtg catgttgcat tcagaagtag   125280
tgctagatac tatcctgtta ctggcagtgc atacatcagt gatcaaagca gattaaagaa   125340
agaccccctg ccttcttgga gtgaagattt tgtttgggatg cgggtaaggg gacagacaat   125400
agaaaagcaa gtgagtgaag tctataccat ggcggctgat caggaacacc gtacagaaga   125460
atccaggagg gaagagagtt aggtggtgtc tgcggtggga gtggcattgt tcagctggtg   125520
atgagaagaa gctttggtga tctggtgaca tttgagtgaa tttgcagaaa ggaaagatac   125580
aagcctagga gatacctggg gaaggaacat tccaggcaga gcaaatagca gtgcaaaggc   125640
cctggcgggg ggcggacatg ctgttagggt acaagcaatg agggtggagg agtggggcag   125700
ccatggggag ggaagggagt gaggcctggt ggggtgaggc cagtgtggag gagccttgag   125760
agggtttgcg ctgatgtggt gtaggtttta gcaggatcat tcttattcct gagttggaaa   125820
tagccttgag ggggaggtga gggcagagca gggccaccca tgtgagaccc ggcactggag   125880
tggaatggcc caagtcagca tcccttggca gcatgaaagc aaaaccagca aggtttgctg   125940
gtggcttaga tgtggcatgt gagagagagc agggctttgg gggtgatttc agggtgagga   126000
cagggtggct gtggacaagg tagggcagac attgggggca gcaggaggtc agagcctgtc   126060
tggatgtagc agttgagacc ccataggtgc ctaatgaggt gaggccagca tcaggtgtat   126120
gagcctggag ttgtcgagag actgtggggc aggggtcag catctgagat gtccactcac   126180
agtggaccca gactggctgg agaggaggag gagcttgaat accgagcctg ctgagtccca   126240
gctccaaggt caggtaggtg aggggagcca gtgctggggc aggggggagta gcaggtgtg   126300
gggttcctaa agccaagatt ttttttaagg cattttgtgc aggagggcga catctgctgt   126360
cagcaccttg gaacttggc ccaggtttgg cagcaccgag ggcactgatg agtgcttttg   126420
gaggagcaaa gggagccaaa ccctaatggg aatgtgttcc tgaaaggaca ggagagagac   126480
```

```
ttgggaaaag gtttracttg aagagggaac ggagaaatag ggcagtagcc agaggaggag   126540
aggagtcggc aatgggttaa gttggcagaa atgaaggcct gtttacgcac tgagggcaga   126600
agcaacaggg aggatcagtt catgacacag gagacacaaa tcgccgttgt ggtgttcaca   126660
gacatgggtt aggattggct gcatggatga cagagcactg tggttctcc cagagttgct    126720 ggggaggagg cagagttggt gagcacaggc gagggtccag gatgcaggaa tcctggagct   126780
caagtcagtt gttcccttgt tgtaagatgt ggccagtgtt gtgagcttca catctgtgcc   126840
ttgaaaaaca ccacatctgt ttgcagagtt gtttactatg tatacacact cagtagaaac   126900
aaaaattgga aacagtcagt gcccaccatc aataagtaat ggttgaacac actgtggtat   126960
aagcttagac tattttagct tgggctattt tgcatgatta aaaatgttct ggccaggtgt   127020
ggtggctcat gcctgtaatc ccagcacttt gggaggccaa ggcaggcaga ttgcttgagc   127080
tcaggagttt gagaccagcc tgggcaacat ggtgaaaccc tgtctctact agaaatacaa   127140
aaagtagctg ggtgtggtgg tgtgcgcctg tagtcctggc taactcagga ggctgaggtg   127200
ggaggatcac ttgagcccat tcgtgcgcca ctgcactcct ggggcacaga gtgagactct   127260
gttagaaaga gagagagaga aagaagagag agggagggag gaaggaagga aggaaataaa   127320
tggaagaaat ggaagggagg aaggggaggg aggaaggaag aaaggaagtt cagccagttg   127380
ccttgggagt tctccattgc actgggttaa gtgagaagag cagagacgtt tatgattttt     127440
caaaacaact aaaacaaaac ctctgtgggt gagggggcaa ggatatggct ataggaacat   127500
ggggcagatt aagaaaggga tatacacaca ccacttagca tttgttacaa ctgttgtggg   127560
agggatggag tgcagaaaaa gaaaaaaaaa agtgcacacc atcccatgta tgtgtataca   127620
aagggacgct tggaagactg gtccccaaaa tgttggtaat gattgtgtca gggtgctgca   127680
gtgctagttg atttttttc acactttgt atatttgagt cttttacaga aagcatttat      127740
tatttatgta ataaaaatct aaatgacaag atttctgtta tgggaaaaat gtagctatac   127800
agtgttgttg taaaaatgtt tgcttggttc accactgaac ttaaaatgct tttaaatgag   127860
ggaaggtgac gatgagatga ttatgatgat ttgcccttga gttacatagc tggtgtacag   127920
gaagctgtcg tttctttgg cttacgtaga aatgtttgtg gtgtctaatt ccacagatgc    127980
acattgactc tcatgaagcc cttggagtgt taaatacatt atttgagatt ttggcccctt    128040 cctcctccg tccggtagac atgctttac ggagtatgtt cgtcactcca aacacaatgg    128100
tgagtctctc gcctggctca gcagatgaat ctggacggct tgttcaggct ctgattactg    128160
ggaccacccc cagaatgtct gagtcagtca gtttgggtag ggcttcttga gagttttgctt  128220 ttttttttt tttttttttt ggtgtggggg tggtgcggaa cagagtctca ctctgtcgcc   128280
caggctggag tacagtgtca tgatctcggc tcactgcaag ctctgccttc cagcttcaca   128340
ccattctcct gcctcagcct cccgagttgc tgggactaca agcgcccacc accacgcccg    128400
gctaattttt ttgtattttt agtagagatg gggtttcacc gtgttagcca ggatggtctt    128460
gatctcctga cctcgtgacc cgcccatctc agcctcccaa agtgctggga ttacaggcgt   128520
gagccaccgc acccggcctt ttattttttt ttggagatgg agccttgctc tgtcacccag    128580
gctggagtac agtggcgcta cctcgactca ctgcaacctc cgcctcccgg gttcaagcaa    128640
ttttcctgcc tcagcctccc gagtagctgg gactacaggt gcgtgccact gtgcccggct   128700 aatttttgt atttttagta gagacggggt ttcactgtgt tagccaggat ggtcgcgatc   128760
tcctgacctt gtgatccgcc cgcctcggcc tcccaaagtg ttgggattac aggtggctct   128820
```

```
cgcaccaagc caagagtttg cattttttagc aaattcccag gtgaaactaa tgcctgcttt    128880
tctgggagca cactttggga ctcagtgata gagaggttta ttggtaggat agtaaaatag    128940
gagttatttt ctttcacaaa attggcaatt gggggaaatt taatcttcct tttttcttca    129000
gctgtgactt atgtattatg tttattttag gcgtccgtga gcactgttca actgtggata    129060
tcgggaattc tggccatttt gagggttctg atttcccagt caactgaaga tattgttctt    129120
tctcgtattc aggagctctc cttctctccg tatttaatct cctgtacagt aattaatagg    129180
ttaagagatg gggacagtac ttcaacgcta gaagaacaca gtgaagggaa acaaataaag    129240
aatttgccag aagaaacatt ttcaaggtat gctttctatc tgagcctata actaacccat    129300
gccttttggg aagtcacgtg atgtttcaca gtcagtaagt ctggaataat acctggtctt    129360
gcttcacttc tgagttgggt aaagaagtct gtatcagtgt aattttctaa tccgtcctgc    129420
attatctatg gctcttggtt catacctgtc ttgaagttct gtcatgttct gtctcttgtc    129480
ctcagtagag atgctacagc agtggctcgc ctcaggcagg gcagggcagt ggggtggctg    129540
tcctggggc aggcagtagg ggcacgctga cgtcagggaa gttgaaaccc aagagaagcc    129600
agtaaaagtg agtctcagat tgtcaccatg tgctggcagt tttacacgct gtcagtaata    129660
aaagtcttct ccctgcaggg cagcctgcct ccaataaata cgtgtagtat caaatcctgt    129720
cttccctcat aaattgtttg gaagctcccc aaggacagtg atgaggcact cgtaagtgct    129780
tgctgcctag atgggtccct ctccaccttt gctagattct gagcattcac tgagttagag    129840
ctgcttctgc aaatgtgctg cttctgctaa gtggctgtga cttcatgcag ccttcacttg    129900
gtttgtcatc agtggagatg ccctgtgttg tcgaaggaga taagcccagt aagcctgctg    129960
ggcaccttt ggtttgcagg ttcagcaggc agcccatggc tttccctgtg tcgcattgaa    130020
gcagctggct aaaattgatg atacattaaa ttcctgtgac agatgatcag cttgtatttg    130080
tgtaatggtg tacagttcac aaagcttaaa aaaatgctac ctgccatttc atcctcagtg    130140
aggaaggtga tacacagaga gaccaagtga ctgtgtccac ggcgacggcg ctctgcattt    130200
cactttagcg gttaatgtac tctacctata ttttttacttt atatttacca tatatctttt    130260
catgtatact tggcgtaagt gctttatagt agtcacctaa ttcactgtca tcttttttgt    130320
ttcttggaag gtttctatta caactggttg gtattctttt agaagacatt gttacaaaac    130380
agctgaaggt ggaaatgagt gagcagcaac atactttcta ttgccaggaa ctaggcacac    130440
tgctaatgtg tctgatccac atcttcaagt ctggtaggtg aatcacatta gtcttcctgg    130500
agtgtctcgt tccccattct gcactataca ctctcagagt gtaggagctg tgctgcccgg    130560
tagaaactct gccttgccca gtgtgccagt tgaaaatatt tgttgctgta agagtacacc    130620
tgataccatg tgacccagca gttccactct tgggtatata cccaaaagaa tggaaagcag    130680
ggtggtgaaa agatatttgc atgccagcat tcatagcagc attattcacg atagctaaaa    130740
tgtgaaccca actgaagtgt ccctcgatgg atgaatggat aagcaaaatc tggtgtatat    130800
ttacagtgga atattattca gccttaaaaa aaggacattc tgacacatgc acaacatgg    130860
gtgacccctta aggacattat gctaaatgaa ataagccagt cacaaaagga caaatactat    130920
gtgattccac ttcatgagg gacctggagt agttaattca tagatataga aagtagaatg    130980
gtggttgcca ggggctgcag gggagggag ttattttttac aagatgaaga gagttattct    131040
agaaatgaat ggtggtgatg gttgtataac attatgaatg tacttaatgc tactgaactg    131100
tacagttaaa aatagttaag aggaccaggt gtcatggctc atgcctgaaa tccaagcact    131160
ttgagaggcc aaggcaggag gattgcttga gccaaggagt ttgagaccag cctcagcaac    131220
```

```
atggtaggac cccatctgta caaacaaact agccggggat agtggtgtgc atgtggtccc   131280
agctactcag gagactgagg ctggaggatc gcttgagccc aggaggttaa gtctctagtg   131340
agatgtgttc atgccactgc actccagcct cggctataga gtaagaccct gcctcaaaaa   131400
aacaaaacaa aacaagacaa gagccaaaaa tggttaagat gggccaatca cagtggctta   131460
tgcctgtaat cccaacactt tgggaggtca aggtaaaagg atcacttgaa gccaggagct   131520
tgggaccagc ctgagcaaca tatcgagacc cctatctcta caagaaaat caaaaactag    131580 ctagatatgg tgggcacatg cctgtagtcc cagctacttg ggaggctgag gtgggaggat   131640
ctcttgagct caggagttcg aggctgcagg gagctattat tgcactccag cctgggctac   131700
agaatgatac cctgcctctt attaaaaaaa aatccaaaaa aaaaaaaag taaacctgag    131760 agcttcctcc tcctgtgtta aatttggagg ccaagatgtt tttgttactt ttacaaatga   131820
tcaaggacgg tgaaggttgg gcatggtagc tcacacctga atcccagca ctttgggagg    131880 ctgaggcggg gtgatcgctt gagcttgaga ccagcctgga caacatagca agagacccca   131940
tctccacaaa aataaaaaaa taaaaaaaaa tagccaggag tagtggcatg agcctgagcc   132000
caggaggtca agctgtagtg agccatgatc atgccactgc actccagcct gggcgagatc   132060
gagaccatgt ctctagagaa agaaaatgac aaggacagtg aacccaagaa agtcataaga   132120
tgccagctgt gcagcaagca tggaaagcag ccagtccaaa ttaggacagt gtgttttcca   132180
agaagaacga tcgtttgtaa tgagaatgct ttgctttaaa taaatgacta aatagctaga   132240
agcctagttc taggggatag gcacgtcttt cttctctcaa gaaatagaa aggcaattct    132300 aatttctagt aacagcaaac agcattaagt catggtccaa atatgaggca aaccaaaatg   132360
tggcttgatt gttcagcagt tgatctgttg gaagcccttg atattaaaaa ggttctcctt   132420
taagcggctt aggagtcacg atcaaagacc tatagaaaga gatgccatcc ttctaggatc   132480
cttggctctc ttgggaacta gattcagata gtcataatgt aaatactgct tgagcttttct  132540 ttctttcttt cttctttct tttttttttt gagacagagt ttcactcttg ttgcccatcc    132600
tggagtgcaa tggtgccatc tcggctcacc gcaacctctg cctcccaggt tcaagcaatt   132660
ctcctgcctc agcctcccga gtagctggga ttacgggcat gcaccaccac gcctggctaa   132720
ttttttgtat ttttagtaga cagggttt ctccatgttg aggctggtct cgaactcctg     132780
acctcaggtg atccacccgc ctcggcctcc caaagtgctg ggattacagg tgtgagccac   132840
cgcacccggc ccgagctttc attttttgaaa tcaatgtatg actgaaacac tgaagactta   132900
ctgacttaat tatggtttca gaacagaatg aaaatgtctt cggttctgat gaatataaaa   132960
ggaaaactaa ccaagttaat ttggcaagta gatggtagag atagaggtgg ggagtggaag   133020
gggaactaaa atcttcacct agcattgttg ggattatatg gttacatcat ctgaagttga   133080
cagaccaaaa tatagaggct tcagaggtct ccaaatagaa ctaaacatgt aattcagatt   133140
gttaggaggt agtataaatg agctaaatct catctttatt acggtagagt taatgggtga   133200
tgtctaaagt tgtctgaagt ctataaatca tgacaaatta tgatgtggtg attgtattca   133260
acagtctttc agttgcaggg ataaaacccc agtttaaact agagtaagag aaagaatgtg   133320
ttggtttaag ctcctggaaa gtgcaggcaa gggtagttgg taggactgca tctagtgttg   133380
taattctgtg gtctgcattg tatatttatg catctcagct ctgctttctt cttttcattt    133440
atataatttt taaattttat tttaaagata gggtctcact ttgtcgccta ggctgaagtg   133500
cagtggcatg aagtgcagtg cgaggctcac tctagcctcg aactcctggg ctctagagtt   133560
```

```
cttcctgcct cagccttcta agtagctgag acaataggca tgtaccaaca tgcctggata  133620
ggttttaaaa ttttttttgta gaaatggaag tcttgctgtg ttgcccaggc gggtctttaa  133680
ctcttagctt caggcgatcc tcctgcctct gcctcccaaa atgctgaggt tataggtgtc  133740
acccaccacg cccagtctca tctctgcttc ctgtgttagt tttgttctct ggtgggctgt  133800
tttcacatga ccgaagatga cctctagcag gctgtgttct cagcccctca agtaggccta  133860
tgtgattggc cttgcatgag taatatgggt gaccataaac ccctgaatgc tctggtccac  133920
atgggccaaa tgggagactg gacagcattc cattgatgag gaggtggggc tggtctccgg  133980
gagtaaggga gaggagcaca tgcagtaact gatggtctgc tgcaagggat agcagcacag  134040
cagttagaat tttggaggta actaccagaa ctgaaaacag aaatgataac aagtagttgc  134100
cttaaaaagg gatgggagca gggtgctttt gtgatcaaag ctccttttctc ttactggatt  134160
tttgtacaca ttttgcatac atatcttaga gtaaaagata gcattttcag ccttggtcca  134220
tttgaggata ctcttggcgt ggcccgcctc catgctagca ggctctggtt gtgccaagtt  134280
cagttgagca tcctggctct tgcctgcacg gaacttccag tcagtgcgtc agtatcacaa  134340
gtcttgatat ttcctatgaa gaagaacagt agtgcagtga cagacgaaat gggtgggcag  134400
gcagaggcag gatttctgag ggagagaagt agctagcttt ttgcagagaa gagttccggc  134460
acccaagaga gcagctgaga gtacaggcag gcaggcagga tgccggtagg gcccggccgc  134520
acggcgccac agaatcctgg agaaggggc ctcttcatgg cctctgcatt cagctgctgt  134580
caccctccgc acaggccatg gccaaaattt aatttcata gtggactcta gttttgagc  134640
cttacttgct attattgaaa taattttctt gtttctttt aaagatcttc ggattatgct  134700
tcactgacca ctgtaataag tttaaagttg agaaaatatg gcttgttaat gaatgatagg  134760
tcaattttag tatgttggtc attttaatat tttgccacca gttggtttgg atttgatgcc  134820
aggaggagac agcctcattt ctaaggacta gtcttgcctt tgtgggataa gggtggtgtg  134880
ttctgtgtcc ttctacatgt ccgagcgatc tctgtgcagc tcaaatgtgg tcactgtctt  134940
attgcgctga tttcctctcc ttccatctca caattgaggc aaaatattgt tactgttgaa  135000
gtgttgtcca ataggacttc cagcagagac aggatgtctg cactgtctaa tttagttgcc  135060
tttagccaca tgtggtgttc tgtacctgaa atgtggctgg tctgattgga tagcttaatt  135120
tataatttta tttaattta attaacttaa atttaaacag ctctgtgtgg atagtggctc  135180
ctgtatgaga cagtgcaggt ctgttgagaa gcagctttac tggtgggagt ggagggcttg  135240
gagagggcac gtgggtttcc tgctggtatc ttttgacctt atttaatctg cccaacattt  135300
gcaagtaagt tgtgtgtgtg tgtatatata aatgtgtgtt tctgtcttct tgtttccttt  135360
gactgcattt atttgaaaga cactaggtgg cagaattact gtatttgatt ggtttcaaga  135420
taagagttga aataattcat ctcgtgtttt tatataagta aggtgtgttt agcatgtaaa  135480
attggtaata tgtattcacg tactgcttaa acaaaggcta tgaattccac ccataaaccg  135540
aaaatgaaga cctttaaatt tgtccatttc aggcgtgggt acttcttaaa taatacctgg  135600
ttcaggaact agtcagaatg gcacccttga ctttttgttt cctgcttttc ctcttgttgg  135660
gagaggaggg tattcatccc aaagtggttt gcctatttca cattccatct aggataagca  135720
gaatagccaa gaaagatagc tgtcctcctg tttacaacat tggggtaac cagcatccct  135780
ctcttttggt ccaagataga ctggtttaga aacagatgat ggcaccagag gcccaggagg  135840
tggaaacatc agctttgttt gttgtccatg tggctgaatt agagctgtct ggccttgtag  135900
cctcaacacg gccttccagc tttgctcacc gtgattttca aggacacatc ttgtgctctt  135960
```

```
ccctgcctgc catccagact atacccagtc agggtggcag gagctgctgc cccttcctcc   136020
ctgagtcctg gtcgtgggtg gtggagatgt gccatgacgc tcacggaggc atgctcaccc   136080
cttcctctgt ggcagagggg atggctgcac gacagctctt ccctgtcctt tccaaagcgt   136140
ctgtggttcc acttttttggg gcaaagcagg aatactggaa gagagagaaa gtggtccttt   136200
ctatagtaat aaagttgaca ttgattcaag ttcatgcttg gggaaaggac agggctacta   136260
acaattataa tgctgggagc aatggaattt tctcatgggt atgtggtagg tttaatttta   136320
attatcccag ttaattctta gaactgctct gtgaagtatt tcccgctttg tgcttaagtt   136380
ctaaaagatc ctgtgccaaa accaagaatg aaaacccaag cattctttct tgcccatcga   136440
tctttctctc atcaggccac ttcttgggtt gatagtggtg agtgtagccg ctgccacttt   136500
cagaatacccc accatgggcc ccagtcactg tgtggcgtgg agaagagatg gttctctctg   136560
tgtcatagct gaacaagccc agcccagaga ggtttctgcc ctaggagctc tcgatggtgg   136620
aattgggatg cgatcccaca tcctgcctgt tttgaaaaca gcattcttta tttccaattc   136680
ctgcttccat tgttcctttt aatatttctt tgtttagctc acaaaaacac ggcttgcgga   136740
gctgctgcgt gcagctgtag ctgtttctct gggtgcagcc tgcatccgcc ttcctgcccg   136800
cctcctttcc tgcactgcca tcgtggtctc cgggcacttg gtccctttct cttccctga    136860
gtccctttgg ctcccctgtg ccaccttgt gatccacagg ctctgcctc tttctgtctc   136920
agactgctgc tcatcactac tcgggaccct aggaagggag gttccaccga gaagcatctt   136980
ctcatctcag ccacgttctc agtgccactg ttgtctttgt taggtaatgg tagctactgt   137040
aacaaataaa ccaacatttc catggcttca caccagagaa ggttgtttct tggttttatg   137100
acaatgtatt gagggtgttc ttggttcacg gatggtttc ctccatgtgg gaattcgggg    137160
acccaggctc cttttccttct tttggttctg ttctccaggc cttcacatcc tctgtgtctg   137220
gttggggaca aggagaggga aggtaaagaa ggctttgtgg ccttggataa gtgacaggca   137280
tgcctttgct ggtgttctct cgtggtgaca ggtcacagcc ccaccctgta aaagggggact  137340
gagagacgtc gtcctgctgc ttcccagcag cagcactgtg gtctctgatg tgttttctgt   137400
gaggataaaa acaggtgatt ccaggatgag gaaagtcagg gaaaccctttg gaaggagggg  137460
accaggcggg tgtcaccatg ggattagtgg tggcttcaga atgagctgca gcgagtgcca   137520
tgccttctaa agcttttgct attctgatat gcccacacca tgcccagcag gtgtctgcct   137580
tgctctccgc agagagagtg atgaatcctt ctcatgagcc tctgtccagt tgttcctccc   137640
tccacctgga agggaccctg ggttcctcat aacatcccag cggaacaggg gaccttctat   137700
cctgtcccca agttcatcct catcctcctg ccggcttcct ggcccctctt atgtctgctt   137760
cctgacgcca catccttctg gattctctgg aattgaattt tgcctttgat gcttatttaa   137820
aaatatccat tgcaggccag gtgtggtggc tcacacctgt aatcctgtgc actttgggaa   137880
gccaaggtgg gcagattgct tgagcccagg agtttgagat tagcctgagc aacatgttga   137940
aatcctgttt ctatagaaaa tacaaaaatt agctgggcat ggtggcgcac acctatactc   138000
ccagctactc aggaacctga gacaggagga tcaattgagc cccggaggcc aaagctacag   138060
tgggctgtga tcgtgccact gtactccagt ctggtcaaac agagtgagac cctgtctgaa   138120
aaaaaaaaaa aaatccattg catacttcac cgtagcgaaa catgtatgtc ttacctttcc   138180
tttcctgcct gtagctgctc ttttacactt aacagccaca ctaagccagc cttaaatgaa   138240
aaacaaacca gcacttcctg tgccctcctg cttccttcat gaggggtccc tccctctgtg   138300
```

```
tacactccat tctcattgcc catggtggtt tgtttccctc ttgtttctca agccatggca    138360
gcctgcctct tgccctcttt actaaaaagg cctttgcaga ggctgcctgt gttctttctt    138420
tctaggtctc tctcatccta ggccctccag cttgattctg tggagctgcc ctcttgtcac    138480
tcagtagctt gtggggtctt ctctgtctag ccacttaatt gattgtgttc ctcgagttgc    138540
tgtccatggt ctctcgttac tgttttctct gtgtttctgc ctctctcctt ggccttggta    138600
ggtccatccc ctttgtgacc ttggctgttg ctctcatgga caactttctc ttgctggtcc    138660
ttgtagtcct ggcatccagc ttctcgacac gggacttgtc ctgccagtac ctcagacttg    138720
cacttaaaat tgaactagca ccactgtcac tctccagggc ctcttcttgt taattagatc    138780
attagggatg ttcagaatcc cagcatcata gtatgttcct cctcccgcta ccccaggaac    138840
cctaacctta cctcctcctc tctatctact aggaggtggc cctcagagtc cgtctcatct    138900
tccacctgaa cttccctaat aggctccagc agctgccacc ccgggggctg agtacttcct    138960
ccatgccttg tgcagtgctg agcccttttac ctgggttctc ctgtttgctc cttattacag    139020
ccctgcgaac agatactgct cttaattcca tcttacacct aaggaagctg aggcccagg    139080 taaggtgcat ccaaggtcac ccaggtagta gacagtagag ccacgatctg aaccaggcag    139140
tctgattcag agcctgtgtt gacactcagc cacctagaac acagcttgga ttgtgggttt    139200
ctattacctg ttcaaaaccc ctacatcccg ggtctgtccc tgcacgtgct ctgtggcctg    139260
gctgcatctt ccttgaaggc agtgcatgcc tcttcactca gggggcccat gcaggaacag    139320
agggccccac agaaggatga ggccagtgca gaatgggctg gaggggacaa tgctgaccag    139380
gaagcaagtg tagagaaatc ccaggaaacc tggaggagcc agagacaagg cattagaact    139440
cctcgtcgtg acctggtctg cattctctga gtgtgctgct tctgttagct cgcttccttg    139500
gtctcaggtt atagtttaag gcattgtgga gccctaaaaa gcctgtactc tgttttacc    139560 tgttttagga ccctttcact ttggggatgt gttgattttt tttttttttt ttttttttt    139620 tttgagatag agtctcgctc cattgcccag gctagagtgc agtggcacga tcttggccac    139680
tgctgcccct gcctcctggg ttcaagcaat tcttgtgctc ccgcctccca aatacctggg    139740
attacaggca cccgccacca cactcggcca attttttgtat ttttagtgga gacagggttt    139800
taccatgttg gtcaggctgg tctcgaactc ctgacctcaa gtgatctgcc caccttggcc    139860
tcccaaagtg ctgtgattat aggcgtgagc caccacaccc ggcctgaaat ttaaatcaga    139920
aataaaattt tgatcccaac agtgatgcca ggcagcccag atctggggga gagggtggcc    139980
ttggccagct gggccttttct ctgtttccca agtcttgctg cctctccctg ctgggctttg    140040
cagcctgtgc atgtctctgt gcctttgacc ttgtttatcc aaaggagagg atagaatgaa    140100
gtcatgattc ctggagccct gagaaggatg ctgtggagaa atttgccggt agaatctagc    140160
tgagtgtgtt gctgaggtgc cagcattgtg tgtggggagg ctgaccgctt ggcctgccta    140220
ggcccaggat gctccatggc cgggcacaga ggccacttgg ctgtcaggtg tcaggagcct    140280
gcagagggca cacagagcct ggaccgcagg ggggtcctgc tttctcacct ggcctccttc    140340
agcatttctg tccctcagtc cttagcaagc ccaggagctg ttgagtttgg caggtgccga    140400
gtgctgttcc tgcctgtgta gctgtggctc agtcctgtgg gggccccgct gtggcccgag    140460
tgcagtgatt cgaggcgctg agtgttccct gactccttct ccaggagctg tgttcagact    140520
ttcgcagctc ttggcttgga gctcctggag ggcttggcat tgccgaccaa tgtggaggtc    140580
gacagtgaga gaggaggaat gctagctttc ttgaccagtc cattaaataa gtgggatatt    140640
ggccaggcac ggcggctcac gccttaatcc cagcactttg ggaggctgag gcgggtggat    140700
```

```
cacgagctca ggagttcaag accagcctgg ccaacatggt gaaacccct ctatactaaa   140760 aatacaaata ttagctgggc gtggtggcag gcgcctgtaa tcctagctac ttgggaggct   140820
gaggcaggag aacagcttga aaccggaagg tggagtttgc agtgagccaa gattgcgcca   140880
ctgcactcca acctgggcaa caagagcaaa actctatctc aaaaaaaaaa aaaaagtag   140940 gatatctgtt tctgcttaga aaatcagaa ttttctaaat gccaggtgtt ctgaatacgt   141000
aagtatggga gacgactcag cctgtttcat ttttatgtaa aatcttcgcg tagccatgtg   141060
gcactggacc gagatgaaag caaagacatt tctccttaac tttgtttcta ggaatgttcc   141120
ggagaatcac agcagctgcc actaggctgt tccgcagtga tggctgtggc ggcagtttct   141180
acaccctgga cagcttgaac ttgcgggctc gttccatgat caccacccac ccggccctgg   141240
tgctgctctg gtgtcagata ctgctgcttg tcaaccacac cgactaccgc tggtgggcag   141300
aagtgcagca gaccccgaag taggttcata atgccccaca gcccagggcg ccagcccagc   141360
accctgtcct gagactccca gtaacctgag ctttggccac cgttaaagca ttttcatttt   141420 ccatttttg tgagggcttg tgaaatttct gctgcatatt aatattcctt tcatggacag   141480
catattattg ggacaaacat gcggtccagc taaaggcatt caaaatagca gttgctttct   141540
aaatgcgatt ttcctttggca ggttctttga caccattgca tcttgtggga tatgcttgtc   141600
atgctctgtg gctcctacta agttctagtc cttaaattgg ttccatagcc agacatgttg   141660
caatgtctta acctcattat aaagtaaatg tggttctggt tatccttaga taatgaagta   141720
acagtgtagc aaatttcaaa acctcttgga aatgttattt taccattcaa aaaggcttac   141780
taaggttctc gttatgggtg gccctctttt tgcaaaaggt tttcaggctt aagctccatt   141840
tctaggtgct ccaacactcc attatttgta tatgtatgga aataaaagct gtgaccaccc   141900
ccaaccctgg ccccgccca gctgaatcct cagcacagta tttctggaag gctcaagatc   141960
ccacgctggg gaaaagaagt tctggagaca aagagggca ggtgctgccg tgcctctctg   142020
ctcagtatgg atactggacc ttgtgctgcc agggctccca gtagggccag ttcatggcac   142080
tcagctggaa agtccactgt tgggaggcat tcttaaccat ccactctgtg ccgtatgtag   142140
tggggtctgg tcattctgtt ggaggagaca gaccagtgac gacatttgaa atgcttggtg   142200
gatgtcttag gcctgttacg atgactgagc actgtggggg caggagacag aaagtcagtg   142260
tctcctagtt ctgtgctgct ttaacgtgca tagaaatcag ctgcggattc agcagatcac   142320
tccttttctg acagatgggc ctgcttactc tgatgttata tcagaaagct ctgaatctgg   142380
gaattgtgtc ccctgaattg gagtaacaga aatgcttaga tgatgagtgt ttaaaagaaa   142440
taaaccaaag gtaaatttag tttggaattc agcaagcgtc ttcattcagc cctctgaggg   142500
caaactacag cttttgtaa atgtaggtaa attctgtgac tgtttcgtga ccccctctga   142560
tccagttttc ctttataacc ttctgtattg ttccttctat tatcctgaaa taacattaat   142620
agattaggct gggcgtggtg gctcatgcct ataatcccag caccttggga agccaaggcg   142680
ggcagatcac ctgaggccag gacttcgaga ccagcctggc caacatgatg aaatgctgtc   142740
tctactgaaa ataacaaaaa ttagccgagc atggtgacag gtgcctgtag tccctgctac   142800
tcagaaggct gaggcgggag aatcgcttga acctaggagg aaaaggttgc agtgagctga   142860
gatcgcgcca ctgcactcta gcctgggtga cagagtgaga ctccatctca aaaaaaaaaa   142920 aaaaaaaaa aaattaatgg atcaatggat ttttaaccta ataattaaat ttcaaaaaat   142980
atcgttcttt aatggtaatg taaaggtaaa attaagataa tatgtaacaa gcatgtgagt   143040
```

```
gtctaaggtg tccccgtggt ggaaggaaaa aataaatccc cataagtgtc caagatgccc    143100
atagagagca gagctgttct ggtttaaacc cctgctctta gcactgtgtt tttccagctg    143160
tgggtggtgg gggatgagta tcttttatt tccatgagat gagaaaatg aattactaga      143220 agtgtgaaat acaaaacaca gctgctcttt ttttagccat agactcagca gccataaaat    143280
tgctgtatcc agttgcagaa attcctgctg cttactcttg accctctctc ggtttgtgtg    143340
catctcctct caggctggct cccagatggg agctggctcc aggcgacact gggtgctctg    143400
ctccaggagg tccttatgtg ggtcctgccc tagcctagcc cctctcttat ggactctgtc    143460
actgtgggtt tatgattcac tctcaatctg tcttacctct tggtgaactg ttagagtcct    143520
gcctatactt tggcgcttgt gggtgtgttg tggtacacat gatgtgttgg tcacttccca    143580
gctcatcttg ttctgagtca ccctagattt gggacattca ttcgccacca gtaccgggcg    143640
gtgtatggcc tgagatttgg gggggcttgt gctgctacaa attggggctg aatttgagtt    143700
gacagtggac cttctttatg tctactgctc atatttgaat tgcaaatact gcctcttctc    143760
tttcagaggc tcattaccct atagctgtat tattgcaaag tgcacaatta cagcttgagt    143820
gtaagtcaca ctgcgctggc aggacggccc actgagaaag ggcacgtttc ctgttcgtta    143880
gttttcacat tgacacataa tttacaatac agtaaaatgt acttttctat caactgtagt    143940
cagtaacagc cccctcccc caaccacatc aagatataga ggagtgctgt cacttcaaac    144000
agttccctct tcctctgcca catcctgccc ctccccaggt ctaaccacca atccgtgctc    144060
tgtccctctg ttcagcccat tgcagaaggc catagaaata gaatctatag gctaggtgtg    144120
gtggctcatg cctgtaatcc cagtattttg agaggctgaa gtgggaggat gacttgaggc    144180
tgggagttca agactagcct gggctgccta gcaagacccc catctccagaa aaaaaaaatt   144240 taaaaattac aatcacgtcc ctgtagttca gctgcttggg aggctgaggc aggaggatca    144300
cttgagctca ggagttagag gttacagtga gctatgatcg tgccactgtg ctccagccta    144360
ggtgacacag caagacgttg tctctgggga aaaagaaag aaacggaacc acgcggtgtg     144420
cagccttctg agtctggccc ctttcggtga gcagtgtcta aagttctgtc gcgtgttgcc    144480
cacgcgtcgg tggctcgctc cttgcaactg ctgagcattg tatggctagg ctgtagtttg    144540
ttttcacttc accagttggg aaacagagaa aaggcacttt ttaaaaagtt taaatctgta    144600
gaattttggt ttttaccagt tctccttctaa atcctgaggg attacaggaa aagttgttgt   144660
atttcagaat attcttagct tgatgtgacc tctgtccccg ttaaggccct tgccgcaat     144720 gggaaggacg tcgctcggtc agaccctgaa ggtcagaggg gcagtttggg agtgtgtcaa    144780
cattttaact gtatggacta gagccaagag tctcaaggtt tataattccc acgtattcaa    144840
aaagaaaaaa acaataaagt gagaagtcag tgtagagtga ataaacctgt gttagtgggg    144900
aagaagtgtt tttaaacagg atttccataa cgtataacat caacatgttt agagtggtga    144960
tgtttcattg ggaaacgaac agtaaaaacat gaaagcaggg aggttttcat tctggcagtt    145020
ggcaactttc acggcagatg gagaaatttca aaagcaattg ctcaattatc aaacatagcc    145080
agtgtgagtt ctgaaataaa ggtgctgatt gaatgtgcag ctttatggtg gattttgcta     145140
ttcaggcaag cattttaatt ttctgcctgt taaattctgt tttctttagt ttttcatatg     145200
tggtttattg tagcttagga atagataact gagagtatat attacacata caacattctg     145260
atatggcaat atttaaaaca acttgtctgt tttagaacta gaattaaaca taatcatctt     145320
cagtattttg caaataagct cactgccatc cagaaacatt gtcaatgcat ctgttgctcc     145380
ttctagaaga cacagtctgt ccagcacaaa gttacttagt ccccagatgt ctggagaaga    145440
```

```
ggaggattct gacttggcag ccaaacttgg aatgtgcaat agagaaatag tacgaagagg   145500
ggctctcatt ctcttctgtg attatgtcgt aagtttgaaa tgcctgtaaa cggggttgag   145560
ggaggtgggg accaggagaa catcctgtgt agatgacact tgcatggacc ctctggaacc   145620
cagaccgccc ggtgtcctgc caagctccat cgaaactaaa tctagaatga atgtttactt   145680
ctgctgtgac atataattgg agaccaggcc tggccttcca gtcactggat tctaagttgg   145740
actgtgagag tttttgcagc tgactcattt atcaaatgcc cggctattgg ctcacgccta   145800
catgatgctg ggtatgtttg ttaatttgag ggaagcaatg gaataataat aactaatgat   145860
ttaaaaaaca aagtaagtgc attgactgta gtggggttct gatttttaaat tttttttaaaa  145920 attaatacca ggagcagtgg cttatgccta aattccagca actcgagagg ctgaggtagg   145980
aagatcactt gagcccagga gtttgagaca agcctgggct atggtgtgag cacccatct    146040 ctaaaaaaat aaaaaataaa aaattatcca agtgtggtgg ctcgtgcctg taatcacagc   146100
tctttgagaa gctgagggcg gaggatggct tgagcctggg agttcgagac cagcctggca   146160
acacagagaa accctgcctc taccaaaaaa agaaagagag gaagaaagaa aaattagcct   146220
ggcgtggtgg tgcatgcctg tggtcccagc cacctgagag actgagaagg gaggattgct   146280
tgagcccaga agtttgaggc tgcagtgagc tgtgactgtg tcactgcact ccggcctggg   146340
tgacaaggcg agaccctgc tctaaaataa tttttttaag ttaatttgta gaaaaggtgt    146400
tagatgttct ttgtcacatt ttatgatgga ttcctgttta aatgccgttc tctttaaaga   146460
aaaaaaaata acttgtggga gtttttaacc ataaaactag catcacatat ttaccatgga   146520
gaatttacaa aaaaacaaat aaacggagga aaataaaacc tcctgtaatc atactactca   146580
gagataactt gctgttagat tttggtctag atttaatact ttttctatat ttatattaaa   146640
aatatttaaa acatatgcat ttctttgtca caaacatggt atcttataga tactactgtc   146700
acatagcaaa acagtgttaa atattctgaa tcagaaaagg aagccgactc tccaactgaa   146760
agaggtgtta tcctagagac ttttttctggt gatgacaatt tattaatagt cacttttgc   146820 tttactttct ctattgaagt agtttttcta ttttgttcta cttttaagga taatataatt    146880
tataatgctg ttttttcacag aaatataaga aaaagatac taattttata agttaataaa   146940
gtttgatcat cccaaatcca aaaatctgaa atccaaaatg ctccaaattc tgaagctttt    147000
tgagtgctga cattatgttc aaaggaaatg ttcattggaa ggtttcagat tttcggattt   147060
agggagctca acaaataagt ataatgcaca tatttcaaaa cctgaaaaaa atcctaaatt   147120
cagaatactt ctgatcccaa acatttcaga taagggttat tcaacctgta ctgtcagatg   147180
atcccaaatg aaaaatatta atcgttaacc aaatatcaag gaattgatca catttacag    147240 tttctgccta ggattatgaa tcaagatgaa aaggctctgc atgttaaaa atatatatt     147300 ttatttttctt ataaatctta aatatctaca cttaagattt atttgatatg tgggatccat   147360 tcatatttg gattcaacag ttctgtcaaa actgtggcag tgataggga ttcttttttt     147420 cccactgaac tatcacaaaa ttggaaaaag agtaattgga gaaccccact ggcttagccg   147480
gcccgaagcc cggagaggg caggcagtgc tgtggatggg gtcatcccag cgcaacgctg    147540
cccctgctac ctgcggatct cgctgaggcc tgcctttgtc ctttgaccct tggccatttg    147600
ttagtgtctc tgagagctgg actgctgtac cctacttccc caggggggcct aacttcacac   147660 agcctctgcc gcagtgcgtg gttggaggtg acggccttgg taaatcgagt ttcctacctc   147720
ctcaattatt tgtgctcata cactgtatat ttttagtgag gtttatattt gggatgtgtt   147780
```

```
ttctccttct tacccttcct ggcctttcta tggcattaat acctggtctc ttcttgtgta   147840
cttgaaaatg aatctctcat catatttttc cttagtgtca gaacctccat gactccgagc   147900
acttaacgtg gctcattgta aatcacattc aagatctgat cagccttttcc cacgagcctc  147960
cagtacagga cttcatcagt gccgttcatc ggaactctgc tgccagcggc ctgttcatcc   148020
aggcaattca gtctcgttgt gaaaaccttt caactgtacg tcttcatcct gccgactatt   148080
gccagttgca gttttccctg ccttaaaaat ggagtattga aatttttaac tttaatttct   148140
gatttgcaaa atagtcatct tttgttcttt tccttcttgc tgttagccaa ccatgctgaa   148200
gaaaactctt cagtgcttgg aggggatcca tctcagccag tcgggagctg tgctcacgct   148260
gtatgtggac aggcttctgt gcacccettt ccgtgtgctg gctcgcatgg tcgacatcct   148320
tgcttgtcgc cgggtagaaa tgcttctggc tgcaaattta caggtattgg gaagagaaac   148380
cctgatattg atttatattg aaaatttagc aggccaagca aaacaggtgg ctggcttttt   148440
cctccgtaag tatggtcttg acatggtcac cgatagaaac atggaaacat ctgcaaactt   148500
gccgttactc gtgtgtccga tctgactgtt tcttgtattt ttttctagtc tgcccttact   148560
aggatgaact gtacacatca gttcatcctt tttaaatgag catgaggtta ttttgggttg   148620
ttaggtgtta caaacacact aatgtgtttt tgtctattag agcagcatgg cccagttgcc   148680
aatggaagaa ctcaacagaa tccaggaata ccttcagagc agcgggctcg ctcagaggta   148740
atgctgaaaa cacaggtcgt ccttgtgtta ggacaaccca ggatataaag gatatagatt   148800
tgtacgggaa taaattcaca ggacaagaaa tcgatgtgcc ttataggtgg gtttactgca   148860
gaagtgccat aatagaacct tcctactttt aaaacaacca gatctcactt tctaaagagt   148920
aaaggatgac cggcaggatc acgtctgtga cgtgagtgga ggcagtttgc actcctggtg   148980
gctgtttgag aggtagcatt tagaatgcct gtattcactg tcctgtgatg agtgggaaaa   149040
taggttatca ggtttatctt agcaaaatca aagcatgtca tctaattgct aaacaagagt   149100
tggcaaatct gagagacatt actcaatcct tggcatgcag gacttacatc tgcatcctgt   149160
tgccatttta tgtcttcaaa gcatttaatc atttagttgt gtttgcaaag tcttttgagaa 149220
gcctttgtca gaaatcccta catctcctat gtgagtgtat ttccatgact gcagaataag   149280
ttaaactttt accttttccc ttcccttgcg gggcggggtg ggggggcaggg attgtgtgtg  149340
tgagagggag agagagacag cagagaagga gaatataatt atcatgctgt gtactttgag   149400
ctgaaactgc aaaaaaggaa aaacacacaa aaattattat gcttttcagt ctttagagta   149460
ccttgtctat tatgcttttc agtcttagtag gtaccttgtt gatggtgttt ttaaatggga  149520
ttgggcacaa ttaggtggac agtttgggat gatttttcag tctgtagggc caagctcttt   149580
tgtaatttgc attatgaagt tgtcactctc atagcagatg gcgggagata aactattatt   149640
acttttgac cctagactta gtcttcagtc cagatgaggg agattaaaag attataaata    149700
tcttgtgcca gatgaggtga ttttattttg aaatgaccat gaattcctat cagttgtctt   149760
actgggatat ttgatagtgg aatttgtgca tttgagtctt agatgatctg ttttacattt   149820
attaagaaag cctttattag cttttatact gtgtattgcc tgttgcagtg tttgagtata   149880
aatgaaattt ctgaaaaata ttaatggagt acaaactgtg atacttaaaa gtaaactagg   149940
gcctgcattt gtatcatgac ctgtttgagt attgatgaga agatagctgt gaagaaaaag   150000
gtttaaacaa gtgtatttttc ctttaagaag ccactaatag tgcatctcct tagagtgtat   150060
atttctagaa tcctagtgtg cagagtttag actaagacta aaaaaaaaaa aaacaaatt    150120
atactgtaat ttcatttttta tttgtatttt agacaccaaa ggctctattc cctgctggac   150180
```

-continued

```
aggtttcgtc tctccaccat gcaagactca cttagtccct ctcctccagt ctcttcccac 150240
ccgctggacg gggatgggca cgtgtcactg gaaacagtga gtccggacaa agtaagtgtc 150300
cagcgtgtct gcatgggagg cacagggcgc tgagtgcctc tgtcacctgt ggcagataca 150360
gagagtgcag aggaggtgcc gtggacccaa ggagttctgg cgctcggctc ggctcagtga 150420
agctgtggtt agagacgtgg ggggccatca aggtctgagg gagccaagca gtgctgatgt 150480 gggaccettt tggtaggagt gtggggtgag tagttagtgg gtgaatcaag gaatagtcgg 150540
ccgtggcctg caggcccctg actgcacagg ccttcaagca catgtcaatg ccgttagcct 150600
ccctccatct cctcatacct tctgccacc tgtgagttgc actgccactg ccagccattc 150660
tggtatgttg tcagcacctc cactgctcat acctcatggt tagggaccac ctggagcctt 150720
ggtagagcct tggtagagcc ttggtactct actttcctgg acaaagttca gcttatgaat 150780
atgaatttag atttcaaaaa ccagcagccc aagtataaga aagcgaaggt tcagtcctgc 150840
cttcttaggc tctattcgct aagcacctgc cctgccctgg ttgctgggga gagatgagta 150900
aagcagacaa cccaggagag gatggcaaag gggccgctaa cccttagtgg tttagctata 150960 tttgaaggc ctattggaag ttcaccaggt gaaggggag gctgtgaggg tgcccaggca 151020
ggtaacagaa gtccaaaggg gaaaacctgt ggtgtggtga gccgtatagc cacagcctgc 151080
cggccggcag ccctctcagc ctagtgcggt gttcccaagc actggcctag gcctgtagct 151140
ccagggatgt gaagtcccct tgaacgccgc ccatcatgtt ccccttatcc atttttttct 151200
tcccaggact ggtacgttca tcttgtcaaa tcccagtgtt ggaccaggtc agattctgca 151260
ctgctggaag gtgcagagct ggtgaatcgg attcctgctg aagatatgaa tgccttcatg 151320
atgaactcgg tacggggga gcagtggagg caaggaatcc tcagcttttc ttgtgacttc 151380
caagtgggat ttgtctcatc atcatgtgac ccacttgttg acaacacatg ttggggactc 151440
cagtctgggc agggacggga tgtcggagag actccactct gaatgggcc gggaagtggg 151500 gaggactcca tttcagatgg ggtcgggaca tgggggttat gctgatcgag acagaaaagc 151560
acattgtttc agccacatta gaatccacgg aggtgttgtt ttgaaatcca gctggcccca 151620
aggctgggtg tatggtttgg gatgagaact atctggcctc cactggagga acaaacacag 151680
gatgttatca tctaagctcc atggccaaga cagaatggaa gtcaaggttg cgtatttgcc 151740
gtagacttca acacagtgtc gtaatgcgtg acgtcaataa cttgtttcta gtgtcttgga 151800
agttgatctt tagtcgtaaa agagaccctt ggatgcagcg agatttcctc tactcacacc 151860
tctgttagat gtagtgaggt tcttcacccc ccaaccccag atgtcagagg gcaccctgcg 151920
cagagctagg aggccatgca aagccttggt gtccctgtcc ctcacccgtg ggcaggtcct 151980
gtgagcagtg gggggccac ctcttgggta tggtgcagcc atggcccaag cagggcttct 152040
tctcagacct actaggacgg gagaaacctc ctggtgcttt agccctgcgt tgatatgcag 152100
caaatgggag ggaagtgggc acctgggagg acaaatgcct gtagaggccg ggagtgacgg 152160
caggtgttca tgaaaagaga ccttgtgggg agggcaacac aacagtgtgt tctgatgtac 152220
tgaagagctc aactgaaaac aacaggagaa ttagcccaaa atccatttac taaaattgtt 152280
tatctttttt tttttttttg agacaaagtc tcgctgttgt cccccaggct ggagtgcaat 152340
ggcgctatct tggctcactg caacctccgc ctcctgggtt catacgattc tcctgcctca 152400
gcctcccaaa tagctggtat taacaggcat gcaccaccac gcccggctaa ttttttgtatt 152460 tttagtagag acgggatttc accatgttgg ccaggctggt ctcaaactcc tgacctcagg 152520
```

```
tgatccgccc acctcggcct cccaaagtgc tgggattata ggcctgagcc accacgcccg   152580
gcctaaaatt gtttatctta agattcatgc agtgaaagct aacttactga gtgataaatt   152640
tgcttagtga tctgtttatt aggttttcca aatttgctaa ttgggctttg aacagctgta   152700
aaagttctga ctgtaaaaga aagcttcaac ttttggcatt catgatgctt ttctgagtat   152760
taaactaaga tagatgtttt acctgaagga tcggccacca atctttaaat ggctaaacaa   152820
aagggttgct aaaacataat ccaaattgac ataagaaata ccattttcc aaccaaaatt    152880 ttggcattca tatggctact tttacgtatt tcagctgcat ttgaacatct ttttcaaact   152940
ttagggtggt tggtgtatca ctgaggtctt ggatgacact ttagctttga ttttgttttt   153000
atgaattaaa attgtcatac caaaattttt atttcaagca aatccaagag cataaaaaat   153060
taaaatatta cttaaaatac taagagagaa cagatatata ttttactaag catatgttga   153120
atgaaattgt tcaaatattt ataacaggca tagagtagaa ttttcttaaa aatattttg    153180 atggtatacc aatttgtatt ttctcagaaa catttgcctt attcttttt ctgttgtgtt    153240 tttcttacct gattgaaagc tcataatctg ttgttattgt ttgttaacct ttaatgctct   153300
gatttcagga gttcaaccta agcctgctag ctccatgctt aagcctaggg atgagtgaaa   153360
tttctggtgg ccagaagagt gcccttttg aagcagcccg tgaggtgact ctggcccgtg    153420
tgagcggcac cgtgcagcag ctccctgctg tccatcatgt cttccagccc gagctgcctg   153480
cagagccggc ggcctactgg agcaagttga atgatctgtt tggtaattaa aattaaaatt   153540
tatcttattt ttaaaaagca ttccagggcc agtatagtac tttgcaccaa gtaaatgtac   153600
aataaaggca gtggatctaa tacattgaaa gcgtttacag aggtagctaa agagcagcac   153660
gggtgtcctc ggctcagaat ttcttcctgt gtgtttgcca ctttgccatt cattgacatg   153720
gtcatggaca tagggctcta agcccttgag gaaggctggg ccagacctca ggggagatgc   153780
agccccaaac cacgtgcagt cctgtggacg gatgtgtaga tgtgccactg aggaacaatg   153840
tcttgagctt tcatcagatt ctcagagaat tgcttgactg cctttcgaag ttgatgcatc   153900
tgtgctcacg tttgcaccca cccacgaggt ccttctgttt caggggatgc tgcactgtat   153960
cagtccctgc ccactctggc ccgggccctg gcacagtacc tggtggtggt ctccaaactg   154020
cccagtcatt tgcaccttcc tcctgagaaa gagaaggaca ttgtgaaatt cgtggtggca   154080
acccttgagg taagaggcag ctcgggagct cagtgttgct gtggggaggg ggcatgggc   154140 tgacactgaa gagggtaaag cagttttatt tgaaaagcaa gatctctgac cagtccagtc   154200
acttttccat ctcagcctgg cagtaagtct tgtcaccgtc aagttattgt agccatcctt   154260
caccctcacc tcgccactcc tcatggtggc ctgtgaggtc agccaggtcc ccttctcatc   154320
tgcacctacc atgttaggtg gatcctaatt ttagagacat gaaaaataat catctggaag   154380
tactttatgt cttaagttgg cctggacatg tcagccaagg aatacttact tggtttgtgt   154440
tagtgcttgt aattcgcccc cagaatgtgt acacgttctg gatgcattaa agtctggcct   154500
gtatccttaa agggccatcg ctgtgctgcc tgccctcagc aaggacacac tttgcagacc   154560
cacagaggct ccgcctccac ctcacaccaa agaaagggag gagtccaaag gcatcagtg    154620 ccattactca caaaatgata aatacaccct tattctgaac cacgtggagt catatggttt   154680
gtgatccctg tccttcaggt ttcagcttag tggggaagtg ggaaagtcag cgtgtgatca   154740
cagcacaggg tgattgctgc tgattatatt atgtgcctgc tgtatgcagg atgaaatact   154800
ttatatgcgt catcttattt gactctcaca accccctgtg ataggctc tgttactccc     154860 atttgacagg tgaggaaagc aaggcttaga gaatttcagt gacttgccca ggtcctctga   154920
```

```
gctaggaagt agccattctg gcatttgaac ccaaggcctg ctatccctag aacccacgct  154980
ctcaaattca acctatgaca gaggcaagcc ctggtgctgt gggagcccca aggaagagcc  155040
tctggcctgg tggccacgta gcccaggaga gatttctaca ggagcccaca gcgctgaagg  155100
agagagaggc agcagagtaa gggggctttg tggcagagag gggactggca ctttgggaa  155160 taggtgggtc aggactgaat gtaatggagc catgtcagag ctgtccttct ggaagggcaa  155220
gggcacctgg acgcgctgcc cctcagtgct ttggacggtt ccacaactgt gattcacacg  155280
gcttccccaa acgaaggtac acgagtgggc attctgtgac tcggtacttc cctttaggcc  155340
ctgtcctgga atttgatcca tgagcagatc ccgctgagtc tggatctcca ggcagggctg  155400
gactgctgct gcctggccct gcagctgcct ggcctctgga gcgtggtctc ctccacagag  155460
tttgtgaccc acgcctgctc cctcatctac tgtgtgcact tcatcctgga ggccggtgag  155520
tccccgtcca tgaacggtgg gttcctatca tagttcctgt ctgcttcacc atgttttat  155580 tttgtgctgc ctgtttgcca ggtactaagc taggaattgg ggatggagag gtagataaaa  155640
tatgcatcag gaagggctgg gccccatctc ttactctcca atatattgga gtctacactg  155700
gaatttaact ggaatttgct ttttttagtca ttttatttag attttgaagt ttcagctttc  155760
atcaaaaata cctctaaact ttatgtctct gtgatctttg gtcttagctg ttttatgtat  155820
ttagtcttat atgatcataa gattaataac attacattca gaagattatt tgttttctgt  155880
cagagttaaa atgtttgttt ttatactgca ttgtaatatt aacgtactgt aaaataaaag  155940
tggcttgttc ttttcaagga acagtatcct caacaagggt cattagccac aatttttaaa  156000
aaattggacg tcatagttta catgttagag ggcgttttga agctttgtat ttttaaatta  156060
aatgttatag agtgatgttt tcatgtttca taattgtttt catctgtgca tttgtagcca  156120
acttgaaaac aaagatccag ggattactac ttaaaagcca gacttcttgg aggttatagt  156180
gatgattttg atagtatctt gagccgtctc ataataacct cagggtgaga gatggccaac  156240
aggagacagt cgagggactt agaaatctga atgaaatctg aagttcaaat cttcagacat  156300
ataccactaa ccaagagatt ggtacctcag tctagtattg tctgtttgtc taaaattggt  156360
tctaaggaat ctaggctagt ctgtctatcc ctttcaactt ttgtgaggct gcacaaatgt  156420
aaaatgttga ataaaagca ctgatggaag tgtgtagaaa ttcttctctt tgttctgttg  156480
taattttagt tgcagtgcag cctggagagc agcttcttag tccagaaaga aggacaaata  156540
ccccaaaagc catcagcgag gaggaggagg aagtagatcc aaacacacag agtaagtctc  156600
aggacccatt tttttcttac atgttgttcc tccaggactt aaaaatcatt cacagagacg  156660
tgcaccgcgg tgagtgtgga ctcctggaag cgcaccgtag ctccgctgtg tcctgctgct  156720
cctccctagc tgtcagggag gctgtagtcc attgctttgc cagctctttt gtttccgagt  156780
gaacacctta tccgtacaca tgcggctgtc tctgacccta cagaccagct gggatgccac  156840
tgggggagcg ctccccttccc cccgcacttc ccacactctg cagttattct gagatccttg  156900
agggcaggga acaggtttgt cttctttgtg ttctcagaaa ttaatgctcg gcctctggtc  156960
agcaagcaac aaccttttgt tgagtgataa tgaataaata aatgtttccc acatgagtat  157020
tcagtaacct cagtgtcagg ttcagccatc tgttttggtg gatatttaaa agaaaattcc  157080
gcttttccta cagaaaaaaa aaaaaatcca aatcccagtg atttaagcca gttatagact  157140
tagacatata ctacggcttt tcatgcactt tcctcccaat tctagagtag gtatttact  157200 aggaaaatgg tggcagtgcc tgttgggagg aagattcttt ggccaagtgt cttttgttct  157260
```

```
tgccagggcc cctaggctgc tggggtgctt cagcttcttt agcccagtgt ctggtgggga 157320
atggcccctg ttgcctgtcc cacagaggtg ggggtgcctc acctggagcc tgtccacaca 157380
ttttacacag cacgcttacc tggagcatca ggcatctttt ccatgctctg tggctcagga 157440
aacacgcctt ttcaatcatg agtgcaccag tgcttttggg cttttctcc ccgcttttgt 157500 gcaatcctgg ttgtggatgg agttttcctg tctttagtct tctgcatagt acttttctct 157560
tctggttccc ggttcaaggt tttgtaatta gagaatgacc cagaagcaat ggcattttaa 157620
tgcacagcca aggacttctc tgaatttgta tctcaaacct ctgtgggtcc ttcaggcttc 157680
agtttgtgat ttcatgattt cttgttgcta cctaaggaat atgaaaacac ccacctccct 157740
actctgcatc ttccagccga gtggcacctc aggctgtgga tcctgtgctt ctgtggtgag 157800
gataagaata gtgccaaccg tgtggattga aatcaatcag ttaatccctc catgtaaagc 157860
acctggaacg gatgacagtc ttgttatgaa tactcaacaa atgctatcat gatttttagt 157920
tagatttcca ttgctttaaa acagttgaga catcttggcg gtttgagtta gagcaacggg 157980
ccctgaagtg ggtctgtttt gggtgaagat gattatgctt attccccatg gccctcttta 158040
ggcaagagtg ggaagctttc tttgtttttt taatcacctc gataggacgt tacttcttaa 158100
aggtcatcca ataaatatta ataggccggg cgcggtggct cacgcctgta atcccagcac 158160
tttgggaggc cgaggcgggc ggatcacgag gtcaggagat cgagaccatc ccagctaaaa 158220
cggtgaaacc ccgtctctac taaaaataca aaaaattagc cgggcgtagt ggcgggcgcc 158280
tgtagtccca gctacttggg aggctgaggc aggagaatgg cgtgaacccg ggaggcggag 158340
cttgcagtga gccgagatcc cgccactgca ctccagcctg ggcgacagag caagactccg 158400
tctcaaaaaa aaaaaaaaat attaataaag ccaactcgtt agcgtggggc ttaattgctt 158460
aagtccaatg agaagtcctt ctctatccta ggaagttgcc caaactgtag aatctcgtgg 158520
cctgtgggta atagccacgt aatacacact cactgcctca acaaatcata ttttagtagg 158580
tatgatattc tagactcaag acaccattct gtggatcttc caagggtgt gaagtgtcca 158640 cagcgtctgc cttgggagtt tccatgccca ccagaaccat gccccaagcc cctcaagcac 158700
tctgacctag gaaagccagt gaagcaagga tgacaacatg gcccttgat actagctgag 158760 ggacagacac aggtcctggg agaccagaga aagacgaggg gcagaggagg tgtcctaaag 158820
gaagtctgag gctgaggagc cacaggatgg cttccagctg tcacaggctg ctgctggcct 158880
tatcacagag agtgggccag agggctggga accaaggcca gagctcaggt tcaggaccat 158940
tccagcaatc ccagcagaaa atggggagaa ttgtatggta taggcggata tgaaggtaga 159000
atctgcaggc cttcagtggc caactcagag tctaagtgga ttccacagtt acagcttgag 159060
cagctggttg taggtcatgc tttctacact gggcatatag gatgtgtttt ttaaaaagtc 159120
ctctcttaac cgttgcttgt ttagatccta agtatatcac tgcagcctgt gagatggtgg 159180
cagaaatggt ggagtctctg cagtcggtgt tggccttggg tcataaaagg aatagcggcg 159240
tgccggcgtt tctcacgcca ttgctaagga acatcatcat cagcctggcc cgcctgcccc 159300
ttgtcaacag ctacacacgt gtgcccccac tggtgagtct gctcgttcct tgcagaagac 159360
caagtacggg gaaaggcacc ggtaggccct gggctgggca cacgtgagag ggcgggacag 159420
aatccccgca gcccagaggc tgcctgctgt ggttctggtg cccactgtgg ttctggtgcc 159480
aggctgcttt cctcaggcac cacgtgtgga ggtcgctagt agaaatactg ggttttctaa 159540
aatgaactga ggccctacat ccctaagaga ttagtgttag acctgattct agagcaacta 159600
gaccactttg cttaatagca gaccagaaac cacacccct cgagtgagtg agattttcct 159660
```

```
ttggagataa ttcatgtttt tctacacagt tttgcagttg tcttcagaat tggtttaaag   159720
taggtgttat tgccaggcgc agtagctcat gcctgtaatc ccagcacttt gggaagccaa   159780
ggtgggcgga tcacttgagg tcaggatttc gagaccagcc tggccaacat ggtgaaaccc   159840
catctctact aaaaatataa aaattagcca ggtgtggtgg tgtacgcctg taatcccagc   159900
tactcaggag actgagacag gagaatcgct tgaacccagg aggcgaaggt tgcagtaagc   159960
cgagatcgcg ccactgcact ctagcctggg caacagagca agactccgtc tcaaaaaaaa   160020
aaaaggtagg tgttattgat cagaacccct gtttcagata acatgaggag cttagcttga   160080
ggagagtgag ggttgatgga gggggactga cttctgccca gtgaaatggc atcatctccc   160140
accagcccgc tgaaataaga tgatgggcc tgttccttag ggcctgcagc atcctcaggc    160200
aggaaagaaa ggccgacctg gcagggtgtg agccagcagg tgtaggtcag ggagaatgga   160260
gccaggtccc agggaagagg cttgtggctg cctgagaagg gtgcgtgcct gcctgtgtgt   160320
gtgtgtgcac gtgtgtgtat gtatgctgga gagtctaggg aggcttgctc caaggacgca   160380
gtattgtttg atcctgagag ataaggattc tgccgcaggg aatgaaggta ttccagatgg   160440
cgggcttatt ccgaagaaga ggccagtgcc tggcggtgct ggaagcagtt gcagaacagg   160500
gagttgtagg cttcctgggg aagagagcag caggggtgct ggagaagcag gccacacttg   160560
ctgcatgggt ttgctctcgg ccccactctt ggtgcacagc gagtcactgt gggttcatta   160620
gcatctggtt atgagacagt aactgctcct ttggaggggc tcgtggagac catgcaggag   160680
ggcacggtct tgaggtcatg ccgtccagag cacacctgag gataggccag gacgggctgc   160740
acgctgtagg taaaattcct ccagcaagct cttcactggc attgaggagt tccctgagtg   160800
cggtcatctg gaaggcagct gtaacaggca ctgcagtctc tccctgggtg ggtaccagag   160860
aggagcatag gggagcataa ccgatttaaa gagagggctt tcctgtggtg aggtaagaga   160920
ttagctggtc attatcatag agcccctct gcctttgtgc agatgggctg tgggaatcct    160980
ggggttccgt tgggtccttt gtcacctcac tgaaggcatg taagctgagc tggccagacc   161040
gtgagctgat cctgccactt gaacagcatc aagcctgcct ctggattctt ctgtgcatgg   161100
cacttgtctg agcacctcac gcacagagaa ctggacttca gagtttacag aaataagctg   161160
tatggttcat tttcatgcct gcttgccaat aaacatatct gagctgaacc tcattgaacg   161220 cctgcccttta ttctagcaca gcacctgctg tttgtgggcg aggggtgctg tctctaactc   161280
ctgcctgctt ctcccagcac tccctgagtg gggtgtgcca gcagcctcag gatgaggaca   161340
ggaagtggga gggcagagca gatttgggag gccacttga tggggaagga agtcccagga    161400
agcagttgga gctgttttct gggggagaag gtgccagctc tgggacagtg ttggggtagt   161460
gaggagggag cccagtggag agaagtcggg cttcctgctt cctcacagta tgtctgtcct   161520
gactcaactc ggatgatgtc acttcctttt catcttctca ggtgtggaag cttggatggt   161580
cacccaaacc gggagggat tttggcacag cattccctga atccccgtg gagttcctcc     161640 aggaaaagga agtctttaag gagttcatct accgcatcaa cacactaggt actcttgggg   161700
cctctccttc aggtcaccat tgtcggacat ctaccgggag gaaatccaga gcccccagta   161760
ctgggatctt ctcatttgac tccagaaaag atttaagcat gataataata caaacctatg   161820
tgaatacatt ttgcagtgtt ggcaaaactc ctttatact gagaaaatag atcccagttc    161880
ctgtgttttg tggcttgaat cccagctttg tgtattccgg gctgtttga agtcaggaaa    161940 ggttcatgtg tagtggacaa cgtgagacca aattctgcct tagattttgc atttaggcta   162000
```

```
aacagtggca gcacttgtct cagaatgttt tcttgtgttc accagtctga tcctgttgtg   162060
tctcagtggt ccattttctc atatgggaac aagcagacgg gagcagatgg agtcaggttt   162120
cttggcactc gccttcccca gagcctagag gcagcatggg gagaaagcag gcttggggct   162180
cagacagtcc tggtctgctt ccagccctcc tacctgagca gcgcagggca agtccgtcta   162240
acctctagag accctcagtt ttgtcatatg taaaatgggg gtcgtgtcta tttcatagaa   162300
ttgttgcaga tttagaaatt acatttctaa acaaatgtta cccttatttt ctaaataagt   162360
gtctaaatga ataagtcacc acttttgccc ctatttgatg gcaagaggtg tgatcttgtg   162420
gtgggactgt aatcagtcag ttctcagtga ctgtgccctg ctgtggtgtt tcctggaatg   162480
ttcctgtctt gtcctagaaa gtctggcagg ggcaccctga ctccactgtc cagtcctctc   162540
cccagtccct cgggcttctg cagatttgag gcttgtttgg atcccagaag gttgtggcag   162600
gagacacctt gcctctactt tcccctttat aattcaatgt ccaaagagag ccctgagcag   162660
gtacctcacg ccagctgcct cacggagctc ctcctcttcc tggctgtgag gatcggtatc   162720
agtggcctcc tgctctctcc cccttgccta acacgagcac ctttgcttac ttgggtgccc   162780
ttgctcttga actgcccatc ggacgtgcgt gacccaagac tgtgccgcag tccttgcctt   162840
gtctgtgctc attttctttg ttcatttttt tccctgtaac gtaaattgtt atatttgtct   162900
gtatctgtgt ctgaatcagt cctgcacgct ctccttctct ctgtctcttg ttctttcttt   162960
accccgttta tcacggggac cccgatgtcc attgctctag ttctcctgtc ctaagcaccc   163020
catcccgtct ctctggcctt accacaagtg gcgtggctgc ctcagacatc atgatgggga   163080
catgaagcac agctgtcaga aacaactgtt cgttagatac actcgaatgc agctcatcaa   163140
tagggatgga gggtctgtcg gatgtatttt cactgaatcc ccgttcctac cttgatacac   163200 tcttttaat ctattcttct agacaggtca gaggaaccat tactttgact tttaaatttt   163260
tagcagcttt attgaggtag aattcacata ctacagattt cacccactct aagcggacag   163320
cttggtggcc attagtttta tccacagagt tgtgcagcca gctgcacagt ctcagggctg   163380
gactccaggg aagattttag cccatttagt gagtggggca gaagtggccc tggccctgca   163440
cgaggttgcc tgcatgggcg tccctgccct gtccctgtgt ctgctccact gggggttgac   163500
caggctgcca gggccgactt gggcctgtgc cacctgcctc tcatgtgtct cggacagtgc   163560
agccgatgtc tatacttcgg tttcctcaat gatgaaatgg aggggatagt gttccccgca   163620
tcatagaact gtgtgaggtt aagggactc actgcccttg gcgtggagcc ttctccaggg   163680
gccgtgctgt gtcggcgtag ctgtcagctc tccgttacag gcttgagaag ggttgacact   163740
ctctcatgta acatttatat ttctaggctg gaccagtcgt actcagtttg aagaaacttg   163800
ggccaccctc cttggtgtcc tggtgacgca gcccctcgtg atggagcagg aggagagccc   163860
accagaagta aggccacacc ctgtgctggt tggcacatgg gcagttatgg ccgcttgcag   163920 gccttttggtg gggaataaaa taaggcagca agctggtgtt ctttttttct cttaccttat   163980
ttttgaaaga gtagctgaat ggtgtcttga ctgatattcc agagcaggga caaagcctgc   164040
tgaggtctgg gggctgcgat taccaatggc tggaatgcat tttattacgg tgcattccat   164100
gttaaggatc aatacgattg tgcccttct ggaaaatatc ttttagttta tcaatattca   164160
gaggagtgta ggttgaatta aaatgaaaag gcactttata aaggccatga gtagtacctg   164220
gtttcatttt tctaatgtct tgcagagatt ttatcaggct tcttgaagtg ttcacgtaca   164280
ttacgctaac acgatattaa taataactgt gctctggtac agcggagcca gcagaatggg   164340
aagttgtgga atgcaggccc ttgattctga tagaaggtgt ggtttgaact cacagaaatg   164400
```

```
acagtttgga gggtagacat atgtcacaag tcatcaagat tgtctttaaa ttcatgcata  164460
gaagctaaca gggtgtcata agcaaggcct gtaaaatgta tgagggaatt caaagataat  164520
ttattaaaaa gtaattcatg tttggagttt tgtgcccaaa ggagtccttg atttgaaaaa  164580
tgggcttttg cccatcagat tgtttcaggg cccgtgtgtg cggaggccct gccttgtgcc  164640
ccgtgagctc agcctgacag aaatcctttg gtagcactta aggctcctct tcctcccatt  164700
gaggcaggga agactctggg ttctgcaggc agaggtggtt gtgggtgtct tgctgctctt  164760
gttgacatgt gggctctcct tccaggaaga cacagagagg acccagatca acgtcctggc  164820
cgtgcaggcc atcacctcac tggtgctcag tgcaatgact gtgcctgtgg ccggcaaccc  164880
agctgtaagc tgcttggagc agcagccccg gaacaagcct ctgaaagctc tcgacaccag  164940
gtttgcttga gttcccacgt gtctctggga catagcaggt gctggggaca gtgggttccc  165000
cgctgaagcg tccagcagct tcaaccaggc cgttttcctt cattgctaga attgaaaaca  165060
ccgtccgtgt ggcctgtgca ggagatgcag acccaaaggt ggcctcctgg tcagtgagaa  165120
gctggaaacg tgacaggaac tgacgtgggg ttattgagca tttaggggaa gacgttagca  165180
gagcaggaat gagcaggcaa ctagtagaac acccacttaa gggctcacgg acaggtgctc  165240
acttaggaag tgagtttcat ttggtattac accaggttcc tttaggcaaa gcggagggaa  165300
agttctggtg tttttcactt gtaagatttt gaaggaaaca aaacactctt taccttttt   165360 ctaaaatgta ggtttgggag gaagctgagc attatcagag ggattgtgga gcaagagatt  165420
caagcaatgg tttcaaagag agagaatatt gccacccatc atttatatca ggcatgggat  165480 cctgtcccctt ctctgtctcc ggctactaca ggtacctgag ggaaagggtg cggggagcg  165540 gttgtacttg ggctagaatg agagaagact ggcatgctca ccacaccagt gatgcgggaa  165600
gacctgagtg tggtctgagt tggaggctgt ggtgctaaat acgctgcccc tttcataagc  165660
aggagtctta gtcaggccca gggaggaagt aaaatctgga aatgaatgag aagcattctc  165720
tcctgccagt caagaaatga gaagcgaaag aattctcacg ggctgtaaga ccagcaggat  165780
ttaaaagttg aattagttgc ttatgttaag aactcaacca agttcatcta cacaagctga  165840
atctccagct tttcctaaga aaccatgtgt ggcagtggct gcagggcagg gcacagctgg  165900
gcctgagcac cccgctccct gcacctctcc cctccctggg ccctgcctgt cactgcccac  165960
tctcccacca agccttccgg ttgtgtgcct gccctatcac aggcatcgga gcttgtcacc  166020
tggtttaaaa gaagagagtt gtgtggggat ttgggatgca cgttttttcac tcaaaagtat  166080 tttagcgtag agctctgtga ttccgtagct atttaggagt ttaagcacct tgaaggcttt  166140
aattgcagaa agttctatgt ggacgtgcaa tgtgttatac gcagtgtcta tgagactcaa  166200
atgtttatta gggcgttgaa gtaaactgag cacttggagg gccatggatc cagccttcaa  166260
ggagctcata agtcaggagg acccaggagc aatgacctgt catagaaggc agaaaagagg  166320
ggcacagagg tgggtgggag gcatacacag gcagctcctg gagctccaag gggagcaagt  166380
gcttccaggg aagggggcgt ggaggcccct ttggaggagg caagttgatc tggggtctgg  166440
cagagggtta gctggggaca tttagcggga ggctggtgcc cgggaattgg ggggatgccc  166500
agcagaaaga catgaggagg ctggcctggg gcgtggggggg gtgtgaaagg ttaagtgggg  166560
gcattatcct gctcccgctc ctgccggctg tatctggtca gcctgggcac cgaggtgggg  166620
ttctggaagc cactgttcac caaaatgctt atctgggtcc cccagagagc ttgcctgcct  166680
ggactgtcgg ctcgcctgca actgctgact cctaagcttt tgcagctcag cccacaacca  166740
```

-continued

```
gttcctattc acagaggtgg gagctgaggg gtgacaagtg actgctgcag tcttatttgt    166800
catagagaaa aagtgacaga gtccagcttg cccactggcc ctgccagctt aactggttat    166860
aaagtgacaa atccccaaga cccacagggc tctgcacaac ctgggccctc ctgccagtgg    166920
cggcgagggc aggtggctca cggctgggtg cctgtctggg caggagctgg gctggtatgg    166980
ggtgggcctg cggccctgcc ccctgtgca gatcaagact cagggtgctg gtgttcacag     167040
gtgccctcat cagccacgag aagctgctgc tacagatcaa ccccgagcgg gagctgggga    167100
gcatgagcta caaactcggc caggtcagtc tcgcgccccc gccgcctggc ctctgtccgt    167160
ttctgtcctc agactttggc gcttgacaca cccaggagaa aagctcagtg cacttttta    167220
atgaaaggaa gttttccttt tttttaaaaa aaatttaat gttcattgtt tttatctgtt     167280
ttattcctag gtcccgcaag cagaggaagc attagttttg tttttattta tgttctgtat    167340
tccagaaagt agttaagaga cctcacatgt agcgatagag atgtgtgtaa agacacagtga    167400
gagggcgtga cttggactta agcaaggacc gtgagacaca aaaggggggg tgaggacaga    167460
gtggagtcag ctgaaatgct caggaggaag tagacgccat gaagggccat ggtatggggg    167520
gccgcaggcg tggccgtgag tgtccctggg gccagctctt ggggggctcc ctgagtgtcc    167580
ctgtccctgt ggcagttct gggtgggagc ccgtgtgca ggcagacagc tcggccactt      167640
cctagcaggt cacattggtc tgtgcttctg tttcctcctc agataagtga agggattcaa    167700
gggtctgggt gtggtggcta acacctgtaa tctataacat tttaggaggc tgaggcagga    167760
ggcttacctg agctcaggag gttgaggctg cagtgagcca tgattgcacc actgcactcc    167820
agcctgggca acagaccagt actctgtccc ttaaaaaaaa atgtaaacag aaacgtaggg    167880
ccatttgcat atgatggcac atggcgtgga gccctacagg tgtatgctgg gcggggcccg    167940
gctgtgctgg ccgacttgca ccttccctc caccccggtg ctgtgtcttt cgctcaccgg     168000
gttcctgatt tagtgaaagc agttgtgcag gacagttctc tttgtagctt ttgtttctgt    168060
ggaaatgggt cagaatatgg tgtttagaaa cacttatgag ctctgagagt ttcctcttct    168120
gagttcctgg cctgcagcct tcacagcaga aaccctgtga tgtcacaagc ctgtttctgt    168180
tccctgctct ctgcctgtac tgtcctgttt tgtgcctgcc ggtttcagtg acaggaagca    168240
gggagctact ggaccagcct gtattttct agacatagtt ggaaaaagaa gtcccactct     168300
tctgtccttt cacctttgac agatgtttcc accccaagat aagtgaaaat gaccaatagg    168360
atgcactgta ttttcatga aagtgtttct gaagggcagg ctgagagtga gaggcctggg     168420
gctcactggg tgcctctggc cttgtcctgg gccagggac actggtctgt gcccgaggta     168480
ttccctatcc ccccaacccc gctgcatttg gccacatcct tcaatgtttg cgttgtgtcc    168540
agcgtccgca aaccaactgt catgggatca tactggggct gaagtacggt cccacccctg    168600
ccctgtctgg ggctgaagta cagtgccacc cctgccctgt ctggggctga aggacagtgc    168660
caccctgcc ctgtctgggg ctgaagtaca gtgccacccc tgccctgtct ggggctgaag     168720
gacagtgcca cccttccct gtctggggct gaaggacagt gccacccctg ccctgtctgg     168780
ggctgaagga cagtgccacc cctgccctgt ctggggctga aggacagtgc accctgcc     168840
ctgtctgggg ctgaaggaca gtgccacccc tgccctgtct ggggctgaag acagtgcca     168900
ccctgccct gtctggggct gaaggacagt gccacccctg ccctgtctgg ggctgaagga    168960
cagtgccacc cctgccctgt ctggggctga aggacagtgc caccctgcc ctgtctgggg     169020
ctgaaggaca gtgccacccc tgccctgtct ggggctgaag acagtgcca ccctgccct      169080
gtctggggct gaaggacagt gccacccctg ccctgtctgg ggctgaagga cagtgccacc    169140
```

```
cctgccctgt ctggggctga aggacagtgc cacccctgcc ctgtctgggg ctgaaggaca   169200
gtgccacccc tgccctgtct gggatgttta gcccctagat gccactggac tgagccgcta   169260
cttgcttttg ggaaagaggg gtggggggtta gggtctggg cgaggggagt gcagggctc    169320 ctccttggcc tgagagctgt tcatacagac tcctcgccca ctccctgcag ggtgctggt   169380 cccaggggg aaatggccct tggtgccaag aacgtgagtt ggggctagtg ccagtgatga    169440
tggagaacag cttttatgg gcacacagcc cacagcactg tgccaagtgc tcgaggcttc    169500
ccgagaacca ggcagaaagg aggacagtcg aggtgtgctg actgcgtggt ggctgcgtga   169560
tctagagcgc gggtcacaaa ggcgcgaggg agctctggcc ttgggtttac cgcaatgact   169620
gccagtgcgg gagactggaa aaggaatctc acgtattggt tccgtgtttt ggggactcca   169680
ttcagatgtc acttaggagt gaaagcatcc cttcgtagag cctctttctg tgtcaccctc   169740
ctcagctgct cctggggttg actggcccct gattcatgcc tttagcatgt gctggagctt   169800
cccagcagct gtccagcccc tgccccaccc tctctgtggg ctcccttgcc cgtaacctgg   169860
ggtgtctgaa cgacccttgc taaggggcag actgttagac ggtaggcatg tgctgagtcc   169920
cagtggccac acccacccac caggagcctg gcactgtggc cgcagcactg agcagtgccc   169980
cgtttctgtg gcaggtgtcc atacactccg tgtggctggg gaacagcatc acaccctga   170040 gggaggagga atgggacgag gaagaggagg aggaggccga cgcccctgca ccttcgtcac   170100
cacccacgtc tccagtcaac tccaggtttt ccaatggcct ttttctttt aacagaaatt   170160 tgaaatttct tatcagtcat ttgatttgtt tgaggtgctt cttgaaatga gcctctcatc   170220
tcatgtactt ggaaaatacc catctcgcat attccacagg aaacaccggg ctggagttga   170280
catccactcc tgttcgcagt ttttgcttga gttgtacagc cgctggatcc tgccgtccag   170340
ctcagccagg aggaccccgg ccatcctgat cagtgaggtg gtcagatccg taagtgagcc   170400
ttcccattcc cctcacacct gcacgtgcca cacgcaccac acacgccaca cacccacac    170460 acacacaccg cccacacaca tgccacttgc acacacaccc ctcatgcatg caacacacac   170520
acaggccaca cgcaccatag acaccacaca cacatgccac atgcacacac atacacggca   170580
tgcaccatac acacaacaca cacagcacac atgccacaca cacgccacac accacatgca   170640
ccacacacat gccacatgca cacacactcc acatgcatgc accacacaca cacacacaca   170700
ccacacacac cacatgcacc acaccacaca ggttacatgc acaacacaca catgccacac   170760
gtgcacacac cccacacacc acatgtatgt gccacacaca gcacacaacc acacacatgc   170820
accacacaca tgccacatgt gcatgcacca gacacatggc acacactaca cacacgccac   170880
gtgcacacac cccacacaca tgtacgcacc acacacatgc cacacacaca tgcaccacac   170940
acatgccaca tgtacacaca tgtatataca caccccacac cacacacaca ccacttgcac   171000
accacgcaca cacaccacat gcgcacacac accacata cgccacatgt acacaccata    171060
cacacaccat acatgcacca cgtgtaccac gcacccacac agacacagca cacgcataca   171120
ccacacacac acgcacacat gcgtcccgca cagtaatgtc tcttgggtgt aagaacacga   171180
cttgccagta gtagcgttct ggatgcgttg cctggattct aacagcgcga ttctcccctt   171240
gccctcctgg ttttccacat ctccagcttc tagtggtctc agacttgttc accgagcgca   171300
accagtttga gctgatgtat gtgacgctga cagaactgcg aagggtgcac ccttcagaag   171360
acgagatcct cgctcagtac ctggtgcctg ccacctgcaa ggcagctgcc gtccttggga   171420
tggtaagtga caggtggcac agaggtttct gtgctgaagc cacgggggcc catctgcctt   171480
```

```
gggacctggt gttggccaga ggtgccgggt gcggctgcct ccttccaaga gttgacccga   171540
accggactcc acggcccacg tgagctgcag tgcttctcag atggagggg ttcagcgacg    171600
gtcagtgcca ttcacaggtc actgtgatgt gggttgtggc ggccaagcca tggtttgggg   171660
tcccgtatcc ctgggcttat gacatcattg tagtagccca tcccacaga accacggtgt    171720
gtggtggcgc tgaggcatcg tagatggtgg aaatgctact ggcttcccca tgctctgccc   171780
tgaggcctga ctgcctcact cccttctca gttatgttcc aggccccg agcttcctgg      171840
ctggacagct tctctcctgg gggccgtttt gtcacagtga ccctgtgttt ctagtcccaa   171900
atctgggtgc tatagtctct ttttagcgtg gtggttgtct tagtcttttt tggctgctac   171960
cacaagttac cttagactgg gtaatttata aacagtggaa atttacttct caccgttctg   172020
ggggctggaa gttttcatgg tcaaggtgcc agcagatttg gtgtgtgatg agggctgctc   172080
tctgcttcat agatggcatc ttctggctgg gtcctcacgg tggaaggagt gaacaagctc   172140
cctcaggcct tttagaaggg ccccaatcca caagggctct cccatcatga cctcatcacc   172200
tcccaaggcc ccaccttctt gtactgtggc actgcaaatt aggtgtcagt gtaggagttt   172260
caggagggat agaaacattc agaccatccc agcggtcaag tgttcatcct cttgagttcc   172320
tccttattct gcttctggtt tatcaggatt cagccagtgc agcatggtac ctgtattctg   172380
tggcacatca ccacatggta tttgccaagt atccatcacc tgcacacgtg aaatcattgc   172440
ccgtgggtcc cgacatctgg cgaagcatat tcaaggatgg cagaactgtc agagctggca   172500
cctctggttc cttgtcatgt ggcattacct agtaatccat tttatgatag caatggaaac   172560
tcatttcttc aacaaacacc tgagtggctg ccgtgtgcca gccgtctggg gcccttggtg   172620
agaatggcat ggtggtgccc atcagggcct gcctagcccg tgctctggac gggctcctgt   172680
gtgtcaggaa cgacaatgct gtcatgacgg tgaatgattt ttttttttgc catcactcca   172740
gccgctaaca tttgcggagc tcttcctccc gcaccccac ctgacaaggc caagggtgac    172800
cttggcccca ccctaggcgg ccaaggtcag aggttagctg gcttgtctgg gtcacacaaa   172860
atgcagcaga ggttgaggtg agcacatgtc cgtgacctgg agcctgactc cctctctgcg   172920
agtcttgact gctcttgcct agactctgtc ctccccgagc ccaaacgcca gtcatcttcc   172980
cttgtgggtg tccttcagcc tggtgccatg ctggtgactc agcagccgtc cagggagtgg   173040
aaacaattga gtgtgtgggt tccctgtgtg ggcatctctc ttcacggcga acaccctctg   173100
ggtgttgccc acacgatgtc aaagcggctc ttggaagggg tccttctcct ttgtgggaag   173160
tttcagctgc tgggctaact tgaattgtaa ctgtggtttt gtgctcaggc ccagatcccc   173220
ctaggcaagt gttgtgccat cagtaatcaa atgagaaata atcattttga aaagcagatc   173280
ctaaggcagg atggtcatgg acactcactc ccagctcttt gtgcactcat gctttctgga   173340
agatggccat cctctgtgaa ggttttcagc gcgtcatgct tggtacccac gtatccagag   173400
catgtcgttt tgaggtattt gcccaccgtt gtgaaatccg tgccacccga gagcaggtcc   173460
tgatgtgggg ctttcagaag tgggacctgg ggccgtacgc agtccttagg gagggccgt    173520
gtggcgttgt gcgtgtgagg ggatagcaca gggtgaggtg ggggcccaag aaggaagtga   173580
cccacaaaga acagcctcct ctttggtcc ttgttcctgg gatggctggg agtggcttct    173640
gtgtcgtccg gccatttccc ctgcggagag gctcctacca ctgccgagaa cctcatcatt   173700
ccacaaaaac aagaggccgc ctggccatcc agcgctccat gggaattctg tgtccccata   173760
gtcttgggct gaaggagggt gacattcctt gctgacttct gcaggggtct cctcactgtt   173820
aaagagcaga ttgaaagtga agaacgtggg ctaagtgttt aggtcgatat ttaaccctgc   173880
```

```
taggttttgg atactaagtg aaattgaggc cattttggtt gaagttgaca gaaaccacta    173940
tcagggatcc ccaagactac cccaggcttt tctagaaaga ctctcagcta agatgtgtta    174000
tggtaaaagc acacaaaaca aaatcagcaa agaaaattag caagggcaga ggcccatggg    174060
gcgatgtccc gaggacacca ggcttgagct tccagaatcc tctcccagcg gggtcgtgca    174120
ggacgcactt aactccccgc acagtgagcc gtgacagcgc gtgtgcagtg tcgtcgccag    174180
gaaagcacac tagagactcg gtgccagggt ttttactggg ggctgggcac atgggcaccc    174240
tctgcctgcc tcgtgcccag actctggact cccggaggga aggcaagttc tcagcaccaa    174300
ccctggtgcc cacacaagca gctgagcaca gggagcccct cctcagtgag gatggtgggc    174360
accgtcccaa caccagccag gggccagcct tgcacacagg cctctcagga tggtctccgg    174420
cctgctgtgt agtctcttct gcacacaagc gtgagggcag cgcccccgcc tcggctgtgg    174480
ggaggagcca ctgggacgtg agctctggtg gcatgcagca gcttttgtct gtgtgtgcct    174540
aggacaaggc cgtggcggag cctgtcagcc gcctgctgga gagcacgctc aggagcagcc    174600
acctgcccag cagggttgga gccctgcacg gcgtcctcta tgtgctggag tgcgacctgc    174660 tggacgcacac tgccaagcag ctcatcccgg tcatcagcga ctatctcctc tccaacctga    174720
aagggatcgc ccagtgagtg ggagcctggc tggggctggg gcggggtct cagaatgagc    174780 tgtgaaggaa gcagcatcac cctctccaag tgcccaggct cctggccaga tgcaggcca    174840 ggtatcagtg ggaacccagg tgggtgccat ggctgaggtc agtgagacgc aagagcacag    174900
gtgcgtccta gaggcttcct cgggcacctc cagcgagctg gagctctcgc ctctgctgct    174960
gtctcatgtg gcgcttagca cactctccca cgtgcccatt cctgactctg ctctcgaggc    175020
catcggctct cattctctgc tcccagaacc ctgttattac ccaggctagc ctcctctctg    175080
caccttcccc gccctggccc agtacctccc tcttgtttcc actgtgattc cgacctcacc    175140
ttatcttaaa gctgctggac ggcaggttct gtacacacgt gtccttgaca aagcacggct    175200
ggtgccgcaa cccctcagcg agcaagtcaa gctcttcaca gcgatgtctt acaagcgcag    175260
agggctctgt gacaccctgg tctcaccgcc actcttccaa agtcgcagag ctttagcag    175320 agatgggccc agcctctctg agtcataggc ttctgcacac gggagctgtc tttagaggga    175380
gggtggaatt tcatcagcca cccacatggg ggagttgagg gcaagaatta ggagcaaaga    175440
tgggaagggg tctgggagga atggccagtg atcccctttg acaagtgggc aggaaacggg    175500
ggctaggtca aagttgagtg gaagacctgg agggagacgg gaaggtctct gtaggcacag    175560
ttcagacagg agggaggtgt gagccagggc acatgccggt ggccgtctgg caggatttgg    175620
gacatgctgg agcagggaca gcggctcatc aggggccatt gccctcatcc aggccagagt    175680
gtcacaagcc cgtggggagg cccttctcgc ctgtcatcct tgctgggcag tgggtgctgt    175740
gctagcagga caggcggacg gctggcaact gtctctgcat ccctggagcc tggcataggg    175800
ccaagtcaca cggggcacag gcctgcaaat caggcacata tgttggtgca gtgacgtgat    175860 tttgggggc agcccagaa caggcccag acacaggcca aagccctgcc tgtgctggtg    175920
tgttgggctg ttctatggct cttgctgtgg gcatggagga ctcagggaag gagagttgag    175980
gtggtccagg agttgcgttt gggatgcaga gagcttgtgg catccaggta gaaatggtgc    176040
gtggggctga cctcagcacc atgggcagag gggccgtgtc acgtgcctcc gaggtggagg    176100
tgggaccacg tggtgacaga tatacgcatc actgggcacg ttttgtggg tgttgggggg    176160 catcgtattg gctcctctgt tcacagtggc cactcattca gtccctggct accaggtcct    176220
```

```
cactgtgcca tggggaaggc cggcgctgtc gggggatcac agaaggcagc acgtcatgat 176280
ggcatgtgcc atgaaggaaa agcacagggc actcaggaag tagaggggac tggcctgggg 176340
tgtgggaatc tagggcctcg ttgagggaca gagagaggaa gtgtgtggtg ccagcatgg 176400 aggtggccac aggggaggct gagttaggcc gagagggcag ggcgttgggg aggtagacgg 176460
gctcagccac tcaggagtg gtcaagcaga ggctgaaggg tcaggccagg ttgcaggggc 176520 ctggggagc cactcaggt aggcgctccc gggagcccgc ctggcccata gctctacact 176580
cccgcgtggg gccggacatg ctgtgaagcc ctctccacgt tggatggggg tggctgagcc 176640
tggatgctgt ctcccgtttt cagctgcgtg aacattcaca gccagcagca cgtactggtc 176700
atgtgtgcca ctgcgtttta cctcattgag aactatcctc tggacgtagg gccggaattt 176760
tcagcatcaa taatacaggt gagtgggccc tggctgtctt cctctgcaca cggggagtgg 176820
gcttcccttc tcttttcctt gcaggatcat accagtgggc cagttttgac ttggtcggga 176880
ggaggcatga acacctgaga ctgtgcagcg attctttgac acagaggcct ttctccctgt 176940
gcagatgtgt ggggtgatgc tgtctggaag tgaggagtcc acccctcca tcatttacca 177000 ctgtgccctc agaggcctgg agcgcctcct gctctctgag cagctctccc gcctggatgc 177060
agaatcgctg gtcaagctga gtgtggacag agtgaacgtg cacagcccgc accgggccat 177120
ggcggctctg ggcctgatgc tcacctgcat gtacacaggt gagcatgtac acggtgccca 177180
taaggccagc ccaagtcctg ttcaagggag gcaggagcat gctcactcaa gggacctcga 177240
ctaggtgccc tctgatttca cacttctggt gttgccccaa gccggcccca tcaccttgca 177300
agaaaggctc tggagccccc agggctggag tacctggtca gggttgaccg tccctgtggt 177360
cactcatccc atgtggctga gctgggctgg gtcctgggca agcaaggggc tgatatcacc 177420
tgctttcaga tctccaggga ctcactggac ccctgtgtac aaagcactgt ctacagagcc 177480
tattgggttg tatagaggta accttcgtac tgaacacttt tgttacagga aaggagaaag 177540
tcagtccggg tagaacttca gaccctaatc ctgcagcccc cgacagcgag tcagtgattg 177600
ttgctatgga gcgggtatct gttcttttg ataggtaaga agcgaagccc catccctcag 177660
ccgttagctt ccctagaact ttggcctgaa gctgtgcttt tgtgtgtgtc tgctgatccc 177720
ctggcgctgt tgctggagtc ctgccagtga ttccccacca cagcctgacc atgggctgcc 177780
ttggctcagg gttccactgg cgagctggtg gtccttggac cccagcactc aggtgtagcg 177840
ttgaccagtt ccaaggttgt cccagtgcct gcccatctct cctgagggct caggacagt 177900 acctggcagt tgggggtgtg gcaggggca ggaatgacca gcctctggga gggtggggca 177960
gaagcctgta cagtgaggag gagctggctc agcctggctg cctatcgtga gagggagcc 178020 cacggggctg tgggaggggg gccgtggtgc ctgtgagcag ggtgaggagc agcggcagga 178080
ggatgaaggt ggaacccaca catgcatctt tgagacccgt gtggtcagtg gcttctgccc 178140
cccaccaccc cccactgctg tgcgtgcata gaattggctt ccctcacctg ctctggaagt 178200
gggttaggag cttggtaggg cttttctca aggacaaggg cccctgattt gctctcaggc 178260
ctcagtcctg gcgacatggt ggatctggag ccttgttgca ctgccttgcc tgtgctctcc 178320
aatcagggtg gccagtgggg agccatttgg ctttttctcaa gagcatactc aggtggacct 178380
tgctccactg tttgaccaga tgaggcattc tgaacagcca agcctgtgct ggtctgtttt 178440
catgttgatt tttttttttc ttttctttt gagatggagt ttttcccttg tcacccaggc 178500
tggagtgcaa tggtgtgatc tcggctcact gcaacctccg cctcccgggt tcaagtgatt 178560
ctcctgcctc agcctcccta gtagctggga ttacaggcac acaccaccat gcccagctaa 178620
```

```
tttttgtgtt tttagtagag acggggtttc accgtgttgg ctgggctggt ctcgaactcc    178680
tgaactcaag tgatccaccc tccttggcct cccaaagtgc tgggattgca ggcgtgagcc    178740
actgcgcccg gcccccatgt cgatttttaa atgcacctct gcatcgttct tcagtcccca    178800
tatgctcact gagcaccact gcgactggca gacgggcaca gggaggcgcc acgaccagtc    178860
ctggccttca aggggcttgt ggtctagtgg gcccaatgct aggtggcgag tgctccaaag    178920
agtgtggtgc acgccttccg cttgaccgct ctccagacgc cacagggagg cacctcgcag    178980
ctgaccacag atttctctct gtggagcagt gtcttcagag cggctgccat gccactgctg    179040
ggcgagggtc tgcgggcggg tagagccagg agcacctgtg aggaagtgca ctgccatttt    179100
cgtagctgct tcccgtgtgt ctcagttaca cacggctggc atgtgtgcac tgatgagacg    179160
ggaacgtgat ggttgctttt cagcactgaa agggatactg ctcaggggc gtgtttcagg    179220 atctggttag ggaagaagca gcgagagcac agatggggcc ctgtgtggta acaagaaaaa    179280
agtcctggtt gacaacagtg ccacgaagcg ttagaacaca tagggatgtt tgtggagcat    179340
ttgcatgtgg aaagcagcaa aaacataatg ggaacgggtt cttttgttat gatttttaaa    179400
aatctctttt gtaacatcct tcccgctgcg ccgtttctgc atattccttt atgtagcttt    179460
caaactcctc ttaggagttc tggtccctac agggcgtggg agcccaggct ttacgtagct    179520
ttcaaactcc tcttaggagt tctggtccct acagggtgtg ggagcccagg cctgtgccg    179580 agcagcctgc ctccacgagc tagacagagg aagggctggg gttttgcctt tttagtctca    179640
aaattcgtac tccagttgct taggctctga cttttccccac ttggaaagtc cctcacggcc    179700
gagggtccct cccagccctg atttcacatc ggcattttcc ccagtattag agccaaggcc    179760
ctccgcgggc aggtggggca gctgtgggag ctggtgccag tctctgacct gcgtccctcc    179820
tcccaggatc aggaaaggct ttccttgtga agccagagtg gtggccagga tcctgcccca    179880
gtttctagac gacttcttcc cacccccagga catcatgaac aaagtcatcg gagagtttct    179940
gtccaaccag cagccatacc cccagttcat ggccaccgtg gtgtataagg tgaggttgca    180000
tgtgggatgg ggatggagtg ggaaagcctg gaggtggagt tgcctccgac ttcccagcag    180060
attcgccagc agagcccagc tcctccgctt taaagcagca atgcctctgg ccccccacccc    180120 acccccgcca cccaggcgca gcaggtgctt cccgtccccc cagccctgac actcaggcac    180180
ctgcttgctc cttgcaggtg tttcagactc tgcacagcac cgggcagtcg tccatggtcc    180240
gggactgggt catgctgtcc ctctccaact tcacgcagag ggccccggtc gccatggcca    180300
cgtggagcct ctcctgcttc tttgtcagcg cgtccaccag cccgtgggtc gcggcgatgt    180360
atcctctctg ggtccctggt gctggccccg tttcccttgt caacaccgag gctcatgttt    180420
catgataagg ttttgaaacc taacctttgc aaaaacccca cagatgccag ggtgacaggc    180480
cctcagcccc agggaagtaa aatgctgaca ggggtacaga aaggagcacg tccagacatt    180540
tgctgaccag ggcctctcag aggggccggt gtatggcagg agggtcgcag ctgagggcc    180600 tttctgtgga gggcctgggt gaggggagcg agggtgggcg gtggtctctg cagacgtccc    180660
gcccactcgc gggctctgtg tggctgggct tctcctgaca ctgcttctca ttagctttgg    180720
tcattgtgcc tcgatcgccc tctcggggaa aggcttaagt aaagatccag ttcccacccc    180780
cagatgctgg ctgccaggag tttccctttc cacagcccctt ccccaagaca gaccacaaga    180840
gcctccaagc agcacagttg tcctggtgct gacagcacag ccttgcccgg cgtgcctggc    180900
acggctctgc cctcactgca ttggagcagg gctagtggag gccagcggaa gcaccggcca    180960
```

```
ccagcgctgc acaggagcca ggccaggtga gtgctgccga gtgggtgccc tgcctgcagg   181020
gcatccagcc agccaagggt tgcaggaatg gaggtggagg cgctgatgca gctggaggca   181080
tccaggtggc ccttccgggg ctctgctcgc tctccaggct ccctggaccc ctttgtagac   181140
tgtttcagga gaggaactcc caggtgagga cagggaggca gcattcccct catttgccgg   181200
ccttttccct taactcctgc accagcctcc cacatgtcat cagcaggatg ggcaagctgg   181260
agcaggtgga cgtgaacctt ttctgcctgg tcgccacaga cttctacaga caccagatag   181320
aggaggagct cgaccgcagg gccttccagt ctgtgcttga ggtggttgca gccccaggaa   181380
gcccatatca ccggctgctg acttgtttac gaaatgtcca caaggtcacc acctgctgag   181440
cgccatggtg ggagagactg tgaggcggca gctggggccg gagcctttgg aagtctgcgc   181500
ccttgtgccc tgcctccacc gagccagctt ggtccctatg ggcttccgca catgccgcgg   181560
gcggccaggc aacgtgcgtg tctctgccat gtggcagaag tgctctttgt ggcagtggcc   181620
aggcagggag tgtctgcagt cctggtgggg ctgagcctga ggccttccag aaagcaggag   181680
cagctgtgct gcaccccatg tgggtgacca ggtcctttct cctgatagtc acctgctggt   181740
tgttgccagg ttgcagctgc tcttgcatct gggccagaag tcctccctcc tgcaggctgg   181800
ctgttggccc ctctgctgtc ctgcagtaga aggtgccgtg agcaggcttt gggaacactg   181860
gcctgggtct ccctggtggg gtgtgcatgc cacgccccgt gtctggatgc acagatgcca   181920
tggcctgtgc tgggccagtg gctggggtg ctagacaccc ggcaccattc tcccttctct   181980
cttttcttct caggatttaa aatttaatta tatcagtaaa gagattaatt ttaacgtaac   182040
tctttctatg cccgtgtaaa gtatgtgaat cgcaaggcct gtgctgcatg cgacagcgtc   182100
cggggtggtg acagggcccc ccggccacgc tccctctcct gtagccactg gcatagccct   182160
cctgagcacc cgctgacatt tccgttgtac atgttcctgt ttatgcattc acaaggtgac   182220
tgggatgtag agaggcgtta gtgggcaggt ggccacagca ggactgagga caggccccca   182280
ttatcctagg ggtgcgctca cctgcagccc ctcctcctcg ggcacagacg actgtcgttc   182340
tccacccacc agtcagggac agcagcctcc ctgtcactca gctgagaagg ccagccctcc   182400
ctggctgtga gcagcctcca ctgtgtccag agacatgggc ctcccactcc tgttccttgc   182460
tagccctggg gtggcgtctg cctaggagct ggctggcagg tgttgggacc tgctgctcca   182520
tggatgcatg ccctaagagt gtcactgagc tgtgttttgt ctgagcctct ctcggtcaac   182580
agcaaagctt ggtgtcttgg cactgttagt gacagagccc agcatccctt ctgcccccgt   182640
tccagctgac atcttgcacg gtgacccctt ttagtcagga gagtgcagat ctgtgctcat   182700
cggagactgc cccacggccc tgtcagagcc gccactccta tccccaggcc aggtccctgg   182760
accagcctcc tgtttgcagg cccagaggag ccaagtcatt aaaatggaag tggattctgg   182820
atggccgggc tgctgctgat gtaggagctg gatttgggag ctctgcttgc cgactggctg   182880
tgagacgagg caggggctct gcttcctcag ccctagaggc gagccaggca aggttggcga   182940
ctgtcatgtg gcttggtttg gtcatgcccg tcgatgtttt gggtattgaa tgtggtaagt   183000
ggaggaaatg ttggaactct gtgcaggtgc tgccttgaga cccccaagct tccacctgtc   183060
cctctcctat gtggcagctg gggagcagct gagatgtgga cttgtatgct gcccacatac   183120 gtgagggga gctgaaaggg agcccctcct ctgagcagcc tctgccaggc ctgtatgagg   183180
cttttcccac cagctcccaa cagaggcctc cccagccag gaccacctcg tcctcgtggc   183240
ggggcagcag gagcggtaga aaggggtccg atgtttgagg aggcccttaa gggaagctac   183300
tgaattataa cacgtaagaa aatcaccatt ccgtattggt tgggggctcc tgtttctcat   183360
```

```
cctagcttt  tcctggaaag  cccgctagaa  ggtttgggaa  cgaggggaaa  gttctcagaa    183420
ctgttggctg  ctccccaccc  gcctcccgcc  tccccccgcag  gttatgtcag  cagctctgag   183480
acagcagtat  cacaggccag  atgttgttcc  tggctagatg  tttacatttg  taagaaataa    183540
cactgtgaat  gtaaaacaga  gccattccct  tggaatgcat  atcgctgggc  tcaacataga    183600
gtttgtcttc  ctcttgttta  cgacgtgatc  taaaccagtc  cttagcaagg  ggctcagaac    183660
accccgctct  ggcagtaggt  gtcccccacc  cccaaagacc  tgcctgtgtg  ctccggagat    183720
gaatatgagc  tcattagtaa  aaatgacttc  acccacgcat  atacataaag  tatccatgca    183780
tgtgcatata  gacacatcta  taattttaca  cacacacctc  tcaagacgga  gatgcatggc    183840
ctctaagagt  gcccgtgtcg  gttcttcctg  gaagttgact  ttccttagac  ccgccaggtc    183900
aagttagccg  cgtgacggac  atccaggcgt  gggacgtggt  cagggcaggg  ctcattcatt    183960
gcccactagg  atcccactgg  cgaagatggt  ctccatatca  gctctctgca  gaagggagga    184020
agactttatc  atgttcctaa  aaatctgtgg  caagcaccca  tcgtattatc  caaattttgt    184080
tgcaaatgtg  attaatttgg  ttgtcaagtt  ttgggggtgg  gctgtgggga  gattgctttt    184140
gttttcctgc  tggtaatatc  gggaaagatt  ttaatgaaac  cagggtagaa  ttgtttggca    184200
atgcactgaa  gcgtgtttct  ttcccaaaat  gtgcctccct  tccgctgcgg  gcccagctga    184260
gtctatgtag  gtgatgtttc  cagctgccaa  gtgctctttg  ttactgtcca  ccctcatttc    184320
tgccagcgca  tgtgtccttt  caaggggaaa  atgtgaagct  gaaccccctc  cagacaccca    184380
gaatgtagca  tctgagaagg  ccctgtgccc  taaaggacac  ccctcgcccc  catcttcatg    184440
gagggggtca  tttcagagcc  ctcggagcca  atgaacagct  cctcctcttg  gagctgagat    184500
gagccccacg  tggagctcgg  gacggatagt  agacagcaat  aactcggtgt  gtggccgcct    184560
ggcaggtgga  acttcctccc  gttgcggggt  ggagtgaggt  tagttctgtg  tgtctggtgg    184620
gtggagtcag  gcttctcttg  ctacctgtga  gcatccttcc  cagcagacat  cctcatcggg    184680 cttttgtccct  ccccccgcttc  ctccctctgc  ggggaggacc  cgggaccaca  gctgctggcc   184740
agggtagact  tggagctgtc  ctccagaggg  gtcacgtgta  ggagtgagaa  gaaggaagat    184800
cttgagagct  gctgagggac  cttggagagc  tcaggatggc  tcagacgagg  acactcgctt    184860
gccgggcctg  ggcctcctgg  gaaggaggga  gctgctcaga  atgccgcatg  acaactgaag    184920
gcaacctgga  aggttcaggg  gccgctcttc  ccccatgtgc  ctgtcacgct  ctggtgcagt    184980
caaaggaacg  ccttcccctc  agttgtttct  aagagcagag  tctcccgctg  caatctgggt    185040
ggtaactgcc  agccttggag  gatcgtggcc  aacgtggacc  tgcctacgga  gggtgggctc    185100
tgacccaagt  ggggcctcct  tgtccaggtc  tcactgcttt  gcaccgtggt  cagagggact    185160
gtcagctgag  cttgagctcc  cctggagcca  gcagggctgt  gatgggcgag  tcccggagcc    185220
ccacccagac  ctgaatgctt  ctgagagcaa  agggaaggac  tgacgagaga  tgtatattta    185280
attttttaac  tgctgcaaac  attgtacatc  caaattaaag  gaaaaaaatg  gaaaccatca    185340
gttgttgctg  tgtgaggctt  gctttgcttc  atgagaacct  agaccttgct  gagctggagt    185400
cttaggaagc  agtctcctaa  gtgcttctcc  agcaggggca  gaaactgtcc  caccagctaa    185460
catctggcat  tatggagggt  ccccaggca  gctgccagca  gggacaggcc  ccgtgttttc    185520
tgtagccagg  gatgaggaag  tggccccagg  gcatgggcct  ggctgggtgc  ttctgcaagg    185580
gccttcccaa  accacagtac  aggtggtctt  cctgccctgc  agatgggagc  tgtgggagct    185640
gctggagctg  ctggagcctt  catggtcaag  tgacatcata  agcttatatg  acatacacaa    185700
```

```
gcctcaggac ttggcccatg gcactgaagc aggtcatcag gcccagcaca gagactagag   185760
ctgtgttctc acagggccca ccacccttcc acctccttgg ccattgacac ctgcgtccct   185820
ggcccagctg ctcccaggta accccccaaag cagctggcac atcccacctc tggtgtggcc   185880
ggggctgctg tgtgtccgca gggcctgccc cgtctattct agcttgtttg tcctgtctga   185940
accagcgcct actccaagaa gcctctgctc agcccagcgg ggatgcttct aagctccgga   186000
cgagcctctc ggaagccttg gtgattggtg gtgtagtcat cttgggatgc agatgtctta   186060
ccaacctgca agaacaaaaa ccctgtggct tcctctggtg cagggtattt agtcaatgtt   186120
tgctgaggtc ccgtctggtt ctggctaatt ggcaggggtc gtccacccat tctttccctg   186180
ctctgctgtc tgtgccagga gagacggggg ccagtcggcc aaggggccag ctcctgctgc   186240
ctgctcctct tgggcacgtg cggggggccc ctttctctga gcaggatag ggatcagtct   186300 gccggaggga tgtggtggac aggcctaaag catttggggc gggggcatgcc acttgagctc   186360 cctaaatctg tctcctcata ggtgacaccg ctccagggcc cccagtggc ctctcctttc   186420 agagctacct aaattctggt cacttcagag aaatggagca ccccccttctc cctggtccag   186480 gtgtggacag cctggcacac tgagcacacc tggcatggct ggtaatttca gaaagaagag   186540
gggccggggt ccagtgggaa gcagcggtga accctcgtg agtgggcttt gcagtccctc   186600
cccatgccac ggcagagctg ccctcaacac agccttcctc ttcctcatcg gagagcacac   186660
cctgtcccct tgccgagctg tgccctgtgc cttcggtggt atttgatttt ggctgctact   186720
ggctttgttg ggatctggaa gtcgcttccc ctgcgtggtg cgtggagcac tgtaagtcag   186780
atgagggaag tagccagggt gaggtgagta ccgggtggag ccgccactga agggactggg   186840
taggggggcc ttgcctctac atgatgtgac acagccaacc gaggacagag aagccccgt   186900 tcctgggggt gtgggggtgca ccccctcaggg aagcctgcag tggggcctga ggaaaggcat   186960
cctccgcgag cccacgagtc tggtccatga gcaccgtgac agtgtctgtg ggtagaggtg   187020
gacccggcct tgtgtcatca ccaggacctc ttttggaaa ccatgtggac atcgcttgcg   187080
ggtcccccag gctctgcagc cccagcagcc tggctgcctt ttgggcaagt ggcttgagcc   187140
acagaggacc cagtcctgtt gcagccacat cctctggggg ggcccgccag tgtggccggc   187200
tttctccacc ctacaccagg cctccaggtg tcctggtcgg gggtgtctgg gccctgggtg   187260
ggccctgtgg acctgtgagg tcagggtcag ggcatcactg gaggcagagg gctgaagttg   187320
tgggtctggg ttccccttgt gtgcacaggc ccctgccctc catgcttggt caggcagcta   187380
cccccaaaac tgctaggaca ggctggtcct gaggtggatc ctggcccctg taccctctgg   187440
acagcccacc cgcccaacct tctaccctgc cccagcggcg gcagtgttgg ccacatcctt   187500
cccctcctgg ccccaattgc tctggggaag tccaggctcc ggagcctgcc caggggcccc   187560
ccgtgatttg ggcccaggac tccacgtggt tctctgcctt cacccaagcc ctgaactcct   187620
cagctgccaa atccccaccc atctgcacag gctgtgctca ccactgctgc tcctggaagg   187680
tgcccctcag tgggacgccc acctcctctc tgggcttctg tgtttgggag ccctgctgcc   187740
cccacccttg gtcagtcccc atgtcctgct ggcctgtcag gcagggcaga aaatccaccc   187800
agaaatgctg agcaggatga gagtctagtt gggcccagcc tcattattta gaagggatgg   187860
aggcctaggg agcatgcttc tagcctgagc ccagcagggc cccgcccatg tcccaggtct   187920
gcaccaggga cagctcctgc cgaggcctga cctgcccctt ctccctcagg tgctgctggt   187980
tgaccagcct ctggccctag gagacccggt agcgactgag ggtcccagca ggccatgcag   188040 cttttgccaag gtacgagccc ctccccagca ggggacagat gtggggaccc tcccaggcag   188100
```

```
gagcagctgg gtgcctggtg ctgccatctg ctgcctgcct ggttcttgtc ctcacattgg    188160
aggtcagtgt gagggctctg cctcgggaaa ggccatggag cttgccctgt ccagggcctc    188220
ccatgtgcac tgagcctggg aagagagggt tggagttgag ccttttaccc tgggaatgct    188280
gcctggagga tggtgcgggt gtggggtggc accctgccag gcagggccct gcctcccgtc    188340
gcccactgga actcgggcag gcaggggtgt aggtgcctcc tctagagccg tccggtgggg    188400
gcccccggca gtggtggtgg tgtccactgg ccagcagctg cccctccagc caggacagta    188460
ggcctgacgc tgtccccagc agctccaagg tggatttgtg aaggggggta gagggcacgt    188520
agaggcccca tgacctcccc agggttctgg gagggctgtg cccccttagc cagcaccatg    188580
ctgggtgata tagtcagatc ctgttacccc tgttgtggag gtgaggaaac aggttagtgg    188640
ggaggacatg actaaggtcc atgctgagtc gctagagctg cacccagaac cactgctggg    188700
accccatgcc tttctgctta ccccttgtgc cgggagatgc caagagatgc tgggagccag    188760
ccccacctct gcccttggag tcatggctac ggaaagggca ttcggaccgg tccctgacct    188820
caccggggag ggccgaaccc tgttcctgag gagccagggc ttcctagagg aggtaggcct    188880
tctagtcact ccttcatctg caggcactcc acagagctct ctgtgccagc ccccagcacg    188940
gagggctgac cttagtcgag tggagatgcc ccagtgccag gcagtaggga tgatgtctcc    189000
tgaggcccag atggaaggga ctggactagt tcatgggcc tgatggtggg gccaggcctt    189060
gaccagggac ccagtgtagg gggtgcagag acccctctga gttcctcaca catccctggg    189120
gccctcccca tacacttcct atcctgactg cgggcaagag ggagcccag ttcgccttcc    189180 ctatgctggg cacccacagt ggggctgggc accccgcca tgccctgcc ctgtccttcc    189240 cctgagagcc tcgtcccac ctccaaggtg cctcagagga cagcaggggc agcgggcaga    189300
ggccgagatg cctcctcatt ccaggctcag ctgcccttct tggggcagcc cacacctgag    189360
agtctcctgc agttggtcag gcctgaggag ggcagggggg tgcctgctgt ccctctgctg    189420
accacagtgg catttagcct gggcaccgcg cccagcacag tccatgctgc acaggtgccg    189480
tgggctccac agagccctgc ctgacatgca tgtgttacgt ttcgggtgcc gatgcccttg    189540
ggcggcactt ctccgggcag aaccccagg ccaccgctcc ggttccggtt ccgctgcatc    189600
tggggctctc ggcaggctgt ggtcctccgg ccagcctggg ggcatctcag tccctcagcc    189660
ccacaggggc ctgccccgca gcctgggcct cgagccccgt ctccgcacgc tgtgccgaat    189720
ctggctgccc atcagctccc tgcgtaccca gactgtgccc tgccatgccc gtggctcttc    189780
ccaggagtgc cctgtggcct cccctggct tgctgggctg attccctcct gtgtctcaaa    189840
cagagctcac ctttgccatc actgctgtcc tcaccggccg gtgccagagg cccgtgtctg    189900
tgtaccctgt gtctgcacct ctgggcaggg cctggctctg accaacccgg gcttccagtg    189960
tccacagacc taaggcccag ggcgcctggg ggctggagca agagaagcaa aaggagccaa    190020
gggtgggggt ttggggttct tgtgagggcc cagcccagg accccaggac caggacaccc    190080
aggagcccca gggcccagcc ccagttcaga aggcaggggc cttctgaggg agcttaaggg    190140
tcccacagcc caggaccccc accagggcca gtggccagcg ttgggggact cagcctcctc    190200
gtcgctcgtc ctctctgttt ctcccacctt ttgcccccctt tctccttgcc tgttcccacc    190260
cgaggccccc tcttggcctg cgtgagccgg ggcggcactg aactgggggc cgatccgcct    190320
gggcggcggt gagaggcagg gccgggagcc gggccgctgg gtttgggcct ggcccgctcg    190380
ccgcaatatt gatggcccgt cagtgcagcc ctgattcctg tgctttcagt taaaaggttt    190440
```

```
ctgttgttgt agcttatgca gttgctctgt tgctatggaa acgtgacatc aaaatgacgt   190500
ttcccgttta aaagctttta actaaattcc tgcctgtcag atgtaggccc cattttgagc   190560
gtggagctgc cttcgagcga gcgtgagcgg cgcctcccgc ccatggtgcg tggggccggg   190620
ccggggccct cgctgagcgc gctctctcac cccacaggcg cctccggcat ggcggcggcc   190680 gagggggcccg gctacctcgt gtctccccag gcggagaagc accggcgggc ccgcaactgg   190740
acggacgccg agatgcgcgg cctcatgctg gtctgggagg agttcttcga cgagctcaag   190800
cagaccaagc gcaacgccaa ggtgtacgag aagatggcca gcaagctctt cgagatgacc   190860
ggcgagcgca ggctgggcga ggagatcaag atcaagatca ccaacatgac cttccagtac   190920
aggtgggcga gcgggcagtg tgggccccac caggacgggg gggcccgggc gtggcgggcc   190980
gctcctgact ttcttggagc tctgagtcgg acgatgtgt gggtcgtggc ctgcctgtcg   191040
gtctcctctg gccgggtatg ggcagaaccc cacgggtga cggggccc acggaaaccg   191100 tgtgtgcagc cttccattgg ggaagtgggg aaactgaggc ccagcaaggg caggaaacca   191160
gtctaagagc tgaggggtag cagggggtggg gctggtgctg gcagaggcc aggatggctc   191220 ccaggacgta tgggcggtct gggcactgtc cctcggaggc agcaacactc atggtggtgc   191280
ccactgacct cacaccctgc tcccccatag ggaggcggcg gctgccagtg ccctcccac   191340 caccaagctc ccaagctcag caggggtttc aggggcctac tgcgtcattg gggaaattga   191400
gactgcaagt gagaaggagg ctcagtgctc tgcgacttgg agcatccact gagcctctgc   191460
catgagccgg tgagccccac tggggctggc cctagggtca cggtggggta tttccagaaa   191520
tcaccaggtg aggtgcagga ccagccagcg catgggtggg gcttacggtg cgaagaagaa   191580
agaggtggag gcctgccctg cccaggact cccagcgtgg gggctcccgg cctggcccca   191640
cctctgctcc tgctacatgg caggtggggcc cttcctgccc tggcaacctg cagggaaggc   191700
cggaggggac cacccagcca gggagatgtt ggcgtctagg aggggacagg tgtggtccca   191760
cacacccagc atcttaaagt gcgtgggtcc ccagcccatt aggacagggt cccgggtggg   191820
caggggtcat ggtggggtga aggtctcagg cacaggcaag gtcacaggtg cggtgagggt   191880
cttgcagggt gtgaaggtca taggtgtgcg gtgaaggtca caggtgtggg gtgatggttt   191940
tgggtgtggg gagggtcttg cacggagcga gggtggcagc aagagctgga agctgcaggg   192000
ggagaatggc agcagagagc acccggccct gtgggcggcc tggacagggc tgggcctggg   192060
gctgccggag agcctgtcag cttccaggat gggagtggcc tcactcagct gctccacctc   192120
cgggtcaggc aggtgagcct ggggcagaga ggctgagagc acctgagcca cttgtgggag   192180
aggccacccc cactgccccc ctcaggcgag gagccggcct ccagcacagc agaagggaac   192240
ccccagtccc cagccctagt gggagtgggg aagaggccca gcaaggcccc ggacagaccg   192300
ccagcctgtg aggtctccgc tttcagttgc gttgatttga ttttttctga gccttgaagg   192360
aggggtccgg ggcctggccc tgcccaaagg cccctaggca ggcccaaagg ccggaccta   192420 gggtgctgag catgacggat gttgggtttg agcggctggc ttgcgacgtg agggctgagg   192480
tgtgagcctg ggtatcttca gaggttcggt ggacacaggc agctgcccgc ggccccactg   192540
ttcccgtggc ctcctagtcc tgctcaggca cctggtgagg aagggacgca gagggcagtg   192600
ggaggtggcc acgactgttc cagcaggctc ccctctgact caggaattca cgggcaccac   192660
ctccctggct ggctctggtt ggtgtctggc caggttattc attatttatg ctgaaagcct   192720
cttcagagtc ccaggggagg gttctctgtct ccattcctgg aggctgagag atgagggtgc   192780
agcagagtgg gggcctccac tccagaccct gcagtctggg ctggccaagg gctgcaccgg   192840
```

```
tgcactgcac gtcatggctg atgaagcact tccacaccgc agcccctcag agctgccaca   192900
gtcagcctta gttcaccgag ggggaagctg aggcccagag catgagaggg acttgcccag   192960
ggccacatag tccttagcag aggaagctgt ggctgggtga ctcgatcttt gtccttttc    193020 tttatacccg cagtctcccc atagcagagg ctttctttt tttttctttt ttcttttttt    193080 ttttttaca agaactcttt atatattaag gctgttgggc tgaagaagcc tgagagggtg    193140
gctggttctg tggagcatgg tttgttgaag tacagtttgg gggcctccta cactgagaat   193200
aggccttttc tcgtttctcc aaagagtggg ctggctcaag tagggcagag agagaagcct   193260
ggggcagagg ttagggatgg gcacccagcg cctgccctca cacgctctgt gctggtgtct   193320
tcacagccac gtgccaccct gggcagcatc ccctgctcac catctggctg tgcctgtttg   193380
ctgggggcac ctcattcaga atccagctta ttgtttccaa cggccaatgg ccacaccctg   193440
gcaggtagca agagtaggag agaggagaca cccactccga gcacaggttg ggtttggagc   193500
ccggccttgg ggcactctgt cactcaaagg cagagtgggg agtgggcact gggccttagg   193560
aggtactggg tccagtgagg cagagatgcc cctgccccac ccccaccttg tggcttcttc   193620
cctggcctgg ccagagctgt ctggccgcca tggggccctg tgtctcctgc cttgacctcc   193680
cagagggcag ccgaggccca ggggaggcct ggggacttag cctctcaggg caggacctgt   193740
ctgcaggagt aggtgggtgc tggggtccc agtggtaatg aggcatcagg cagtgtggga    193800
aggggcccat ccggcccacc ccagggcctc tgggcaggtt gcaggttgta gcgctggatc   193860
taggctcctg cccagactgt aggttcaacc aagaatggca tgggagccca gcctgctgtt   193920
tgctttatta aatctgccct gtagctgggg gagggcttta ctttgatcat cactatgtca   193980
ttgatataaa aatagaggct cagagaggtg aatgaacctg cccaaagtca cacagcaaag   194040
tgtggagatg agatactgac tcagggctgt ggacactgaa gcctgtgctc taacgccagt   194100
ggctgtcgct ccctgaggca ttctctcccg aacaacacag ttattatatt acaaaatatt   194160
atcactatat ttatatatct tataatacct tattattaca ataaaacctt attactctac   194220 cttttcaaaat gaattattta aaaagcagta tttgctcatt gcagagagtc tagaaactat   194280
agaaaagcaa gggaaaagca ataggaccag ccccaaggtc ccagcatgca cagataacct   194340
tagtaatact gggacgtgtg cttccttttt aacatctgag cccgtgtagg tcctgaagcc   194400
cagcttcttt ctaagtccat tgtcatcttg accctggagc ctggccgatt ttgctgggga   194460
ggcccttgcc agccgagagc ggctcctgcc tgtgccggcg tggcgcgccc ctctgctgag   194520
gctgggcagg acaggggctg ggccagctct gtttctcacc cttggctctt gtgtctctcg   194580
tttcaggaaa ttaaaatgca tgacagatag cgagtccgcc ccgcccgact ggccctatta   194640
cctagccatt gatgggattc tggccaaggt ccccgagtcc tgtgatggca aactgccgga   194700
cagccagccg ccggggccct ccacgtccca gaccgaggcg tccctgtcgc cgcccgctaa   194760
gtccacccct ctgtacttcc cgtataacca gtgctcctac gaaggccgct tcgaggatga   194820
tcgctccgac agctcctcca gcttactgtc ccttaagttc aggtagtgtg tctgcttgtc   194880
cttcccctgc cctggggtat ctcagccccc accatttaga gaaagggact gggagtggca   194940
aggccggcgc cggcggccac agtggttgca gaggccgtgg ctgcgggcag cgcctccagg   195000
gacaggcggc ctcagaccag ggagggcttt agtgtccaca ggcagaccga gtttgtctcc   195060
cagctccatc acttttgagc tgcacggaaa gttccttgac ttctctgcc tcagtctccc     195120 tcctataaaa tgggggtaaa tcagtacctt tctcagaggg tggctgggag catcacagga   195180
```

```
gagaagacgc agcatggggc ccggcacacg gagggagacc aagccccaga ccccagaatg    195240
cgccccctgg cctcccttag cccacacaga ccccaccctc acaggctagc tgccctctca    195300
gcactgggga gggtgtcggg ctgcacctca tcacgtgttg ccgtgggcat gacccgtccc    195360
ctctgccatc catcccacac ctcagacccg tcccgtgctg gccacgtgac tgtgcctgca    195420
agatgctcac agggcagccg ggagccaggc agcatgcagg acagacacct gcggggtggg    195480
cctggggagc ccagagaagg tgcttttgag gaggggacat ttggggtggg ctttcaaggt    195540
aaaatagaag ttggccattt ggaggcaaga acaggaagat tgtggatttg agtcacagct    195600
tctcccctgc cctggtcttc aagtctttct gacaggaggt gtcagaaaag tatctttagt    195660
agagaaggcg tctccgagga gggtccctct catgccgggg gccgctgctt gactcaggat    195720
ttctcattga agacctgaga caaaaacgct tttgctggca gctagaagga accagcagga    195780
ggcctgagat ttgtggctgt tgttcccgtg gactgagccc agttctcaga ctcagctgcc    195840
tggggccttg cacaggactg gggcgtgggg gctgccctcc ctgatcaggc ccaaagcgcg    195900
gatctcacgc ccctgaggtt ggctgtaccc tctcagctca gagcagagtg tgggccaggg    195960
atgagcaggc actggagcag ggccctgggg tctgtgggtt ttggcagctc cctgcccttc    196020
agggaggtct gctgagacca cggggtgggccc ctaccccagc agcagagctc tcaggaggcg    196080
cccacagggc tggactgcct ttactcacca cctctaccag agctctgagg tcctggggag    196140
agagcccagg cctcttgtgg gccccacacc ctctaggtgc ctgtccttct gcctctctac    196200
caaggtgtgc cggccccatt tctaggccgc cgggagataa gggggctcac atctcaggcc    196260
cttccttctg ggacctcagt ttccccatct gcctaaggcc gggtgggggct ggtggtcttg    196320 gcttccctac aggggtcctg agtactctgc actacccagc accccccacc cctgccttca    196380
tctctccctg ggggtggtct ctccacccct ggccccaac tggggctgag ccccccacctg    196440 cccagtttgg tgggtgaagg gtgctccctg gcaggatatg cccctctgca gcccagaaca    196500
tcccaccctt tccagaccga aggggtgtgg attgtcctgg gacccggtc attggggtca    196560 tccgctagtc gcaaaggacg gcaatgcctg tggcctctct ttctttcttt ttctttttttt    196620 tttttttttga gacggagtct cgctcttgtg cagagagcag tggcgcgatc ttggctcact    196680
gcaacctccg cctcgtgggt tcaagcgatt ctcctgcctc agcctcccga gtagctggga    196740
ttacaggcac ccgccacaac gcctggctaa ttttttgtatt tttagtagag atgggggttt    196800
accatgttgg ccaggctggt cttgaactcc tgacctcagg tgatccacct gcctctgcct    196860
cccaaagtgc tgggattaca ggcataagcc tccacacccg gccacccctg ttactttctg    196920
tcaaaggcgg tgggttctgg cccctccttt gcacatggaa tatgagaccc tgagtaagtg    196980
acctgactcc ctggggcctc agtttcccca tttgcccagt aggattgtcg ggagggtccg    197040
gtgaggcccc tggtgtgccc aggctctgtg gccagcacgt ccacagccgg cactgtcctt    197100
ccaggtcgga ggagcggccg gtgaagaagc gcaaggtgca gagctgccac ctgcagaaga    197160
agcagctgcg gctgctggag gccatggtgg aggagcagcc ccggctgagc cgcgccgtgg    197220
aggagacctg ccgcgaggtg cgccgcgtgc tggaccagca gcacatcctg caggtgcaga    197280
gcctgcagct gcaggagcgc atgatgagtc tgctggagag gatcatcacc aagtccagcg    197340
tctaggccag caggcggcgg cggcggcggg gccgggcggc tggtggtact gctcaggcca    197400
cccagggcag gccactcagg ccaggcgggc aaggggccg ccccgcgagc ggagaccgcg    197460
ttccacctgg cctctggcag gatgtccctt ctgaggggta ttttgaggaa cccccaggcc    197520
ctggggaccg tgaggctcca gtctccagca tgaatgccct tcctcggaca caggccaggg    197580
```

```
cctctggggt tcactccgag taagaacgtc ctagagccac tctccagtgt cgttactatc   197640
aatgatactt gacgtggctt tgatattaaa cgtatacttt ttcattcttg cctggaacgc   197700
acagtttgct gttgctggct tggtgaggat gccctgattg atggatcccg aaaatgaaag   197760
cagatggaaa cggttggggg caggctggag ctggggagc tctctcctga agggaaccct    197820
gtgtcctccc tcaccaggac ctctgcgtct ctccttaaat ggcctctgac gcctgatgaa   197880
aaccccagcg accttccagg aggcttttat tcagctctgt ttggagcatc aggtgtttcc   197940
actgcctcct tagcaatgac actaataaaa gtcgtaacac ctgttcacat gcacagccct   198000
gttgagtgtt ctgggtgctg gagatatcat ggtggatgac acaaaggccc tggcctcttg   198060
gagcttatgc tcccatgcgg ggaagacaca tgggtcagta gagaaatggt tgcaggttgt   198120
gataagtgct ggaagggagg ggttggcctg aggacacgga ggcagacata cgtggagctg   198180
ggaacagtgg ccacacaggg aacggccagt gcgaaggccc agaggcagag gacactggag   198240
caagcccagg agcagctagg aggctggtgg ccagcagcca ggccacggaa gcccgtgcag   198300
cccgtgggga ggagtgttca tgcttttcaa gcttagtggg agtcttttgg ccagtgcagc   198360
tctgggtctg acatcggtgg gggacagagg ggtggtggag cggccacagc tgcaagctca   198420
cctcactgcc ggcccttcca ccagtttcaa actctttcta gaagctccag ctttcccaaa   198480
gctgaattct ctatgagcct ccttggccgg gactcgggcg tctggttgcc ctggctgcaa   198540
aggaggctgg ggccaggtgt gttttgagtca cctcctggaa ttaggcaagt tgctgcccaa   198600
atagaaggtt gttggcaggt gggtcagcag gtgaacagca tggtttgact cagggttcag   198660
aaaaatctcc ctctggctgc caagcgagca ggccgtggag acaggtgcag aggcaggtgt   198720
ggcagcaggc atcctgccag gcagtgctgc agtcatcctg cgacaagcag cagcagctca   198780
tcctacccte taggggtct tgaggtcagc caggcaagag agcagcttgg actccactgg    198840
gtgtgggacc agcctgtgga ccatggtggt gtggagggtg ccctcggcct gcctgtgtga   198900
aggagaggcc ggcgtgttct gtggagccca aaggggagct gggcaagcag gattcacttc   198960
actctgaggg tcctggagct cccaccctcc tcagccatct ccccagagcc tgtgtgccga   199020
ggactcggcc catgttgctg tgggatgaga ggcagagtgt cgtgagggtg taaggagcgg   199080
cggcagtggt gggaggaggg agcagcagcc agcgctacgg tgccagtttc cagctgccag   199140
atgacgccgc tgaccctgtg gttgagaaga gatgcacaga gccagctctt gcaagccagt   199200
gtggctgcca tagcacctgc cgagaagcag aaggaagggt ggcccagga ggacagagga    199260
tgcgggcaca tctgatgcgg gcctgagttt tgggagcttt tgctctagcc agtttccagc   199320
tccgggaccc acccgcctcg taggcaagac accacccaag aaatcatttg cttaacaaac   199380
acactgggct ccaactggac acctgtgcca ccctagatgc tgggaaccca gccatgcaca   199440
aggcacctgc ccccagctgc tgaccactga ggctggctag cagctcccat ggggccagtg   199500
tggggttccc cagcctccta acagggagcc agtcacaagc cctcgagagg gaagggtgcc   199560
cgcggccctg gcaggaaggt taggctggac gctcccacaa gacataacag atggaggttc   199620
taaatgatgt agcaacttct tcaccctgaa actgctgtag agtcagccat gacgcaccgg   199680
tacttcagta actgccaggc atccgggaca gcacaccgcg agtcgctgct gtgcttggt    199740
tagaagtggt ttggtctgtt ttcttctcgc cctctctaat cagagtcagt gattcatgcc   199800
cttccatcac cttagagaag gggcaggcgc tgcccgacct tctccaggct ggagcagcat   199860
cgcctcatgt cagcagaact cagctgtaga atatcgtggg gttggtgcct ttcatcagca   199920
```

```
gcatgtcctt aacaactttc tgatttcttc cttagttgtt ggtccattaa ggagaaaaaa    199980
aatgatctca gccattgcta aaatatttga taagattcag caaagcagca tgttaacatt    200040
gaaaactaga atcaggagcc aggcagatgt gcttgctttt cacctgtagt atttcatgtt    200100
gttttgacgt ttttagctaa tgcattaaga taaataaaca aaagccgggc acggtggttc    200160
acgcctgtaa tcccagcact ttgggaggct gaggcgggag gatcctctga ggtcaggagt    200220
tcaagaccag cctgaccaac atggagaaac ctcgtcatta ctaaaaatac aaaattagct    200280
gggcgtggtg gtgcatgcct gtaatcccag ctacttggga ggctgaggca ggagaatcgc    200340
ttgaacccgg gaggcggagg ttgcagtgag ctgagattgc accactgcac tccagcctgg    200400
gtgacagtga aactcggtct caaaaaaaaa aaaaaattaa aaaagataa ataaaataag     200460 caggataaga aatgaagaaa gtagagttac ctttgttttc agatttcatt tttgtatacc    200520
cagaaagcca aatgtacaaa agactgggag ctctttaaac cagcttaaac ttgttgaaaa    200580
tgaggatgaa gaaatatccc attcagagtt ggaatgaatt taacccagaa ggaacaggac    200640
ctctactgaa gagaactatg cagtcttact gaaaaatcta aataatacct gagcgctgga    200700
gaaacttcgc acactcctga aagctccaaa gtcaatgtca tcatttttatt aatgtcattc    200760 caaacatagt ctcaataata tcacttcttg gttttgacat ggacgcgatg atgtttaaat    200820
tcatatgaaa aaagaacggg gccaaaagtc caaggccagt cagcgtgaga agaccgctcg    200880
gcctccctcg gagtcgggga gttggaaccg cagactgaga tcatgtggct gctgaggcc    200940 aggacgaacg tcgggaaatg gagactcctg cgttgctggt gggatgtggt gcagccgctt    201000
ccaggagcaa tttggtgtcc cgtcctaaag ctgaagaaac gcatttcctc tggtcagtgc    201060
cactcctaga caggccaccc tgcggcagcc gtcctcaaac tggtctgagg accctcaac    201120 gctcttaaaa atcattaaaa gtgggccagg tgcggtggct cacacctgta atcccagcac    201180
tttgggaggc caagacaggc ggatcacgag gtcaggacat tgagatcatc ctggctaaca    201240
cggtgaaacc ccgtctctac taaaaataca aaaaattagc cgggcgtggt ggcgggcgcc    201300
tgtagtccca gctacttggg aggctgagcc aggagaatgg cgtgaaccca ggaggtggag    201360
cttgcagtga gctgagatca ctccactgca ctccagcctg ggcagcagag cgagactctg    201420
tctcaaaaaa aaataataaa taaataaata aaaataaaat aaaataaaat tcattaaaag    201480
tgccaaagaa cttttgctta tgtgagttct aatgaccaat attaatacac attagaatat    201540
cttattagaa attaaacctg agacctttag aaaacatgta ttcatttcaa aatagcaata    201600
aacccatgac atattaacat aaataacaat tgtatgaaaa atatattttc caaaacaaaa    201660
agttttcggg agaagtgtgg catagttta catggtcgta aatctctggc ttaagagaag    201720
cccactggcc tctcagcagg ctctgggtcc gtccactttg ggggtgtttt ggttgtgaag    201780
tataggagtg aatggagaag ctcattctta cccagatgtg tatttgaaaa gaaaaggaac    201840 atttaataa cctttgcaaa taatcggtat attcttccgt gatcctattc caacactgga    201900
caggtggtgg tttgttttt tttttggag acggagtccc gctctgtcac tcaggctgga    201960
gtgcagtggc gcgatttcag ctcactgcaa gctccgcctc c                      202001
```

<210> SEQ ID NO 9
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 9

-continued

```
ataaattgtc atcacca                                                    17

<210> SEQ ID NO 10
<211> LENGTH: 13481
<212> TYPE: DNA
<213> ORGANISM: Homo sapiens
<220> FEATURE:
<221> NAME/KEY: CDS
<222> LOCATION: (146)..(9580)

<400> SEQUENCE: 10
gctgccggga cgggtccaag atggacggcc gctcaggttc tgcttttacc tgcggcccag     60
agccccattc attgccccgg tgctgagcgg cgccgcgagt cggcccgagg cctccgggga   120
ctgccgtgcc gggcgggaga ccgcc atg gcg acc ctg gaa aag ctg atg aag    172
                              Met Ala Thr Leu Glu Lys Leu Met Lys
                                1               5 gcc ttc gag tcc ctc aag tcc ttc cag cag cag cag cag cag cag cag    220
Ala Phe Glu Ser Leu Lys Ser Phe Gln Gln Gln Gln Gln Gln Gln Gln
 10              15                  20                  25 cag cag cag cag cag cag cag cag cag cag cag cag caa cag ccg        268
Gln Gln Gln Gln Gln Gln Gln Gln Gln Gln Gln Gln Gln Gln Pro
             30                  35                  40 cca ccg ccg ccg ccg ccg ccg ccg cct cct cag ctt cct cag ccg ccg    316
Pro Pro Pro Pro Pro Pro Pro Pro Pro Pro Gln Leu Pro Gln Pro Pro
                 45                  50                  55 ccg cag gca cag ccg ctg ctg cct cag ccg cag ccg ccc ccg ccg ccg    364
Pro Gln Ala Gln Pro Leu Leu Pro Gln Pro Gln Pro Pro Pro Pro Pro
             60                  65                  70 ccc ccg ccg cca ccc ggc ccg gct gtg gct gag gag ccg ctg cac cga    412
Pro Pro Pro Pro Pro Gly Pro Ala Val Ala Glu Glu Pro Leu His Arg
 75                  80                  85 cca aag aaa gaa ctt tca gct acc aag aaa gac cgt gtg aat cat tgt    460
Pro Lys Lys Glu Leu Ser Ala Thr Lys Lys Asp Arg Val Asn His Cys
 90                  95                 100                 105 ctg aca ata tgt gaa aac ata gtg gca cag tct gtc aga aat tct cca    508
Leu Thr Ile Cys Glu Asn Ile Val Ala Gln Ser Val Arg Asn Ser Pro
                110                 115                 120 gaa ttt cag aaa ctt ctg ggc atc gct atg gaa ctt ttt ctg ctg tgc    556
Glu Phe Gln Lys Leu Leu Gly Ile Ala Met Glu Leu Phe Leu Leu Cys
            125                 130                 135 agt gat gac gca gag tca gat gtc agg atg gtg gct gac gaa tgc ctc    604
Ser Asp Asp Ala Glu Ser Asp Val Arg Met Val Ala Asp Glu Cys Leu
        140                 145                 150 aac aaa gtt atc aaa gct ttg atg gat tct aat ctt cca agg tta cag    652
Asn Lys Val Ile Lys Ala Leu Met Asp Ser Asn Leu Pro Arg Leu Gln
    155                 160                 165 ctc gag ctc tat aag gaa att aaa aag aat ggt gcc cct cgg agt ttg    700
Leu Glu Leu Tyr Lys Glu Ile Lys Lys Asn Gly Ala Pro Arg Ser Leu
170                 175                 180                 185 cgt gct gcc ctg tgg agg ttt gct gag ctg gct cac ctg gtt cgg cct    748
Arg Ala Ala Leu Trp Arg Phe Ala Glu Leu Ala His Leu Val Arg Pro
                190                 195                 200 cag aaa tgc agg cct tac ctg gtg aac ctt ctg ccg tgc ctg act cga    796
Gln Lys Cys Arg Pro Tyr Leu Val Asn Leu Leu Pro Cys Leu Thr Arg
            205                 210                 215 aca agc aag aga ccc gaa gaa tca gtc cag gag acc ttg gct gca gct    844
Thr Ser Lys Arg Pro Glu Glu Ser Val Gln Glu Thr Leu Ala Ala Ala
        220                 225                 230 gtt ccc aaa att atg gct tct ttt ggc aat ttt gca aat gac aat gaa    892
```

```
Val Pro Lys Ile Met Ala Ser Phe Gly Asn Phe Ala Asn Asp Asn Glu
    235                 240                 245 att aag gtt ttg tta aag gcc ttc ata gcg aac ctg aag tca agc tcc       940
Ile Lys Val Leu Leu Lys Ala Phe Ile Ala Asn Leu Lys Ser Ser Ser
250                 255                 260                 265 ccc acc att cgg cgg aca gcg gct gga tca gca gtg agc atc tgc cag       988
Pro Thr Ile Arg Arg Thr Ala Ala Gly Ser Ala Val Ser Ile Cys Gln
                    270                 275                 280 cac tca aga agg aca caa tat ttc tat agt tgg cta cta aat gtg ctc      1036
His Ser Arg Arg Thr Gln Tyr Phe Tyr Ser Trp Leu Leu Asn Val Leu
            285                 290                 295 tta ggc tta ctc gtt cct gtc gag gat gaa cac tcc act ctg ctg att      1084
Leu Gly Leu Leu Val Pro Val Glu Asp Glu His Ser Thr Leu Leu Ile
        300                 305                 310 ctt ggc gtg ctg ctc acc ctg agg tat ttg gtg ccc ttg ctg cag cag      1132
Leu Gly Val Leu Leu Thr Leu Arg Tyr Leu Val Pro Leu Leu Gln Gln
    315                 320                 325 cag gtc aag gac aca agc ctg aaa ggc agc ttc gga gtg aca agg aaa      1180
Gln Val Lys Asp Thr Ser Leu Lys Gly Ser Phe Gly Val Thr Arg Lys
330                 335                 340                 345 gaa atg gaa gtc tct cct tct gca gag cag ctt gtc cag gtt tat gaa      1228
Glu Met Glu Val Ser Pro Ser Ala Glu Gln Leu Val Gln Val Tyr Glu
                    350                 355                 360 ctg acg tta cat cat aca cag cac caa gac cac aat gtt gtg acc gga      1276
Leu Thr Leu His His Thr Gln His Gln Asp His Asn Val Val Thr Gly
            365                 370                 375 gcc ctg gag ctg ttg cag cag ctc ttc aga acg cct cca ccc gag ctt      1324
Ala Leu Glu Leu Leu Gln Gln Leu Phe Arg Thr Pro Pro Pro Glu Leu
        380                 385                 390 ctg caa acc ctg acc gca gtc ggg ggc att ggg cag ctc acc gct gct      1372
Leu Gln Thr Leu Thr Ala Val Gly Gly Ile Gly Gln Leu Thr Ala Ala
    395                 400                 405 aag gag gag tct ggt ggc cga agc cgt agt ggg agt att gtg gaa ctt      1420
Lys Glu Glu Ser Gly Gly Arg Ser Arg Ser Gly Ser Ile Val Glu Leu
410                 415                 420                 425 ata gct gga ggg ggt tcc tca tgc agc cct gtc ctt tca aga aaa caa      1468
Ile Ala Gly Gly Gly Ser Ser Cys Ser Pro Val Leu Ser Arg Lys Gln
                    430                 435                 440 aaa ggc aaa gtg ctc tta gga gaa gaa gaa gcc ttg gag gat gac tct      1516
Lys Gly Lys Val Leu Leu Gly Glu Glu Glu Ala Leu Glu Asp Asp Ser
            445                 450                 455 gaa tcg aga tcg gat gtc agc agc tct gcc tta aca gcc tca gtg aag      1564
Glu Ser Arg Ser Asp Val Ser Ser Ser Ala Leu Thr Ala Ser Val Lys
        460                 465                 470 gat gag atc agt gga gag ctg gct gct tct tca ggg gtt tcc act cca      1612
Asp Glu Ile Ser Gly Glu Leu Ala Ala Ser Ser Gly Val Ser Thr Pro
475                 480                 485 ggg tca gca ggt cat gac atc atc aca gaa cag cca cgg tca cag cac      1660
Gly Ser Ala Gly His Asp Ile Ile Thr Glu Gln Pro Arg Ser Gln His
490                 495                 500                 505 aca ctg cag gcg gac tca gtg gat ctg gcc agc tgt gac ttg aca agc      1708
Thr Leu Gln Ala Asp Ser Val Asp Leu Ala Ser Cys Asp Leu Thr Ser
                    510                 515                 520 tct gcc act gat ggg gat gag gag gat atc ttg agc cac agc tcc agc      1756
Ser Ala Thr Asp Gly Asp Glu Glu Asp Ile Leu Ser His Ser Ser Ser
            525                 530                 535 cag gtc agc gcc gtc cca tct gac cct gcc atg gac ctg aat gat ggg      1804
Gln Val Ser Ala Val Pro Ser Asp Pro Ala Met Asp Leu Asn Asp Gly
        540                 545                 550
```

| | | | | | | | | | | | | | | |
|---|---|---|---|---|---|---|---|---|---|---|---|---|---|---|
| acc | cag | gcc | tcg | tcg | ccc | atc | agc | gac | agc | tcc | cag | acc | acc | acc | gaa | 1852
| Thr | Gln | Ala | Ser | Ser | Pro | Ile | Ser | Asp | Ser | Ser | Gln | Thr | Thr | Thr | Glu |
| 555 | | | | 560 | | | | | 565 | | | | | | ggg cct gat tca gct gtt acc cct tca gac agt tct gaa att gtg tta  1900
Gly Pro Asp Ser Ala Val Thr Pro Ser Asp Ser Ser Glu Ile Val Leu
570             575                 580                 585 gac ggt acc gac aac cag tat ttg ggc ctg cag att gga cag ccc cag  1948
Asp Gly Thr Asp Asn Gln Tyr Leu Gly Leu Gln Ile Gly Gln Pro Gln
                590                 595                 600 gat gaa gat gag gaa gcc aca ggt att ctt cct gat gaa gcc tcg gag  1996
Asp Glu Asp Glu Glu Ala Thr Gly Ile Leu Pro Asp Glu Ala Ser Glu
            605                 610                 615 gcc ttc agg aac tct tcc atg gcc ctt caa cag gca cat tta ttg aaa  2044
Ala Phe Arg Asn Ser Ser Met Ala Leu Gln Gln Ala His Leu Leu Lys
        620                 625                 630 aac atg agt cac tgc agg cag cct tct gac agc agt gtt gat aaa ttt  2092
Asn Met Ser His Cys Arg Gln Pro Ser Asp Ser Ser Val Asp Lys Phe
    635                 640                 645 gtg ttg aga gat gaa gct act gaa ccg ggt gat caa gaa aac aag cct  2140
Val Leu Arg Asp Glu Ala Thr Glu Pro Gly Asp Gln Glu Asn Lys Pro
650                 655                 660                 665 tgc cgc atc aaa ggt gac att gga cag tcc act gat gat gac tct gca  2188
Cys Arg Ile Lys Gly Asp Ile Gly Gln Ser Thr Asp Asp Asp Ser Ala
                670                 675                 680 cct ctt gtc cat tgt gtc cgc ctt tta tct gct tcg ttt ttg cta aca  2236
Pro Leu Val His Cys Val Arg Leu Leu Ser Ala Ser Phe Leu Leu Thr
            685                 690                 695 ggg gga aaa aat gtg ctg gtt ccg gac agg gat gtg agg gtc agc gtg  2284
Gly Gly Lys Asn Val Leu Val Pro Asp Arg Asp Val Arg Val Ser Val
        700                 705                 710 aag gcc ctg gcc ctc agc tgt gtg gga gca gct gtg gcc ctc cac ccg  2332
Lys Ala Leu Ala Leu Ser Cys Val Gly Ala Ala Val Ala Leu His Pro
    715                 720                 725 gaa tct ttc ttc agc aaa ctc tat aaa gtt cct ctt gac acc acg gaa  2380
Glu Ser Phe Phe Ser Lys Leu Tyr Lys Val Pro Leu Asp Thr Thr Glu
730                 735                 740                 745 tac cct gag gaa cag tat gtc tca gac atc ttg aac tac atc gat cat  2428
Tyr Pro Glu Glu Gln Tyr Val Ser Asp Ile Leu Asn Tyr Ile Asp His
                750                 755                 760 gga gac cca cag gtt cga gga gcc act gcc att ctc tgt ggg acc ctc  2476
Gly Asp Pro Gln Val Arg Gly Ala Thr Ala Ile Leu Cys Gly Thr Leu
            765                 770                 775 atc tgc tcc atc ctc agc agg tcc cgc ttc cac gtg gga gat tgg atg  2524
Ile Cys Ser Ile Leu Ser Arg Ser Arg Phe His Val Gly Asp Trp Met
        780                 785                 790 ggc acc att aga acc ctc aca gga aat aca ttt tct ttg gcg gat tgc  2572
Gly Thr Ile Arg Thr Leu Thr Gly Asn Thr Phe Ser Leu Ala Asp Cys
    795                 800                 805 att cct ttg ctg cgg aaa aca ctg aag gat gag tct tct gtt act tgc  2620
Ile Pro Leu Leu Arg Lys Thr Leu Lys Asp Glu Ser Ser Val Thr Cys
810                 815                 820                 825 aag tta gct tgt aca gct gtg agg aac tgt gtc atg agt ctc tgc agc  2668
Lys Leu Ala Cys Thr Ala Val Arg Asn Cys Val Met Ser Leu Cys Ser
                830                 835                 840 agc agc tac agt gag tta gga ctg cag ctg atc atc gat gtg ctg act  2716
Ser Ser Tyr Ser Glu Leu Gly Leu Gln Leu Ile Ile Asp Val Leu Thr
            845                 850                 855 ctg agg aac agt tcc tat tgg ctg gtg agg aca gag ctt ctg gaa acc  2764
Leu Arg Asn Ser Ser Tyr Trp Leu Val Arg Thr Glu Leu Leu Glu Thr
        860                 865                 870

| | |
|---|---|
| ctt gca gag att gac ttc agg ctg gtg agc ttt ttg gag gca aaa gca<br>Leu Ala Glu Ile Asp Phe Arg Leu Val Ser Phe Leu Glu Ala Lys Ala<br>875                   880                   885 | 2812 |
| gaa aac tta cac aga ggg gct cat cat tat aca ggg ctt tta aaa ctg<br>Glu Asn Leu His Arg Gly Ala His His Tyr Thr Gly Leu Leu Lys Leu<br>890                   895                   900                   905 | 2860 |
| caa gaa cga gtg ctc aat aat gtt gtc atc cat ttg ctt gga gat gaa<br>Gln Glu Arg Val Leu Asn Asn Val Val Ile His Leu Leu Gly Asp Glu<br>910                   915                   920 | 2908 |
| gac ccc agg gtg cga cat gtt gcc gca gca tca cta att agg ctt gtc<br>Asp Pro Arg Val Arg His Val Ala Ala Ala Ser Leu Ile Arg Leu Val<br>925                   930                   935 | 2956 |
| cca aag ctg ttt tat aaa tgt gac caa gga caa gct gat cca gta gtg<br>Pro Lys Leu Phe Tyr Lys Cys Asp Gln Gly Gln Ala Asp Pro Val Val<br>940                   945                   950 | 3004 |
| gcc gtg gca aga gat caa agc agt gtt tac ctg aaa ctt ctc atg cat<br>Ala Val Ala Arg Asp Gln Ser Ser Val Tyr Leu Lys Leu Leu Met His<br>955                   960                   965 | 3052 |
| gag acg cag cct cca tct cat ttc tcc gtc agc aca ata acc aga ata<br>Glu Thr Gln Pro Pro Ser His Phe Ser Val Ser Thr Ile Thr Arg Ile<br>970                   975                   980                   985 | 3100 |
| tat aga ggc tat aac cta cta cca agc ata aca gac gtc act atg  gaa<br>Tyr Arg Gly Tyr Asn Leu Leu Pro Ser Ile Thr Asp Val Thr Met  Glu<br>990                   995                   1000 | 3148 |
| aat aac ctt tca  aga gtt att gca gca  gtt tct cat gaa cta  atc<br>Asn Asn Leu Ser  Arg Val Ile Ala Ala  Val Ser His Glu Leu  Ile<br>             1005                   1010                   1015 | 3193 |
| aca tca acc acc  aga gca ctc aca ttt  gga tgc tgt gaa gct  ttg<br>Thr Ser Thr Thr  Arg Ala Leu Thr Phe  Gly Cys Cys Glu Ala  Leu<br>             1020                   1025                   1030 | 3238 |
| tgt ctt ctt tcc  act gcc ttc cca gtt  tgc att tgg agt tta  ggt<br>Cys Leu Leu Ser  Thr Ala Phe Pro Val  Cys Ile Trp Ser Leu  Gly<br>             1035                   1040                   1045 | 3283 |
| tgg cac tgt gga  gtg cct cca ctg agt  gcc tca gat gag tct  agg<br>Trp His Cys Gly  Val Pro Pro Leu Ser  Ala Ser Asp Glu Ser  Arg<br>             1050                   1055                   1060 | 3328 |
| aag agc tgt acc  gtt ggg atg gcc aca  atg att ctg acc ctg  ctc<br>Lys Ser Cys Thr  Val Gly Met Ala Thr  Met Ile Leu Thr Leu  Leu<br>             1065                   1070                   1075 | 3373 |
| tcg tca gct tgg  ttc cca ttg gat ctc  tca gcc cat caa gat  gct<br>Ser Ser Ala Trp  Phe Pro Leu Asp Leu  Ser Ala His Gln Asp  Ala<br>             1080                   1085                   1090 | 3418 |
| ttg att ttg gcc  gga aac ttg ctt gca  gcc agt gct ccc aaa  tct<br>Leu Ile Leu Ala  Gly Asn Leu Leu Ala  Ala Ser Ala Pro Lys  Ser<br>             1095                   1100                   1105 | 3463 |
| ctg aga agt tca  tgg gcc tct gaa gaa  gaa gcc aac cca gca  gcc<br>Leu Arg Ser Ser  Trp Ala Ser Glu Glu  Glu Ala Asn Pro Ala  Ala<br>             1110                   1115                   1120 | 3508 |
| acc aag caa gag  gag gtc tgg cca gcc  ctg ggg gac cgg gcc  ctg<br>Thr Lys Gln Glu  Glu Val Trp Pro Ala  Leu Gly Asp Arg Ala  Leu<br>             1125                   1130                   1135 | 3553 |
| gtg ccc atg gtg  gag cag ctc ttc tct  cac ctg ctg aag gtg  att<br>Val Pro Met Val  Glu Gln Leu Phe Ser  His Leu Leu Lys Val  Ile<br>             1140                   1145                   1150 | 3598 |
| aac att tgt gcc  cac gtc ctg gat gac  gtg gct cct gga ccc  gca<br>Asn Ile Cys Ala  His Val Leu Asp Asp  Val Ala Pro Gly Pro  Ala<br>             1155                   1160                   1165 | 3643 |
| ata aag gca gcc  ttg cct tct cta aca  aac ccc cct tct cta  agt<br>Ile Lys Ala Ala  Leu Pro Ser Leu Thr  Asn Pro Pro Ser Leu  Ser | 3688 |

```
                1170              1175              1180
ccc atc cga cga aag ggg aag gag aaa gaa cca gga gaa caa gca    3733
Pro Ile Arg Arg Lys Gly Lys Glu Lys Glu Pro Gly Glu Gln Ala
            1185              1190              1195 tct gta ccg ttg agt ccc aag aaa ggc agt gag gcc agt gca gct    3778
Ser Val Pro Leu Ser Pro Lys Lys Gly Ser Glu Ala Ser Ala Ala
        1200              1205              1210 tct aga caa tct gat acc tca ggt cct gtt aca aca agt aaa tcc    3823
Ser Arg Gln Ser Asp Thr Ser Gly Pro Val Thr Thr Ser Lys Ser
    1215              1220              1225 tca tca ctg ggg agt ttc tat cat ctt cct tca tac ctc aaa ctg    3868
Ser Ser Leu Gly Ser Phe Tyr His Leu Pro Ser Tyr Leu Lys Leu
1230              1235              1240 cat gat gtc ctg aaa gct aca cac gct aac tac aag gtc acg ctg    3913
His Asp Val Leu Lys Ala Thr His Ala Asn Tyr Lys Val Thr Leu
            1245              1250              1255 gat ctt cag aac agc acg gaa aag ttt gga ggg ttt ctc cgc tca    3958
Asp Leu Gln Asn Ser Thr Glu Lys Phe Gly Gly Phe Leu Arg Ser
        1260              1265              1270 gcc ttg gat gtt ctt tct cag ata cta gag ctg gcc aca ctg cag    4003
Ala Leu Asp Val Leu Ser Gln Ile Leu Glu Leu Ala Thr Leu Gln
    1275              1280              1285 gac att ggg aag tgt gtt gaa gag atc cta gga tac ctg aaa tcc    4048
Asp Ile Gly Lys Cys Val Glu Glu Ile Leu Gly Tyr Leu Lys Ser
1290              1295              1300 tgc ttt agt cga gaa cca atg atg gca act gtt tgt gtt caa caa    4093
Cys Phe Ser Arg Glu Pro Met Met Ala Thr Val Cys Val Gln Gln
            1305              1310              1315 ttg ttg aag act ctc ttt ggc aca aac ttg gcc tcc cag ttt gat    4138
Leu Leu Lys Thr Leu Phe Gly Thr Asn Leu Ala Ser Gln Phe Asp
        1320              1325              1330 ggc tta tct tcc aac ccc agc aag tca caa ggc cga gca cag cgc    4183
Gly Leu Ser Ser Asn Pro Ser Lys Ser Gln Gly Arg Ala Gln Arg
    1335              1340              1345 ctt ggc tcc tcc agt gtg agg cca ggc ttg tac cac tac tgc ttc    4228
Leu Gly Ser Ser Ser Val Arg Pro Gly Leu Tyr His Tyr Cys Phe
1350              1355              1360 atg gcc ccg tac acc cac ttc acc cag gcc ctc gct gac gcc agc    4273
Met Ala Pro Tyr Thr His Phe Thr Gln Ala Leu Ala Asp Ala Ser
            1365              1370              1375 ctg agg aac atg gtg cag gcg gag cag gag aac gac acc tcg gga    4318
Leu Arg Asn Met Val Gln Ala Glu Gln Glu Asn Asp Thr Ser Gly
        1380              1385              1390 tgg ttt gat gtc ctc cag aaa gtg tct acc cag ttg aag aca aac    4363
Trp Phe Asp Val Leu Gln Lys Val Ser Thr Gln Leu Lys Thr Asn
    1395              1400              1405 ctc acg agt gtc aca aag aac cgt gca gat aag aat gct att cat    4408
Leu Thr Ser Val Thr Lys Asn Arg Ala Asp Lys Asn Ala Ile His
1410              1415              1420 aat cac att cgt ttg ttt gaa cct ctt gtt ata aaa gct tta aaa    4453
Asn His Ile Arg Leu Phe Glu Pro Leu Val Ile Lys Ala Leu Lys
            1425              1430              1435 cag tac acg act aca aca tgt gtg cag tta cag aag cag gtt tta    4498
Gln Tyr Thr Thr Thr Thr Cys Val Gln Leu Gln Lys Gln Val Leu
        1440              1445              1450 gat ttg ctg gcg cag ctg gtt cag tta cgg gtt aat tac tgt ctt    4543
Asp Leu Leu Ala Gln Leu Val Gln Leu Arg Val Asn Tyr Cys Leu
    1455              1460              1465 ctg gat tca gat cag gtg ttt att ggc ttt gta ttg aaa cag ttt    4588
```

```
Leu Asp Ser Asp Gln Val Phe Ile Gly Phe Val Leu Lys Gln Phe
        1470            1475            1480 gaa tac att gaa gtg ggc cag ttc agg gaa tca gag gca atc att       4633
Glu Tyr Ile Glu Val Gly Gln Phe Arg Glu Ser Glu Ala Ile Ile
        1485            1490            1495 cca aac atc ttt ttc ttc ttg gta tta cta tct tat gaa cgc tat       4678
Pro Asn Ile Phe Phe Phe Leu Val Leu Leu Ser Tyr Glu Arg Tyr
        1500            1505            1510 cat tca aaa cag atc att gga att cct aaa atc att cag ctc tgt       4723
His Ser Lys Gln Ile Ile Gly Ile Pro Lys Ile Ile Gln Leu Cys
        1515            1520            1525 gat ggc atc atg gcc agt gga agg aag gct gtg aca cat gcc ata       4768
Asp Gly Ile Met Ala Ser Gly Arg Lys Ala Val Thr His Ala Ile
        1530            1535            1540 ccg gct ctg cag ccc ata gtc cac gac ctc ttt gta tta aga gga       4813
Pro Ala Leu Gln Pro Ile Val His Asp Leu Phe Val Leu Arg Gly
        1545            1550            1555 aca aat aaa gct gat gca gga aaa gag ctt gaa acc caa aaa gag       4858
Thr Asn Lys Ala Asp Ala Gly Lys Glu Leu Glu Thr Gln Lys Glu
        1560            1565            1570 gtg gtg gtg tca atg tta ctg aga ctc atc cag tac cat cag gtg       4903
Val Val Val Ser Met Leu Leu Arg Leu Ile Gln Tyr His Gln Val
        1575            1580            1585 ttg gag atg ttc att ctt gtc ctg cag cag tgc cac aag gag aat       4948
Leu Glu Met Phe Ile Leu Val Leu Gln Gln Cys His Lys Glu Asn
        1590            1595            1600 gaa gac aag tgg aag cga ctg tct cga cag ata gct gac atc atc       4993
Glu Asp Lys Trp Lys Arg Leu Ser Arg Gln Ile Ala Asp Ile Ile
        1605            1610            1615 ctc cca atg tta gcc aaa cag cag atg cac att gac tct cat gaa       5038
Leu Pro Met Leu Ala Lys Gln Gln Met His Ile Asp Ser His Glu
        1620            1625            1630 gcc ctt gga gtg tta aat aca tta ttt gag att ttg gcc cct tcc       5083
Ala Leu Gly Val Leu Asn Thr Leu Phe Glu Ile Leu Ala Pro Ser
        1635            1640            1645 tcc ctc cgt ccg gta gac atg ctt tta cgg agt atg ttc gtc act       5128
Ser Leu Arg Pro Val Asp Met Leu Leu Arg Ser Met Phe Val Thr
        1650            1655            1660 cca aac aca atg gcg tcc gtg agc act gtt caa ctg tgg ata tcg       5173
Pro Asn Thr Met Ala Ser Val Ser Thr Val Gln Leu Trp Ile Ser
        1665            1670            1675 gga att ctg gcc att ttg agg gtt ctg att tcc cag tca act gaa       5218
Gly Ile Leu Ala Ile Leu Arg Val Leu Ile Ser Gln Ser Thr Glu
        1680            1685            1690 gat att gtt ctt tct cgt att cag gag ctc tcc ttc tct ccg tat       5263
Asp Ile Val Leu Ser Arg Ile Gln Glu Leu Ser Phe Ser Pro Tyr
        1695            1700            1705 tta atc tcc tgt aca gta att aat agg tta aga gat ggg gac agt       5308
Leu Ile Ser Cys Thr Val Ile Asn Arg Leu Arg Asp Gly Asp Ser
        1710            1715            1720 act tca acg cta gaa gaa cac agt gaa ggg aaa caa ata aag aat       5353
Thr Ser Thr Leu Glu Glu His Ser Glu Gly Lys Gln Ile Lys Asn
        1725            1730            1735 ttg cca gaa gaa aca ttt tca agg ttt cta tta caa ctg gtt ggt       5398
Leu Pro Glu Glu Thr Phe Ser Arg Phe Leu Leu Gln Leu Val Gly
        1740            1745            1750 att ctt tta gaa gac att gtt aca aaa cag ctg aag gtg gaa atg       5443
Ile Leu Leu Glu Asp Ile Val Thr Lys Gln Leu Lys Val Glu Met
        1755            1760            1765
```

```
agt gag cag caa cat act ttc tat tgc cag gaa cta ggc aca ctg       5488
Ser Glu Gln Gln His Thr Phe Tyr Cys Gln Glu Leu Gly Thr Leu
        1770            1775                1780 cta atg tgt ctg atc cac atc ttc aag tct gga atg ttc cgg aga       5533
Leu Met Cys Leu Ile His Ile Phe Lys Ser Gly Met Phe Arg Arg
        1785            1790                1795 atc aca gca gct gcc act agg ctg ttc cgc agt gat ggc tgt ggc       5578
Ile Thr Ala Ala Ala Thr Arg Leu Phe Arg Ser Asp Gly Cys Gly
        1800            1805                1810 ggc agt ttc tac acc ctg gac agc ttg aac ttg cgg gct cgt tcc       5623
Gly Ser Phe Tyr Thr Leu Asp Ser Leu Asn Leu Arg Ala Arg Ser
        1815            1820                1825 atg atc acc acc cac ccg gcc ctg gtg ctg ctc tgg tgt cag ata       5668
Met Ile Thr Thr His Pro Ala Leu Val Leu Leu Trp Cys Gln Ile
        1830            1835                1840 ctg ctg ctt gtc aac cac acc gac tac cgc tgg tgg gca gaa gtg       5713
Leu Leu Leu Val Asn His Thr Asp Tyr Arg Trp Trp Ala Glu Val
        1845            1850                1855 cag cag acc ccg aaa aga cac agt ctg tcc agc aca aag tta ctt       5758
Gln Gln Thr Pro Lys Arg His Ser Leu Ser Ser Thr Lys Leu Leu
        1860            1865                1870 agt ccc cag atg tct gga gaa gag gag gat tct gac ttg gca gcc       5803
Ser Pro Gln Met Ser Gly Glu Glu Glu Asp Ser Asp Leu Ala Ala
        1875            1880                1885 aaa ctt gga atg tgc aat aga gaa ata gta cga aga ggg gct ctc       5848
Lys Leu Gly Met Cys Asn Arg Glu Ile Val Arg Arg Gly Ala Leu
        1890            1895                1900 att ctc ttc tgt gat tat gtc tgt cag aac ctc cat gac tcc gag       5893
Ile Leu Phe Cys Asp Tyr Val Cys Gln Asn Leu His Asp Ser Glu
        1905            1910                1915 cac tta acg tgg ctc att gta aat cac att caa gat ctg atc agc       5938
His Leu Thr Trp Leu Ile Val Asn His Ile Gln Asp Leu Ile Ser
        1920            1925                1930 ctt tcc cac gag cct cca gta cag gac ttc atc agt gcc gtt cat       5983
Leu Ser His Glu Pro Pro Val Gln Asp Phe Ile Ser Ala Val His
        1935            1940                1945 cgg aac tct gct gcc agc ggc ctg ttc atc cag gca att cag tct       6028
Arg Asn Ser Ala Ala Ser Gly Leu Phe Ile Gln Ala Ile Gln Ser
        1950            1955                1960 cgt tgt gaa aac ctt tca act cca acc atg ctg aag aaa act ctt       6073
Arg Cys Glu Asn Leu Ser Thr Pro Thr Met Leu Lys Lys Thr Leu
        1965            1970                1975 cag tgc ttg gag ggg atc cat ctc agc cag tcg gga gct gtc ctc       6118
Gln Cys Leu Glu Gly Ile His Leu Ser Gln Ser Gly Ala Val Leu
        1980            1985                1990 acg ctg tat gtg gac agg ctt ctg tgc acc cct ttc cgt gtg ctg       6163
Thr Leu Tyr Val Asp Arg Leu Leu Cys Thr Pro Phe Arg Val Leu
        1995            2000                2005 gct cgc atg gtc gac atc ctt gct tgt cgc cgg gta gaa atg ctt       6208
Ala Arg Met Val Asp Ile Leu Ala Cys Arg Arg Val Glu Met Leu
        2010            2015                2020 ctg gct gca aat tta cag agc agc atg gcc cag ttg cca atg gaa       6253
Leu Ala Ala Asn Leu Gln Ser Ser Met Ala Gln Leu Pro Met Glu
        2025            2030                2035 gaa ctc aac aga atc cag gaa tac ctt cag agc agc ggg ctc gct       6298
Glu Leu Asn Arg Ile Gln Glu Tyr Leu Gln Ser Ser Gly Leu Ala
        2040            2045                2050 cag aga cac caa agg ctc tat tcc ctg ctg gac agg ttt cgt ctc       6343
Gln Arg His Gln Arg Leu Tyr Ser Leu Leu Asp Arg Phe Arg Leu
        2055            2060                2065
```

```
tcc acc atg caa gac tca ctt agt ccc tct cct cca gtc tct tcc        6388
Ser Thr Met Gln Asp Ser Leu Ser Pro Ser Pro Pro Val Ser Ser
            2070                2075                2080 cac ccg ctg gac ggg gat ggg cac gtg tca ctg gaa aca gtg agt        6433
His Pro Leu Asp Gly Asp Gly His Val Ser Leu Glu Thr Val Ser
    2085                2090                2095 ccg gac aaa gac tgg tac gtt cat ctt gtc aaa tcc cag tgt tgg        6478
Pro Asp Lys Asp Trp Tyr Val His Leu Val Lys Ser Gln Cys Trp
                2100                2105                2110 acc agg tca gat tct gca ctg ctg gaa ggt gca gag ctg gtg aat        6523
Thr Arg Ser Asp Ser Ala Leu Leu Glu Gly Ala Glu Leu Val Asn
            2115                2120                2125 cgg att cct gct gaa gat atg aat gcc ttc atg atg aac tcg gag        6568
Arg Ile Pro Ala Glu Asp Met Asn Ala Phe Met Met Asn Ser Glu
        2130                2135                2140 ttc aac cta agc ctg cta gct cca tgc tta agc cta ggg atg agt        6613
Phe Asn Leu Ser Leu Leu Ala Pro Cys Leu Ser Leu Gly Met Ser
    2145                2150                2155 gaa att tct ggt ggc cag aag agt gcc ctt ttt gaa gca gcc cgt        6658
Glu Ile Ser Gly Gly Gln Lys Ser Ala Leu Phe Glu Ala Ala Arg
                2160                2165                2170 gag gtg act ctg gcc cgt gtg agc ggc acc gtg cag cag ctc cct        6703
Glu Val Thr Leu Ala Arg Val Ser Gly Thr Val Gln Gln Leu Pro
            2175                2180                2185 gct gtc cat cat gtc ttc cag ccc gag ctg cct gca gag ccg gcg        6748
Ala Val His His Val Phe Gln Pro Glu Leu Pro Ala Glu Pro Ala
        2190                2195                2200 gcc tac tgg agc aag ttg aat gat ctg ttt ggg gat gct gca ctg        6793
Ala Tyr Trp Ser Lys Leu Asn Asp Leu Phe Gly Asp Ala Ala Leu
    2205                2210                2215 tat cag tcc ctg ccc act ctg gcc cgg gcc ctg gca cag tac ctg        6838
Tyr Gln Ser Leu Pro Thr Leu Ala Arg Ala Leu Ala Gln Tyr Leu
                2220                2225                2230 gtg gtg gtc tcc aaa ctg ccc agt cat ttg cac ctt cct cct gag        6883
Val Val Val Ser Lys Leu Pro Ser His Leu His Leu Pro Pro Glu
            2235                2240                2245 aaa gag aag gac att gtg aaa ttc gtg gtg gca acc ctt gag gcc        6928
Lys Glu Lys Asp Ile Val Lys Phe Val Val Ala Thr Leu Glu Ala
        2250                2255                2260 ctg tcc tgg cat ttg atc cat gag cag atc ccg ctg agt ctg gat        6973
Leu Ser Trp His Leu Ile His Glu Gln Ile Pro Leu Ser Leu Asp
    2265                2270                2275 ctc cag gca ggg ctg gac tgc tgc tgc ctg gcc ctg cag ctg cct        7018
Leu Gln Ala Gly Leu Asp Cys Cys Cys Leu Ala Leu Gln Leu Pro
                2280                2285                2290 ggc ctc tgg agc gtg gtc tcc tcc aca gag ttt gtg acc cac gcc        7063
Gly Leu Trp Ser Val Val Ser Ser Thr Glu Phe Val Thr His Ala
            2295                2300                2305 tgc tcc ctc atc tac tgt gtg cac ttc atc ctg gag gcc gtt gca        7108
Cys Ser Leu Ile Tyr Cys Val His Phe Ile Leu Glu Ala Val Ala
        2310                2315                2320 gtg cag cct gga gag cag ctt ctt agt cca gaa aga agg aca aat        7153
Val Gln Pro Gly Glu Gln Leu Leu Ser Pro Glu Arg Arg Thr Asn
    2325                2330                2335 acc cca aaa gcc atc agc gag gag gag gaa gta gat cca aac        7198
Thr Pro Lys Ala Ile Ser Glu Glu Glu Glu Val Asp Pro Asn
                2340                2345                2350 aca cag aat cct aag tat atc act gca gcc tgt gag atg gtg gca        7243
Thr Gln Asn Pro Lys Tyr Ile Thr Ala Ala Cys Glu Met Val Ala
```

-continued

|     |     |     |     |     |     |     |     |     |     |     |     |     |     |     |      |
|-----|-----|-----|-----|-----|-----|-----|-----|-----|-----|-----|-----|-----|-----|-----|------|
|     |     | 2355 |     |     |     | 2360 |     |     |     | 2365 |     |     |     |     |      |
| gaa | atg | gtg | gag | tct | ctg | cag | tcg | gtg | ttg | gcc | ttg | ggt | cat | aaa | 7288 |
| Glu | Met | Val | Glu | Ser | Leu | Gln | Ser | Val | Leu | Ala | Leu | Gly | His | Lys |      |
|     |     | 2370 |     |     |     | 2375 |     |     |     | 2380 |     |     |     |     |      |
| agg | aat | agc | ggc | gtg | ccg | gcg | ttt | ctc | acg | cca | ttg | cta | agg | aac | 7333 |
| Arg | Asn | Ser | Gly | Val | Pro | Ala | Phe | Leu | Thr | Pro | Leu | Leu | Arg | Asn |      |
|     |     | 2385 |     |     |     | 2390 |     |     |     | 2395 |     |     |     |     |      |
| atc | atc | atc | agc | ctg | gcc | cgc | ctg | ccc | ctt | gtc | aac | agc | tac | aca | 7378 |
| Ile | Ile | Ile | Ser | Leu | Ala | Arg | Leu | Pro | Leu | Val | Asn | Ser | Tyr | Thr |      |
|     |     | 2400 |     |     |     | 2405 |     |     |     | 2410 |     |     |     |     |      |
| cgt | gtg | ccc | cca | ctg | gtg | tgg | aag | ctt | gga | tgg | tca | ccc | aaa | ccg | 7423 |
| Arg | Val | Pro | Pro | Leu | Val | Trp | Lys | Leu | Gly | Trp | Ser | Pro | Lys | Pro |      |
|     |     | 2415 |     |     |     | 2420 |     |     |     | 2425 |     |     |     |     |      |
| gga | ggg | gat | ttt | ggc | aca | gca | ttc | cct | gag | atc | ccc | gtg | gag | ttc | 7468 |
| Gly | Gly | Asp | Phe | Gly | Thr | Ala | Phe | Pro | Glu | Ile | Pro | Val | Glu | Phe |      |
|     |     | 2430 |     |     |     | 2435 |     |     |     | 2440 |     |     |     |     |      |
| ctc | cag | gaa | aag | gaa | gtc | ttt | aag | gag | ttc | atc | tac | cgc | atc | aac | 7513 |
| Leu | Gln | Glu | Lys | Glu | Val | Phe | Lys | Glu | Phe | Ile | Tyr | Arg | Ile | Asn |      |
|     |     | 2445 |     |     |     | 2450 |     |     |     | 2455 |     |     |     |     |      |
| aca | cta | ggc | tgg | acc | agt | cgt | act | cag | ttt | gaa | gaa | act | tgg | gcc | 7558 |
| Thr | Leu | Gly | Trp | Thr | Ser | Arg | Thr | Gln | Phe | Glu | Glu | Thr | Trp | Ala |      |
|     |     | 2460 |     |     |     | 2465 |     |     |     | 2470 |     |     |     |     |      |
| acc | ctc | ctt | ggt | gtc | ctg | gtg | acg | cag | ccc | ctc | gtg | atg | gag | cag | 7603 |
| Thr | Leu | Leu | Gly | Val | Leu | Val | Thr | Gln | Pro | Leu | Val | Met | Glu | Gln |      |
|     |     | 2475 |     |     |     | 2480 |     |     |     | 2485 |     |     |     |     |      |
| gag | gag | agc | cca | cca | gaa | gaa | gac | aca | gag | agg | acc | cag | atc | aac | 7648 |
| Glu | Glu | Ser | Pro | Pro | Glu | Glu | Asp | Thr | Glu | Arg | Thr | Gln | Ile | Asn |      |
|     |     | 2490 |     |     |     | 2495 |     |     |     | 2500 |     |     |     |     |      |
| gtc | ctg | gcc | gtg | cag | gcc | atc | acc | tca | ctg | gtg | ctc | agt | gca | atg | 7693 |
| Val | Leu | Ala | Val | Gln | Ala | Ile | Thr | Ser | Leu | Val | Leu | Ser | Ala | Met |      |
|     |     | 2505 |     |     |     | 2510 |     |     |     | 2515 |     |     |     |     |      |
| act | gtg | cct | gtg | gcc | ggc | aac | cca | gct | gta | agc | tgc | ttg | gag | cag | 7738 |
| Thr | Val | Pro | Val | Ala | Gly | Asn | Pro | Ala | Val | Ser | Cys | Leu | Glu | Gln |      |
|     |     | 2520 |     |     |     | 2525 |     |     |     | 2530 |     |     |     |     |      |
| cag | ccc | cgg | aac | aag | cct | ctg | aaa | gct | ctc | gac | acc | agg | ttt | ggg | 7783 |
| Gln | Pro | Arg | Asn | Lys | Pro | Leu | Lys | Ala | Leu | Asp | Thr | Arg | Phe | Gly |      |
|     |     | 2535 |     |     |     | 2540 |     |     |     | 2545 |     |     |     |     |      |
| agg | aag | ctg | agc | att | atc | aga | ggg | att | gtg | gag | caa | gag | att | caa | 7828 |
| Arg | Lys | Leu | Ser | Ile | Ile | Arg | Gly | Ile | Val | Glu | Gln | Glu | Ile | Gln |      |
|     |     | 2550 |     |     |     | 2555 |     |     |     | 2560 |     |     |     |     |      |
| gca | atg | gtt | tca | aag | aga | gag | aat | att | gcc | acc | cat | cat | tta | tat | 7873 |
| Ala | Met | Val | Ser | Lys | Arg | Glu | Asn | Ile | Ala | Thr | His | His | Leu | Tyr |      |
|     |     | 2565 |     |     |     | 2570 |     |     |     | 2575 |     |     |     |     |      |
| cag | gca | tgg | gat | cct | gtc | cct | tct | ctg | tct | ccg | gct | act | aca | ggt | 7918 |
| Gln | Ala | Trp | Asp | Pro | Val | Pro | Ser | Leu | Ser | Pro | Ala | Thr | Thr | Gly |      |
|     |     | 2580 |     |     |     | 2585 |     |     |     | 2590 |     |     |     |     |      |
| gcc | ctc | atc | agc | cac | gag | aag | ctg | ctg | cta | cag | atc | aac | ccc | gag | 7963 |
| Ala | Leu | Ile | Ser | His | Glu | Lys | Leu | Leu | Leu | Gln | Ile | Asn | Pro | Glu |      |
|     |     | 2595 |     |     |     | 2600 |     |     |     | 2605 |     |     |     |     |      |
| cgg | gag | ctg | ggg | agc | atg | agc | tac | aaa | ctc | ggc | cag | gtg | tcc | ata | 8008 |
| Arg | Glu | Leu | Gly | Ser | Met | Ser | Tyr | Lys | Leu | Gly | Gln | Val | Ser | Ile |      |
|     |     | 2610 |     |     |     | 2615 |     |     |     | 2620 |     |     |     |     |      |
| cac | tcc | gtg | tgg | ctg | ggg | aac | agc | atc | aca | ccc | ctg | agg | gag | gag | 8053 |
| His | Ser | Val | Trp | Leu | Gly | Asn | Ser | Ile | Thr | Pro | Leu | Arg | Glu | Glu |      |
|     |     | 2625 |     |     |     | 2630 |     |     |     | 2635 |     |     |     |     |      |
| gaa | tgg | gac | gag | gaa | gag | gag | gag | gcc | gac | gcc | cct | gca | cct | 8098 |
| Glu | Trp | Asp | Glu | Glu | Glu | Glu | Glu | Ala | Asp | Ala | Pro | Ala | Pro |      |
|     |     | 2640 |     |     |     | 2645 |     |     |     | 2650 |     |     |     |     |      |
| tcg | tca | cca | ccc | acg | tct | cca | gtc | aac | tcc | agg | aaa | cac | cgg | gct | 8143 |

-continued

| | | | | | | | | | | | | |
|---|---|---|---|---|---|---|---|---|---|---|---|---|
| Ser | Ser | Pro | Pro<br>2655 | Thr | Ser | Pro | Val<br>2660 | Asn | Ser | Arg | Lys | His<br>2665 | Arg | Ala |

```
gga gtt gac atc cac tcc tgt tcg cag ttt ttg ctt gag ttg tac       8188
Gly Val Asp Ile His Ser Cys Ser Gln Phe Leu Leu Glu Leu Tyr
            2670                2675                2680 agc cgc tgg atc ctg ccg tcc agc tca gcc agg agg acc ccg gcc       8233
Ser Arg Trp Ile Leu Pro Ser Ser Ser Ala Arg Arg Thr Pro Ala
            2685                2690                2695 atc ctg atc agt gag gtg gtc aga tcc ctt cta gtg gtc tca gac       8278
Ile Leu Ile Ser Glu Val Val Arg Ser Leu Leu Val Val Ser Asp
            2700                2705                2710 ttg ttc acc gag cgc aac cag ttt gag ctg atg tat gtg acg ctg       8323
Leu Phe Thr Glu Arg Asn Gln Phe Glu Leu Met Tyr Val Thr Leu
            2715                2720                2725 aca gaa ctg cga agg gtg cac cct tca gaa gac gag atc ctc gct       8368
Thr Glu Leu Arg Arg Val His Pro Ser Glu Asp Glu Ile Leu Ala
            2730                2735                2740 cag tac ctg gtg cct gcc acc tgc aag gca gct gcc gtc ctt ggg       8413
Gln Tyr Leu Val Pro Ala Thr Cys Lys Ala Ala Ala Val Leu Gly
            2745                2750                2755 atg gac aag gcc gtg gcg gag cct gtc agc cgc ctg ctg gag agc       8458
Met Asp Lys Ala Val Ala Glu Pro Val Ser Arg Leu Leu Glu Ser
            2760                2765                2770 acg ctc agg agc agc cac ctg ccc agc agg gtt gga gcc ctg cac       8503
Thr Leu Arg Ser Ser His Leu Pro Ser Arg Val Gly Ala Leu His
            2775                2780                2785 ggc gtc ctc tat gtg ctg gag tgc gac ctg ctg gac gac act gcc       8548
Gly Val Leu Tyr Val Leu Glu Cys Asp Leu Leu Asp Asp Thr Ala
            2790                2795                2800 aag cag ctc atc ccg gtc atc agc gac tat ctc ctc tcc aac ctg       8593
Lys Gln Leu Ile Pro Val Ile Ser Asp Tyr Leu Leu Ser Asn Leu
            2805                2810                2815 aaa ggg atc gcc cac tgc gtg aac att cac agc cag cag cac gta       8638
Lys Gly Ile Ala His Cys Val Asn Ile His Ser Gln Gln His Val
            2820                2825                2830 ctg gtc atg tgt gcc act gcg ttt tac ctc att gag aac tat cct       8683
Leu Val Met Cys Ala Thr Ala Phe Tyr Leu Ile Glu Asn Tyr Pro
            2835                2840                2845 ctg gac gta ggg ccg gaa ttt tca gca tca ata ata cag atg tgt       8728
Leu Asp Val Gly Pro Glu Phe Ser Ala Ser Ile Ile Gln Met Cys
            2850                2855                2860 ggg gtg atg ctg tct gga agt gag gag tcc acc ccc tcc atc att       8773
Gly Val Met Leu Ser Gly Ser Glu Glu Ser Thr Pro Ser Ile Ile
            2865                2870                2875 tac cac tgt gcc ctc aga ggc ctg gag cgc ctc ctg tct gag           8818
Tyr His Cys Ala Leu Arg Gly Leu Glu Arg Leu Leu Leu Ser Glu
            2880                2885                2890 cag ctc tcc cgc ctg gat gca gaa tcg ctg gtc aag ctg agt gtg       8863
Gln Leu Ser Arg Leu Asp Ala Glu Ser Leu Val Lys Leu Ser Val
            2895                2900                2905 gac aga gtg aac gtg cac agc ccg cac cgg gcc atg gcg gct ctg       8908
Asp Arg Val Asn Val His Ser Pro His Arg Ala Met Ala Ala Leu
            2910                2915                2920 ggc ctg atg ctc acc tgc atg tac aca gga aag gag aaa gtc agt       8953
Gly Leu Met Leu Thr Cys Met Tyr Thr Gly Lys Glu Lys Val Ser
            2925                2930                2935 ccg ggt aga act tca gac cct aat cct gca gcc ccc gac agc gag       8998
Pro Gly Arg Thr Ser Asp Pro Asn Pro Ala Ala Pro Asp Ser Glu
            2940                2945                2950
```

| | | | | | | | | | | | | |
|---|---|---|---|---|---|---|---|---|---|---|---|---|
| tca | gtg | att | gtt | gct | atg | gag | cgg | gta | tct | gtt | ctt | ttt | gat | agg | 9043 |
| Ser | Val | Ile | Val | Ala | Met | Glu | Arg | Val | Ser | Val | Leu | Phe | Asp | Arg | |
| | | | 2955 | | | | 2960 | | | | | 2965 | | | |

| atc | agg | aaa | ggc | ttt | cct | tgt | gaa | gcc | aga | gtg | gtg | gcc | agg | atc | 9088 |
| Ile | Arg | Lys | Gly | Phe | Pro | Cys | Glu | Ala | Arg | Val | Val | Ala | Arg | Ile | |
| | | | 2970 | | | | 2975 | | | | | 2980 | | | |

| ctg | ccc | cag | ttt | cta | gac | gac | ttc | ttc | cca | ccc | cag | gac | atc | atg | 9133 |
| Leu | Pro | Gln | Phe | Leu | Asp | Asp | Phe | Phe | Pro | Pro | Gln | Asp | Ile | Met | |
| | | | 2985 | | | | 2990 | | | | | 2995 | | | |

| aac | aaa | gtc | atc | gga | gag | ttt | ctg | tcc | aac | cag | cag | cca | tac | ccc | 9178 |
| Asn | Lys | Val | Ile | Gly | Glu | Phe | Leu | Ser | Asn | Gln | Gln | Pro | Tyr | Pro | |
| | | | 3000 | | | | 3005 | | | | | 3010 | | | |

| cag | ttc | atg | gcc | acc | gtg | gtg | tat | aag | gtg | ttt | cag | act | ctg | cac | 9223 |
| Gln | Phe | Met | Ala | Thr | Val | Val | Tyr | Lys | Val | Phe | Gln | Thr | Leu | His | |
| | | | 3015 | | | | 3020 | | | | | 3025 | | | |

| agc | acc | ggg | cag | tcg | tcc | atg | gtc | cgg | gac | tgg | gtc | atg | ctg | tcc | 9268 |
| Ser | Thr | Gly | Gln | Ser | Ser | Met | Val | Arg | Asp | Trp | Val | Met | Leu | Ser | |
| | | | 3030 | | | | 3035 | | | | | 3040 | | | |

| ctc | tcc | aac | ttc | acg | cag | agg | gcc | ccg | gtc | gcc | atg | gcc | acg | tgg | 9313 |
| Leu | Ser | Asn | Phe | Thr | Gln | Arg | Ala | Pro | Val | Ala | Met | Ala | Thr | Trp | |
| | | | 3045 | | | | 3050 | | | | | 3055 | | | |

| agc | ctc | tcc | tgc | ttc | ttt | gtc | agc | gcg | tcc | acc | agc | ccg | tgg | gtc | 9358 |
| Ser | Leu | Ser | Cys | Phe | Phe | Val | Ser | Ala | Ser | Thr | Ser | Pro | Trp | Val | |
| | | | 3060 | | | | 3065 | | | | | 3070 | | | |

| gcg | gcg | atc | ctc | cca | cat | gtc | atc | agc | agg | atg | ggc | aag | ctg | gag | 9403 |
| Ala | Ala | Ile | Leu | Pro | His | Val | Ile | Ser | Arg | Met | Gly | Lys | Leu | Glu | |
| | | | 3075 | | | | 3080 | | | | | 3085 | | | |

| cag | gtg | gac | gtg | aac | ctt | ttc | tgc | ctg | gtc | gcc | aca | gac | ttc | tac | 9448 |
| Gln | Val | Asp | Val | Asn | Leu | Phe | Cys | Leu | Val | Ala | Thr | Asp | Phe | Tyr | |
| | | | 3090 | | | | 3095 | | | | | 3100 | | | |

| aga | cac | cag | ata | gag | gag | gag | ctc | gac | cgc | agg | gcc | ttc | cag | tct | 9493 |
| Arg | His | Gln | Ile | Glu | Glu | Glu | Leu | Asp | Arg | Arg | Ala | Phe | Gln | Ser | |
| | | | 3105 | | | | 3110 | | | | | 3115 | | | |

| gtg | ctt | gag | gtg | gtt | gca | gcc | cca | gga | agc | cca | tat | cac | cgg | ctg | 9538 |
| Val | Leu | Glu | Val | Val | Ala | Ala | Pro | Gly | Ser | Pro | Tyr | His | Arg | Leu | |
| | | | 3120 | | | | 3125 | | | | | 3130 | | | |

| ctg | act | tgt | tta | cga | aat | gtc | cac | aag | gtc | acc | acc | tgc | tga | | 9580 |
| Leu | Thr | Cys | Leu | Arg | Asn | Val | His | Lys | Val | Thr | Thr | Cys | | | |
| | | | 3135 | | | | 3140 | | | | | | | | | gcgccatggt gggagagact gtgaggcggc agctggggcc ggagcctttg gaagtctgcg 9640 cccttgtgcc ctgcctccac cgagccagct tggtccctat gggcttccgc acatgccgcg 9700 ggcggccagg caacgtgcgt gtctctgcca tgtggcagaa gtgctctttg tggcagtggc 9760 caggcaggga gtgtctgcag tcctggtggg gctgagcctg aggccttcca gaaagcagga 9820 gcagctgtgc tgcaccccat gtgggtgacc aggtcctttc tcctgatagt cacctgctgg 9880 ttgttgccag gttgcagctg ctcttgcatc tgggccagaa gtcctccctc ctgcaggctg 9940 gctgttggcc cctctgctgt cctgcagtag aaggtgccgt gagcaggctt tgggaacact 10000 ggcctgggtc tccctggtgg ggtgtgcatg ccacgccccg tgtctggatg cacagatgcc 10060 atggcctgtg ctgggccagt ggctgggggt gctagacacc cggcaccatt ctcccttctc 10120 tcttttcttc tcaggattta aaatttaatt atatcagtaa agagattaat tttaacgtaa 10180 ctctttctat gcccgtgtaa agtatgtgaa tcgcaaggcc tgtgctgcat gcgacagcgt 10240 ccggggtggt ggacagggcc cccggccacg ctccctctcc tgtagccact ggcatagccc 10300 tcctgagcac ccgctgacat ttccgttgta catgttcctg tttatgcatt cacaaggtga 10360 ctgggatgta gagaggcgtt agtgggcagg tggccacagc aggactgagg acaggccccc 10420

```
attatcctag gggtgcgctc acctgcagcc cctcctcctc gggcacagac gactgtcgtt   10480
ctccacccac cagtcaggga cagcagcctc cctgtcactc agctgagaag gccagccctc   10540
cctggctgtg agcagcctcc actgtgtcca gagacatggg cctcccactc ctgttccttg   10600
ctagccctgg ggtggcgtct gcctaggagc tggctggcag gtgttgggac ctgctgctcc   10660
atggatgcat gccctaagag tgtcactgag ctgtgttttg tctgagcctc tctcggtcaa   10720
cagcaaagct tggtgtcttg gcactgttag tgacagagcc cagcatccct tctgcccccg   10780
ttccagctga catcttgcac ggtgacccct tttagtcagg agagtgcaga tctgtgctca   10840
tcggagactg ccccacggcc ctgtcagagc cgccactcct atccccaggc caggtccctg   10900
gaccagcctc ctgtttgcag gcccagagga gccaagtcat taaaatggaa gtggattctg   10960
gatggccggg ctgctgctga tgtaggagct ggatttggga gctctgcttg ccgactggct   11020
gtgagacgag gcagggctc tgcttcctca gccctagagg cgagccaggc aaggttggcg   11080
actgtcatgt ggcttggttt ggtcatgccc gtcgatgttt gggtattga atgtggtaag   11140
tggaggaaat gttggaactc tgtgcaggtg ctgccttgag accccaagc ttccacctgt   11200
ccctctccta tgtggcagct ggggagcagc tgagatgtgg acttgtatgc tgcccacata   11260
cgtgaggggg agctgaaagg gagcccctcc tctgagcagc ctctgccagg cctgtatgag   11320
gcttttccca ccagctccca acagaggcct ccccagcca ggaccacctc gtcctcgtgg   11380
cggggcagca ggagcggtag aaaggggtcc gatgtttgag gaggcccta agggaagcta   11440
ctgaattata acacgtaaga aaatcaccat tccgtattgg ttgggggctc ctgtttctca   11500
tcctagcttt ttcctggaaa gcccgctaga aggtttggga acgaggggaa agttctcaga   11560
actgttggct gctccccacc cgcctcccgc ctcccccgca ggttatgtca gcagctctga   11620
gacagcagta tcacaggcca gatgttgttc ctggctagat gtttacattt gtaagaaata   11680
acactgtgaa tgtaaaacag agccattccc ttggaatgca tatcgctggg ctcaacatag   11740
agtttgtctt cctcttgttt acgacgtgat ctaaaccagt ccttagcaag gggctcagaa   11800
caccccgctc tggcagtagg tgtcccccac ccccaaagac ctgcctgtgt gctccggaga   11860
tgaatatgag ctcattagta aaaatgactt cacccacgca tatacataaa gtatccatgc   11920
atgtgcatat agacacatct ataatttac acacacacct ctcaagacgg agatgcatgg   11980
cctctaagag tgcccgtgtc ggttcttcct ggaagttgac tttccttaga cccgccaggt   12040
caagttagcc gcgtgacgga catccaggcg tgggacgtgg tcagggcagg gctcattcat   12100
tgcccactag gatcccactg gcgaagatgg tctccatatc agctctctgc agaagggagg   12160
aagactttat catgttccta aaaatctgtg gcaagcaccc atcgtattat ccaaattttg   12220
ttgcaaatgt gattaatttg gttgtcaagt tttgggggtg ggctgtgggg agattgcttt   12280
tgttttcctg ctggtaatat cgggaaagat tttaatgaaa ccagggtaga attgtttggc   12340
aatgcactga gcgtgttttc tttcccaaaa tgtgcctccc ttccgctgcg ggcccagctg   12400
agtctatgta ggtgatgttt ccagctgcca agtgctcttt gttactgtcc accctcattt   12460
ctgccagcgc atgtgtcctt tcaaggggaa aatgtgaagc tgaaccccct ccagacaccc   12520
agaatgtagc atctgagaag gccctgtgcc ctaaaggaca cccctcgccc ccatcttcat   12580
ggagggggtc atttcagagc cctcggagcc aatgaacagc tcctcctctt ggagctgaga   12640
tgagccccac gtggagctcg ggacggatag tagacagcaa taactcggtg tgtgccgcc   12700
tggcaggtgg aacttcctcc cgttgcgggg tggagtgagg ttagttctgt gtgtctggtg   12760
```

| | | | | | |
|---|---|---|---|---|---|
| ggtggagtca | ggcttctctt | gctacctgtg | agcatccttc | ccagcagaca | tcctcatcgg 12820 |
| gctttgtccc | tcccccgctt | cctccctctg | cggggaggac | ccgggaccac | agctgctggc 12880 |
| cagggtagac | ttggagctgt | cctccagagg | ggtcacgtgt | aggagtgaga | agaaggaaga 12940 |
| tcttgagagc | tgctgaggga | ccttggagag | ctcaggatgg | ctcagacgag | gacactcgct 13000 |
| tgccgggcct | gggcctcctg | ggaaggaggg | agctgctcag | aatgccgcat | gacaactgaa 13060 |
| ggcaacctgg | aaggttcagg | ggccgctctt | cccccatgtg | cctgtcacgc | tctggtgcag 13120 |
| tcaaaggaac | gccttcccct | cagttgtttc | taagagcaga | gtctcccgct | gcaatctggg 13180 |
| tggtaactgc | cagccttgga | ggatcgtggc | caacgtggac | ctgcctacgg | agggtgggct 13240 |
| ctgacccaag | tggggcctcc | ttgtccaggt | ctcactgctt | tgcaccgtgg | tcagagggac 13300 |
| tgtcagctga | gcttgagctc | ccctggagcc | agcagggctg | tgatgggcga | gtcccggagc 13360 |
| cccacccaga | cctgaatgct | tctgagagca | aagggaagga | ctgacgagag | atgtatattt 13420 |
| aattttttaa | ctgctgcaaa | cattgtacat | ccaaattaaa | ggaaaaaaat | ggaaaccatc 13480 |
| a | | | | | 13481 |

The invention claimed is:

1. A gapped oligomeric compound comprising a contiguous sequence of linked monomer subunits having a gap region located between a 5'-region and a 3'-region wherein the 5' and 3'-regions each, independently, have from 2 to 8 contiguous RNA-like modified nucleosides that each adopt a 3'-endo conformational geometry when put into an oligomeric compound and wherein the gap region has from 6 to 14 contiguous monomer subunits selected from β-D-2'-deoxyribonucleosides and 5'-substituted β-D-2'-deoxyribonucleosides having Formula I:

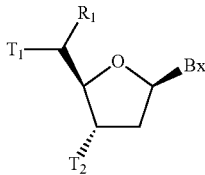

I wherein independently for each 5'-substituted β-D-2'-deoxyribonucleoside having Formula I:
  $T_1$ and $T_2$ are each, independently, an internucleoside linking group linking the 5'-substituted β-D-2'-deoxyribonucleoside having Formula I to the remainder of the gapped oligomeric compound;
  Bx is a heterocyclic base moiety;
  $R_1$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and
  wherein said gap region comprises at least one 5'-substituted β-D-2'-deoxyribonucleoside having Formula I and a plurality of β-D-2'-deoxyribonucleosides.

2. The gapped oligomeric compound of claim 1 wherein each substituted group comprises one or more optionally protected substituent groups independently selected from halogen, $OJ_1$, $NJ_1J_2$, $=NJ_1$, $SJ_1$, $N_3$, CN, $OC(=L)J_1$, $OC(=L)NJ_1J_2$ and $NJ_3C(=L)NJ_1J_2$, wherein each $J_1$, $J_2$ and $J_3$ is, independently, H, $C_1$-$C_6$ alkyl or a protecting group, and L is O, S or $NJ_1$.

3. The gapped oligomeric compound of claim 1 wherein each $R_1$ is independently selected from $C_1$-$C_6$ alkyl, substituted $C_1$-$C_6$ alkyl, $C_2$-$C_6$ alkenyl and $C_2$-$C_6$ alkynyl.

4. The gapped oligomeric compound of claim 1 wherein each $R_1$ is independently selected from $CH_3$, $CH_2CH_3$, $CH_2CH_2OH$, $CH_2CHCH_2$ and $CHCH_2$.

5. The gapped oligomeric compound of claim 1 wherein each $R_1$ is $CH_3$.

6. The gapped oligomeric compound of claim 1 having only one 5'-substituted β-D-2'-deoxyribonucleoside of Formula I.

7. The gapped oligomeric compound of claim 1 having only two 5'-substituted β-D-2'-deoxyribonucleosides of Formula I.

8. The gapped oligomeric compound of claim 1 wherein each 5'-substituted β-D-2'-deoxyribonucleoside has the configuration of Formula Ia:

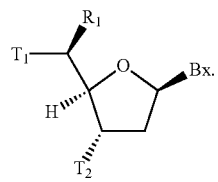

Ia

9. The gapped oligomeric compound of claim 1 wherein each 5'-substituted β-D-2'-deoxyribonucleoside has the configuration of Formula Ib:

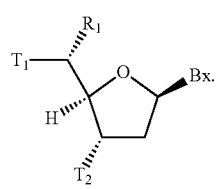

Ib

10. The gapped oligomeric compound of claim 1 wherein each internucleoside linking group that links adjacent monomer subunits is independently selected from a phosphodiester or phosphorothioate internucleoside linking group.

11. The gapped oligomeric compound of claim 1 wherein each internucleoside linking group that links adjacent monomer subunits is a phosphorothioate internucleoside linking group.

12. The gapped oligomeric compound of claim 1 wherein each monomer subunit comprises a heterocyclic base moiety independently selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

13. The gapped oligomeric compound of claim 1 wherein each modified nucleoside in the 5' and 3'-regions is independently selected from a bicyclic nucleoside comprising a bicyclic furanosyl sugar moiety or a modified nucleoside comprising a furanosyl sugar moiety having at least one substituent group.

14. The gapped oligomeric compound of claim 13 comprising one or more 2'-modified nucleosides that each have a 2'-substituent group independently selected from halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2—CH=CH_2$, $O(CH_2)_2—OCH_3$, $O(CH_2)_2—SCH_3$, $O(CH_2)_2—OCF_3$, $O(CH_2)_3—N(R_3)(R_4)$, $O(CH_2)_2—ON(R_3)(R_4)$, $O(CH_2)_2—O(CH_2)_2—N(R_3)(R_4)$, $OCH_2C(=O)—N(R_4)(R_4)$, $OCH_2C(=O)—N(R_5)—(CH_2)_2—N(R_3)(R_4)$ and $O(CH_2)_2—N(R_5)—C(=NR_6)[N(R_3)(R_4)]$ wherein $R_3$, $R_4$, $R_5$ and $R_6$ are each, independently, H or $C_1$-$C_6$ alkyl.

15. The gapped oligomeric compound of claim 14 wherein each 2'-substituent group is independently selected from F, $OCH_3$, $O(CH_2)_2—OCH_3$ and $OCH_2C(=O)—N(H)CH_3$.

16. The gapped oligomeric compound of claim 15 wherein each 2'-substituent group is $O(CH_2)_2—OCH_3$.

17. The gapped oligomeric compound of claim 13 comprising one or more bicyclic nucleosides wherein each bicyclic nucleoside has a bridging group independently selected from 4'-$(CH_2)$—O-2', 4'-$(CH_2)$—S-2', 4'-$(CH_2)_2$—O-2', 4'-$CH(CH_3)$—O-2', 4'-$CH(CH_2OCH_3)$—O-2', 4'-$C(CH_3)_2$—O-2', 4'-$CH_2$—N($OCH_3$)-2', 4'-$CH_2$—O—N($CH_3$)-2', 4'-$CH_2$—$NCH_3$—O-2', 4'-$CH_2$—C(H)($CH_3$)-2' and 4'-$CH_2$—C(=$CH_2$)-2'.

18. The gapped oligomeric compound of claim 17 wherein each bridging group is 4'-CH[(S)—($CH_3$)]—O-2'.

19. The gapped oligomeric compound of claim 1 comprising at least two different types of modified nucleosides in the 5' and 3'-regions comprising at least two different modified ribofuranosyl sugar moieties.

20. The gapped oligomeric compound of claim 19 wherein the 5' and 3'-regions include only 4'-CH[(S)—($CH_3$)]—O-2' bicyclic nucleosides and 2'-$O(CH_2)_2$—$OCH_3$ substituted nucleosides.

21. The gapped oligomeric compound of claim 1 wherein the modified nucleosides in the 5' and 3'-regions each have the same modified sugar moiety.

22. The gapped oligomeric compound of claim 1 wherein the 5' and 3'-regions each, independently, have from 3 to 6 monomer subunits and the gap region has from 6 to 10 monomer subunits.

23. A method of inhibiting gene expression comprising contacting one or more cells, a tissue or the animal with the oligomeric compound of claim 1 wherein said oligomeric compound is complementary to a target RNA.

24. The method of claim 23 wherein said cells are in a human.

25. The method of claim 23 wherein said target RNA is human mRNA.

26. The method of claim 23 wherein said target RNA is cleaved thereby inhibiting the function of said target RNA.

* * * * *